US009750801B2

(12) United States Patent
Barouch et al.

(10) Patent No.: US 9,750,801 B2
(45) Date of Patent: Sep. 5, 2017

(54) REPLICATING RECOMBINANT ADENOVIRUS VECTORS, COMPOSITIONS, AND METHODS OF USE THEREOF

(71) Applicants: Beth Israel Deaconess Medical Center, Inc., Boston, MA (US); Crucell Holland B.V., Leiden (NL)

(72) Inventors: Dan Barouch, Newton, MA (US); Peter Abbink, Winthrop, MA (US)

(73) Assignees: Janssen Vaccines & Prevention B.V., Leiden (NL); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/632,433

(22) Filed: Feb. 26, 2015

(65) Prior Publication Data
US 2015/0246112 A1    Sep. 3, 2015

Related U.S. Application Data

(60) Provisional application No. 61/946,091, filed on Feb. 28, 2014.

(51) Int. Cl.
C12N 15/00 (2006.01)
A61K 39/21 (2006.01)
A61K 39/235 (2006.01)
C12N 7/00 (2006.01)
C12N 15/86 (2006.01)
A61K 39/00 (2006.01)

(52) U.S. Cl.
CPC ............... *A61K 39/21* (2013.01); *C12N 7/00* (2013.01); *C12N 15/86* (2013.01); *A61K 2039/5256* (2013.01); *A61K 2039/53* (2013.01); *C12N 2710/10052* (2013.01); *C12N 2710/10143* (2013.01); *C12N 2710/10171* (2013.01); *C12N 2710/10343* (2013.01); *C12N 2710/16143* (2013.01); *C12N 2710/16171* (2013.01); *C12N 2740/16134* (2013.01); *C12N 2740/16171* (2013.01)

(58) Field of Classification Search
None
See application file for complete search history.

(56) References Cited

U.S. PATENT DOCUMENTS

| 3,608,030 | A | * | 9/1971 | Tint | A61K 9/2886 264/113 |
| 5,670,488 | A | | 9/1997 | Gregory et al. | |
| 8,227,243 | B2 | * | 7/2012 | Vogels | C07K 14/005 424/455 |
| 2005/0196384 | A1 | * | 9/2005 | Vogels | C07K 14/005 424/93.2 |
| 2005/0221493 | A1 | * | 10/2005 | Vogels | A61K 39/12 435/456 |
| 2006/0115456 | A1 | | 6/2006 | Peng et al. | |
| 2006/0233756 | A1 | * | 10/2006 | Eloit | C12N 15/86 424/93.2 |
| 2007/0298051 | A1 | * | 12/2007 | Barouch | A61K 38/18 424/199.1 |
| 2010/0047282 | A1 | * | 2/2010 | Nabel | A61K 39/12 424/233.1 |
| 2010/0143302 | A1 | * | 6/2010 | Havenga | C12N 7/00 424/93.2 |
| 2011/0311580 | A1 | * | 12/2011 | Vogels | C07K 14/005 424/199.1 |
| 2012/0076812 | A1 | * | 3/2012 | Barouch | A61K 39/21 424/188.1 |
| 2013/0122038 | A1 | * | 5/2013 | Radosevic | A61K 35/761 424/199.1 |
| 2014/0302080 | A1 | * | 10/2014 | Barouch | C07K 14/005 424/188.1 |
| 2014/0348791 | A1 | * | 11/2014 | Barouch | C07K 14/005 424/93.2 |
| 2015/0291935 | A1 | * | 10/2015 | Barouch | A61K 39/12 424/199.1 |
| 2016/0024156 | A1 | * | 1/2016 | Barouch | A61K 39/21 424/186.1 |

FOREIGN PATENT DOCUMENTS

| WO | 2004018627 A2 | 3/2004 |
| WO | 2005012537 A2 | 2/2005 |
| WO | 2011014794 A1 | 2/2011 |

OTHER PUBLICATIONS

Gray GE, et. al; HVTN 503/Phambili study team. Safety and efficacy of the HVTN 503/Phambili study of a clade-B-based HIV-1 vaccine in South Africa: a double-blind, randomised, placebo-controlled test-of-concept phase 2b study. Lancet Infect Dis. Jul. 2011;11(7):507-15. Epub May 11, 2011. Erratum in: Lancet Infect Dis. Jul. 2011;11(7):495.*

Abbink P. et. al. Human adenovirus type 26, complete genome. Apr. 18, 2007. GenBank: EF153474.1.*

Zhang XY, et. al. Human cytomegalovirus major immediate-early gene, enhancer. Aug. 2, 1993. GenBank: K03104.1.*

Patterson LJ, Prince GA, Richardson E, Alvord WG, Kalyan N, Robert-Guroff M. Insertion of HIV-1 genes into Ad4DeltaE3 vector abrogates increased pathogenesis in cotton rats due to E3 deletion. Virology. Jan. 5, 2002;292(1):107-13.*

Huang MM, Hearing P. Adenovirus early region 4 encodes two gene products with redundant effects in lytic infection. J Virol. Jun. 1989;63(6):2605-15.*

(Continued)

*Primary Examiner* — Stacy B Chen
(74) *Attorney, Agent, or Firm* — Panitch Schwarze Belisario & Nadel LLP

(57) ABSTRACT

Replicating recombinant adenovirus vectors derived from human adenovirus serotype 26 or human adenovirus serotype 35 are described. The replicating recombinant adenovirus vectors have attenuated replicative capacity as compared to that of the corresponding wild-type adenovirus. They can be used for stable expression of heterologous genes in vivo. Also described are compositions and methods of using these recombinant adenovirus vectors to induce an immune response in a subject, and vaccinate a subject against an immunogenic human immunodeficiency virus (HIV) infection.

20 Claims, 26 Drawing Sheets

(56) References Cited

OTHER PUBLICATIONS

Bridge E, Ketner G. Redundant control of adenovirus late gene expression by early region 4. J Virol. Feb. 1989;63(2):631-8.*

Santra, S., et al., Mosaic vaccines elicit CD8+ T lymphocyte responses that confer enhanced immune coverage of diverse HIV strains in monkeys. Nat Med, 2010. 16(3): p. 324-8.

Li, Q., et al., Visualizing antigen-specific and infected cells in situ predicts outcomes in early viral infection. Science, 2009. 323(5922): p. 1726-9.

Baden, L.R., et al., First-in-human evaluation of the safety and immunogenicity of a recombinant adenovirus serotype 26 HIV-1 Env vaccine (IPCAVD 001). J Infect Dis, 2013. 207(2): p. 240-7.

Barouch, D.H., et al., Characterization of humoral and cellular immune responses elicited by a recombinant adenovirus serotype 26 HIV-1 Env vaccine in healthy adults (IPCAVD 001). J Infect Dis, 2013. 207(2): p. 248-56.

Alexander, J. et al., Pre-clinical evaluation of a replication-competent recombinant adenovirus serotype 4 vaccine expressing HIV-1 Envelope 1086 Clade C. PloS one 7:e31177.

Thomas, et al., Effects of the Deletion of Early Region 4(E4) Open Reading Frame 1 (orf1), orf1-2, orf1-3 and orf1-4 on Virus-Host Cell Interation, Transgene Expression, and Immunogenicity of Replicating Adenovirus HIV Vaccine Vectors, PLOS ONE 2013. 8(10) p. e76344.

Kim, et al., Evaluation of E1B gene-attenuated replicating adenoviruses for cancer gene therapy, Cancer Gene Therapy, 2012. 9: p. 725-736.

Centers for Disease, Control, and Prevention, Vital signs: HIV prevention through care and treatment—United States. MMWR Morb Mortal Wkly Rep, 2011. 60(47): p. 1618-23.

Centlivre, M., et al., In HIV-1 pathogenesis the die is cast during primary infection. AIDS, 2007. 21(1): p. 1-11.

Flynn, N.M., et al., Placebo-controlled phase 3 trial of a recombinant glycoprotein 120 vaccine to prevent HIV-1 infection. J Infect Dis, 2005. 191(5): p. 654-65.

Chen, H., et al., Adenovirus-based vaccines: comparison of vectors from three species of adenoviridae. J Virol, 2010. 84(20): p. 10522-32.

Liu, J., et al., Immune control of an SIV challenge by a T-cell-based vaccine in rhesus monkeys. Nature, 2009. 457(7225): p. 87-91.

Diarrhea: Why children are still dying and what can be done, 2009, The United Nations Chidlren's Fund (UNICEF)/World Health Organization (WHO): New York, NY.

Ramani, S. and G. Kang, Viruses causing childhood diarrhoea in the developing world. Curr Opin Infect Dis, 2009. 22(5): p. 477-82.

Gurwith, M., et al., Safety and immunogenicity of an oral, replicating adenovirus serotype 4 vector vaccine for H5N1 influenza: a randomised, double-blind, placebo-controlled, phase 1 study. Lancet Infect Dis, 2013. 13(3): p. 238-50.

Centers for Disease, Control, and Prevention, Vital signs: HIV prevention through care and treatment-United States. MMWR Morb Mortal Wkly Rep, 2011. 60(47): p. 1618-23.

Centlivre, M., et al., in HIV-1 pathogenesis the die is cast during primary infection. AIDS, 2007. 21(1): pp. 1-11.

Wawer, M.J., et al., Rates of HIV-1 transmission per coital act, by stage of HIV-1 infection, in Rakai, Uganda. J Infect Dis, 2005. 191(9): p. 1403-9.

Flynn, n. M., et al., Placebo-controlled phase 3 trial of a recombinant glycoprotein 120 vaccine to prevent HIV-1 infection. J Infect Dis, 2005. 191(5): p. 654-65.

Pitisuttithum, P., et al., Randomized, double-blind, placebo-controlled efficacy trial of a bivalent recombinant glycoprotein 120 HIV-1 vaccine among injection drug users in Bangkok, Thailand. J Infect Dis, 2006. 194(12): p. 1661-71.

Buchbinder, S.P., et al., Efficacy assessment of a cell-mediated immunity HIV-1 vaccine (the Step Study): a double-blind, randomised, placebo-controlled, test-of-concept trial. Lancet, 2008. 372(9653): p. 1881-93.

Rerks-Ngarm, S., et al., Vaccination with ALVAC and AIDSVAX to prevent HIV-1 infection in Thailand. N Engl J Med, 2009. 361(23): p. 2209-20.

McElrath, M.J., et al., HIV-1 vaccine-induced immunity in the test-of-concept Step Study: a case-cohort analysis. Lancet, 2008. 372(9653): p. 1894-905.

Abbink, P., et al., Comparative seroprevalence and immunogenicity of six rare serotype recombinant adenovirus vaccine vectors from subgroups B and D. J Virol, 2007. 81(9): p. 4654-63.

Vogels, R., et al., Replication-deficient human adenovirus type 35 vectors for gene transfer and vaccination: efficient human cell infection and bypass of preexisting adenovirus immunity. J Virol, 2003. 77(15): p. 8263-71.

Farina, S.F., et al., Replication-defective vector based on a chimpanzee adenovirus. J Virol, 2001. 75(23): p. 11603-13.

Barouch, D.H., et al., International seroepidemiology of adenovirus serotypes 5, 26, 35, and 48 in pediatric and adult populations. Vaccine, 2011. 29: p. 5203-5209.

Chen, H. et al., Adenovirus-based vaccines: comparison of vectors from three species of adenoviridae. J Virol, 2010. 84(20): p. 10522-32.

Thorner, A.R., et al., Age dependence of adenovirus-specific neutralizing antibody titers in individuals from sub-Saharan Africa. J Clin Microbiol, 2006. 44(10): p. 3781-3.

Sprangers, M.C., et al., Quantifying adenovirus-neutralizing antibodies by luciferase transgene detection: addressing preexisting immunity to vaccine and gene therapy vectors. J Clin Microbiol, 2003. 41(11): p. 5046-52.

Waddington, S.N., et al., Adenovirus serotype 5 hexon mediates liver gene transfer. Cell, 2008. 132(3): p. 397-409.

Liu, J., et al., Magnitude and phenotype of cellular immune responses elicited by recombinant adenovirus vectors and heterologous prime-boost regimens in rhesus monkeys. J Virol, 2008. 82(10): p. 4844-52.

Liu, J., et al., Immune control of an SIV challenge by a T-cell-based vaccine in rhesus monkeys. Nature, 2009. 457 (7225): p. 87-91.

Lore, K., et al., Myeloid and plasmacytoid dendritic cells are susceptible to recombinant adenovirus vectors and stimulate polyfunctional memory T cell responses. J Immunol, 2007. 179(3): p. 1721-9.

Kuschner, R.A., et al., A phase 3, randomized, double-blind, placebo-controlled study of the safety and efficacy of the live, oral adenovirus type 4 and type 7 vaccine, in U.S. military recruits. Vaccine, 2013. 31(28): p. 2963-71.

Masopust, D. And L.J. Picker, Hidden memories: frontline memory T cells and early pathogen interception. J Immunol, 2012. 188(12): p. 5811-7.

Bell, J.A., et al., Illness and microbial experiences of nursery children at junior village. American Journal of Hygiene, 1961. 74: p. 267-292.

Brandt, C.D., et al., Infections in 18,000 infants and children in a controlled study of respiratory tract disease. I. Adenovirus pathogenicity in relation to serologic type and illness syndrome. Am J Epidemiol, 1969. 90(6): p. 484-500.

Fox, J.P., et al., the virus watch program: a continuing surveillance of viral infections in metropolitan New York families. VI. Observations of adenovirus infections: virus excretion patterns, antibody response, efficiency of surveillance, patterns of infections, and relation to illness. Am J Epidemiol, 1969. 89(1): p. 25-50.

Fox, J.P., C.E. Hall, and M.K. Cooney, the Seattle Virus Watch. VII. Observations of adenovirus infections. Am J Epidemiol, 1977. 105(4): p. 362-86.

Noel, J., et al., Identification of adenoviruses in faeces from patients with diarrhoea at the Hospitals for Sick Children, London, 1989-1992. J Med Virol, 1994. 43(1): p. 84-90.

Faden, H., et al., Pediatric adenovirus infection: relationship of clinical spectrum, seasonal distribution, and serotype. Clin Pediatr (Phila), 2011. 50(6): p. 483-7.

Abbas, K.Z., et al., Temporal changes in respiratory adenovirus serotypes circulating in the greater Toronto area, Ontario, during Dec. 2008 to Apr. 2010. Virol J, 2013. 10: p. 15.

(56) References Cited

OTHER PUBLICATIONS

Diarrhea: Why children are still dying and what can be done, 2009, the United Nations Chidlren's Fund (UNICEF)/ World Health Organization (WHO): New York, NY.
Ramani, S. And G. Kang, Viruses causing childhood diarrhoea in the developing world. Curr Opin Infect Dis, 2009. 22 (5): p. 477-82.
Kotloff, K.L., et al., Burden and aetiology of diarrhoeal disease in infants and young children in developing countries (the Global Enteric Multicenter Study, GEMS): a prospective, case-control study. Lancet, 2013. 382(9888): p. 209-22.
Magwalivha, M., et al., High prevalence of species D human adenoviruses in fecal specimens from Urban Kenyan children with diarrhea. J Med Virol, 2010. 82(1): p. 77-84.
Liu, L.Y., et al., [Investigation of adenovirus infection in hospitalized children with diarrhea during 2010 in Beijing, China]. Zhonghua Er Ke Za Zhi, 2012. 50(6): p. 450-4 (English Abstract Only).
Ouyang, Y., et al., Etiology and epidemiology of viral diarrhea in children under the age of five hospitalized in Tianjin, China. Arch Virol, 2012. 157(5): p. 881-7. (English Abstract Only).
Lee, J.I., et al., Detection and molecular characterization of adenoviruses in Korean children hospitalized with acute gastroenteritis. Microbiol Immunol, 2012. 56(8): p. 523-8.
Espinola, E.E., et al., Genetic diversity of human adenovirus in hospitalized children with severe acute lower respiratory infections in Paraguay. J Clin Virol, 2012. 53(4): p. 367-9.
Mast, T.C., et al., International epidemiology of human pre-existing adenovirus (Ad) type-5, type-6, type-26 and type-36 neutralizing antibodies: correlates of high Ad5 titers and implications for potential HIV vaccine trials. Vaccine, 2010. 28: p. 950-957.
Kasel, J.A., et al., Conjunctivitis and enteric infection with adenovirus types 26 and 27: responses to primary, secondary and reciprocal cross-challenges. Am J Hyg, 1963. 77: p. 265-82. (Abstract Only).
Hierholzer, J.C., et al., Adenoviruses from patients with AIDS: a plethora of serotypes and a description of five new serotypes of subgenus D (types 43-47). J Infect Dis, 1988. 158(4): p. 804-13 (Abstract Only).
Khoo, S.H., et al., Adenovirus infections in human immunodeficiency virus-positive patients: clinical features and molecular epidemiology. J Infect Dis, 1995. 172(3): p. 629-37 (Abstract Only).
Curlin, M.E., et al., Frequent detection of human adenovirus from the lower gastrointestinal tract in men who have sex with men. PLoS One, 2010. 5(6): p. e11321.
Dubberke, E.R., et al., Acute meningoencephalitis caused by adenovirus serotype 26. J Neurovirol, 2006. 12(3): p. 235-40.
Koneru, B., et al., Adenoviral infections in pediatric liver transplant recipients. JAMA, 1987. 258(4): p. 489-92.
Venard, V., et al., Genotyping of adenoviruses isolated in an outbreak in a bone marrow transplant unit shows that diverse strains are involved. J Hosp Infect, 2000. 44(1): p. 71-4.
Al Qurashi, Y.M., M. Guiver, and R.J. Cooper, Sequence typing of adenovirus from samples from hematological stem cell transplant recipients. J Med Virol, 2011. 83(11): p. 1951-8.
Janes, H., et al., MRKAd5 HIV-1 Gag/Pol/Nef vaccine-induced T-cell responses inadequately predict distance of breakthrough HIV-1 sequences to the vaccine or viral load. PLoS One, 2012. 7(8): p. e43396.
Fischer, W., et al., Polyvalent vaccines for optimal coverage of potential T-cell epitopes in global HIV-1 variants. Nat Med, 2007. 13(1): p. 100-6.
Barouch, D.H., et al., Mosaic HIV-1 vaccines expand the breadth and depth of cellular immune responses in rhesus monkeys. Nat Med, 2010. 16(3): p. 319-23.
Written Opinion dated Oct. 6, 2015 in Int'l Application No. PCT/EP2015/054031.
Int'l Search Report issued Oct. 6, 2015 in Int'l Application No. PCT/EP2015/054031.
Peng et al, "Replicating Rather than Nonreplicating Adenovirus-Human Immunodeficiency Virus Recombinant Vaccines are Better at Eliciting Potent Cellular Immunity and Priming Higher-Titer Antibodies," Journal of Virology, vol. 79, No. 16, pp. 10200-10209 (Aug. 2005).
Neill et al, "Genetic Analysis of the Adenovirus E4 6/7 trans Activator: Interaction with E2F and Induction of a Stable DNA-Protein Complex Are Critical for Activity," Journal of Virology, vol. 65, No. 10, pp. 5364-5373 (Oct. 1991).
Patterson "The "STEP-Wise" Future of Adenovirus-Based HIV Vaccines," Current Medicinal Chemistry, vol. 18, pp. 3981-3986 (2011).
Patterson et al, "Replicating Adenovirus Vector Prime/Protein Boost Strategies for HIV Vaccine Development," Expert Opin. Biol. Ther, vol. 8, No. 9, pp. 1347-1363 (2008).
Alexander et al, "Pre-Clinical Development of a Recombinant, Replication-Competent Adenovirus Serotype 4 Vector Vaccine Expressing HIV-1 Envelope 1086 Clade C," PLOS ONE, vol. 8, Issue 12, pp. 1-16 (2013).
Office Action dated Jun. 22, 2017 in EP Application No. 15707112.7.
"AIDS Vaccine 2013 Oct. 7-10, 2013 Barelona Spain", Aids Research and Human Retroviruses, vol. 29, No. 11, 4 pgs. (Nov. 2013).

\* cited by examiner

FIG. 12

RT-PCR Results on Serum Samples from Monkeys Immunized with Replicating E1(+) and Non-Replicating E1(-) Ad26-SIVGag Vectors.

| Serum Monkey | Wk-1 | Wk1 | Wk4 | Wk6 | Wk8 | Wk10 | Wk12 | Wk16 |
|---|---|---|---|---|---|---|---|---|
| 415-08 | 0 | 0 | 0 | 0 | 0 | 0 | 0 | 0 |
| 421-08 | 0 | 0 | 0 | 0 | 0 | 0 | 0 | 0 |
| 451-08 | 0 | 0 | 0 | 0 | 0 | 0 | 0 | 0 |
| 427-08 | 0 | 0 | 0 | 0 | 0 | 0 | 0 | 0 |
| 429-08 | 0 | 0 | 0 | 0 | 0 | 0 | 0 | 0 |
| 432-08 | 0 | 0 | 0 | 0 | 0 | 0 | 0 | 0 |
| Control | 3.0E+05 | 2.8E+05 | 4.4E+05 | 3.2E+05 | 3.8E+05 | 3.6E+05 | 3.7E+05 | 3.1E+05 |

REPLICATING RECOMBINANT ADENOVIRUS VECTORS, COMPOSITIONS, AND METHODS OF USE THEREOF

CROSS-REFERENCE TO RELATED APPLICATIONS

This application is entitled to priority pursuant to 35 U.S.C. §119(e) to U.S. Provisional Patent Application No. 61/946,091, filed Feb. 28, 2014, which is incorporated by reference herein in its entirety.

STATEMENT REGARDING FEDERALLY SPONSORED RESEARCH OR DEVELOPMENT

This invention was made with government support under Grant Nos. AI078526 and AI096040 awarded by the National Institutes of Health. The government has certain rights in the invention. This invention was also made with support from the Bill and Melinda Gates Foundation Grant No. OPP1033091.

REFERENCE TO SEQUENCE LISTING SUBMITTED ELECTRONICALLY

This application contains a sequence listing, which is submitted electronically via EFS-Web as an ASCII formatted sequence listing with a file name "688097-34U1 Sequence Listing.txt", creation date of Feb. 27, 2014, and having a size of 381 KB. The sequence listing submitted via EFS-Web is part of the specification and is herein incorporated by reference in its entirety.

FIELD OF THE INVENTION

The invention relates to replicating recombinant adenovirus vectors. In particular, the invention provides replicating recombinant adenovirus vectors derived from human adenovirus serotype 26 (Ad26) or serotype 35 (Ad35) that can be used to induce immune response or provide protective immunity against an HIV infection.

BACKGROUND OF THE INVENTION

Human Immunodeficiency Virus (HIV) affects millions of people worldwide, and the prevention of HIV remains a very high priority, even in an era of widespread antiretroviral treatment. In the United States, the Center for Disease Control (CDC) estimates that of all HIV-positive US residents, approximately one fifth are unaware of their status, and this small proportion is responsible for transmitting half the new infections each year [2]. Worldwide, the gap in prompt diagnosis and treatment is far greater. At the end of 2010, an estimated 34 million people were living with HIV worldwide, up 17% from 2001. Although the majority of new HIV infections continue to occur in sub-Saharan Africa, the CDC estimated that the annual incidence of HIV infection from 2008-2011 in the United States has remained stable at around 15-16/100,000, with over 40,000 new infections each year. Thus, it is an urgent global health priority to find a safe and potent HIV vaccine that would prevent HIV infection or blunt its initial impact prior to diagnosis, including both destruction of the gut CD4 pool [3] and high risk of transmission [4].

Live attenuated vaccines have proven to be highly efficacious in humans and in non-human primates (NHP) against certain viral diseases, such as a live attenuated simian immunodeficiency virus (SIV) based vaccine for preventing SIV infection. Unfortunately, due to safety risks associated with live attenuated HIV, such a strategy is not applicable for HIV human vaccine.

As an alternative to live attenuated viral vaccines, the use of replication incompetent recombinant viral vectors has been explored for vaccines and other types of gene therapy. In particular, replication incompetent recombinant adenoviral vectors, particularly adenovirus serotypes 2 and 5 (Ad2 and Ad5) have been extensively studied for gene delivery applications, including vaccination. Although such replication incompetent Ad5 vector-based vaccines have been shown to elicit protective immune responses in a variety of animal models, the utility of recombinant Ad5 vector-based vaccines for human immunodeficiency virus (HIV) and other pathogens is likely to be limited by the high seroprevalence of Ad5-specific neutralizing antibodies (NAbs) in human populations [17]. For example, in a seroepidemiology study of 4,381 subjects worldwide, it was observed that Ad5 NAb titers were nearly universal and high titer in sub-Saharan Africa, with the majority of individuals exhibiting Ad5 NAb titers >200 [14].

Even though Ad5 has high seroprevalence in humans, several HIV-1 vaccine efficacy trials have been conducted using vaccines based on recombinant Ad5 vector-based vaccines. These studies include the HVTN 502/STEP (Merck Ad5), HVTN 503/Phambili (Merck Ad5), and HVTN 505 (NIH VRC DNA/Ad5) HIV-1 vaccine efficacy trials. However, all three of these HIV-1 vaccine efficacy studies, which utilized nonreplicating Ad5 and DNA/Ad5 vaccines, showed no efficacy against HIV-1 infection. Moreover, a trend towards increased HIV-1 infection was observed in vaccinees with the Merck Ad5 vaccine from the STEP study as compared with placebos. Experience to date with replication incompetent vectors such as adenovirus subtype 5 for HIV vaccine has been disappointing, with failure to show benefit in several efficacy trials [5-8].

Accordingly, concerns regarding the safety of Ad5 vectors, particularly from the STEP study [8, 10], have led to the exploration of biologically substantially different Ad vectors from alternative serotypes as viral vaccine vectors [11-13]. One example of an alternative adenovirus serotype to Ad5 is Adenovirus serotype 26 (Ad26). Ad26 is a non-enveloped DNA virus that is a relatively uncommon virus in humans. Ad26 is not known to replicate in any other species. A number of surveys for adenovirus in different populations have shown it to be isolated only rarely, and even when isolated, seldom associated with symptoms. Experimental inoculation, likewise, showed little evidence for serious infection. See, e.g., [14, 27-43]. Thus, there is no evidence from observational studies that Ad26 causes clinical symptoms in healthy adults, and experimental data from an Ad26 challenge study also suggested that enteric Ad26 infection does not produce symptoms [44].

In terms of at least receptor usage, in vivo tropism, interactions with dendritic cells, innate immune profiles, adaptive immune phenotypes, and protective efficacy against SIV in rhesus monkeys, Ad26 has proven to be biologically very different from Ad5 [11, 12, 15, 19-22]. Moreover, the safety and immunogenicity of nonreplicating Ad26 vector in humans has been demonstrated (ClinicalTrials.Gov NCT01215149). Furthermore, many of the advantageous biological differences between Ad5 and Ad26, such as lower seroprevalance and low neutralizing antibody titers in humans are also present between Ad5 and Ad35.

Replication-incompetent Ad26 has been tested in a GLP toxicology study and three Phase I clinical trials with no significant pattern of adverse effects. Although replication incompetent viral vectors are preferred for gene therapy and related applications, such as vaccination, since replicating viral vectors can produce multiple copies of the virus, which can go on to infect other cells, setting of an infections cycle, there are some possible drawbacks to the use of replication incompetent viral vectors. One possible drawback of replication-incompetent viral vectors is that expression of the target gene to be delivered to the host from the viral vector can decrease following administration of the vector. Being unable to replicate or propagate in the host, the viral vector cannot produce any new copies that can subsequently be used to augment gene expression, requiring re-administration of the viral vector. If the same adenovirus serotype is re-administered to the host, the host may generate neutralizing antibodies to that particular adenovirus serotype, resulting in a serotype specific anti-adenovirus response. Such a serotype specific anti-adenovirus response may prevent effective re-administration of the viral vector, rendering it less effective as a vaccine or gene delivery vehicle.

Accordingly, there is a need in the art for new recombinant viral vectors that can be used as vaccine vectors that overcome certain disadvantages associated with replication-incompetent recombinant viral vectors. In particular, there exists a need for new recombinant viral vectors that can be used as vaccine vectors against infectious diseases, such as HIV infection. Such a vaccine preferably would be simple to administer, long-acting, with minimal adverse effects. In the case of an HIV vaccine, the HIV vaccine further would preferably be effective against a wide scope of the diversity of circulating types of HIV transmission, including the most frequent.

BRIEF SUMMARY OF THE INVENTION

The invention satisfies this need by providing a replicating recombinant adenovirus vector comprising a recombinant adenovirus genome derived from a human adenovirus serotype 26 or serotype 35 genome. In particular, the invention provides a replicating recombinant adenovirus vector that can be used to induce an immune response or provide protective immunity in a subject, e.g. against an HIV infection.

In one general aspect, the invention provides a replicating recombinant adenovirus vector, comprising a recombinant adenovirus genome having:
  (a) a promoter operably linked to a heterologous nucleic acid sequence;
  (b) a functional E1 coding region;
  (c) a deletion in the E3 coding region; and
  (d) a deletion in the E4 coding region, provided that E4 open reading frame 6/7 is not deleted,
wherein the adenovirus genome is human adenovirus serotype 26 or 35 genome.

According to a preferred embodiment of the invention, the heterologous nucleic acid sequence is located between a left inverted terminal repeat (ITR) and the 5'-end of the functional E1 coding region of the replicating recombinant adenovirus vector.

In an embodiment of the invention, the replicating recombinant adenovirus vector comprises a heterologous nucleic acid sequence encoding an immunogenic polypeptide. The heterologous nucleic acid sequence can encode an HIV antigen, preferably an HIV antigen derived from the sequences of the HIV gag, pol, and/or env gene products, and more preferably a mosaic HIV antigen. In particular embodiments, the heterologous nucleic acid sequence encodes a polypeptide comprising the amino acid sequence of SEQ ID NO: 48 or SEQ ID NO: 50. In more particular embodiments, the heterologous nucleic acid sequence comprises the nucleotide sequence of SEQ ID NO: 47 or SEQ ID NO: 49.

In embodiments of the invention, the replicating recombinant adenovirus vector comprises a functional E1 coding region encoding the amino acid sequences of SEQ ID NOs: 14, 15, and 16. In a particular embodiment, the functional E1 coding region comprises the nucleotide sequence of SEQ ID NO: 13.

In one embodiment of the invention, the replicating recombinant adenovirus vector comprises a partially deleted E3 coding region, and the partially deleted E3 coding region consists of the nucleotide sequence encoding the amino acid sequence of SEQ ID NO: 6. In a particular embodiment, the partially deleted E3 coding region consists of the nucleotide sequence of SEQ ID NO: 5.

In one embodiment of the invention, the replicating recombinant adenovirus vector comprises a partially deleted E4 coding region, and the partially deleted E4 coding region consists of the nucleotide sequence encoding the amino acid sequence of SEQ ID NO: 22. In a particular embodiment, the partially deleted E4 coding region consists of the nucleotide sequence of SEQ ID NO: 23.

In one embodiment of the invention, the replicating recombinant adenovirus vector comprises a CMV promoter operably linked to a heterologous nucleic acid sequence. In a particular embodiment, the CMV promoter has the nucleotide sequence of SEQ ID NO: 51.

According to embodiments of the invention, a replicative capacity of a replicating recombinant adenovirus vector of the invention is attenuated as compared to a replicative capacity of a wild-type human adenovirus serotype 26 or serotype 35. In particular embodiments, the replicative capacity of a replicating recombinant adenovirus vector of the invention is attenuated by at least about 80-fold to 100-fold, as compared to the replicative capacity of a wild-type human adenovirus serotype 26 or 35.

In a particular embodiment, the invention provides a replicating recombinant adenovirus vector comprising a recombinant human adenovirus serotype 26 genome having:
  (a) a promoter operably linked to a heterologous nucleic acid sequence encoding the amino acid sequence of SEQ ID NO: 48 or SEQ ID NO: 50;
  (b) a functional E1 coding region encoding the amino acid sequences of SEQ ID NOs: 14, 15 and 16;
  (c) a partially deleted E3 coding region consisting of the nucleotide sequence encoding the amino acid sequence of SEQ ID NO: 6; and
  (d) a partially deleted E4 coding region consisting of the nucleotide sequence encoding the amino acid sequence of SEQ ID NO: 22.

In an embodiment of the invention, the replicating recombinant adenovirus vector comprises the heterologous nucleic acid sequence located between a left ITR and the 5'-end of the functional E1 coding region encoding the amino acid sequences of SEQ ID NOs: 14, 15, and 16.

In another particular embodiment of the invention, a replicating recombinant adenovirus vector comprises a recombinant human adenovirus serotype 26 genome having:
  (a) a CMV promoter having the nucleotide sequence of SEQ ID NO: 51 operably linked to a heterologous nucleic acid sequence comprising the nucleotide sequence of SEQ ID NO: 47 or SEQ ID NO: 49;
  (b) a functional E1 coding region comprising the nucleotide sequence of SEQ ID NO: 13;

(c) a partially deleted E3 coding region consisting of the nucleotide sequence of SEQ ID NO: 5; and
(d) a partially deleted E4 coding region consisting of the nucleotide sequence of SEQ ID NO: 23,
wherein the heterologous nucleic acid sequence is located between left ITR and 5'-end of the functional E1 coding region.

In another general aspect, the invention provides a composition comprising a replicating recombinant adenovirus vector according to an embodiment of the invention and a pharmaceutically acceptable carrier, preferably the vector is isolated. In one embodiment, a composition of the invention is formulated for oral administration to a subject. In another embodiment, a composition of the invention is an enteric-coated capsule.

In yet another general aspect, the invention provides a method of producing a replicating adenovirus particle. The method comprises introducing a replicating recombinant adenovirus vector according to an embodiment of the invention into a cell under conditions sufficient for replication of the recombinant adenovirus genome of the vector and packaging of the adenovirus particle in the cell; and collecting the adenovirus particle.

Other general aspects of the invention relate to a method of producing an immune response in a subject, and a method of vaccinating a subject against an infection comprising administering to the subject an immunogenically effective amount of a composition comprising a pharmaceutically acceptable carrier and a replicating recombinant adenovirus vector according to the invention. Preferably, the composition is orally administered to the subject.

According to embodiments of the invention, a method of producing an immune response in a human subject or vaccinating a human subject against an HIV infection comprises orally administering to the subject an immunogenically effective amount of a composition comprising a pharmaceutically acceptable carrier and a replicating recombinant adenovirus vector comprising a recombinant serotype 26 adenovirus genome.

In one embodiment of a method of producing an immune response in a human subject or vaccinating a human subject against an HIV infection, the composition administered to the subject comprises a replicating recombinant adenovirus vector comprising a recombinant serotype 26 adenovirus genome having:
(a) promoter operably linked to a heterologous nucleic acid sequence encoding the amino acid sequence of SEQ ID NO: 48 or SEQ ID NO: 50;
(b) a functional E1 coding region encoding the amino acid sequences of SEQ ID NOs: 14, 15, and 16;
(c) a partially deleted E3 coding region consisting of the nucleotide sequence encoding the amino acid sequence of SEQ ID NO: 6; and
(d) a partially deleted E4 coding region consisting of the nucleotide sequence encoding the amino acid sequence of SEQ ID NO: 22.

Preferably, in the method of producing an immune response in a human subject or vaccinating a human subject against an HIV infection according to an embodiment of the present invention, the heterologous nucleic acid sequence is located between left ITR and 5'-end of the functional E1 coding region In another embodiment of a method of producing an immune response in a human subject or vaccinating a human subject against an HIV infection, the composition administered to the subject comprises a replicating recombinant adenovirus vector comprising a recombinant serotype 26 adenovirus genome having:
(a) a CMV promoter having the nucleotide sequence of SEQ ID NO: 51 operably linked to a heterologous nucleic acid sequence comprising the nucleotide sequence of SEQ ID NO: 47 or SEQ ID NO: 49;
(b) a functional E1 coding region comprising the nucleotide sequence of SEQ ID NO: 13;
(c) a partially deleted E3 coding region consisting of the nucleotide sequence of SEQ ID NO: 5; and
(d) a partially deleted E4 coding region consisting of the nucleotide sequence of SEQ ID NO: 23
wherein the heterologous nucleic acid sequence is located between left ITR and 5'-end of the functional E1 coding region.

The invention also relates to a replicating recombinant adenovirus vector according to the invention for use in producing an immune response in a subject, or for use in the vaccination of a subject against an infection. Any of the replicating recombinant adenovirus vectors according to the invention, including but not limited to those described herein, can be used in producing an immune response in a subject, or in the vaccination of a subject against an infection. Preferably, the replicating recombinant adenovirus vector according to the invention is for use in producing an immune response in a human subject or vaccinating a human subject against an HIV infection.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 3A: adaptor Ad26 plasmid vector (AdApt26.26E1.Mos1-HIVEnv; SEQ ID NO: 72) containing a heterologous nucleic acid sequence encoding the mosaic HIV antigen Mos1-HIVEnv in the transgene cassette cloned upstream of the E1 coding region (which encodes E1A, E1B 19K and E1B 55K proteins); FIG. 3B: cosmid vector (pWeAd26.pIX-rITR.dE3.dE4.260RF6; SEQ ID NO: 2) containing a partially deleted E3 coding region (E3-12.2K), a partially deleted E4 coding region where all E4 open reading frames have been deleted except for E4 open reading frame 6/7 (E4 Orf6/7), and the remaining portion of the Ad26 genome; the adaptor Ad26 plasmid vector shown in FIG. 3A and the cosmid vector in FIG. 3B contain overlapping regions of nucleic acid sequence (marked as "Overlap with cosmid" and "Overlap with AdApter", respectively) that facilitate homologous recombination in a host cell to produce a replicating recombinant Ad26 vector according to embodiments of the invention;

FIG. 4A: assessment of transgene region integrity by PCR using primers CMV.fwd (Ad26_1) (SEQ ID NO: 73) and E1.rev (Ad26_7) (SEQ ID NO: 74) (expected size of PCR product: 3.3 kb); FIG. 4B: identity PCR for the E1 coding region using primers polyA.fwd (Ad26_8) (SEQ ID NO: 75) and Ad26.pIX.rev (Ad26_9) (SEQ ID NO: 76) (expected size of PCR product: 3 kb), the E3 coding region using primers Ad26.E3.fwd (Ad26_3) (SEQ ID NO: 77) and Ad26.E3.rev (Ad26_4) (SEQ ID NO: 78) (expected size of PCR product: 0.5 kb), and the E4 coding region (primers Ad26.E4.fwd (Ad26_5) (SEQ ID NO: 79) & AdE4.rev (Ad26_6) (SEQ ID NO: 80)) (expected size of PCR product: 1.5 kb); FIG. 4C: analysis of Mos1-HIVEnv expression (140 kDa) by Western blot using primary antibody anti-HIV-1 gp120 (cat#NEA-9301, Virus Research Products) and secondary antibody Goat anti-mouse IgG-HRP (cat#170-6516, Biorad);

FIG. 5A: PCR analysis of the E1 coding region (primers polyA.fwd (Ad26_8) (SEQ ID NO: 75) and Ad26.pIX.rev (Ad26_9) (SEQ ID NO: 76)), E3 coding region (primers Ad26.E3.fwd (Ad26_3) (SEQ ID NO: 77) and Ad25.E3.rev (Ad26_4) (SEQ ID NO: 78) and E4 coding region (primers Ad26.E4.fwd (Ad26_5) (SEQ ID NO: 79) & Ad26.E4.rev (Ad26_6) (SEQ ID NO: 80); FIG. 5B: PCR analysis of transgene region integrity using primers CMV.fwd (Ad26_1) (SEQ ID NO: 73) and Ad26_10 (SEQ ID NO: 81)); FIG. 5C: Western Blot analysis of protein expression of mosaic HIV antigen (Mos1-HIVEnv) using primary antibody anti-HIV-1 gp120 (cat#NEA-9301, Virus Research Products) and secondary antibody Goat anti-mouse IgG-HRP (cat#170-6516, Biorad);

FIG. 6A: in vitro infectivity in A549 cells (human, non-complementing); FIG. 6B: in vitro infectivity in HuTu 80 cells (human, non-complementing); FIG. 6C: in vitro infectivity in PER.55K cells (human, complementing);

FIG. 7A: in vitro infectivity in A549 cells (human, non-complementing) and PER.55K (human, complementing) of Ad26.WT, rcAd26.dE3.empty, and replication-incompetent vector non-rcAd26.dE3.empty; FIG. 7B: in vitro infectivity in rhesus monkey kidney cells (MK-2 cell line) of Ad26.WT, rcAd26.dE3.dE4.empty, rcAd26.dE3.dE4.Mos1Env, and replication-competent simian Ad vector derived from rhesus monkeys (rcSAd.SIVgag); the replication-competent simian Ad vector rcSAd-SIVgag is labeled with an asterik (*);

FIG. 8A: in vitro infectivity of Ad26.WT, rcAd26.dE3.Empty, rcAd26.dE3.dE4.Empty, rcAd26.dE3.Mos1Env, and rcAd26.dE3.dE4.Mos1Env in A549 (human, non-complementing) cells after $1^{st}$ reinfection and $2^{nd}$ reinfection; FIG. 8B: in vitro infectivity of Ad26.WT, rcAd26.dE3.Empty, rcAd26.dE3.dE4.Empty, rcAd26.dE3.Mos1Env, and rcAd26.dE3.dE4.Mos1Env in HuTu80 (human, noncomplementing) cells after $1^{st}$ reinfection and $2^{nd}$ reinfection; FIG. 8C: comparison of viral titers for Ad26.WT, rcAd26.dE3.dE4.Empty, and rcAd26.dE3.dE4.Mos1Env lysates harvested at full CPE from cultures infected with each vector at an MOI of 1000; lysates from either infected A549 or HuTu80 cells were compared by performing a plaque assay in both A549 and PER.55K cells;

FIG. 9A: in vitro infectivity in A549 cells (human, non-complementing); FIG. 9B: in vitro infectivity in HuTu80 cells (human, non-complementing); and FIG. 9C: in vitro infectivity in PER.55K cells;

Figure 11A:
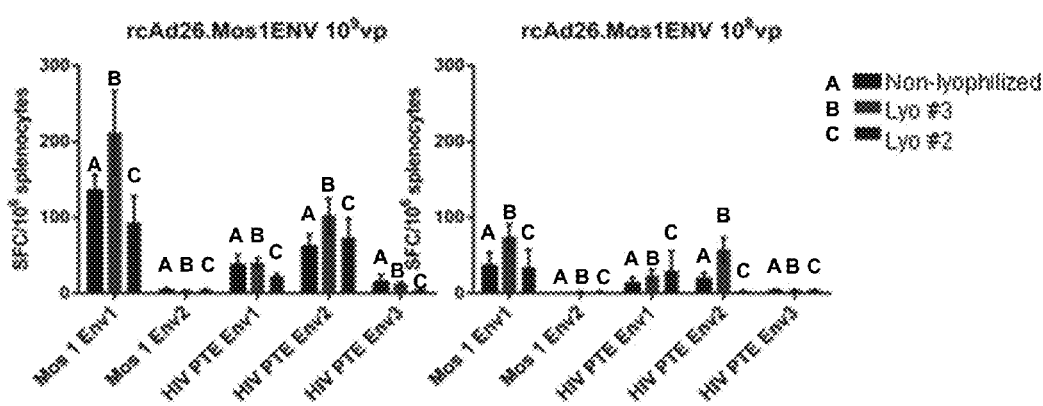
Figure 11B:
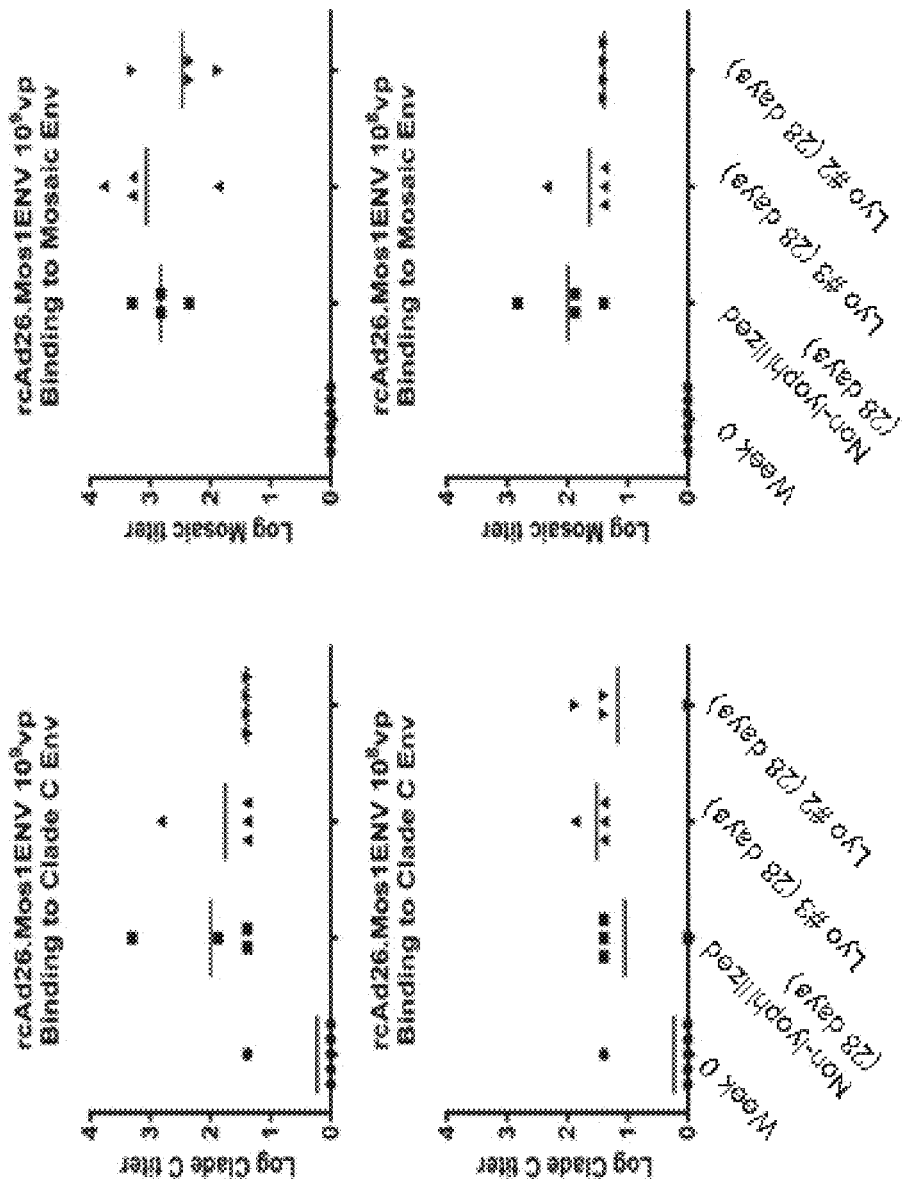
Figure 13A:
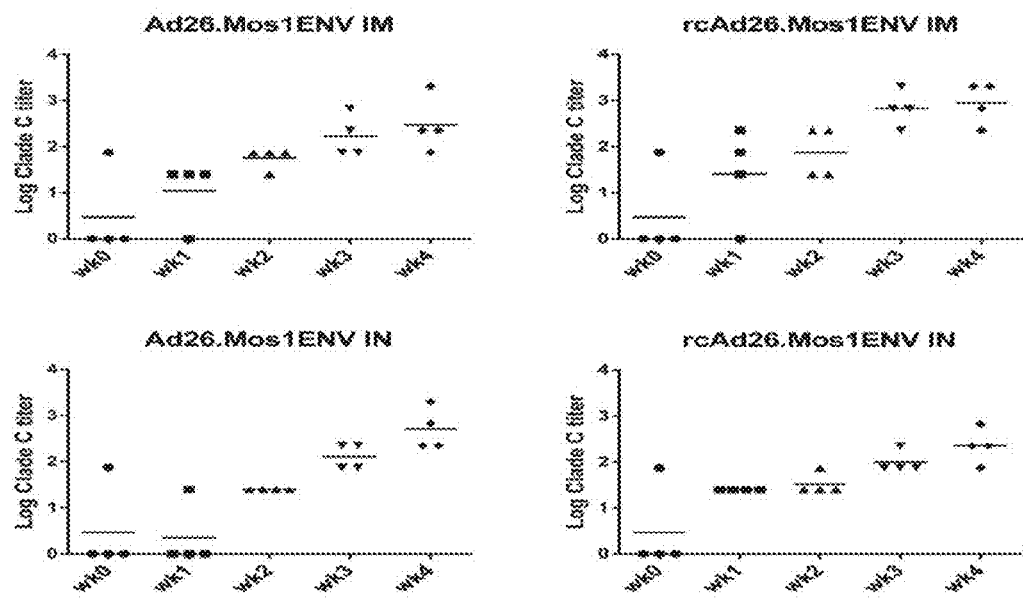
Figure 13B:
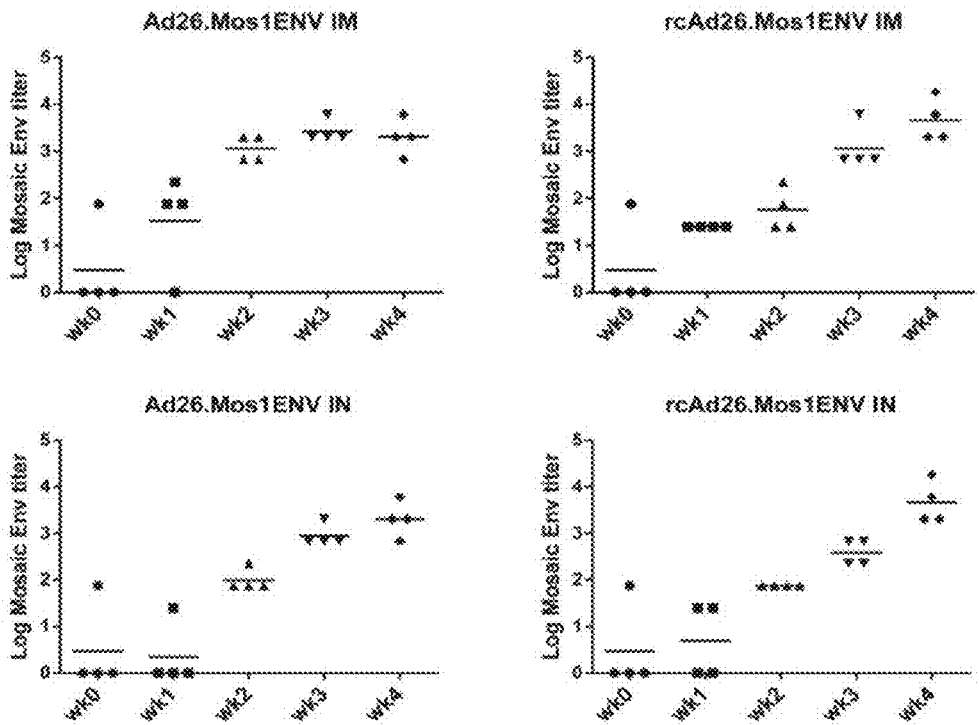
Figure 14:
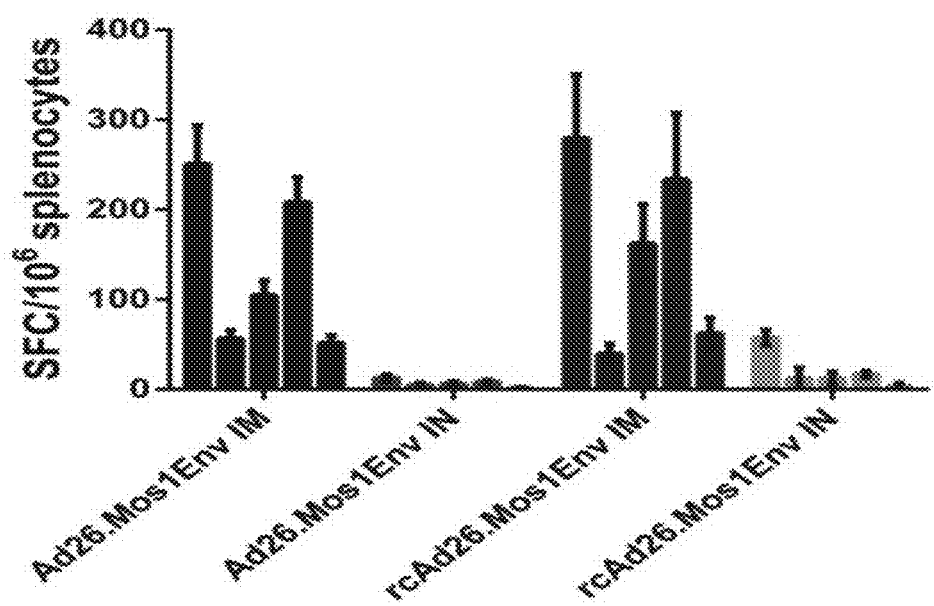
Figures 15A, 15B:
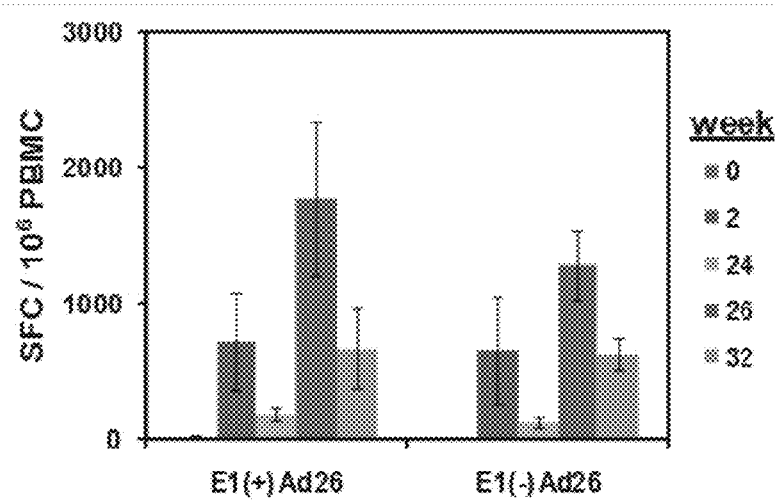
Figure 16A:
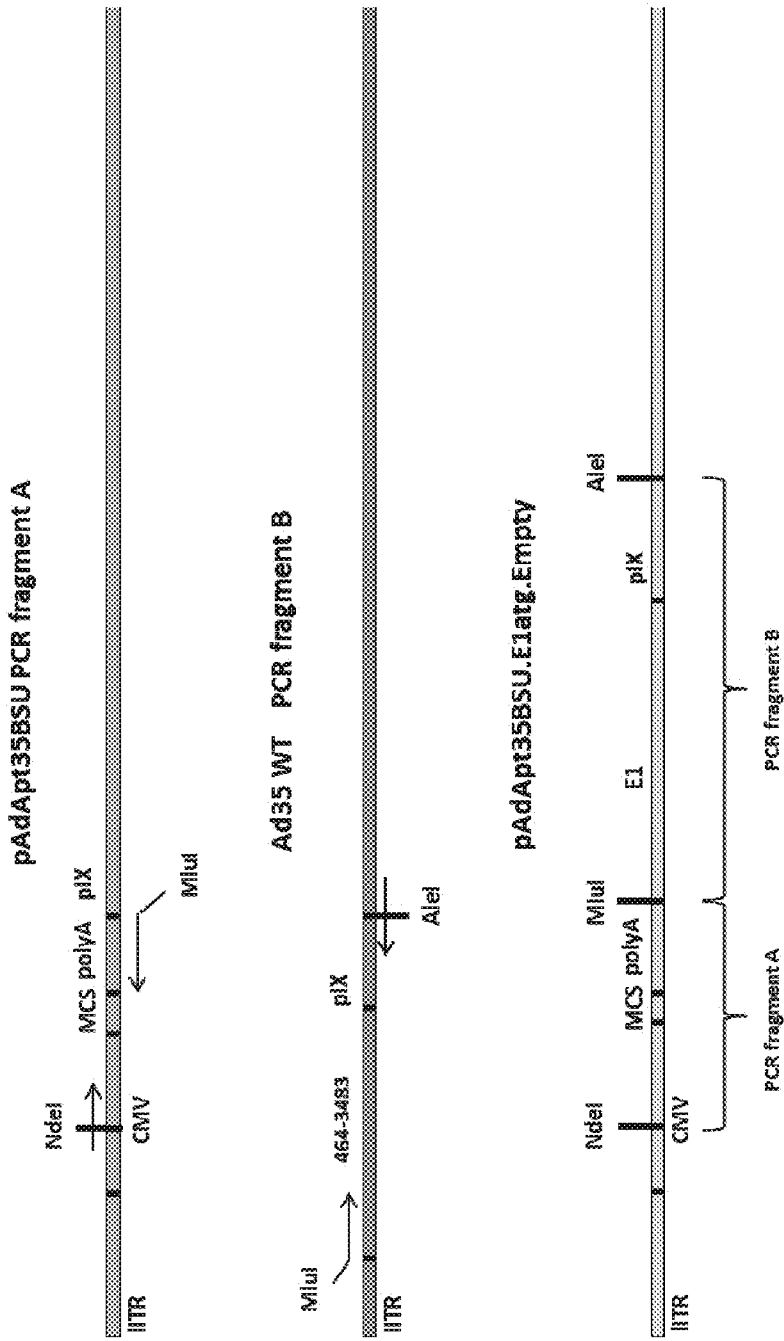
Figure 16B:
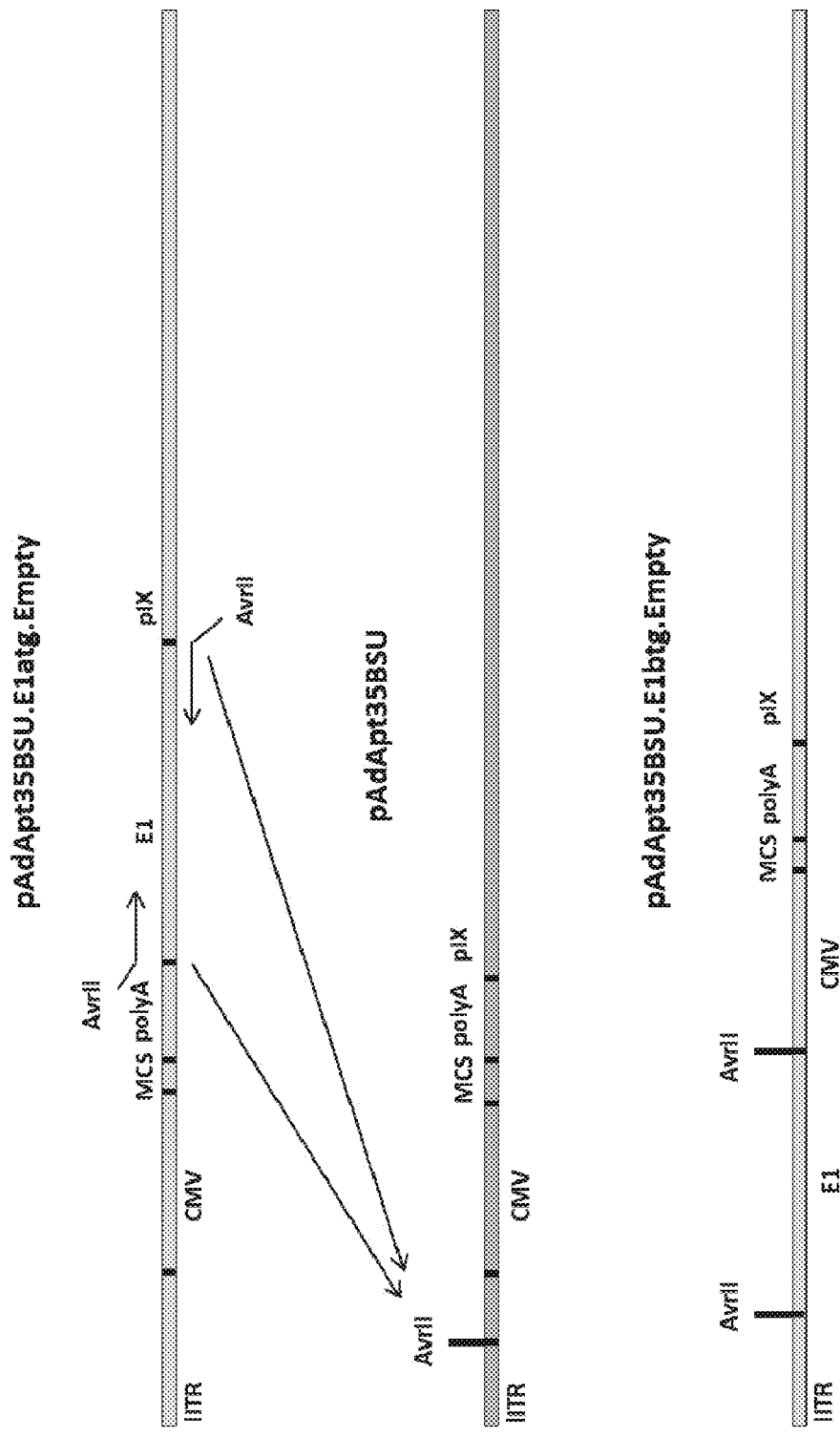
Figure 17:
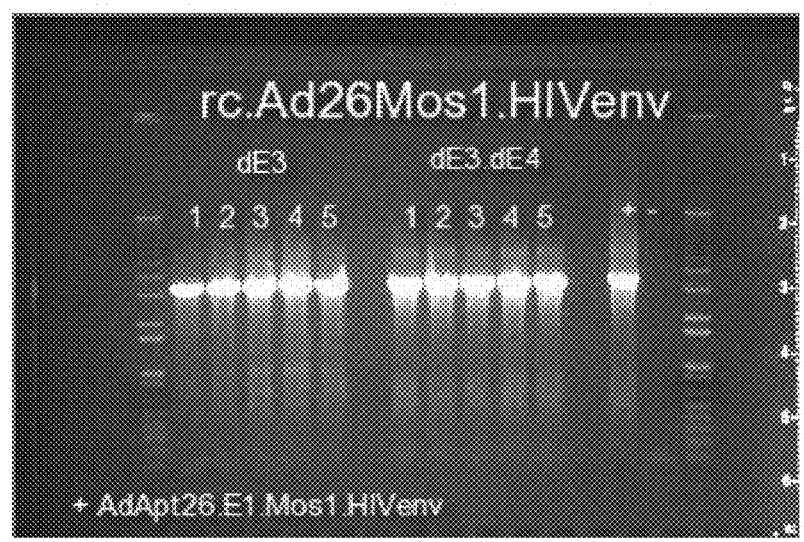

rcAd26Mos1GagPol; rcAd26Mos2GagPol) in Balb/C mice; results are reported as spot forming cells (SFC) per $10^6$ splenocytes;

FIGS. 11A and 11B show immunogenicity of lyophilized rcAd26.Mos1Env vector (injected with $10^8$ or $10^9$ virus particles) and binding antibody titers to HIV-1 Clade C envelope protein and Mosaic envelope protein in Balb/C mice; FIG. 11A: mouse immunogenicity as determined by IFNγ-ELISPOT assay using Mos1ENV and HIV PTE Env peptide pools; FIG. 11B: binding antibody titers to HIV-1 Clade C envelope and Mosaic Env as determined by ELISA prior to dosing with rcAd26.Mos1Env vector and 28 days after immunization;

Figure 12:
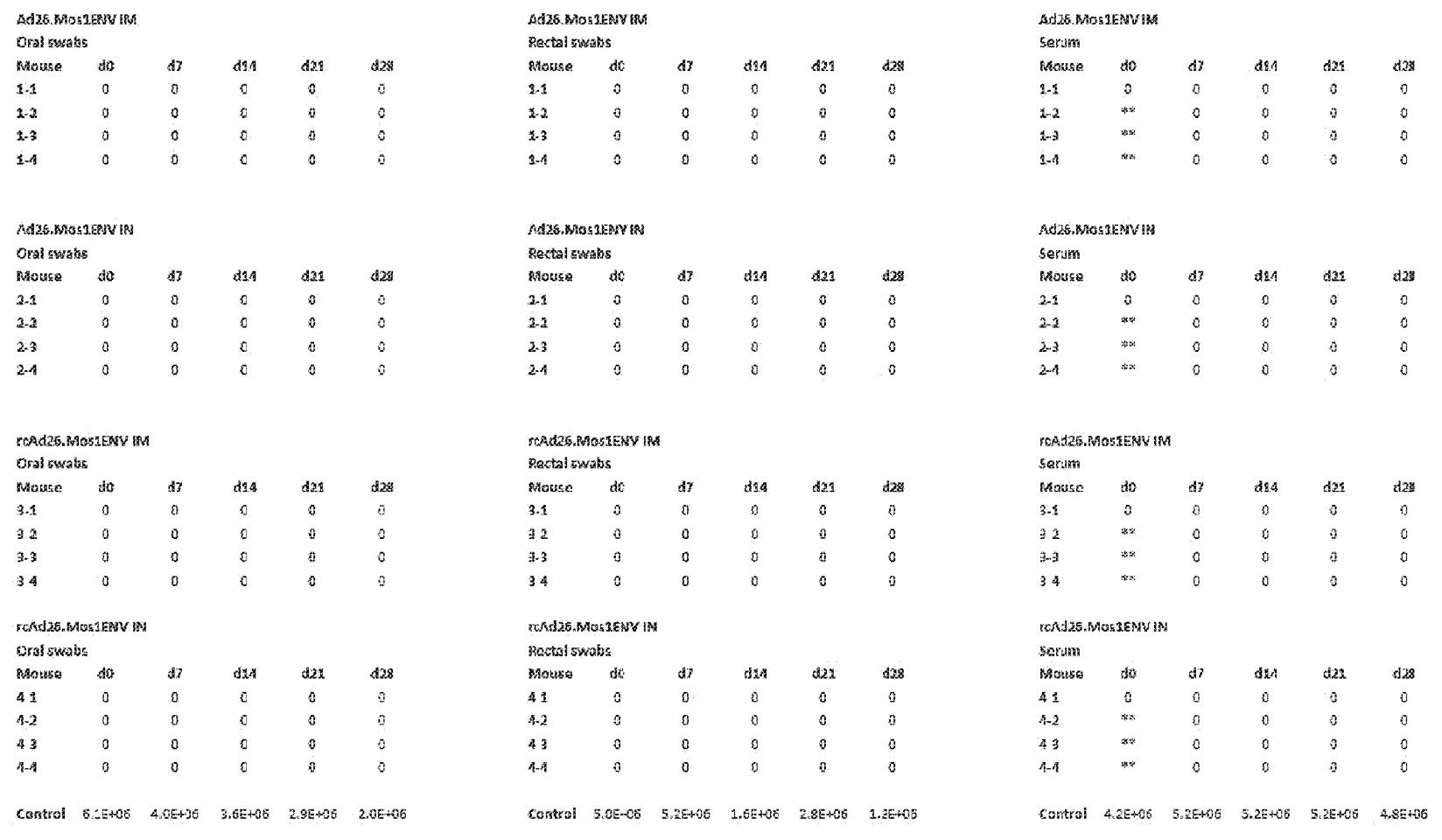

FIG. 12 is a table of the results from RT-PCR performed on mouse serum, oral swab and rectal swab samples taken at days 0, 7, 14, 21, and 28 after intramuscular (IM) or intranasal (IN) immunization with either a replication incompetent recombinant Ad26 vector (Ad26.Mos1Env) (made replication incompetent by deletion in E1 coding region) or replication-competent recombinant Ad26 vector according to the invention (rcAd26.Mos1Env), with both vectors containing a nucleic acid sequence encoding the mosaic HIV antigen Mos1-HIVEnv; results are reported in copies/mL and control samples were spiked with $5.04 \times 10^6$ copies/mL of plasmid DNA; "**" indicates that no sample was taken;

FIGS. 13A and 13B show the binding antibody titers in mice serum after IM or IN immunization with replication-incompetent recombinant Ad26 vector (Ad26.Mos1Env) and replication-competent recombinant Ad26 vector (rcAd26.Mos1Env) as determined by ELISA; FIG. 13A: binding antibody titers to HIV-1 *Clade C* envelope protein; FIG. 13B: binding antibody titers to Mosaic Env protein;

FIG. 14 depicts the response to peptide pools in Balb/C Mice four weeks post-immunization with either replication-incompetent recombinant Ad26 vector (Ad26.Mos1ENV) or replication-competent recombinant Ad26 vector according to the invention (rcAd26.Mos1ENV) administered intramuscularly (IM) or intranasally (IN) as determined by IFNγ-ELISPOT; for each regimen tested, the peptide pools from left to right are Mos1 Env, Mos2 Env, PTE Env 1, PTE Env 2, and PTE Env 3;

FIGS. 15A and 15B show immunogenicity and replication of replication-competent Ad26-SIVGag (containing E1 coding region, "E1 (+)") and replication-incompetent Ad26-SIVGag (lacking E1 coding region, "E1 (−)") vectors in non-human primates (Indian-origin rhesus monkeys *Macaca Mulatta*); FIG. 15A: results of IFNγ-ELISPOT to determine immune response reported as spot forming cells (SFC) per $10^6$ peripheral blood mononuclear cells (PMBC); for each vector tested, the data for weeks 0, 2, 24, 26, and 32 is shown from left to right, respectively; FIG. 15B: RT-PCR results to assess virus replication; monkeys 415-08, 421-08, and 451-08 received replication-incompetent Ad26.SIVgag vector, and monkeys 427-08, 429-08, and 432-08 received replication-competent Ad26.SIVgag vector; RT-PCR results are reported as copies/mL, and control samples are spiked with $5.04 \times 10^5$ copies/mL of plasmid DNA;

FIGS. 16A and 16B are schematic representations of the cloning strategy used to construct a recombinant Ad35 adaptor plasmid vector that can be used to produce a replicating recombinant Ad35 vector according to embodiments of the invention, containing a transgene cassette before the E1 coding region and after the E1 coding region; FIG. 16A: cloning of replicating recombinant Ad35 vector pAdApt35BSU.E1atg.Empty, which is designed to contain part of the Ad35 genome, including the E1 coding region located downstream of the transgene cassette; FIG. 16B: cloning of replicating recombinant Ad35 vector pAdApt35BSU.E1btg.Empty (SEQ ID NO: 26), which is designed to contain part of the Ad35 genome, including the E1 coding region located upstream of the transgene cassette; and FIG. 17 is an agarose gel image assessing recombinant adenovirus vector stability by PCR analysis of the transgene region; the vectors screened by PCR include rcAd26.dE3.Mos1HIVEnv ("dE3," containing deletion in E3 coding region), rcAd26.dE3.dE4.Mos1HIVEnv ("dE3.dE4" containing deletions in both E3 and E4 coding regions), and as positive control AdApt26.E1Mos1HIVenv ("+" Ad26 adaptor plasmid with coding sequence for Mos1HIVEnv cloned into the transgene cassette of pAdApt26—see FIG. 2); five passages of the virus post-production (labeled 1, 2, 3, 4, and 5) were screened by PCR using primers CMV.fwd (Ad26_1) (SEQ ID NO: 73) and E1.rev (Ad26_7) (SEQ ID NO: 74) with an expected PCR product size of 3.3 kb.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, "subject" means any animal, preferably a mammal, most preferably a human, to whom will be or has been administered a composition or replicating recombinant adenovirus vector according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, the term "adenovirus," abbreviated "Ad," refers to viruses of the adenoviridae family. Adenovirus is a medium-sized (90-100 nm), nonenveloped icosahedral virus containing double-stranded DNA. The term "adenoviridae" refers collectively to adenoviruses of the genera *Atadenovirus, Aviadenovirus, Ichtadenovirus, Mastadenovirus*, and *Siadenovirus*. "Adenovirus" includes, but is not limited to human, bovine, ovine, equine, canine, porcine, murine and simian adenovirus species. Human adenoviruses, i.e., adenoviruses that can infect humans, can be classified into subgenera, or species, A-G.

As used herein, "human adenovirus" collectively refers to all human adenoviruses of subgenera A-G as well as the individual serotypes thereof.

The term "adenovirus serotype" means the individual members of a viral genus that are defined and identified by their expression of at least one serotype-specific epitope. Currently, there are over 60 known immunologically different types of adenovirus that can cause human infection including, but not limited to, human adenovirus serotypes 1, 2, 3, 4, 4a, 5, 6, 7, 7a, 7d, 8, 9, 10, 11A, 11P, 12, 13, 14, 15, 16, 17, 18, 19, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 51.

Preferably, an adenovirus used in accordance with the invention is derived from adenovirus serotype 26 (Ad26) having a wild-type genome of SEQ ID NO: 1, or adenovirus serotype 35 (Ad35) having a wild-type genome of SEQ ID NO: 27. Adenovirus 26 is part of subgroup D and adenovirus 35 is part of subgroup B.

The various regions of the adenovirus genome have been mapped and are understood by those skilled in the art (see, e.g., Fields et al., *Virology* Volume 2, chapters 67 and 68, $3^{rd}$ Edition, Lippincoft-Raven Publishers). The genomic sequences of the various adenovirus serotypes, as well as the nucleotide sequence of the particular coding regions of the adenovirus genome, are known in the art and can be accessed e.g., from GenBank and NCBI. In general, adenovirus genomes contain replication-essential genes, whose gene functions are required for replication and are encoded by, for example, the adenoviral early regions (e.g., E1, E2, and E4 regions) and late regions (e.g., the L1-L5 regions). Adenovirus genomes also contain genes involved in viral packaging (e.g., the Iva2 gene), and virus-associated RNAs (e.g., VA-RNA1 and/or VA-RNA-2).

The term "inverted terminal repeat sequence" or "ITR" refers to the common usage of the term with respect to adenoviruses and includes all ITR sequences and variations thereof that are functionally equivalent. The ITRs are the sets of sequences (motifs) which flank the linear adenovirus genome on the 5'-end ("left ITR" or "lITR") and 3'-end ("right ITR" or "rITR"), and are necessary for replication of the adenovirus genome. There is a high degree of sequence conservation within the ITR sequences between adenoviruses of different serotypes. A replicating recombinant adenovirus vector according to the invention can comprise any known adenovirus ITR sequence.

As used herein, the term "early gene 1 coding region" or "E1 coding region" refers to the full-length nucleic acid sequence in a human adenovirus genome that is first transcribed following infection, and that encodes the three human adenovirus E1 proteins known to be important for replication of the viral genome: E1A protein, E1B-19K protein, and E1B-55K protein.

As used herein, "early gene 3 coding region" or "E3 coding region" refers to the full-length nucleic acid sequence in a human adenovirus genome that encodes the seven human adenovirus E3 proteins: E3 13.2K, E3 CR1-alpha, E3 19K, E3 CR1-beta, E3 CR1-gamma, E3 RID-beta and E3 14.7K. Most of the E3 proteins have immunomodulatory functions. The human adenovirus E3 coding region is dispensable for viral replication in tissue culture. However, some of the E3 proteins may be involved in the evasion of host immune defenses, and deletion of some or all of the E3 coding region may induce stronger pro-inflammatory responses in animal models (Sparer et al., 1996, *J. Virol.* 70: 2431-2439).

As used herein, "early gene 4 coding region" or "E4 coding region" refers to the full-length nucleic acid sequence in a human adenovirus genome that encodes at least the five human adenovirus E4 proteins: E4 orf1, E4 orf2, E4 orf3, E4 orf4 and E4 orf6/7. Adenovirus vectors lacking the E4 coding region may not be effective in delivery and long term retention of transgene expression under all circumstances (Leppard, *Journal of General Virology* (1997), 78, 2131-2138.).

The terms "deleted" and "deletion" as used herein with respect to a coding region of a nucleic acid sequence, such as an E3 or E4 coding region of an adenovirus genome, mean that at least one nucleotide is omitted from the full-length wild-type nucleotide sequence. Deletions can be greater than about 1, 10, 50, 100, 200, or even 500 nucleotides. Deletions in the relevant coding region of the adenovirus genome can be about 1%, 5%, 10%, 25%, 50%, 75%, 80%, 90%, 99% or more of the coding region. Alternatively, the entire coding region can be deleted, meaning that all the nucleotides of the relevant coding region are omitted. A coding region that is "partially deleted" or "partly deleted" means that nucleotides of a portion of the coding region that is less than the entire coding region are omitted.

As used herein, the term "heterologous" in the context of nucleic acid sequences, amino acid sequences, and antigens refers to nucleic acid sequences, amino acid sequences, and antigens that are foreign and are not naturally found associated with a particular adenovirus. A "heterologous nucleic acid sequence" can be any transgene. As used herein, a "transgene" broadly refers to any gene or genetic material isolated from one source, either natural (e.g., cell) or synthetic (e.g., genetically engineered in a vector, recombinant DNA), and transferred to another source.

As used herein, the term "transgene cassette" refers to a region of a nucleic acid vector that contains a promoter and a multiple cloning site. The transgene cassette is designed such that a heterologous nucleic acid sequence can be cloned into the multiple cloning site and placed under control of the promoter region. A transgene cassette does not necessarily have to contain a transgene or heterologous nucleic acid sequence, and can be "empty," meaning that it lacks a transgene or heterologous nucleic acid sequence. One of ordinary skill in the art will recognize that a transgene cassette can contain additional genetic regulatory elements, e.g., transcription termination signals, etc.

The term "recombinant adenovirus" refers to an adenovirus whose genome has been modified through conventional recombinant DNA techniques. As used herein, the term "recombinant adenovirus vector" refers to a vector construct comprising nucleotide sequences derived from an adenovirus genome and optionally, one or more heterologous nucleic acid sequences. According to embodiments of the invention, a recombinant adenovirus vector comprises adenoviral nucleotide sequences that are modified such that the recombinant adenovirus vector is replication competent, but the replication efficiency is attenuated as compared to the replication efficiency of the corresponding wild-type adenovirus. In accordance with this embodiment, a recombinant adenovirus vector can be engineered to comprise a mutated adenovirus genome by introducing one or more mutations in an adenovirus genome, e.g., introducing deletions in one or more coding regions for adenoviral proteins.

As used herein, "replicating recombinant adenovirus vector" and "replication competent recombinant adenovirus vector" refer to a recombinant adenovirus vector that can replicate or propagate upon introduction into a non-complementing cell. In one particular embodiment of the invention, a "replicating recombinant adenovirus vector" or "replication competent recombinant adenovirus vector" can replicate or propagate upon introduction into a non-complementing human cell. The terms "replicate" and "propagate" are used interchangeably, referring to the ability of the adenovirus vector to reproduce or proliferate. These terms are well understood in the art. The propagation or replication of a viral vector can be measured using assays standard in the art and described herein, such as a burst assay or plaque assay.

As used herein "replicative capacity" refers to the relative ability of a recombinant adenovirus vector to replicate or propagate in a non-complementing cell.

As used herein, a "non-complementing cell" refers to a cell that does not supply a particular genetic element, e.g., gene product, protein, etc. in trans. When referring to a recombinant adenovirus vector, wherein the coding region for a particular viral gene product is fully or partially deleted on the vector such that one or more of the functional viral gene products cannot be expressed by the vector, a non-complementing host cell specifically refers to a cell that does not supply the deleted functional gene product in trans. For example, if the E1 gene of the adenovirus genome is deleted to produce a recombinant adenovirus vector, a cell that does not supply a functional E1 gene in trans would be considered a non-complementing host cell. According to embodiments of the invention, a non-complementing cell is a human cell. Examples of non-complementing human cells include, but are not limited to, HuTu 80 cells (duodenum carcinoma, ATCC #HTB-40) and A549 cells (lung carcinoma, ATCC #CCL-185).

As used herein the terms "replication deficient," "replication incompetent" and "non-replicating," when used with reference to a recombinant adenovirus vector, are all intended to refer to a recombinant vector comprising a recombinant adenovirus genome that lacks certain genetic information necessary for replication and formation of a genome-containing capsid in a non-complementing cell. Replication deficient, replication incompetent and non-replicating recombinant vectors cannot replicate under physiological conditions either in vivo or in vitro, unless the missing viral genetic elements necessary for replication are provided by a second source, e.g., a complementing host cell.

As used herein, the term "operably linked" is to be taken in its broadest reasonable context, and refers to a linkage of polynucleotide elements in a functional relationship. A nucleic acid sequence is "operably linked" when it is placed into a functional relationship with another nucleic acid sequence. For instance, a promoter is operably linked to a coding sequence if it affects the transcription of the coding sequence.

The term "promoter" is used in its conventional sense, and refers to a nucleotide sequence that initiates the transcription of an operably linked nucleotide sequence. A promoter is located on the same strand near the nucleotide sequence they transcribe. Promoters may be naturally occurring or synthetic. When the vector to be employed is a viral vector, the promoters can be endogenous to the virus or derived from other sources.

The terms "attenuated" and "attenuation" refer to reduced pathogenicity and replicative capacity of a recombinant adenovirus vector as compared to the corresponding wild-type adenovirus. In one embodiment, attenuation refers to preventing replication in mammalian (e.g., human) cells. In another embodiment, attenuation refers to reducing, but not eliminating, replicative capacity of the virus, such that it can replicate in mammalian cells, but to a lesser degree as compared to the corresponding wild-type virus. In yet another embodiment, attenuation refers to the inability to cause disease e.g., viral infection, or to cause disease, but to a lesser extent than wild-type virus. Attenuation can be achieved by using a variety of methods known in the art. For example, serial passage of viruses in animals, eggs, or tissue culture can lead to the acquisition of a variety of mutations that can result in reduced pathogenicity and replicative capacity. Attenuation can also be achieved by the complete or partial deletion of nucleic acid sequence from the genome of the virus, e.g., complete or partial deletions of E1, E3, or E4 coding regions of the adenovirus genome. Virus attenuation can be measured by any method known in the art, e.g., by the virus titer required to infect cells, RT-PCR, or the time required to achieve maximum cytopathic effect (CPE).

As used herein, the term "infection" refers to the invasion of a host by a disease causing agent. A disease causing agent is considered to be "infectious" when it is capable of invading a host, and replicating or propagating within the host. Examples of infectious agents include viruses, e.g., HIV and certain species of adenovirus, prions, bacteria, fungi, protozoa and the like.

In one general aspect, the invention provides a replicating recombinant adenovirus vector comprising a recombinant adenovirus genome. According to embodiments of the invention, a replicating recombinant adenovirus vector is replication competent, meaning that it can replicate in a non-complementing human cell. This is in contrast to many other known recombinant adenovirus vectors that have been used for vaccines, which are typically replication incompetent, thus cannot replicate or propagate in a non-complementing human cell.

The replicative capacity of a replicating recombinant adenovirus vector according to embodiments of the invention in a non-complementing cell is attenuated, or reduced, as compared to the replicative capacity of an otherwise identical wild-type adenovirus. According to embodiments of the invention, the attenuation in replicative capacity of a replicating recombinant adenovirus vector relative to the wild-type adenovirus can be between 2-fold and 1000-fold lower than the replicative capacity of the corresponding wild-type adenovirus. For example, the replicative capacity of the recombinant adenovirus vector can be decreased by 2-fold, 5-fold, 10-fold, 50-fold, 60-fold, 70-fold, 80-fold, 90-fold, 100-fold, 150-fold, 200-fold, 250-fold, 500-fold, 750-fold or 1000-fold relative to the replicative capacity of the wild-type adenovirus the replicating recombinant adenovirus vector is derived from. Preferably, the replicative capacity of the recombinant adenovirus vector is about 50-fold lower, and more preferably about 80-fold to about 100-fold lower than the replicative capacity of the wild-type adenovirus the replicating recombinant adenovirus vector derived from.

Figure 1:
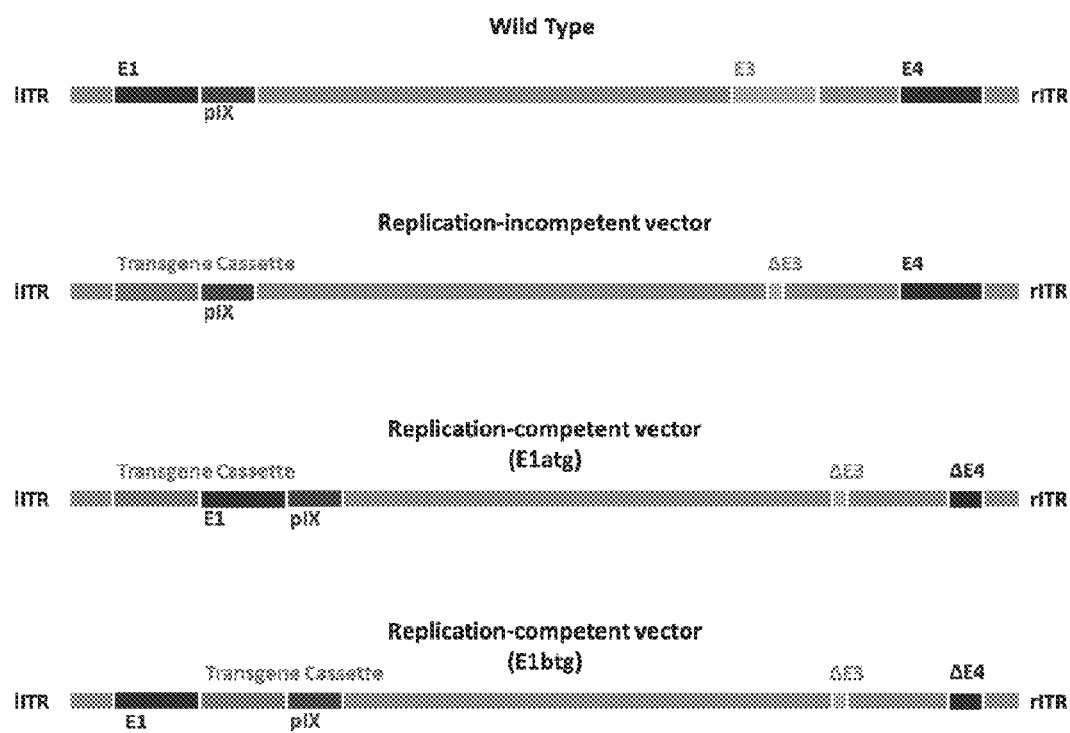
FIG. 1 shows schematic representations of a wild-type adenovirus genome, a genome of a replication-incompetent recombinant adenovirus vector, a genome of replication-competent recombinant adenovirus vector containing an E1 coding region after the transgene cassette according to an embodiment of the invention, and a genome or a replication-competent recombinant adenovirus vector containing an E1 coding region before the transgene cassette according to another embodiment of the invention.

According to embodiments of the invention, a replicating recombinant adenovirus vector comprises a recombinant adenovirus genome. The recombinant adenovirus genome comprises (a) a promoter operably linked to a heterologous nucleic acid sequence; (b) a functional E1 coding region; (c) a deletion in the E3 coding region; and (d) a deletion in the E4 coding region, provided that E4 open reading frame 6/7 is not deleted. See, e.g., FIG. 1, which is a schematic representation of a replicating recombinant adenovirus vector according to an embodiment of the invention as compared to a wild-type adenovirus genome and non-replicating recombinant adenovirus vector lacking an E1 coding region. By deleting or partially deleting the E3 and E4 coding regions and retaining a functional E1 coding region in the recombinant adenovirus genome, the replicative capacity of the vector was attenuated as compared to wild-type, but the recombinant adenovirus vector was still replication competent. See, e.g., FIGS. 6A-6C.

According to embodiments of the invention, the recombinant adenovirus genome is derived from the genome of human adenovirus serotype 26 or the genome of human adenovirus serotype 35, and preferably human adenovirus serotype 26.

In one embodiment of the present invention, a wild-type human adenovirus serotype 26 genome, such as that having the nucleotide sequence of SEQ ID NO: 1, comprises, inter alia, the E1 coding region (SEQ ID NO: 13), the E3 coding region (SEQ ID NO: 4), and the E4 coding region (SEQ ID NO: 17). The E1 coding region encodes three proteins: E1A protein (SEQ ID NO: 14); the E1B 19K protein (SEQ ID NO: 15); and the E1B 55K protein (SEQ ID NO: 16). The E3 coding region encodes 7 proteins: E3 13.2K (SEQ ID NO: 6); E3 CR1-alpha (SEQ ID NO: 7); E3 19K (SEQ ID NO: 8); E3 CR1-beta (SEQ ID NO: 9); E3 CR1-gamma (SEQ ID NO: 10); E3 RID-beta (SEQ ID NO: 11); and E3 14.7K (SEQ ID NO: 12). The E4 coding regions encodes 5 proteins: E4 ORF1 (SEQ ID NO: 18); E4 ORF2 (SEQ ID NO: 19); E4 ORF3 (SEQ ID NO: 20); E4 ORF 4 (SEQ ID NO: 21); and E4 ORF6/7 (SEQ ID NO: 22).

Likewise, in another embodiment of the present invention, a wild-type human adenovirus serotype 35 genome, such as that having the nucleotide sequence of SEQ ID NO: 24, comprises, inter alia, the E1 coding region (SEQ ID NO: 36); the E3 coding region (SEQ ID NO: 27); and the E4 coding region (SEQ ID NO: 40). The E1 coding region encodes three proteins: E1A protein (SEQ ID NO: 37); the E1B 19K protein (SEQ ID NO:38); and the E1B 55K protein (SEQ ID NO: 39). The E3 coding region encodes 7 proteins: E3 13.2K (SEQ ID NO: 29); E3 CR1-alpha (SEQ ID NO: 30); E3 19K (SEQ ID NO: 31); E3 CR1-beta (SEQ ID NO: 32); E3 CR1-gamma (SEQ ID NO: 33); E3 RID-beta (SEQ ID NO: 34); and E3 14.7K (SEQ ID NO: 35). The E4 coding regions encodes 5 proteins: E4 ORF1 (SEQ ID NO: 42); E4 ORF2 (SEQ ID NO: 43); E4 ORF3 (SEQ ID NO: 44); E4 ORF 4 (SEQ ID NO: 45); and E4 ORF6/7 (SEQ ID NO: 46).

Deletion of the E1 coding region from the Ad26 or Ad35 genome results in a replication incompetent recombinant adenovirus genome, meaning that the virus is unable to replicate in a non-complementing cell. Thus, a replicating recombinant adenovirus vector according to the invention comprises a functional E1 coding region.

The term "functional E1 coding region" is intended to encompass a nucleic acid sequence on the adenovirus vector that encodes active forms of E1A protein, E1B-19K protein, and E1B-55K protein, sufficient for viral replication. According to embodiments of the invention, a recombinant adenovirus vector can be engineered such that the functional E1 coding region is transferred to a different location within the recombinant viral vector as compared to the location of the E1 coding region in the wild-type adenovirus genome.

In one embodiment of the invention, a "functional E1 coding region" encodes active forms of E1A protein, E1B-19K protein, and E1B-55K protein, each of which has substantially identical activity as the wild-type human adenovirus E1A protein, E1B-19K protein, and E1B-55K protein, respectively.

In one embodiment of the invention, a functional E1 coding region of an Ad26 replicating recombinant adenovirus vector comprises a nucleotide sequence encoding Ad26 E1A protein (SEQ ID NO: 14), E1B-19K protein (SEQ ID NO: 15), and E1B-55K protein (SEQ ID NO: 16). In a particular embodiment of the invention, a functional E1 coding region of an Ad26 replicating recombinant adenovirus vector comprises the nucleotide sequence of SEQ ID NO: 13.

In another particular embodiment of the invention, a functional E1 coding region of an Ad35 replicating recombinant adenovirus vector comprises a nucleotide sequence encoding Ad35 E1A protein (SEQ ID NO: 37), E1B-19K protein (SEQ ID NO: 38) and E1B-55K protein (SEQ ID NO: 39). In a particular embodiment of the invention, a functional E1 coding region of an Ad35 replicating recombinant adenovirus vector comprises the nucleotide sequence of SEQ ID NO: 36.

According to embodiments of the invention, a replicating recombinant adenovirus vector comprises a heterologous nucleic acid sequence that is located between a left ITR and the 5'-end of a functional E1 coding region. The heterologous nucleic acid sequence and the left ITR or the 5'-end of the E1 coding region can optionally be separated by a linker region of nucleic acid sequence. The present inventors surprisingly found that by placing the functional E1 coding region after the heterologous nucleic acid sequence, rather than before, both vector stability and expression of the heterologous nucleic acid sequence were increased, which was an unexpected effect.

According to embodiments of the invention, a replicating recombinant adenovirus vector comprises a deletion in the E3 coding region. A deletion in the E3 coding region can be, e.g., a partial deletion, such that the replicating recombinant adenovirus vector comprises a partially deleted E3 coding region.

According to a particular embodiment, in a partially deleted E3 coding region, all nucleic acid sequence of the E3 coding region with the exception of the nucleic acid sequence encoding the E3 12.5K protein product is deleted. When a recombinant adenovirus vector comprises a recombinant Ad26 genome, in one embodiment a partially deleted E3 coding region encodes the amino acid sequence of SEQ ID NO: 6, and in a particular embodiment, consists of the nucleotide sequence of SEQ ID NO: 5. When a recombinant adenovirus vector comprises a recombinant Ad35 genome, in one embodiment a partially deleted E3 coding region encodes the amino acid sequence of SEQ ID NO: 29, and in a particular embodiment, consists of the nucleotide sequence of SEQ ID NO: 28.

In certain embodiments of the invention, the E3 coding region of the recombinant adenovirus vector can be completely deleted. According to embodiments of the invention, a recombinant adenovirus vector with a completely deleted E3 coding region is replication competent, i.e., can replicate in a non-complementing human cell.

According to embodiments of the invention, a replicating recombinant adenovirus vector comprises a deletion in the E4 coding region, except E4 open reading frame 6/7. According to a particular embodiment, a replicating recombinant adenovirus vector comprises a partially deleted E4 coding region, wherein all E4 open reading frames have been deleted except open reading frame 6/7. Thus, in a particular embodiment, when a recombinant adenovirus vector comprises a recombinant Ad26 genome, a partially deleted E4 coding region encodes the amino acid sequence of SEQ ID NO: 22, and consists of the nucleotide sequence of SEQ ID NO: 23. In another particular embodiment, when a recombinant adenovirus vector comprises a recombinant Ad35 genome, a partially deleted E4 coding region encodes the amino acid of SEQ ID NO: 41, and consists of the nucleotide sequence of SEQ ID NO: 46.

The present inventors have surprisingly found that a partial deletion of the E4 coding region, in addition to an at least partial deletion of the E3 coding region, produced a recombinant replicating adenovirus vector with increased stability, as compared to a recombinant replicating adenovirus vector containing the deletion of the E3 coding region and without the partial deletion of the E4 coding region. See, e.g., FIG. 17. In the experiment for FIG. 17, stability of the transgene of recombinant adenovirus vectors was determined by transgene PCR after 5 passages of the virus. A recombinant replicating adenovirus vector with both partial deletions of the E3 and E4 coding regions showed stability at all five passages of the virus post-production as determined by PCR analysis of the transgene region, whereas partial deletion of only the E3 coding region showed faint lower molecular weight bands at all passages post the first infection, indicating decreased stability of the transgene.

The present inventors have also surprisingly discovered that a replicating recombinant adenovirus vector according to the invention has attenuated replicative capacity. Attenuation of replicating adenovirus vectors comprising an E1 coding region containing both the E1B-19K protein and E1B-55K protein has not previously been demonstrated to the best of the knowledge of the inventors. Moreover, to the best of the knowledge of the inventors, attenuation of replicating Ad26 or Ad35 vectors has not previously been demonstrated. There is no a priori reason to predict that a construction of the recombinant adenovirus vector would have resulted in attenuated replicative capacity yet preserved stability. This achievement of attenuation and stability has practical value from a clinical, regulatory, and manufacturing perspective.

According to a preferred embodiment of the invention, a replicating recombinant adenovirus vector comprises a heterologous nucleic acid sequence located between the left ITR and the 5'-end of the E1 coding region, i.e., upstream of the E1 coding region. A heterologous nucleic acid sequence for use in the invention can comprise any transgene, including but not limited to nucleic acid sequence useful for gene therapy, nucleic acid sequence encoding a therapeutically active protein or immunogenic polypeptide (e.g., antigen), and synthetic nucleic acid sequences encoding genetically engineered or computationally designed protein or peptide sequences with potential therapeutic effects (e.g., mosaic antigens or proteins).

According to embodiments of the invention, a heterologous nucleic acid sequence encodes an immunogenic polypeptide or immunogen. In one embodiment, an immunogenic polypeptide or immunogen is any polypeptide or protein suitable for protecting a subject (e.g., human) against a pathogenic disease or infection including, but not limited to, bacterial, protozoan, fungal, and viral diseases. In another embodiment, an immunogen or immunogenic peptide is any protein or polypeptide capable of inducing an immune response, e.g., a humoral and/or cellular mediated response, in a subject. In yet another embodiment, an immunogen or immunogenic peptide is any protein or polypeptide that can be used to vaccinate a subject, i.e., produce immunity against a disease or infection in subject. In yet another embodiment, an immunogenic peptide is an antigen or portion thereof, or a combination of multiple antigens or portions thereof, that can induce an immune response or produce an immunity against a disease or infection in a subject.

Preferably, an immunogenic polypeptide is capable of raising in a host a protective immune response, e.g., inducing an immune response against a viral disease or infection, and/or produces an immunity in (i.e., vaccinates) a subject against a viral disease or infection, that protects the subject against the viral disease or infection. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen can also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen can further be a polio immunogen, a herpes immunogen (e.g., CMV, EBV, HSV immunogens), a papillomavirus (e.g., HPV16 or HPV18) immunogen, a respiratory syncytial virus immunogen (such as F or G protein), a mumps immunogen, a measles immunogen, a rubella immunogen, a diptheria toxin or other diptheria immunogen, a pertussis immunogen, a hepatitis (e.g., hepatitis A or hepatitis B) immunogen, or any other vaccine immunogen known in the art in view of the present disclosure.

In a preferred embodiment, an immunogenic polypeptide induces an immune response or produces an immunity against human immunodeficiency virus (HIV). HIV is divided into two major types, HIV type 1 (HIV-1) and HIV type 2 (HIV-2). HIV-1 is the most common strain of HIV virus, and is known to be more pathogenic than HIV-2. HIV as used herein broadly refers to HIV type 1, HIV type 2, and subtypes thereof. In a preferred embodiment, an immunogenic polypeptide produces immunity against or induces an immune response against HIV-1.

According to embodiments of the invention, a heterologous nucleic acid sequence can encode an immunogenic polypeptide that is an HIV antigen. The HIV antigen can be an HIV-1 or HIV-2 antigen. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. Other examples of HIV antigens include gene regulatory proteins Tat and Rev; accessory proteins Nef, Vpr, Vif and Vpu; capsid proteins, nucleocapsid proteins, and p24 viral protein. A heterologous nucleic acid sequence according to the invention can encode any HIV antigen, and preferably encodes a gag, env, and/or pol gene product, or portion thereof.

According to a preferred embodiment, a heterologous nucleic acid sequence encodes an immunogenic polypeptide comprising an HIV Gag, Env, or Pol antigen, or any portion or combination thereof, more preferably an HIV-1 Gag, Env, or Pol antigen or any portion or combination thereof.

According to another preferred embodiment, a replicating recombinant adenovirus vector according to the invention comprises a heterologous nucleic acid sequence encoding a mosaic HIV antigen. As used herein, a "mosaic antigen" refers to a recombinant protein comprising fragments of natural sequences, and the recombinant protein is capable of eliciting immune responses against multiple naturally occurring antigenic or immunogenic determinants. The amino acid sequence of a "mosaic antigen" can be computationally generated and optimized using a genetic algorithm. Mosaic antigens resemble natural antigens, but are optimized to increase the coverage of potential epitopes, more preferably T-cell epitopes, found in the natural sequences, thereby improving the breadth and coverage of the immune response. The term "mosaic antigen," when used with respect to HIV, refers to a recombinant protein comprising fragments of natural sequences of HIV immunogens.

A mosaic HIV antigen according to embodiments of the invention is preferably a mosaic antigen comprising multiple immunogenic fragments from one or more of the HIV Gag, Pol, and/or Env polypeptide sequences, preferably from one or more of the Gag, Pol, and/or Env polypeptide sequences of HIV-1.

According to embodiments of the invention, a mosaic HIV antigen is optimized to include a broader array of immunogenic sequences to increase coverage of epitopes, more preferably T-cell epitopes, found in circulating HIV strains.

In one embodiment, a mosaic HIV antigen according to the invention is a mosaic HIV antigen with multiple immunogenic sequences derived from one of Gag, Pol, and Env polypeptide sequences from one or more HIV types or subtypes, preferably from one or more subtypes of HIV-1. For example, the mosaic HIV antigen can be a mosaic HIV Gag antigen with multiple immunogenic sequences derived from the sequences of HIV gag gene products; a mosaic HIV Pol antigen with multiple immunogenic sequences derived from the sequences of HIV pol gene products; or a mosaic HIV Env antigen with multiple immunogenic sequences derived from the sequences of HIV env gene products.

In another embodiment, a mosaic HIV antigen according to the invention comprises a combination of immunogenic sequences derived from two of Gag, Pol, and Env polypeptide sequences from one or more HIV types or subtypes, preferably from one or more subtypes of HIV-1. Illustrative and non-limiting examples include a mosaic HIV Env-Pol antigen with epitopes derived from the sequences of HIV env and pol gene products; a mosaic HIV Env-Gag antigen with epitopes derived from the sequences of HIV env and gag gene products; a mosaic HIV Gag-Pol antigen with epitopes derived from the sequences of HIV gag and pol gene products; and a mosaic HIV Gag-Env antigen with epitopes derived from the sequences of HIV gag and env gene products.

In yet another embodiment, a mosaic HIV antigen according to the invention comprises a combination of immunogenic sequences derived from all three of Gag, Pol, and Env polypeptide sequences from one or more HIV types or subtypes, preferably from one or more subtypes of HIV-1.

Preferably, the mosaic HIV antigen is a mosaic HIV Env antigen, or a mosaic HIV Gag-Pol antigen.

In a particular embodiment of the invention, an immunogenic polypeptide is a mosaic HIV Env antigen comprising the amino acid sequence of SEQ ID NO: 48 (hereinafter referred to as "Mos1-HIVEnv"). In a more particular embodiment of the invention, a heterologous nucleic acid sequence of a replicating recombinant adenovirus according to the invention comprises the nucleotide sequence of SEQ ID NO: 47.

In another particular embodiment of the invention, an immunogenic polypeptide is a mosaic HIV Gag-Pol antigen comprising the amino acid sequence of SEQ ID NO: 50 (hereinafter referred to as "Mos1-HIVGagPo1"). In a more particular embodiment of the invention, a heterologous nucleic acid sequence used in a replicating recombinant adenovirus according to the invention comprises the nucleotide sequence of SEQ ID NO: 49.

According to other particular embodiments of the invention, an immunogenic polypeptide is a mosaic HIV Env antigen comprising the amino acid sequence of SEQ ID NO: 69 (hereinafter referred to as "Mos2-HIVEnv"), or a mosaic HIV Gag-Pol antigen comprising the amino acid sequence of SEQ ID NO: 71 (hereinafter referred to as "Mos2-GagPol"). In more particular embodiments of the invention, heterologous nucleic acid sequences used in a replicating recombinant adenovirus according to the invention can comprise the nucleotide sequence of SEQ ID NO: 70 or SEQ ID NO: 72.

Studies of the T cell responses induced by previous vaccines using natural HIV sequences have shown that there is relatively limited breadth of recognition of epitopes on HIV, compared to the wide variety of circulating strains. For example, in the STEP trial, a median of approximately 1-2 epitopes per each of the Gag, Pol, and Nef proteins were recognized by each individual, but when this number is corrected for epitope frequency in the pool of HIV to which a participant might have been exposed, the number would be considerably less [52]. Accordingly, the use of mosaic HIV antigens, and preferably mosaic HIV-1 antigens comprising multiple immunogenic fragments from one or more of HIV-1 Gag, Pol, and Env polypeptide sequences in a replicating recombinant adenovirus vector according to the invention provides for increased breadth of recognition of epitopes, optimizing immunologic coverage of global HIV-1 virus diversity [53-55].

According to embodiments of the invention, a promoter is operably linked to a heterologous nucleic acid sequence. The promoter directs expression of the heterologous nucleic acid sequence within a eukaryotic cell, such as a mammalian or human cell, and preferably in a non-complementing human cell. The promoter can be a mammalian promoter or a viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, b-actin promoter and other constitutive promoters. Inducible mammalian promoters include, but are not limited to, promoters that are strongly induced in the presence of environmental stimulus, such as a nutrient (e.g., sugar, amino acid), a change in temperature, pH, etc. Exemplary viral promoters which function in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. The promoter can also be a tissue specific promoter that has activity in only certain cell types. Examples of tissue specific promoters include promoters specific to epithelial tissues, such as the promoter of the E-cadherin gene or promoters of other genes that are specifically expressed in epithelial cells. Other promoters that can be used in the invention are known to those of ordinary skill in the art in view of the present disclosure.

Preferably, the promoter is a cytomegalovirus (CMV) promoter. In a particular embodiment, the promoter is a CMV promoter having the nucleic acid sequence of SEQ ID NO: 51.

In addition to the promoter, other regulatory sequences can also be included in the recombinant vector to regulate the expression of heterologous genes. Examples of such regulatory sequences include, but are not limited to, an enhancer, an upstream regulatory domain, a splicing signal, a polyadenylation signal, a transcriptional termination sequence, a translational regulatory sequence, a ribosome binding site and a translational termination sequence, etc.

Accordingly, the invention provides a novel adenovirus vector construct that is replication competent (see, e.g., FIGS. 6A-6C, FIGS. 7A-7B, and FIGS. 8A-8C), and can thus overcome certain disadvantages associated with replication incompetent vectors. A recombinant adenovirus vector according to the invention is replication competent, and can propagate in non-complementing human cells, albeit with lower efficiency than the wild-type adenovirus, thus amplifying transgene expression in the infected non-complementing host cells. Accordingly, transgene expression occurs not only from the recombinant adenovirus vectors present in the initial infecting virus, but also from additional copies of the recombinant adenovirus vectors that are produced by replication of the viral genome within the non-complementing host cell. This is in contrast to a replication-deficient recombinant adenovirus vector, such as an E1 deletion adenovirus vector, wherein all transgene expression is derived from the recombinant vectors present in the viral particles used for infection.

Replicating recombinant adenovirus vectors according to the invention can be produced by any method known in the art in view of the present disclosure. The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression or propagation system can be used, including mammalian cells, bacterial, yeast, insect or plant systems.

Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments can then be obtained either by synthesizing the complementary strand and annealing the strands together under appropriate conditions, or by adding the complementary strand using DNA polymerase with an appropriate primer sequence.

Techniques for the manipulation of nucleic acids, such as, e.g., generating mutations in sequences, deleting portions of sequences, subcloning, labeling probes, sequencing, hybridization and the like are well described in the scientific and patent literature, see, e.g., Sambrook, ed., Molecular Cloning: A Laboratory Manual ($2^{nd}$ Ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization with Nucleic Acid Probes, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of ordinary skill in the art. These include, e.g., analytical biochemical methods such as NMR, electron microscopy, spectrophotometry, radiography, electrophoresis, capillary electrophoresis, high performance liquid chromatography (HPLC), thin layer chromatography (TLC), and hyperdiffusion chromatography; various immunological methods, e.g. fluid or gel precipitation reactions, immunodiffusion, immuno-electrophoresis, radioimmunoassays (RIAs), enzyme-linked immunosorbent assays (ELISAs), enzyme-linked immunosorbent spot (ELISPOT) assays, immuno-fluorescent assays; virus quantification assays, e.g., plaque forming unit (PFU) assays, focus forming assays; nucleic acid and protein analytical techniques, e.g., Southern analysis, Northern analysis, Western blot analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography, etc.

Methods to generate and replicate viral vector constructs are well known in the scientific and patent literature, see, e.g., U.S. Pat. No. 5,981,225; U.S. Pat. No. 5,922,576; U.S. Pat. No. 5,880,102; Graham (1995) Mol. Biotechnol. 3:207-220, and for general methodologies, e.g., Sambrook, Ausubel, Tijssen. Viral genome genetic engineering, transformation and infection techniques in cell culture, viral manipulation and isolation techniques, Ad replication competent cell lines and permissive conditions for Ad replication, and the like, are all well known and described in the scientific and patent literature, see e.g., Krougliak (1995) Hum. Gene Ther. 6:1575-1586; Gorziglia (1999) J. Virol. 73:6048-6055; Cote (1998) Biotechnol. Bioeng. 59:567-575; Hartigan-O'Connor (1999) J. Virol. 73:7835-7841; U.S. Pat. No. 5,851,806; U.S. Pat. No. 5,880,102; U.S. Pat. No. 5,882,877; U.S. Pat. No. 5,891,690; U.S. Pat. No. 5,965,541; U.S. Pat. No. 5,981,225; U.S. Pat. No. 5,985,846; U.S. Pat. No. 5,994,106; U.S. Pat. No. 5,955,281.

For example, recombinant adenoviral vectors can be generated by a variety of known procedures, e.g., in vivo homologous recombination method (see, e.g., He (1999) Proc. Natl. Acad. Sci. USA 95:2509-2514; Aoki (1999) Mol. Med. 5:224-231; Souza (1999) Biotechniques 26:502-508; U.S. Pat. No. 5,919,676); by the in vitro direct ligation method (see, e.g., Mizuguchi (1998) Hum. Gene Ther. 9:2577-2583); or using circular adenoviral DNA (see, e.g., Tashiro (1999) Hum. Gene Ther. 10:1845-1852). As another technique, the altered sequences can be inserted in a bacterial clone taking advantage of a bacterial recombination system, e.g., as the method described by Chartier (1996) J. Virol 70:4805-4810. This system uses a bacterial plasmid that contains a full length copy of an Ad genome coupled with a simple gene replacement method in E. coli. This allows manipulation of any portion of the Ad genome in a prokaryotic or eukaryotic expression vector followed by insertion into a full length copy of an Ad genome. The full length Ad chromosome is cut once with a restriction enzyme in the region to be replaced. Bacteria are co-transformed with this linearized molecule. Homologous recombination yields a circular molecule that is competent for replication in the bacterial cell. Presence of the altered Ad sequence can be confirmed by PCR and Southern blotting.

Figure 2:
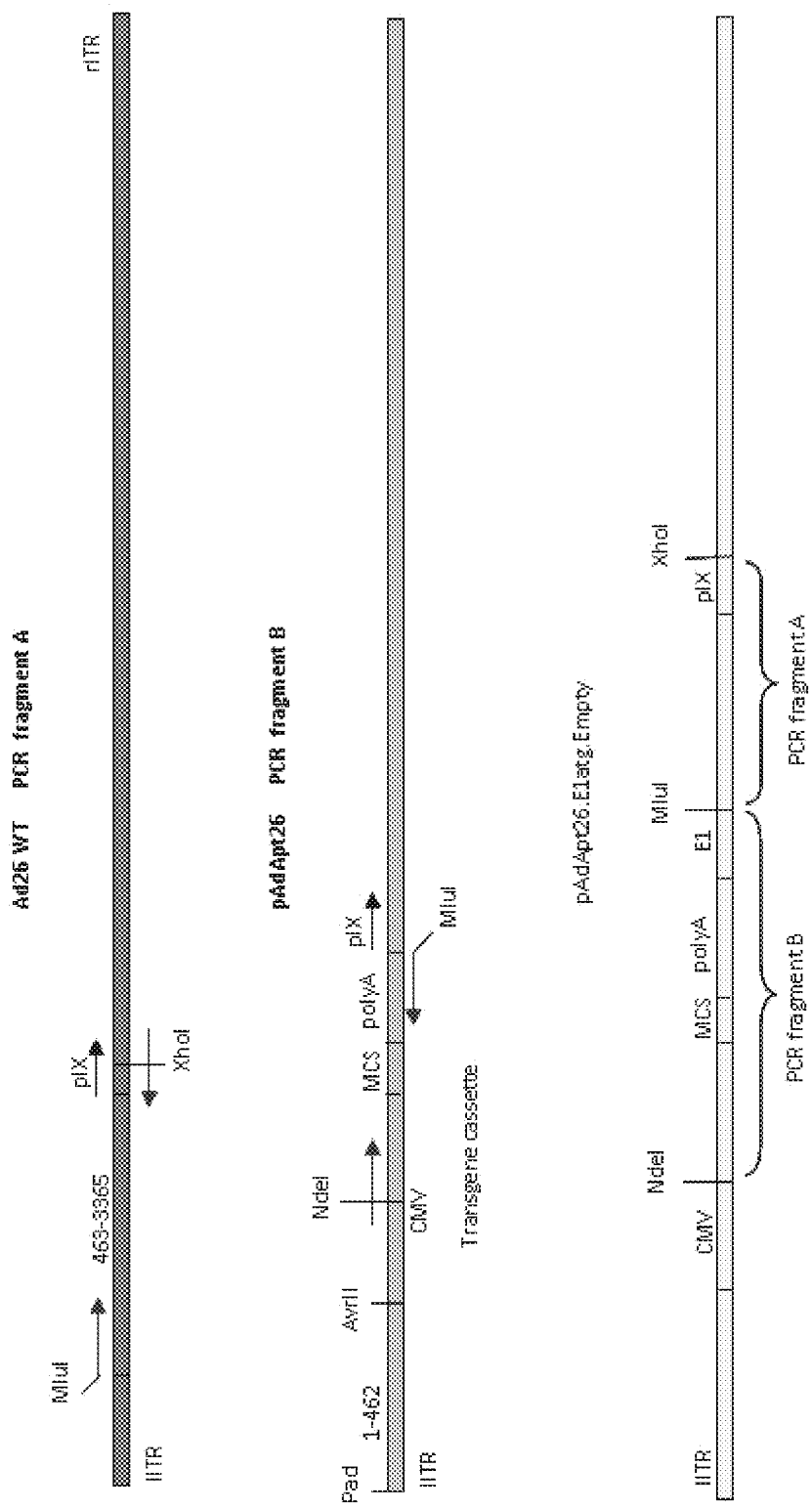
FIG. 2 is a schematic representation of a cloning strategy for constructing an adaptor Ad26 plasmid vector that can be used to produce a replicating recombinant Ad26 vector according to embodiments of the invention; the plasmid vector (pAdApt26.E1atg.Empty; SEQ ID NO: 3) is designed to contain part of the Ad26 genome, including the E1 coding region which is located downstream of the transgene cassette.

Preferably, a recombinant adenoviral vector of the invention is obtained through homologous recombination in a host cell, the homologous recombination being between two linearized plasmids containing regions of sequence homology. In this method, a plasmid/cosmid vector system can be used (FIG. 2). The plasmid contains part of the adenovirus genome, starting from the left end of the genome at the left ITR to a site within the pIX coding region. The plasmid includes a transgene cassette containing a promoter, and a multiple cloning site (MCS) for insertion of a heterologous nucleic acid sequence under control of the promoter in the transgene cassette. One of ordinary skill in the art will appreciate that the transgene cassette can comprise other regulatory elements to control expression, stability, etc. of the heterologous nucleic acid sequence from the transgene cassette, e.g., signal sequences such as a polyadenylation (polyA) transcription termination signal. The adaptor plasmid also contains the E1 coding region, which according to embodiments of the invention, is downstream of the transgene cassette. The 3'-end of the adaptor plasmid contains nucleic acid sequence that is homologous to a portion of the cosmid vector sequence for facilitating homologous recombination, and is preferably about 2.0 to 2.5 kb. The cosmid vector contains the remaining majority of the adenovirus genome spanning from a site within the pIX coding region to the right ITR, including the E3 and E4 coding region. The region of homology with the adaptor plasmid is at the 5' end of the cosmid vector and includes the pIX sequence.

The adenovirus sequence can be manipulated, e.g., by deleting the E3 coding region, completely or partially, and partially deleting the E4 coding region, and the heterologous nucleic acid sequence cloned into the MCS of the adapter plasmid prior to homologous recombination of the plasmid and cosmid to obtain the recombinant adenovirus vector using any method known in the art in view of the present disclosure.

Any plasmid/cosmid system can be used to generate a recombinant adenovirus vector in view of the present disclosure. Cosmids are commercially available hybrid plasmids that contain the Lamda phage Cos sequence. Cosmids allow for stable insertion of large DNA fragments (up to approximately 50 kb), whereas other plasmids carrying a DNA fragment of this size can become instable. The adenovirus 26 or adenovirus 35 genome can be cloned into the plasmid/cosmid using methods known in the art in view of the present disclosure. The adenovirus plasmid/cosmid, such as pAdApt26 or pAdApt35 plasmid, allows for insertion of heterologous nucleic acid sequences into the respective backbone of the adenovirus 26 or adenovirus 35 genome. The adenovirus plasmid/cosmid can also serve as the template or source for amplification or manipulation of Ad genes of interest. In accordance with the invention, recombinant adenovirus vector can be produced by homologous recombination upon co-transfecting an appropriate cell type with the plasmid vector, containing part of the adenovirus genome and the transgene cassette with the inserted heterologous nucleic acid sequence, and the cosmid vector containing the remaining adenovirus genome. Co-transfection can be performed by any method known in the art, e.g., the DEAE dextran method (McCutchan and Pagano, 1968), the calcium phosphate procedure (Graham and van der Eb, 1973), microinjection, lipofection (liposome transfection), electroporation, etc.

Amounts of plasmid and cosmid used in the co-transfection can vary depending on the particular plasmid and cosmid constructs, cell types, etc., and typically range between approximately 0.2 to 10 μg of DNA per $10^6$ cells. For example, a plasmid:cosmid ratio of 1:3 (e.g., 2 μg plasmid: 6 μg cosmid) can be used, although the ratio of plasmid: cosmid can be adjusted as necessary to optimize the co-transfection. The plasmid and cosmid are linearized before transfection, e.g., by restriction enzyme digest. Cells suitable for transfection include any cell line permissive for adenovirus infection, including but not limited to HEK-293 cells, HeLa cells, 293-D22 cells, A549 cells, HuTu 80 cells, HCT-15 cells, IGROV-1 cells, U87 cells, W162 cells, PER.55K cells, and PER.C6 cells (Fallaux, et al., New helper cells and matched early region 1-deleted adenovirus vectors prevent generation of replication-competent adenoviruses. *Hum Gene Ther* 9, 1909-1917, 1998) or derivatives thereof. In certain embodiments, PER.C6 cells are used for transfection of plasmid/cosmid and subsequent generation of the recombinant adenovirus vector.

The transfected cells can be cultured in any suitable vessel known in the art. For example, cells can be grown and the infected cells can be cultured in a biogenerator or a bioreactor. Generally, "biogenerator" or "bioreactor" means a culture tank, generally made of stainless steel or glass, with a volume of 0.5 liter or greater, comprising an agitation system, a device for injecting a stream of $CO_2$ gas, and an oxygenation device. Typically, it is equipped with probes measuring the internal parameters of the biogenerator, such as the pH, the dissolved oxygen, the temperature, the tank pressure or certain physicochemical parameters of the culture (for instance the consumption of glucose or of glutamine or the production of lactate and ammonium ions). The pH, oxygen, and temperature probes are connected to a bioprocessor which permanently regulates these parameters. In other embodiments, the vessel is a spinner flask, a roller bottle, a shaker flask, or in a flask with a stir bar providing mechanical agitation.

The cells can be passaged, and incubated until the development of cytopathic effect (CPE), or the virus-containing cells can be frozen for storage and subsequently used for re-infection of cells, or for virus isolation. The recombinant adenovirus vector can be isolated and purified by any method known in the art in view of the present disclosure, e.g, purification from plaques. Isolated and purified recombinant adenovirus vector can be stored in liquid form, e.g., aqueous buffer, and frozen, or it can be lyophilized and stored in dry form.

The invention also provides a method of producing a replicating adenovirus particle. According to embodiments of the invention, the method comprises introducing a replicating recombinant adenovirus vector according to the invention into a cell under conditions sufficient for replication of the recombinant adenovirus genome and packaging of the adenovirus particle in the cell. Thereafter, the adenovirus particles can be collected from the cell.

As used herein, "viral particle" or "virion" refers to a viral genome enclosed in a protein coat or shell. A viral particle is essentially an inert carrier of a viral genome. Viral particles are assembled inside cells from virus-specific components and carry the viral genome from cell to cell e.g., by infection. Viral particles themselves are not capable of growth or replication, and thus serve as carriers of the viral genome. An "adenovirus particle" specifically refers to a viral particle containing a wild-type adenovirus genome, recombinant adenovirus genome, or recombinant adenovirus vector.

As used herein, the term "collecting," with reference to the production of adenovirus particles, means the isolation of a population of recombinant virus particles from cells used to produce the viral particles. Viral particles can be collected from the virus-containing cells, from the growth medium of cells, or both. To collect viral particles from the cells used to produce the particles, the cells are lysed to release the particles. Thereafter, the particles can be purified according to any of the methods known in the art and described herein.

Any appropriate cell line for propagating adenovirus vectors can be used in a method for producing an adenovirus particle in view of the present disclosure, including, but not limited to PER.C6 cells or HEK293 cells. The produced adenoviral particles can be collected from the cell culture supernatant or from the cells after lysis (e.g., by chemical means, freeze/thawing, osmotic shock, mechanic shock, sonication and the like). Host cell DNA can be degraded by treatment with a DNAse/RNAse, such as Benzonase (American International Chemicals, Inc.). The viral particles can be isolated by consecutive rounds of plaque purification. The collected viral particles can be purified using any suitable technique known in the art in view of the present disclosure (e.g., chromatographic methods, ultracentrifugation on a cesium chloride or sucrose gradient).

Alternatively, virus-containing cells, wherein a recombinant adenovirus vector was introduced into the cell, can be frozen prior to collecting the adenoviral particles. These cells can be used to propagate a new batch of cells for producing replicating adenoviral particles, or they can be stored and the adenoviral particles can subsequently be collected from the cells.

In another general aspect, the invention provides a composition comprising a replicating recombinant adenovirus vector according to the invention and a pharmaceutically acceptable carrier. Preferably, the replicating recombinant adenovirus vector is isolated. It will be appreciated that a pharmaceutical composition or vaccine comprising the recombinant adenovirus may contain adjuvants, excipients, and carriers.

According to embodiments of the invention, a composition can be a vaccine. As used herein, the term "vaccine" refers to a composition comprising a replicating recombinant adenovirus vector of the invention that can provide active acquired immunity to a particular disease. In a preferred embodiment, a vaccine is a composition comprising a replicating recombinant adenovirus vector of the invention that can provide active acquired immunity to an HIV infection.

Compositions of the invention can be formulated in any matter suitable for administration to a subject to facilitate administration and improve efficacy, including, but not limited to, oral (enteral) administration and parenteral injections. The parenteral injections include intravenous injection or infusion, intra-arterial injection, subcutaneous injection, intramuscular injection, and intra-articular injection. Compositions of the invention can also be formulated for other routes of administration including transmucosal, ocular, rectal, long acting implantation, sublingual administration, under the tongue, from oral mucosa bypassing the portal circulation, inhalation, or intranasal.

In a preferred embodiment, a composition is formulated for oral administration. Compositions suitable for oral administration include, but are not limited to, powders, capsules, caplets, gelcaps, granules, and tablets. In one preferred embodiment, enteric coated capsules or tablets are formulated for oral administration. Further detail may be found, e.g. in Remington's Pharmaceutical Sciences," 1990, 18th ed., Mack Publishing Co., Easton, Pa. In another preferred embodiment, a composition is formulated for injection, e.g., intramuscular or subcutaneous, as a liquid preparation. Compositions suitable for injection include solutions, suspensions, and emulsions.

Oral vaccine compositions can be taken in the form of solutions, suspensions, tablets, pills, capsules, sustained release formulations, or powders, containing from about 10% to about 95% of the active ingredient, preferably about 25% to about 70%. Oral and/or intranasal vaccination may be preferable to raise mucosal immunity (which plays an important role in protection against pathogens infecting the respiratory and gastrointestinal tracts) in combination with systemic immunity. Excipients that can be included in oral formulations include, for example, pharmaceutical grades of mannitol, lactose, starch, sucrose, histidine, glycine, gelatin, magnesium stearate, sodium saccharin cellulose, magnesium carbonate, sodium chloride, magnesium chloride, and the like. Additional ingredients, such as alcohol, detergent (e.g., Tween), ethylenediamine-tetraacetic acid (EDTA), can also be included in the oral composition.

Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. Carriers can take a wide variety of forms depending on the form of preparation desired for administration. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

A vaccine composition can be prepared from freshly harvested viral cultures by methods that are standard in the art. For example, the growth of the virus is monitored by standard techniques (observation of cytopathic effect, immunofluorescence or other antibody-based assays), and harvested when a sufficiently high viral titer has been achieved. The viral stocks can be further concentrated or lyophilized by conventional methods before inclusion in the vaccine formulation. Other methods, such as those in described in Thomas, et al., Agri-Practice, V. 7 No. 5, pp. 26-30, can also be employed.

According to embodiments of the invention, a recombinant adenovirus vector can be lyophilized prior to formulation for administration as either a solid preparation or liquid preparation. The present inventors have found that the design of a replicating recombinant adenovirus vector according to the invention increases the stability of the vector and allows the vector to survive lyophilization without decay of virus particles/plaque forming unit (vp/PFU) titers or reduced immunogenicity (FIGS. 11A and 11B). The lyophilized vector can be packaged into capsules to obtain a solid preparation for oral administration. The lyophilized vector can also be resuspended in a suitable buffer to obtain a liquid preparation for parenteral administration.

According to embodiments of the invention, compositions for administration will commonly comprise a buffered solution in a pharmaceutically acceptable carrier, e.g., an aqueous carrier such as buffered saline and the like. The compositions can also contain pharmaceutically acceptable substances as required to approximate physiological conditions such as pH adjusting and buffering agents.

Accordingly, the stability of a replicating recombinant adenovirus vector according to the invention in lyophilized form allows the vector to be packaged into capsules, tablets, and other solid preparations suitable for oral administration. Thus, compositions of the invention are easy to administer and allow for simple, efficient delivery to a subject.

According to an embodiment of the invention, the composition is a capsule comprising a purified recombinant vector, such as rcAd26.Mos1Env, rcAd26.Mos2Env, rcAd26.Mos1GagPol and/or rcAd26.Mos2GagPol; a buffer, such as Tris buffer, phosphate buffer; one or more salts, such as NaCl, $MgCl_2$; a nonionic surfactant, such as a polysorbate, e.g., Tween 20, Tween 40, Tween 60 or Tween 80; a bulking agent, such as lactose, sucrose, or hydroxypropyl methylcellulose (HPMC); and one or more additional ingredients such as EDTA, histidine, lactate, mannitol, ethanol, etc. The composition is buffered at a pH of 6.0 and 8.0, preferably 6.5 to 7.5, more preferably 7.0 to 7.4. In a particular embodiment, the composition is enteric-coated. The composition can be stored frozen, for example at a temperature of less than −65° C.

In another general aspect, the invention provides a method of producing an immune response in a subject. According to embodiments of the invention, the method comprises administering to a subject an immunogenically effective amount of a composition comprising a replicating recombinant adenovirus vector of the invention and a pharmaceutically acceptable carrier. Any of the replicating recombinant adenovirus vectors described herein and compositions thereof can be used in a method of producing an immune response in a subject according to the invention.

The invention also relates to a method of vaccinating a subject, e.g., human. A method of vaccination can be against an infection, e.g., bacterial, protozoan, fungal and viral diseases, etc., and is preferably against a viral infection, more preferably an HIV infection. A method of vaccination according to the invention comprises administering to the subject an immunogenically effective amount of a composition comprising a pharmaceutically acceptable carrier and a replicating recombinant adenovirus vector. Any of the replicating recombinant adenovirus vectors described herein and compositions thereof can be used in a method of vaccination according to the invention.

As used herein, "HIV infection" specifically refers to the invasion of a host organism, such as the cells and tissues of the host organism, by the HIV virus.

As used herein, "vaccinating" or "vaccination" means to produce an immune response or immunity against a disease or infection (bacterial, viral, etc.) in a subject, e.g., human. According to embodiments of the invention, a composition of the invention is administered to vaccinate a subject against an HIV infection.

As used herein, "an immunogenically effective amount" means an amount of a composition sufficient to induce a desired immune effect or immune response in a subject. In one embodiment, an immunogenically effective amount means an amount sufficient to induce an immune response in a subject. In another embodiment, an immunogenically effective amount means an amount sufficient to produce immunity in a subject, e.g., provide a protective effect against a disease such as a viral infection. An immunogenically effective amount can vary depending upon a variety of factors, such as the physical condition of the subject, age, weight, health, etc.; route of administration, such as oral or parenteral; the particular application, whether inducing immune response or providing protective immunity; the specific replicating recombinant adenovirus vector administered; the immunogen encoded by the replicating recombinant adenovirus vector, and the particular disease, e.g., viral infection, for which immunity is desired. An immunogenically effective amount can readily be determined by one of ordinary skill in the art in view of the present disclosure.

As general guidance, an immunogenically effective amount can range from about $10^8$ viral particles to about $10^{12}$ viral particles, for example $10^8$, $10^9$, $10^{10}$, $10^{11}$, or $10^{12}$ viral particles. An immunologically effective amount can be administered in a single composition, or in multiple compositions, such as 1, 2, 3, 4, 5, 6, 7, 8, 9, or 10 compositions (e.g., tablets or capsules), wherein the administration of the multiple capsules collectively provides a subject with the immunologically effective amount. It is also possible to administer a immunogenically effective amount to a subject, and subsequently administer another dose of an immunogenically effective amount to the same subject, in a so-called prime-boost regimen. This prime-boost regime is well known to s a person of ordinary skill in the vaccine field. Further booster administrations can optionally be added to the regimen, as needed.

According to preferred embodiments, in a method of producing an immune response or a method of vaccination, a composition according to the invention is administered orally, preferably as a solid composition (tablet, capsule, etc.), to a human subject. However in some embodiments, a composition is administered by injection in liquid formulation, e.g., intramuscular injection.

According to embodiments of the invention, a replicating recombinant adenovirus vector elicits an immune response against an HIV infection. An immune response can be a cellular response or a humoral response. In general, cellular response refers to the activity of the CD4 and CD8+ T cells, whereas humoral response refers to antibody production and activity. More particularly, a cellular immune response includes a response that enables host CD8+ T cells to limit replication of HIV and kill HIV-infected cells, thus dampening or eliminating a first local, muscosal focus of HIV infection during the early stages of infection.

The ability to induce or stimulate an anti-HIV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELISPOT), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay).

The ability to stimulate a humoral response can be determined by antibody binding and/or competition in binding (see for example Harlow, 1989, Antibodies, Cold Spring Harbor Press). For example, titers of antibodies produced in response to administration of a composition providing an immunogen can be measured by ELISA. ELISPOT can also be used to assess humoral immune response to identify and enumerate the number of cells secreting an antibody produced in response to administration of an antigen.

According to embodiments of the invention, upon administration to a subject, a replicating recombinant adenovirus vector expresses an immunogenic polypeptide. Any of the immunogenic polypeptides described herein can be encoded by a recombinant viral vector and administered to a subject in a method of the invention. The expressed immunogenic polypeptide is presented to the immune system of the subject, thereby inducing the required response to produce immunity, or induce an immune response to treat or prevent a disease or infection. For example, the response can be the production of antibodies specific to the immunogenic polypeptide.

Preferably, upon administration to a subject, a replicating recombinant adenovirus vector expresses a mosaic HIV antigen. Presentation of a mosaic HIV antigen according to the invention to the immune system of a subject can induce the production of antibodies specific to the HIV, such as antibodies specific to HIV gag, pol, and/or env gene products, depending on the sequence composition of the expressed mosaic HIV antigen.

According to embodiments of the invention, in a method of producing an immune response in a subject or vaccination of a subject, a replicating recombinant adenovirus vector encodes a mosaic HIV antigen comprising the amino acid sequence of SEQ ID NO: 48 (Mos1-HIVEnv) or SEQ ID NO: 50 (Mos1-HIVGagPo1). A replicating recombinant adenovirus vector according to the invention can also encode a mosaic HIV antigen comprising the amino acid sequence of SEQ ID NO: 69 (Mos2-HIVEnv) or SEQ ID NO: 71 (Mos2-GagPol).

According to embodiments of the invention, compositions comprising replicating recombinant adenovirus vectors can be administered to a subject prior to an HIV infection, or after the onset of an HIV infection. When administered prior to an HIV infection, e.g., for vaccination of a subject, an immune response can be induced that provides protective immunity to the subject, effectively immunizing the subject to any future HIV infection. When administered after the onset of an HIV infection, an immune response can be induced that treats the HIV infection, e.g., by destroying HIV infected cells, preventing the HIV virus from replicating, and/or inhibiting viral entry of the HIV virus into cells.

Compositions of the invention can be administered in a variety of dosage forms, and dosing regimens. The appropriate dosing regimen, including the frequency of administration, mode of administration, and the immunogenically effective amount, will vary, and can be affected by the particular condition of the patient (e.g., age, health, condition), time of administration (e.g., prior to infection or after the onset of infection), etc. One of ordinary skill in the art would readily be able to determine the appropriate dosing regimen in view of the present disclosure. For example, in a method of vaccinating a subject, compositions can be administered in two doses, an initial dose and a second dose, wherein the second dose is administered several days, weeks or months after the initial dose. As another non-limiting and illustrative example, in a method of producing an immune response, a daily or weekly dosing regimen can be established, wherein a determined immunogenically effective amount of the composition is administered once daily, or once weekly, for a set period of time, e.g., several weeks or months. The dosing regimen can be adjusted accordingly depending on the response of the subject, e.g., improvement or worsening in condition.

Without wishing to be bound by any theories, it is hypothesized that a replicating recombinant adenovirus vector of the invention can induce immune responses that differ in their location and cellular phenotype from replication-incompetent, parenteral (injectable) vaccines. This is thought to be in part due to the stability of the recombinant adenovirus vector to lyophilization, thus allowing the recombinant vector to be administered orally as a solid composition. Specifically, replicating recombinant adenovirus vectors of the invention are believed to induce potent immune responses in the Gut-Associated Lymphoid Tissue (GALT), which is an early target for HIV infection and destruction of CD4+ cells [56]. Thus, the replicating recombinant adenovirus vectors may function by preventing or limiting HIV replication on first entry.

The following examples of the invention are to further illustrate the nature of the invention. It should be understood that the following examples do not limit the invention and that the scope of the invention is to be determined by the appended claims.

EXAMPLES

Example 1

Cloning of Empty Ad26 Adaptor Plasmid (pAdApt26.E1atg.Empty) with E1 Coding Region after Transgene Cassette The empty Ad26 recombinant vector, pAdAp26.E1atg.Empty (SEQ ID NO: 3) was constructed as shown in FIG. 2. The pAdApt26.E1atg.Empty vector contains the E1 coding region after the transgene cassette. "Empty" denotes that the vector does not contain a heterologous nucleic acid sequence or transgene, however any heterologous nucleic acid sequence of interest can be inserted into the multiple cloning site of the transgene cassette of the pAdApt26.E1atg.Empty vector under control of the CMV promoter, and upstream of the E1 coding region.

Production of "PCR Fragment A" and "PCR Fragment B"

Two polymerase chain reactions (PCRs) were set up. The first PCR was to amplify the E1 coding region from the wild-type adenovirus vector genome ("Ad26 WT"), and was performed using the following primer pair: forward primer, Ad26WT.463.MluI.fwd 5'-CACAGACGCGTATCAGCT-GATCCGCAGGGTATTTA-3' (SEQ ID NO: 54); and reverse primer, Ad26WT.XhoI.rev 5'-CTGGGCATG-TAGCTCGAGGCCAGT-3' (SEQ ID NO: 55). The forward primer was designed to introduce an MluI site at the start of the E1 coding region, and the reverse primer was designed to overlap with the existing XhoI is the pIX region of the Ad26 viral genome. This resulted in a PCR product flanked by a MluI and a XhoI site ("PCR fragment A").

The second PCR was to amplify part of the transgene cassette from the pAdApt26 vector (Abbink et al. Comparative seroprevalence and immunogenicity of six rare serotype recombinant adenovirus vaccine vectors from subgroups B and D. *J. Virology* (2007) 81(9), 4654-4663) and was performed using the following primer pair: forward primer, AdApt26.NdeI.fwd primer 5'-GTGTATCATATGCCAAG-TACGCCC-3' (SEQ ID NO: 52); and reverse primer, AdApt26.MluI.rev 5'-CGATCACGCGTATCTAGACAT-GATAAGATACATTGATG-3' (SEQ ID NO: 53). The forward primer was designed to overlap with the existing NdeI site in the CMV promoter of the pAdApt26 vector, and the reverse primer was designed to introduce a MluI site immediately after the polyA sequence. This resulted in a PCR product flanked by a NdeI and a MluI site ("PCR fragment B").

Cloning of AdApt26.E1atg.Empty (E1 Region Put after Transgene Cassette)

PCR fragment A was digested with NdeI and MluI, and PCR fragment B was digested with MluI and XhoI. pAdApt26 vector was digested with NdeI and XhoI. All fragments were gel purified. A triple ligation was set up with these digested fragments and clones were screened by restriction enzyme analysis and sequencing to confirm pAdApt26.26E1.empty was obtained.

Example 2

Cloning of Ad26 Adaptor Plasmid Containing a Heterologous Nucleic Acid Sequence Encoding a Mosaic HIV Antigen (pAdApt26.26E1.Mos1-HIVEnv)

Figure 3A:
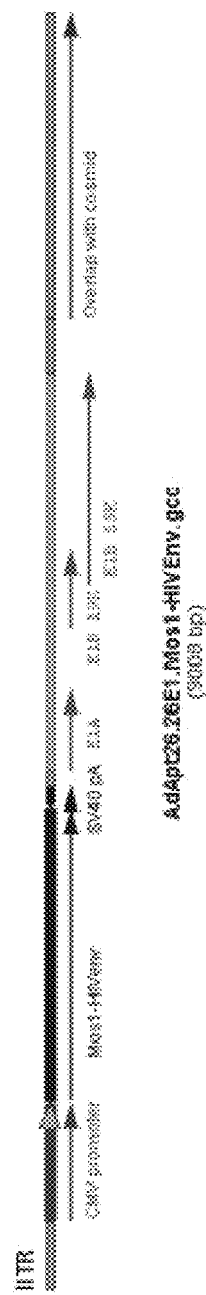
FIGS. 3A and 3B show a schematic representation of an adaptor Ad26 plasmid vector and cosmid vector for producing a replicating recombinant Ad26 vector according to embodiments of the invention.

The Ad26 adaptor plasmid containing a heterologous nucleic acid sequence encoding the mosaic HIV antigen Mos1HIVEnv (SEQ ID NO: 48) cloned into the transgene cassette under control of the CMV promoter, pAdApt26.26E1.Mos1-HIVEnv (FIG. 3A) was constructed as follows.

Mos1-HIVEnv was digested from a plasmid that was synthetically generated by GeneART® that contained the Mos1-HIVEnv transgene (SEQ ID NO: 47) in a bacterial backbone. KpnI and BamHI sites were designed flanking the transgene sequence. pAdApt26.26E1.Empty was digested with KpnI and BamHI. After purification, both DNA fragments were ligated together using T4 DNA ligase. Clones were sequenced to verify integrity.

Example 3

Cloning of Ad26 Cosmid Vector (pWe.Ad26.pIX-rITR.dE3dE426orf6)

Figure 3B:
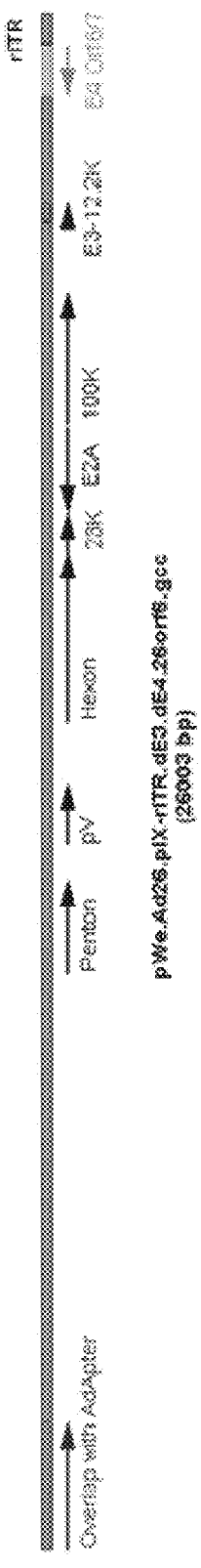

The Ad26 cosmid vector pWe.Ad26.pIX-rITR.dE3dE426orf6 (SEQ ID NO: 2) (FIG. 3B) containing a partially deleted Ad26 E3 coding region (SEQ ID NO: 5) and a partially deleted Ad26 E4 coding region (SEQ ID NO: 22) was constructed as follows.

Cloning of pWe/Ad26.pIX-rITR.dE3.26orf6 Ad26 Cosmid (Ad26 Cosmid Containing Native Ad26E4Orf6)

The E4orf6 region of adenovirus serotype 5 (Ad5E4orf6) present in the cosmid vector pWe/Ad26.pIX-rITR.dE3.5orf6 (Abbink et al. 2007, supra) was first replaced with the native E4orf6 region of adenovirus 26 (Ad26E4orf6). A PCR fragment was generated from the EcoRI site present in the Ad26 fiber protein coding region to the MluI site in the E4orf3 of Ad26. Ad26 WT was used as the template for the PCR reaction, with the following primer pair was used: forward primer, Ad26.E4orf6.fwd 5'-CTATTTGAT-GAGAATGGAATTCTATTA-3' (SEQ ID NO: 56); and reverse primer, Ad26.E4orf6.rev 5'-CTTATGCTGGATG-TACGCGTAGAG-3' (SEQ ID NO: 57). This PCR fragment was ligated into the pWe/Ad26.pIX-rITR.dE3.5orf6 cosmid (digested with EcoRI and partially with MluI) thereby replacing the Ad5orf6 part to provide pWe/Ad26.pIX-rITR.dE3.26orf6.

Cloning of pWe/Ad26.pIX-rITR.dE3.dE4.26orf6 (Ad26 Cosmid Vector Containing Partially Deleted E3 Coding Region and a Partially Deleted E4 Coding Region)

Two PCR fragments were generated. The first was generated starting at the EcoRI site in the Ad26 fiber protein coding region until the start of the E4orf6 region with a designed MluI site at the start of the E4orf6 using the following primer pair: forward primer, Ad26.dE4.EcoRI-MluI.fwd 5'-GACTGCTACTACAAAGAAGGATGTA-3' (SEQ ID NO: 58); and reverse primer Ad26.dE4.EcoRI-MluI.rev 5'-TATTCAACGCGTAGTACGACAAGGTACG-CAAGAGAAT-3' (SEQ ID NO: 59). pBr/Ad26.dE3.26orf6 (Abbink et al. 2007, supra) was used as the template.

The second PCR fragment was generated at the start of the E4orf1 with a designed MluI site until the SrfI site using the following primer pair: forward primer, Ad26.dE4.MluI-SrfI.fwd5'-TATTCAACGCGTAGCTCAGCCCGCTTAC-CAGTAGA-3' (SEQ ID NO: 60); and reverse primer, Ad26.dE4.MluI-SrfI.rev 5'-GCGTCTGGCGCGGCGCA-GCAGA-3' (SEQ ID NO: 61). pBr/Ad26.dE3.26orf6 was used as the template.

Both of the generated PCR fragments were digested with EcoRI/MluI or MluI/SrfI. pBr/Ad26.dE3.26orf6 was digested with EcoRI/SrfI. Before the E4orf6 was swapped with that of Ad5, this plasmid had its native Ad26 E4orf6 gene still present. The EcoRI/MluI and MluI/SrfI digested PCR fragments were ligated into the digested pBr/Ad26.dE3.26orf6 by triple ligation, providing pBr/Ad26.dE3.dE4.26orf6, in which E4orf1 through E4orf4 were deleted.

Finally, the pBr/Ad26.dE3.dE4.26orf6 and the pBr/Ad26.SfiI (Abbink et al., 2007, supra) plasmids were digested with SrfI and PacI and ligated into a pWe cosmid backbone that was digested with PacI resulting in pWe/Ad26.pIX-rITR.dE3.dE4.26orf6 cosmid vector.

Example 4

Production of a Replicating Recombinant Adenovirus 26 Vector rcAd26.Mos1-HIVEnv

The adaptor plasmid pAdApt26.26E1.Mos1-HIVEnv obtained in Example 2, and the cosmid vector pWe.Ad26.pIX-rITR.dE3dE426orf6 obtained in Example 3 (FIGS. 3A and 3B) were first cleaned and amplified to ensure that the plasmid and cosmids were free of any animal components. The plasmids were cleaned with chaotropic salt, which is present in the NT buffer in the Nucleospin Extract II kit of Macherey-Nagel. These cleaned plasmids were electroporated into MegaX DH10B bacteria, which were subsequently grown on animal component free LB agar containing 50 µg/mL ampicillin. After the electroporation, one single colony was isolated and a streak was performed on animal component free LB agar containing 50 µg/mL ampicillin. This streak was repeated one more time. After the second streak, three colonies were grown in animal component free LB broth with 50 µg/mL ampicillin and subsequently tested by miniprep analysis. One culture was selected and used to inoculate a maxiprep culture, again using animal component free LB broth containing 50 µg/mL ampicillin. The plasmids were subsequently isolated using an Endotoxin free maxiprep kit of Macherey-Nagel. The RNAse present in the kit was not used as it is of animal origin. Instead the RNAse Ti of Roche, which is derived from the fungus called *Aspergillus oryzae*, was used. The integrity of pAdApt26.26E1.Mos1-HIVEnv plasmid and pWe/Ad26.dE3.dE4.26orf6 cosmid vector were confirmed by restriction enzyme analysis.

The rcAd26.Mos1-HIVEnv replicating recombinant vector was generated by transient transfection. The DNA solution for transfection was produced by mixing 1 µg of linearized plasmid pAdApt26.26E1.Mos1-HIVEnv and 5 µg of linearized cosmid pWe/Ad26.dE3.dE4.26orf6.

To rescue the virus, Lipofectamine 2000CD was added to the DNA mixture at a DNA:Lipofectamine 2000CD ratio of 1 µg: 2.5 µl, and incubated at room temperature for 30-40 min. PER.C6 cells were seeded in a T25 flask one day prior to transfection, washed with DMEM, and the transfection mixture was incubated on the cells for 4 hours at 37° C. and 10% $CO_2$. After 4 hours, the transfection mixture was removed and culture medium was added. After incubation at 37° C. and 10% $CO_2$ for 2 days, the transfected cells were passaged to a T75 flask and incubated until the development of cytopathic effect (CPE).

Figure 4A:
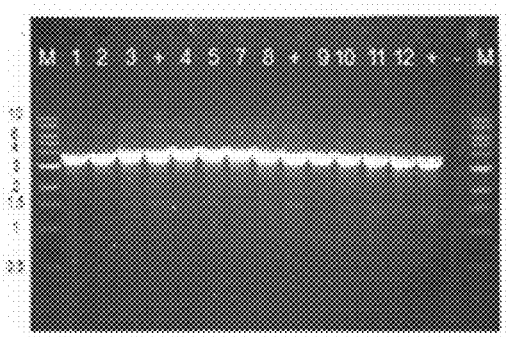
FIGS. 4A-4C depict gel images from the PCR and Western Blot analysis of plaques from the first round of purification of a replicating recombinant Ad26 vector according to an embodiment of the invention, rcAd26.Mos1-HIVEnv; at the top of the lanes, "+" indicates positive control, "−" and E indicate the negative controls, the rest of the lanes are labeled with the identifying number of the plaque tested, in FIGS. 4A and 4B "M" represents the 1 kb size marker (NEB, numbers indicate the size in kb, 0.3, 0.5, 0.7, 1.0, 1.5, 2.0, 2.5, 3.0, 4.0, 5.0, 6.0, 8.0 and 10.0 kb), and in FIG. 4C "M" represents Magic marker (Invitrogen, numbers indicate the size in kD)
Figure 4C:
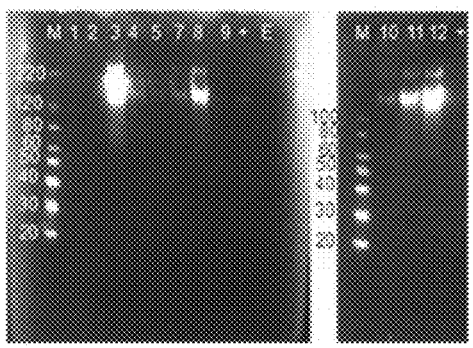
Figure 4B:
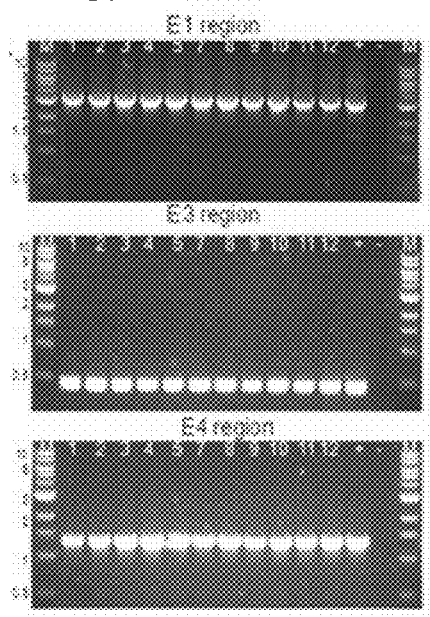

As CPE development did not progress to full CPE, the total crude material was harvested, stored at −20° C. and subsequently used for reinfection of PER.C6 seeded in a T75 flask. By the reinfection process full CPE was obtained and the total crude material was harvested and stored at −20° C. This material was used to perform the first plaque purification. A total of 12 plaques were picked from the highest dilutions and propagated on PER.C6 cells seeded in a 24 well plate. The propagated plaques were tested for integrity of the transgene region by PCR using the proofreading polymerase Pfu (Promega; cat#M7745) and primer set Ad26-1 (SEQ ID NO: 73) and Ad26-7 (SEQ ID NO: 74) (see FIGS. 4A-4C). The PCR product includes the CMV promoter, polyA sequence, the start of the coding region of E1A protein, which has an expected size of 3.3 kb. Sequences were analyzed by alignment of the obtained transgene region sequences from PCR of the rcAd26.Mos1-HIVEnv vector to the reference sequence for the PCR product (SEQ ID NO: 93).

Figure 5A:
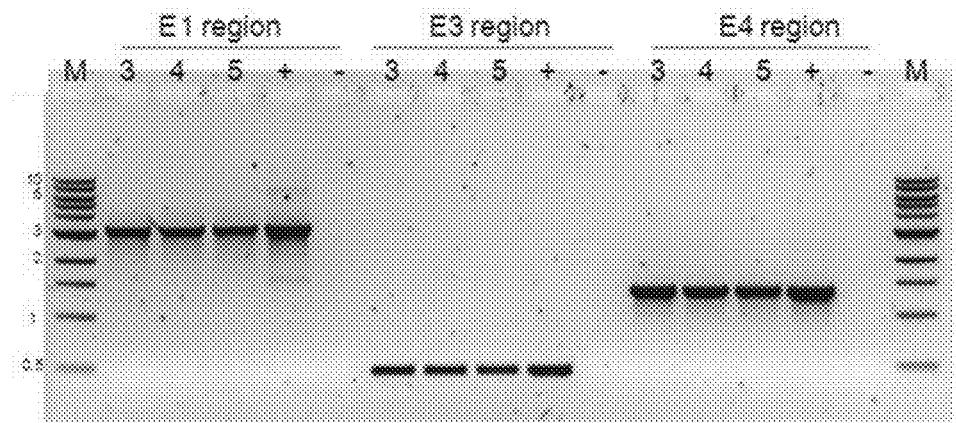
FIGS. 5A-5C depict images from PCR and Western Blot analysis of plaques from the second round of purification of a replicating recombinant Ad26 vector according to embodiments of the invention, rcAd26.Mos1-HIVEnv; on the top of the lanes "+" indicates positive control, "−" indicates negative control, and "U" indicates uninfected A549 cells, the rest of the lanes are labeled with the identifying number of the plaque tested; "M" indicates 1 kb marker (NEB, numbers indicate the size in kb) in FIGS. 5A and 5B, and Magic marker (Invitrogen, numbers indicate the amount of kD) in FIG. 5C.
Figure 5B:
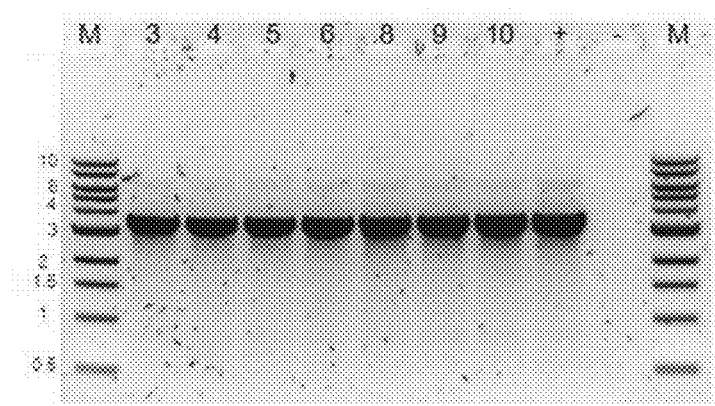
Figure 5C:
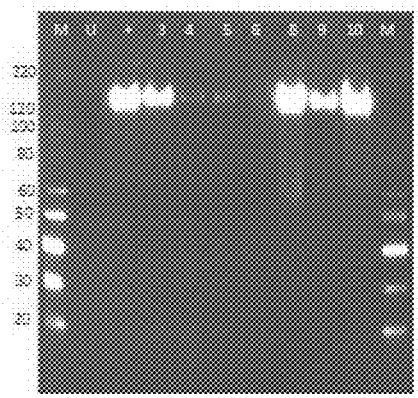

Plaque 3 was prioritized and subjected to a second round of plaque purification. Twenty plaques from the highest dilutions were selected from round two. A total of 12 plaques were propagated on PER.C6 cells seeded in a MW24 plate format and analyzed. Transgene region integrity for subsequent rounds of plaque purification was analyzed by PCR using the proofreading polymerase Pfu (Promega; cat#M7745) and the transgene region primers Ad26-1 (SEQ ID NO: 73) and Ad26-10 (SEQ ID NO: 81) (located in the CMV promoter and E1 coding region, respectively), rather than Ad26-1 and Ad26-7, as it gave more specific product bands (see FIG. 5B). Alignment of the obtained transgene region sequences of the rcAd26.Mos1-HIVEnv vector was compared with the Mos1-HIVEnv reference sequence (SEQ ID NO: 93).

Based on the results obtained, plaque number 3 (see FIG. 5B, lane 2) was selected to continue with. The virus was subsequently expanded, and the rcAd26.Mos1-HIVEnv vector was purified from the cell pellet by a three-step freeze/thaw cycle and a two-step cesium chloride (CsCl) centrifugation procedure. The host cell DNA was degraded by Benzonase treatment. The vector was aliquoted into cryovials, snap frozen on liquid nitrogen and stored at −80° C.

Example 5

Characterization of the rcAd26.Mos1 HIVEnv Recombinant Adenovirus Vector

Determination of Infectious Titer of the Virus.

The viral particle (vp) amount (vp/mL) of the purified rcAd26.Mos1-HIVEnv was initially determined using spectrophotometric methods by measuring the optical density at 260 nm in the presence of 1% SDS. Alternatively, HPLC was also used to determine vp/mL. The infectious particle amount was determined by TCID50 assay using 911 cells, or plaque forming unit (PFU) assay. For the PFU assay, cells permissive to adenovirus growth, such as 293 or PER.55K cells, were seeded at day 1 in 6 well plates at a density of $8.5 \times 10^5$ cells per well. On day 0, the cells were infected with log dilutions of purified adenovirus vector followed by agar overlay after an infection period of 24 hours. At day 14, the plaques were counted in the wells in which the plaques were sufficiently separated so there was no overlap of multiple plaques. Virus particles per plaque forming unit (vp/PFU) was calculated as follows:

# of plaques at day 14/dilution=PFU/ml

Average of all dilutions counted on a plate is calculated.

(Average PFU/ml)/viral titer(vp/ml)=vp/PFU

Transgene PCR and Sequence Analysis

Transgene and PCR sequence analysis was performed as described above in Example 4.

Transgene Expression

Expression levels of the transgene encoding the Mos1-HIVEnv mosaic HIV antigen were determined by Western blot analysis. A549 cells were infected at increasing multiplicity of infections (MOIs: 1000, 2500, 5000, 10000, 25000 and 50000 vp per cell) with the obtained purified rcAd26.Mos1HIVEnv vector. After 3 days of incubation, lysates were prepared from the infected A549 cells and one uninfected control sample. Mos1-HIVEnv expression for rcAd26.Mos1HIVEnv was confirmed by Western blot analysis using a primary antibody anti-HIV-1 gp120 (Virus Research Products; cat#NEA-9301) and secondary antibody goat anti-mouse IgG-HRP (Biorad; cat#170-6516).

Purity Determination

The purity of rcAd26.Mos1-HIVEnv was determined by SDS-PAGE analysis under denaturing conditions, which results in disintegration of the adenoviral particle and separation of the individual proteins that constitute the rcAd26.Mos1HIVEnv vector. Four different vp amounts ($5 \times 10^8$ vp, $1 \times 10^9$ vp, $3 \times 10^9$ vp and $6 \times 10^9$ vp) were analyzed with varying concentrations of bovine serum albumin (BSA) (0.5 µg, 0.1 µg, 0.05 µg and 0.01 µg).

The size of the observed protein bands was compared to the Novex Sharp Pre-stained Marker migration pattern. The apparent sizes were used to putatively assign the bands on the gel to specific proteins. After instant blue staining (Expedeon; cat#194-ISB1L), the gel was scanned and the intensity of the bands were determined by the Gel Pro 6.0 software. BSA was used as an internal marker of known concentration. The protein band pattern observed for the rcAd26.Mos1-HIVEnv was as expected for adenovirus, as the visible bands are comparable to known adenoviral related proteins (118 kD: Hexon; 60 kD: Penton base; 59 kD: pIIIa (minor capsid protein); 45 kD: pV (minor core protein); 26 kD: pVI (minor capsid protein); 20 kD: pVII (core protein). No unexpected or unknown bands were detected.

Example 6

In Vitro Infectivity and Growth of Ad26 Vectors in Various Cell Lines

The infectivity and growth kinetics of replication competent Ad26 vectors (rcAd26) were analyzed. Specifically, the deletion of E3/E4 and insertion of the Mos1-HIVEnv transgene was assessed in terms of attenuation, as defined by the virus titer required to infect cells and the time to achieve maximum cytopathic effect (CPE) of replication-competent Ad26 vectors.

The rcAd26 vectors tested are shown below in Table 1, and the infectivity and growth kinetics of each of these vectors was compared to wild-type Ad26 (Ad26.WT) in the following cell lines: A549 (human epithelial lung carcinoma cell line; ATCC #CCL-185, Manassas, Va.), HuTu 80 (human duodenum adenocarcinoma cell line; ATCC #HTB-40), and PER.55K (Human epithelial cell line that complements the Ad E1 region [12]). The rcAd26 vectors were made replication competent by adding the E1 region back into the replication-incompetent Ad26 behind the transgene cassette. Versions of the vector that were compared had either part of the E3 region deleted, or part of both the E3 and E4 region deleted, and were with or without the Mos1-HIVEnv transgene. For comparison, the replication incompetent version of wild-type Ad26 was also tested.

TABLE 1

Ad26 Vectors Used for In Vitro Infectivity and Growth Study

| Vector | Replication Competent | E3 Deleted | E4 Deleted | Transgene |
|---|---|---|---|---|
| rcAd26.dE3.dE4.Mos1.Env | Yes | Yes | E4 orf 1-4 | HIVMos1.Env |
| rcAd26.dE3.Mos1.Env | Yes | Yes | No | HIVMos1.Env |
| rcAd26.dE3.dE4.empty | Yes | Yes | E4 orf 1-4 | No |
| rcAd26.dE3.empty | Yes | Yes | No | No |
| Ad26.WT | Yes | No | No | No |
| non-rcAd26.dE3.Empty | No | Yes | No | No |
| non-rcAd26.dE3.Mos1.Env | No | Yes | No | HIVMos1.Env |

Figure 6A:
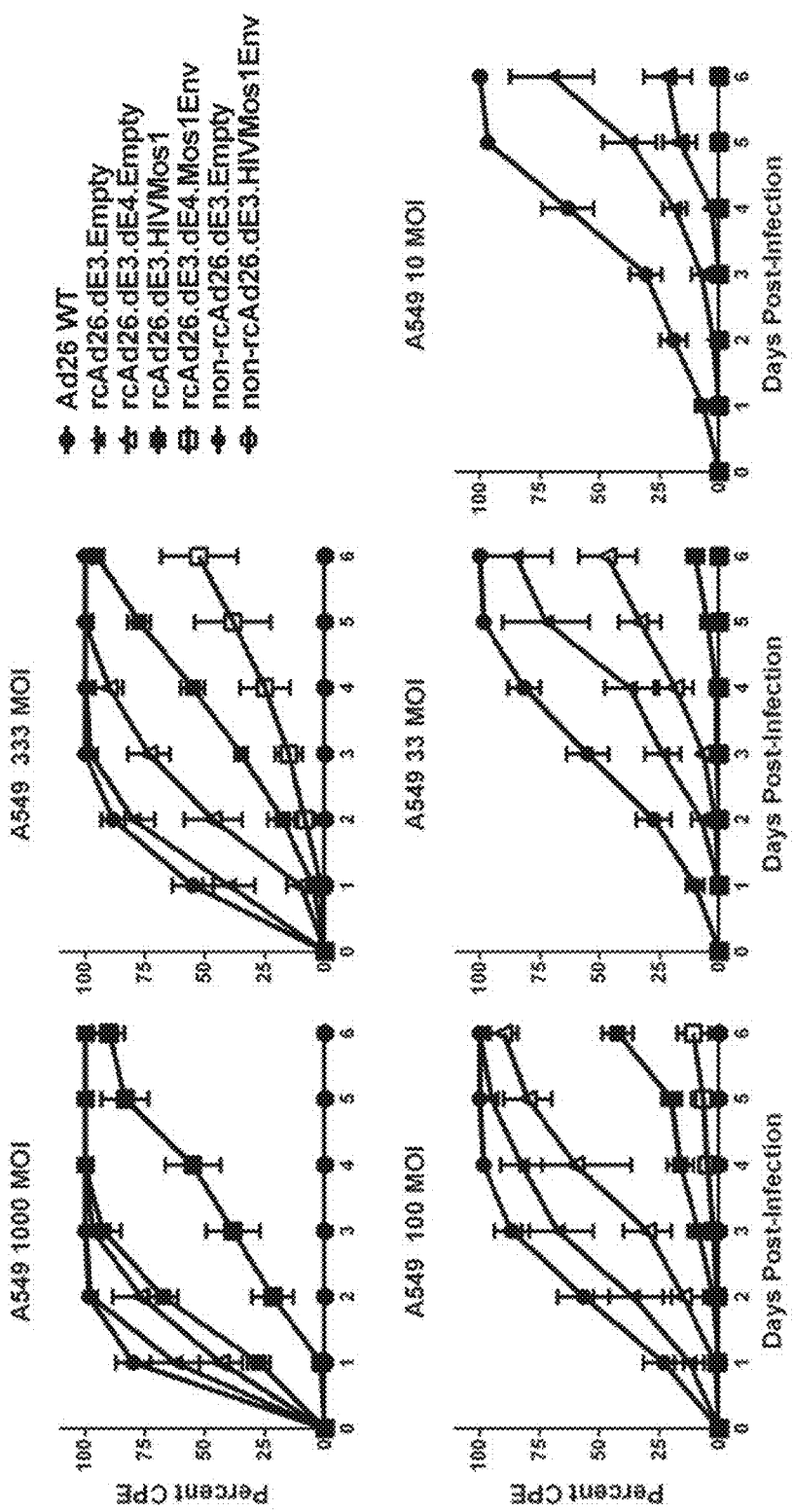
FIGS. 6A-6C compare the in vitro replication and infectivity reported as percent cytopathic effect (CPE) of replicating recombinant Ad26 vectors according to embodiments of the invention containing either (i) a deletion in the E3 coding region and lacking a transgene (rcAd26.dE3.empty), (ii) a deletion in the E3 and E4 coding regions and lacking a transgene (rcAd26.dE3.dE4.empty), (iii) a deletion in the E3 coding region and containing a transgene (rcAd26.dE3.Mos1Env), (iv) a deletion in the E3 coding region and E4 coding region, and containing a transgene (rcAd26.dE3.Mos1Env), and (v) wild-type Ad26 (Ad26.WT) in various cell lines; replication and infectivity was also compared to replication incompetent recombinant Ad26 vectors non-rcAd26.dE3.empty (deletion in E1 coding region, deletion in the E3 coding region, no transgene) and non-rcAd26.dE3.Mos1Env (deletion in E1 coding region, deletion in E3 coding region, containing a transgene)
Figure 6B:
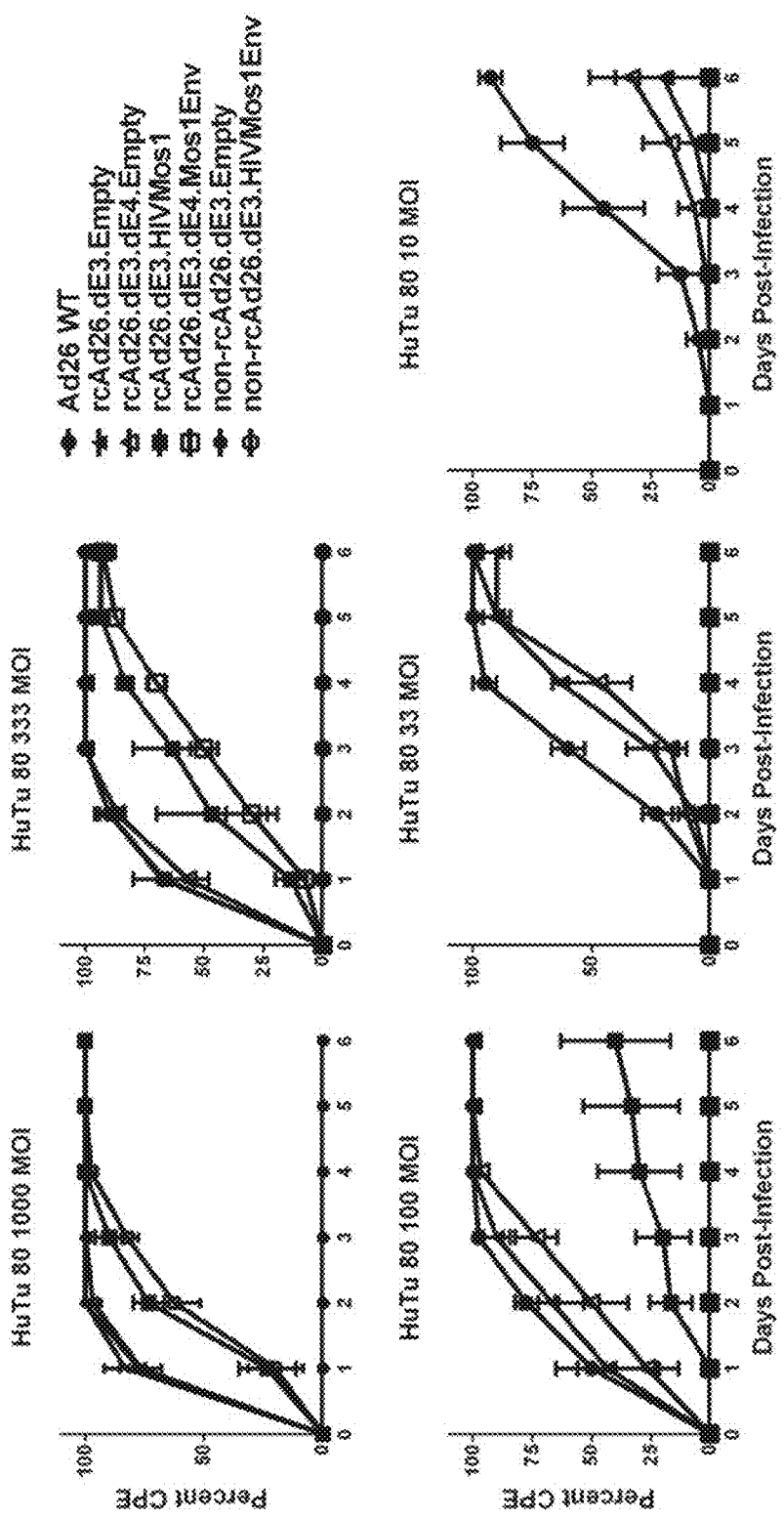
Figure 6C:
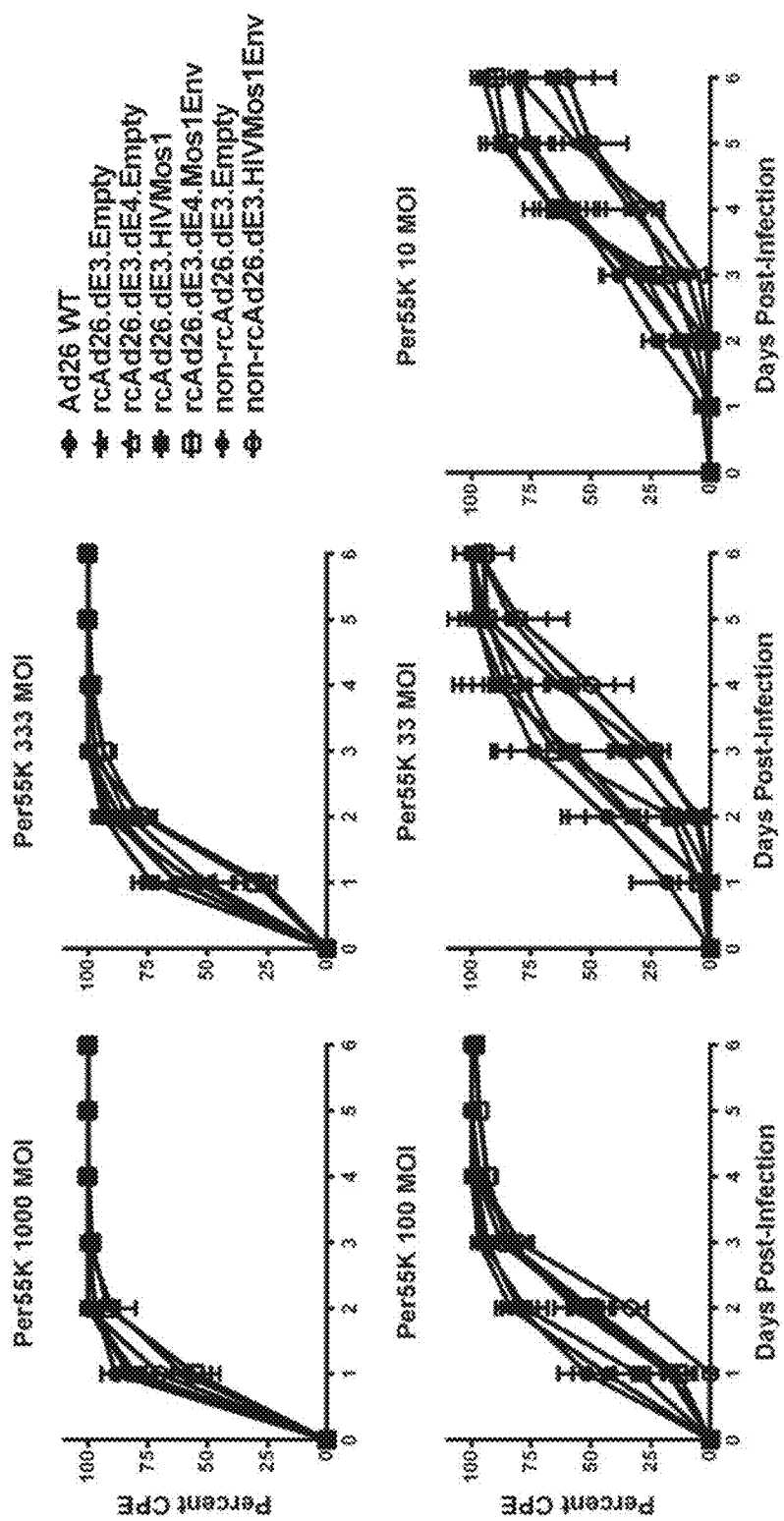

The infectivity assays were performed by first seeding A549, HuTu 80, or PER.55K cells into 6-well plates the day before infection. The next day, the cells were infected with the Ad26 vectors at various multiplicity of infection (MOI) (1000, 333, 100, 33, 10, and 0). The cultures were then monitored and scored daily for the percentage cytopathic effect (CPE) observed out to 6 days post-infection. Each vector and cell line combination was tested in 3 replicate experiments. The results of the in vitro infectivity experiments for each of the tested cell lines are shown in FIGS. 6A-6C.

For all rcAd26 vectors, the in vitro replicative capacity was significantly reduced (required more virus to infect the monolayer and took longer to cause maximum CPE) in the non-complementing A549 cells (FIG. 6A) and HuTu 80 cells (FIG. 6B) as compared to wild-type Ad26 in both of these cell lines. Decreased in vitro replicative capacity occurred in a step-wise fashion with vectors containing only the partial E3 deletion having only a slight reduction, then becoming more reduced as both E3 and E4 were partially deleted. Replicative capacity was most reduced in vectors containing the transgene encoding Mos1-HIVEnv, with rcAd26.dE3.dE4.Mos1Env (partial E3/E4 deletion, and encoding Mos1-HIVEnv) having the most pronounced decrease in replicative capacity. Approximately 100-fold more virus was needed to achieve the same virus growth compared to wild-type Ad26. As expected, the non-replicating Ad26 vectors did not replicate in either the A549 or HuTu 80 cell lines.

As a control, the vector growth in E1-complementing PER.55K cells was evaluated. The data demonstrated that there was no significant difference in growth between the various Ad26 vectors as compared to wild-type when PER.55K cells were infected (FIG. 6C).

The results of these experiments indicate that the replicating recombinant rcAd26 vectors had a significant decrease in infectious titer, and increase in time to achieve full CPE as compared to wild-type Ad26 when used to infect A549 and HuTu80 cell lines, but had no decrease in growth when used to infect PER.55K cells. The decreased in vitro replicative capacity of the replicating recombinant rcAd26 vectors in non-complementing cells was most pronounced with partial deletions of both the E3 and E4 coding regions, and when the vector contained a transgene, e.g., nucleic acid sequence encoding Mos1-HIVEnv. The replicative capacity of the rcAd26.Mos1Env vector was at least 100-fold less than the replicative capacity of wild-type Ad26. This reduction in replicative capacity (i.e., attenuation) had not been previously observed in other adenovirus vectors, and could not be predicted based on the structure of the vector construct.

Example 7

Comparison of In Vitro Infectivity and Growth of Replicating Recombinant Ad26 Vectors in Human Cell Lines and Rhesus Monkey Cell Lines The infectivity and growth kinetics of the replicating recombinant Ad26 vector rcAd26.dE3.Empty, and replication incompetent Ad26 vector non-rcAd26.dE3.Empty, both as described above in Table 1, were analyzed in A549 cells and PER.55K cells. The infectivity assays were performed as described above in Example 6 by infecting cells at various MOIs (1000, 100, or 10). Wild-type Ad26 (Ad26.WT) was tested as a control. The results are reported as percent CPE, and are shown in FIG. 7A.

The infectivity and growth kinetics of replicating recombinant Ad26 vectors rcAd26.dE3.dE4.Empty and rcAd26.dE3.dE4.Mos1Env were analyzed in MK-2 cells (rhesus monkey kidney cell line). For the controls, Ad26.WT and replication competent simian Ad vector derived from rhesus monkeys (rcSAd.SIVgag) were tested. The infectivity assays were performed also as described above in Example 6 by infecting cells at MOIs of 1000, 333, and 100. The results are reported as percent CPE, and are shown in FIG. 7B.

Figure 7A:
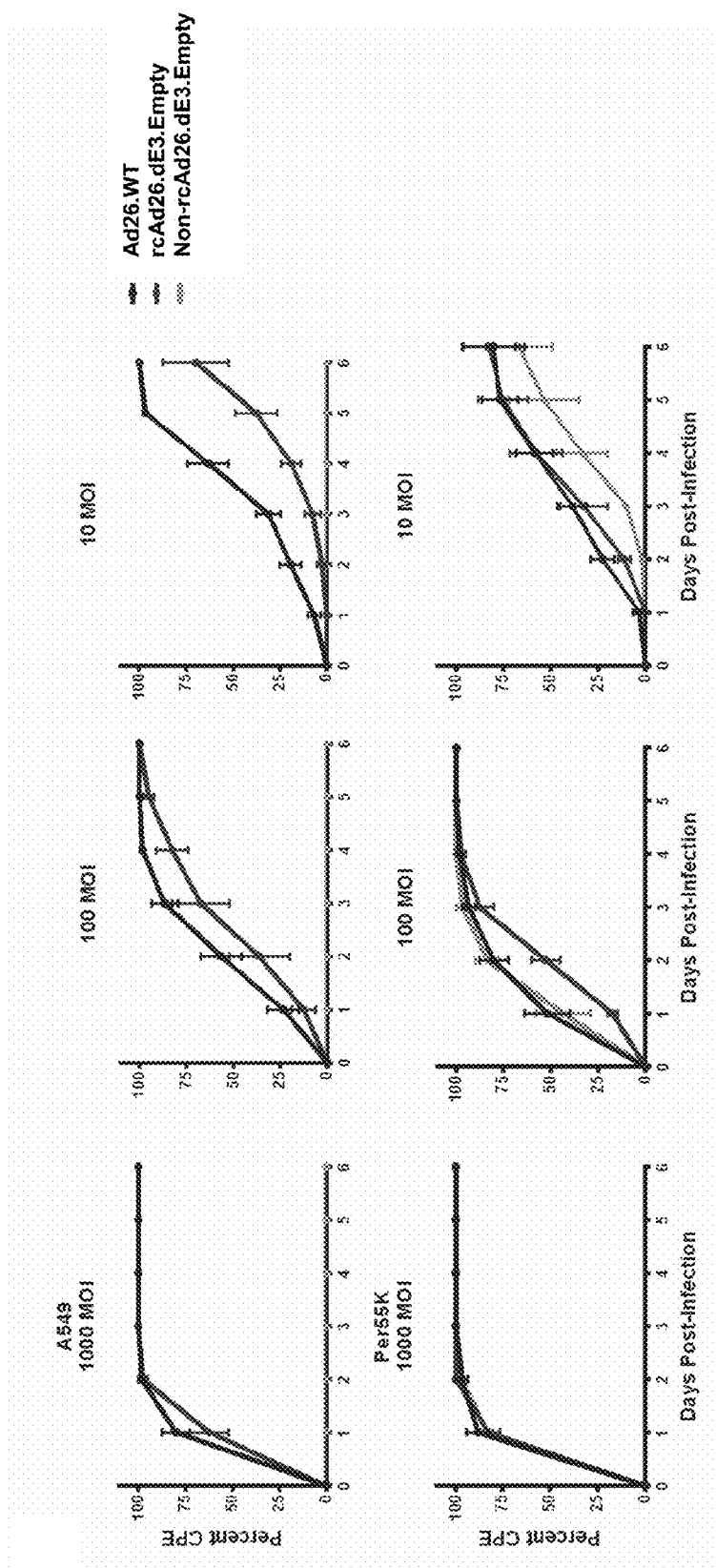
FIGS. 7A and 7B compare the in vitro replication and infectivity reported as percent cytopathic effect (CPE) of replicating recombinant Ad26 vectors according to embodiments of the invention in human cell lines and rhesus cell lines.
Figure 7B:
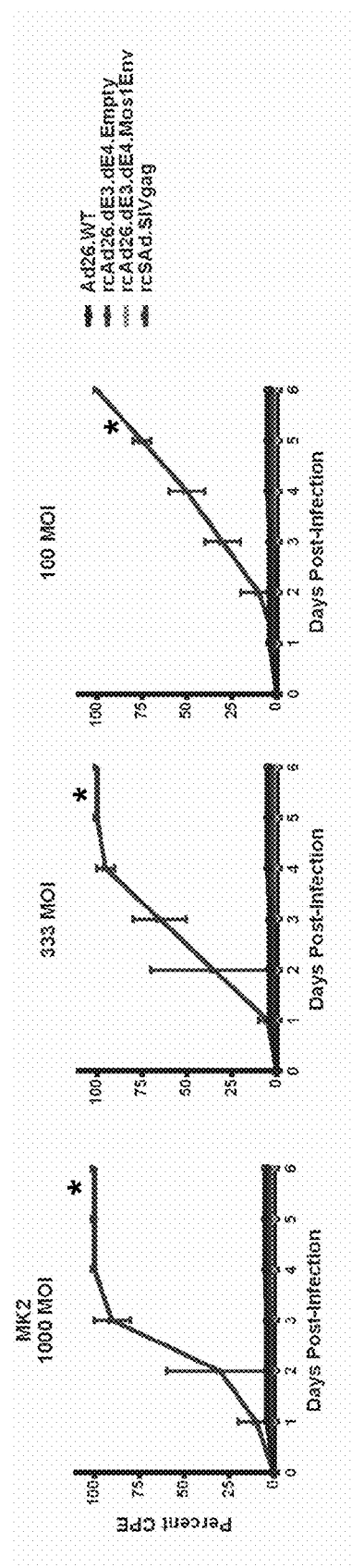

The results of the above experiments demonstrate that wild-type Ad26 and the replicating recombinant Ad26 vectors tested grew efficiently in A549 cells, whereas the replication-incompetent Ad26 vector did not, as expected (FIG. 7A). Moreover, all three vectors grew well in the adenovirus E1 protein complementing cell line, PER.55K cells, as expected. Additionally, the results confirm that replication of the replicating recombinant Ad26 vectors is species specific, as none of these vectors replicated in the rhesus monkey cell line MK2, whereas the replication competent simian Ad vector replicated well in MK-2 cells (FIG. 7B).

Example 8

In Vitro Infectivity and Growth of Replicating Recombinant rcAd26 Vectors after Multiple Cell Passages To verify that the CPE observed above in Examples 6 and 7 indicated that the recombinant Ad26 vectors were indeed replicating viruses, the replication kinetics of the replicating recombinant rcAd26 vectors rcAd26.dE3.Empty, rcAd26.dE3.dE4.Empty, rcAd26.dE3.Mos1Env, and rcAd26.dE3.dE4.Mos1Env (Table 1), were compared through two additional passages of the virus in either A549 or HuTu80 cell cultures.

Primary cell cultures were harvested at full CPE by harvesting both the cells and supernatant by pipetting and freezing at −20° C. Subsequent re-infections were performed by thawing, and then clarifying each lysate by centrifugation. To re-infect cells, 100 μL of each cell lysate was added to cells that had been seeded at $8.5 \times 10^5$ cell per well into a 6-well plate the day before. Cultures were then monitored and scored daily for percent CPE for 6 days post-infection, and infected cell lysates harvested the day of full CPE. PFU assays were performed by infecting either PER.55K cells or A549 cells that had been seeded into 6-well plates at a concentration of $8.5 \times 10^5$ cells per well the day before with serial dilutions of adenovirus. The next day, an agar overlay was added, and plaques were counted at day 7 and day 14 post infection. All serial dilutions were done in duplicate.

Figure 8A:
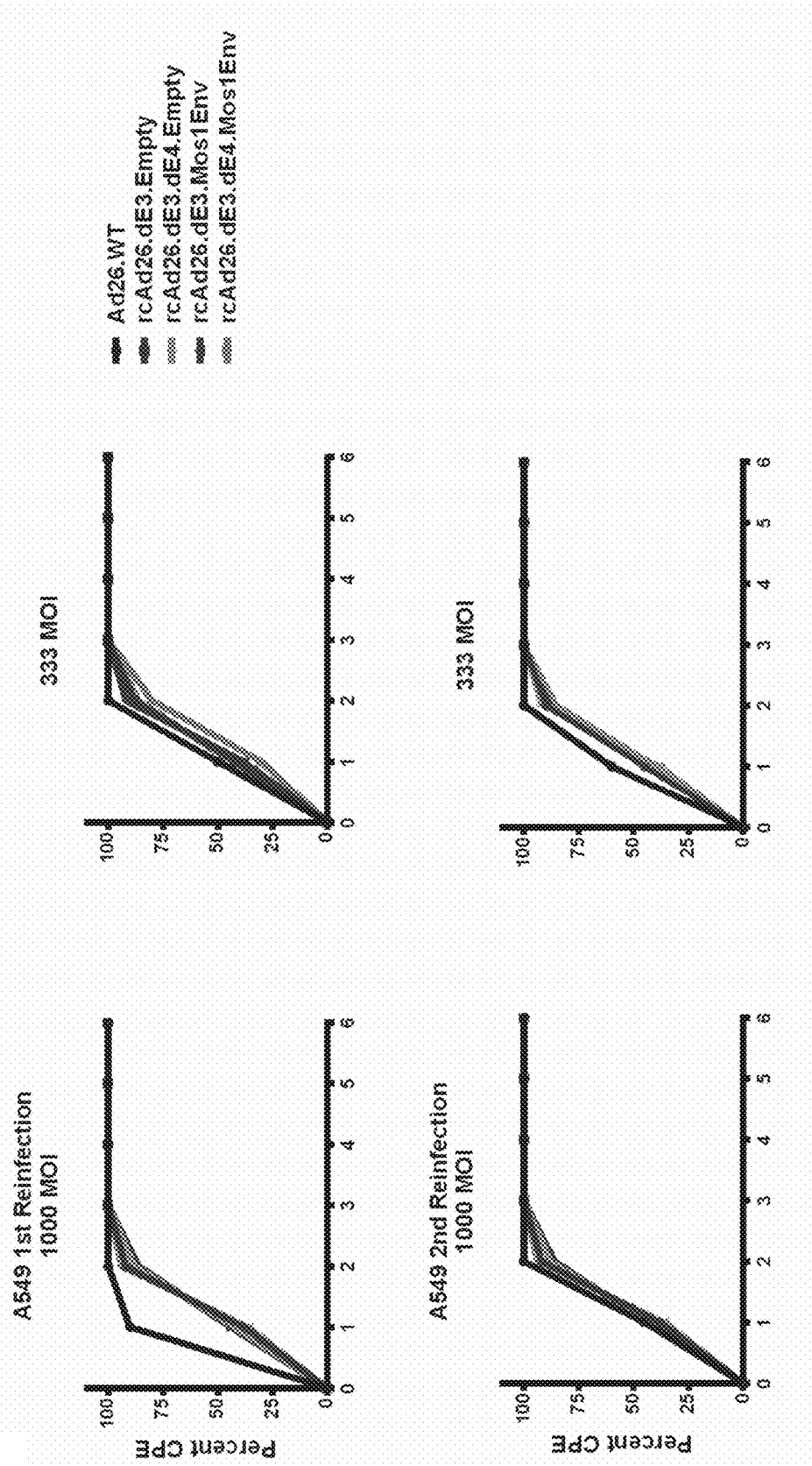
FIGS. 8A-8C show the in vitro replication and infectivity reported as percent cytopathic effect (CPE) of replicating recombinant adenovirus vectors according to embodiments of the invention in human cell lines after two passages in cell culture.
Figure 8B:
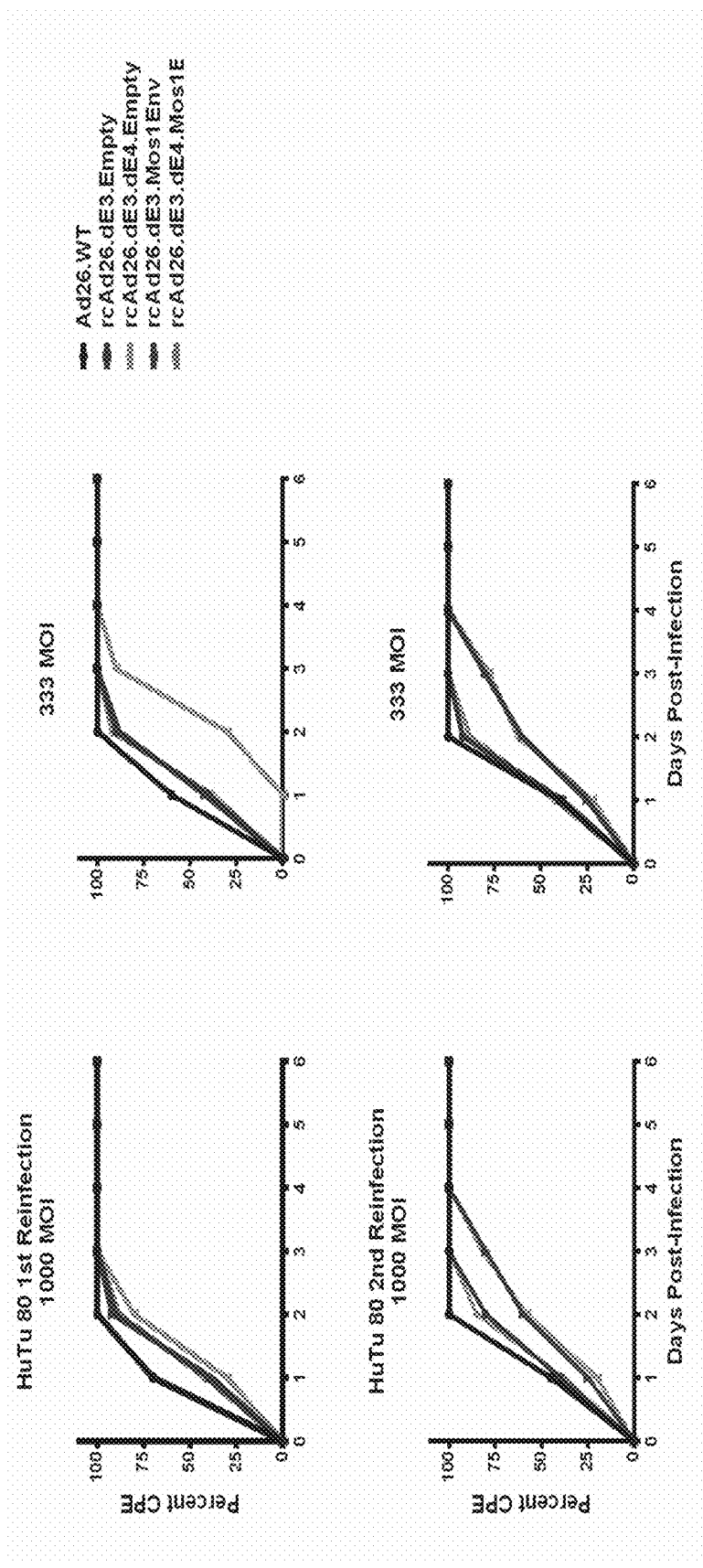

The results are shown in FIGS. 8A-8B, and demonstrate that all replication competent recombinant rcAd26 vectors tested replicated well through 2 passages in both A549 and HuTu80 cell lines, confirming that the CPE observed reflected vector replication, rather than some other effect, e.g., nonspecific cell lysis.

To determine the viral titer of the lysates harvested at full CPE in the in vitro infectivity assays, a plaque forming unit (PFU assay was performed using the same samples as above. Lysates were harvested at full CPE from A549 and HuTu80 cell cultures infected with 1000 MOI of each vector, and then assessed for viral titers using A549 cells (non-complementing E1 cells). Experiments with PER.55K cells (E1 complementing cells) were performed as a control.

Figure 8C:
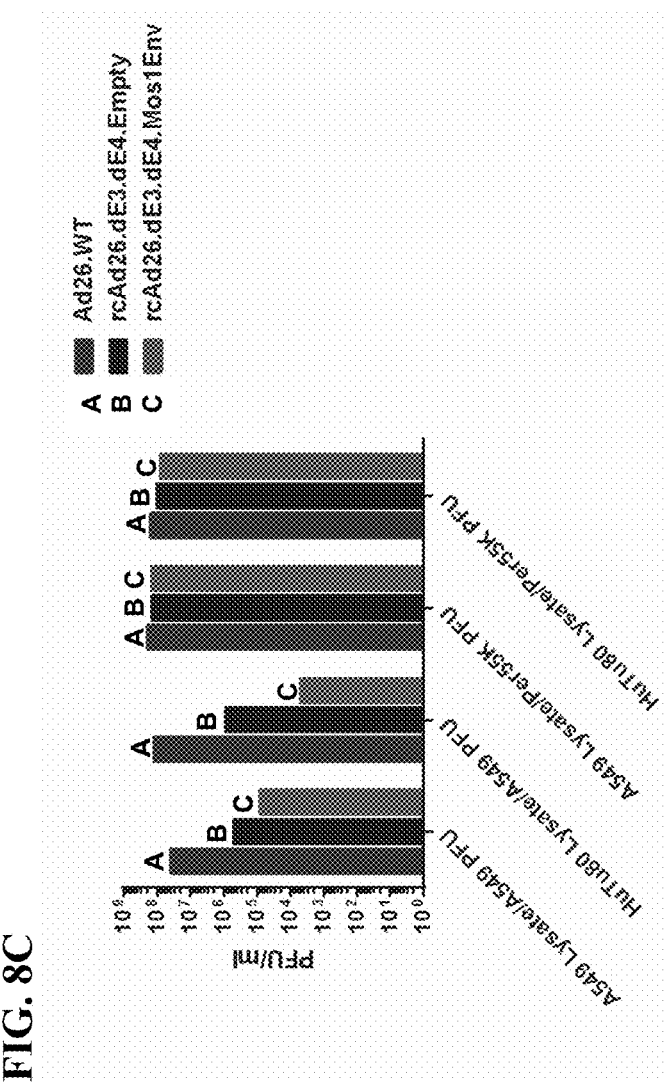

From the results of the PFU assays shown in FIG. 8C, it can be seen that titers closely mimicked the results obtained in the in vitro infectivity assays, with attenuation occurring in a step-wise fashion. More specifically, the rcAd26.dE3.dE4.Empty vector had a PFU titer 1.9 logs lower than wild-type Ad26, and with the addition of the Mos1Env transgene (rcAd26.dE3.dE4.Mos1Env), the titer decreased to 2.7 logs lower than the wild-type virus. This effect was even more pronounced with lysates from HuTu80 cells, in which the rcAd26.dE3.dE4.Empty vector had a titer 2.2 logs lower than wild-type Ad26, and with addition of the transgene, the titer dropped to 4.4 logs lower than the wild-type virus. In the control experiments with PER.55K cells, no significant differences were observed among the vectors tested, as expected.

Example 9

Comparison of In Vitro Infectivity of Replicating Recombinant Ad26 Vectors and Replicating Recombinant Ad4 Vector Experiments were performed using the in vitro infectivity assay to compare the infectivity of the rcAd26.dE3.dE4.Mos1Env vector to that of the replicating recombinant adenovirus 4 (Ad4)-based vector expressing influenza H5, which is the hemagglutinin protein from H1N1 (rcAd4.H5) in A549, HuTu80, and PER.55K cells. The rcAd4.H5 vector, developed by PaxVax, has previously proven safe and immunogenic in a Phase 1 clinical trial[1, 59]. The rcAd4.H5 and wild-type Ad4 (Ad4.WT) vectors were obtained from PaxVax (San Diego, Calif.). Wild-type Ad26 (Ad26.WT) was also tested as a control. The experiments were carried out as described above in more detail in Example 6 using varying MOIs (100–, 333, 100, 33, and 10).

Figure 9A:
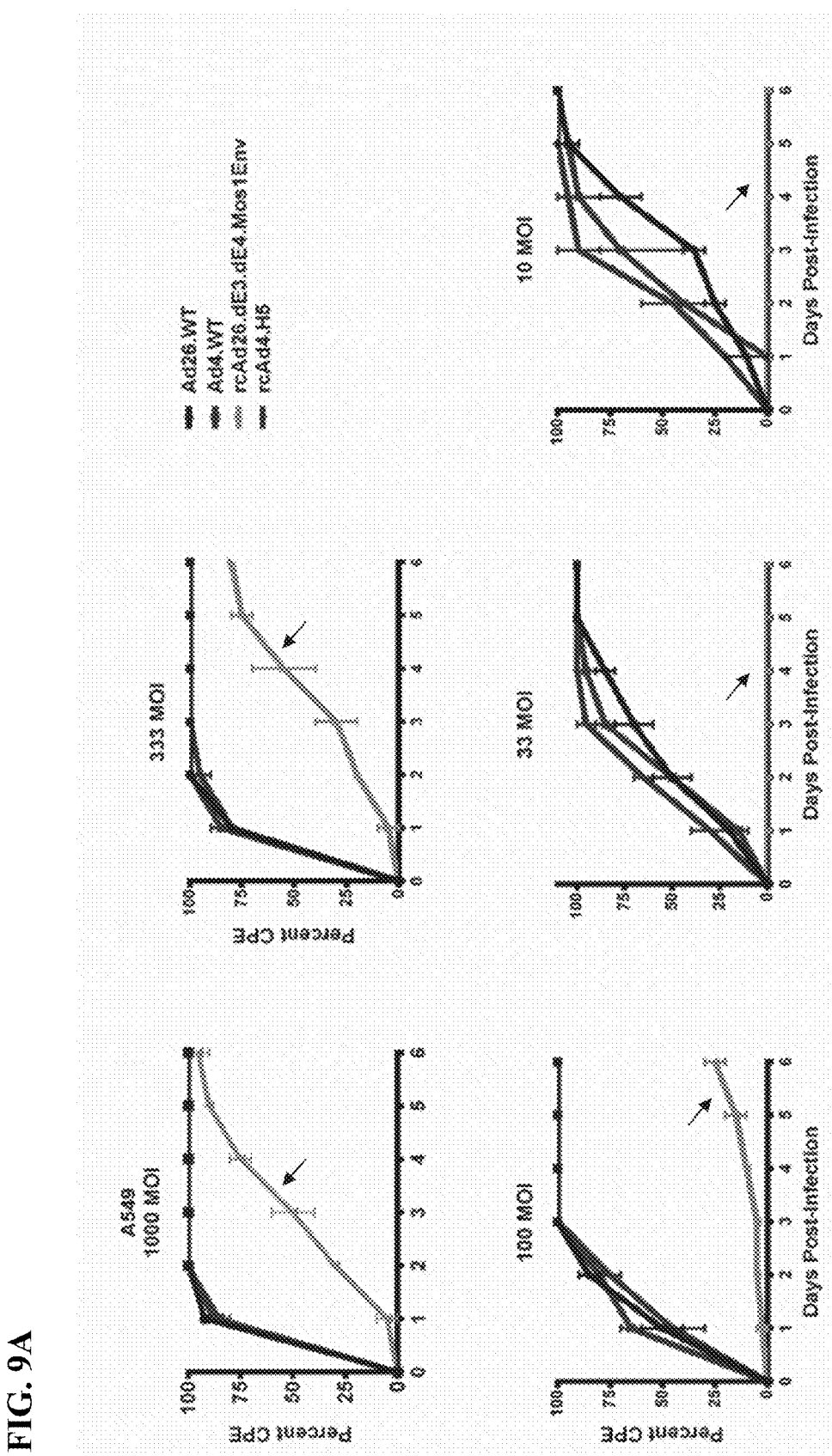
FIGS. 9A-9C compare in vitro replication and infectivity reported as percent cytopathic effect (CPE) of replicating recombinant Ad26 vector rcAd26.dE3.dE4.Mos1Env and an Ad4-based vector expressing influenza H5 (rcAd4.H5), which has previously proven safe and immunogenic in phase 1 clinical trials; replication and infectivity was also compared to wild-type Ad26 (Ad26.WT) and Ad4 (Ad4.WT) vectors; the replicating recombinant Ad26 vector rcAd26.dE3.dE4.Mos1Env is pointed to by an arrow.
Figure 9B:
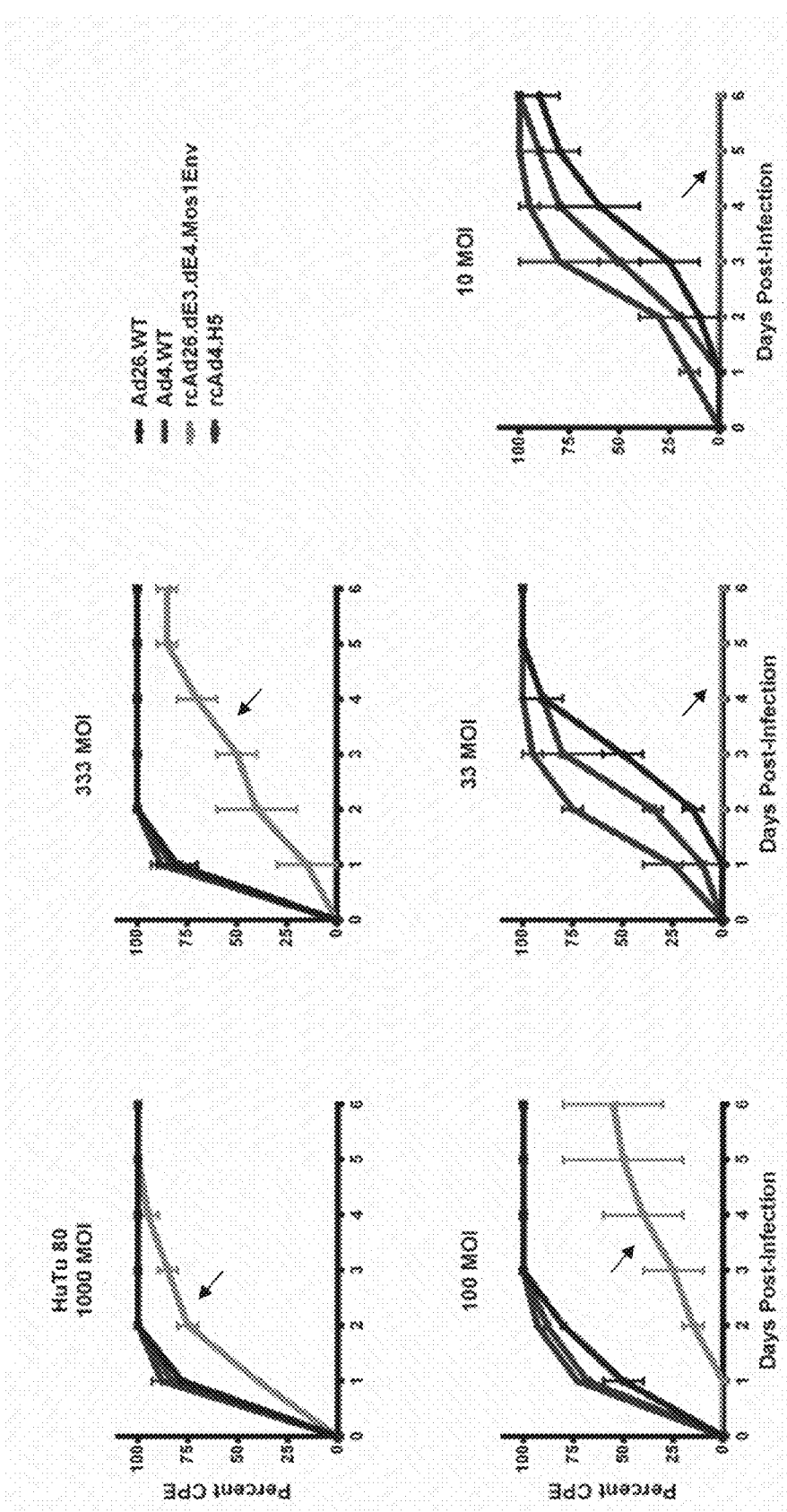
Figure 9C:
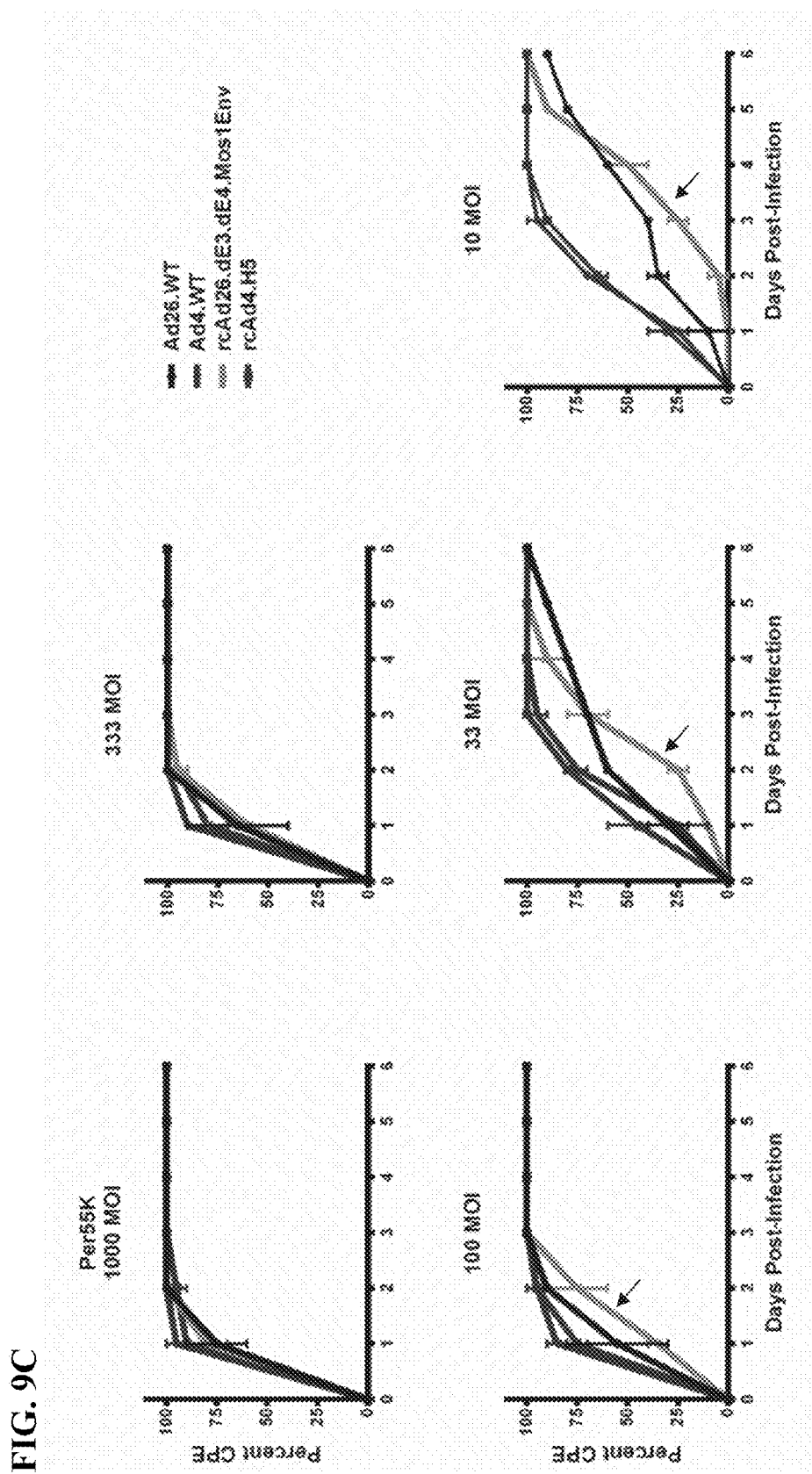

The results are shown in FIGS. 9A-9C for each cell line tested: A549 (FIG. 9A), HuTu 80 (FIG. 9B), and PER.55K (FIG. 9C). The results show that the rcAd26.Mos1Env vector exhibited a 91-fold reduced replicative capacity as compared to rcAd4.H5 on day 3 after infection of A549 cells (FIG. 9A; p<0.0001), and a 72.5-fold reduced replicative capacity than rcAd4.H5 on day 3 after infection of HuTu80 cells (FIG. 9B; p=0.009). As expected, all vectors tested grew well in PER.55K cells (FIG. 9C).

Example 10

Mouse Immunogenicity and Infectivity of Replicating Recombinant rcAd26 Vectors

The immunogenicity of the following replicating recombinant Ad26 vectors according to the invention expressing different mosaic HIV antigens in mice was assessed: rcAd26.Mos1Env; rcAd26.Mos2Env; rcAd26.Mos1GagPol; and rcAd26.Mos2GagPol.

Balb/c mice (n=4) were injected intramuscularly (IM) with $10^9$ viral particles (vp) of purified adenovirus rcAd26 vector in PBS (50 μL injection). Mice were sacrificed 28 days after immunization, and the spleen was harvested. Immunogenicity was determined by assessing the splenocytes by IFN-γ ELISPOT assay. The splenocytes were stimulated with overlapping peptide pools matching the mosaic HIV-1 Gag, Pol, or Env sequences in the rcAd26 vectors in a 96-well multiscreen plate. Each peptide pool consisted of peptides 15 amino acids in length that overlap by 11 amino acids covering the entire amino acid sequence of the corresponding mosaic antigen. After incubation the wells were washed, labeled and developed to visualize spot forming cells. Cells that responded to the mosaic protein expressed from the injected vector in vivo showed up as a spot in the well after in vitro stimulation by excreting IFN-γ, which is labeled and visualized using streptavidin-alkaline phosphatase and chromogen.

Figure 10:
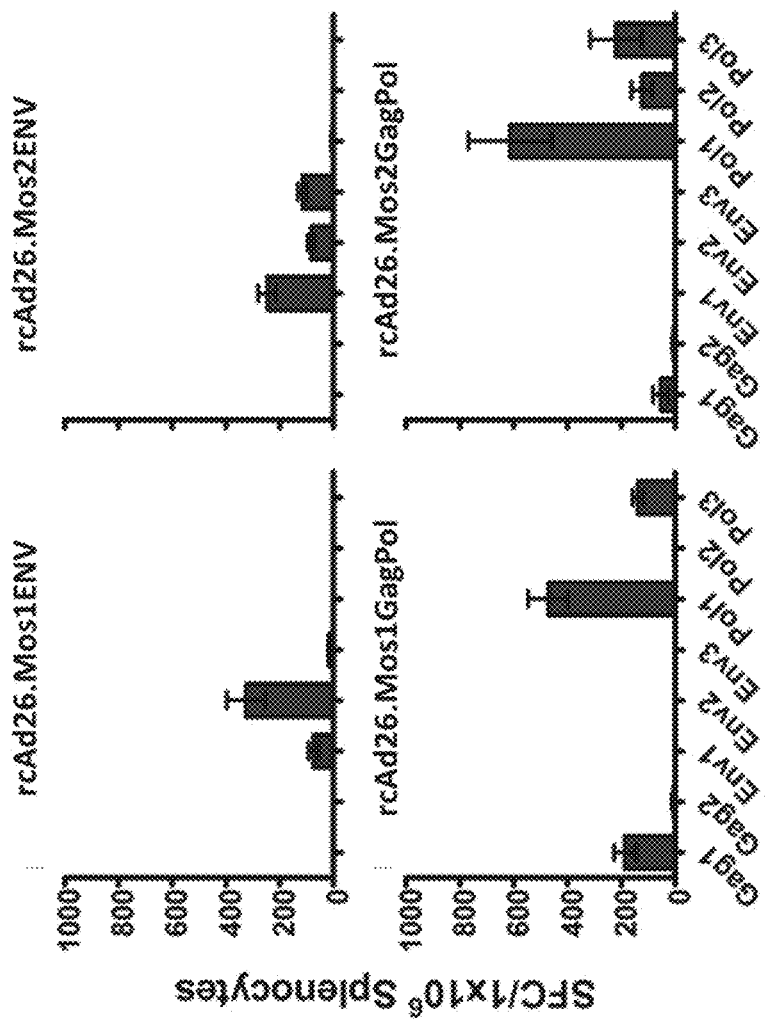
FIG. 10 shows the results of IFNγ-ELISPOT assay used to assess the immunogenicity of each of the replicating recombinant rcAd26 vectors according to embodiments of the invention (rcAd26.Mos1ENV; rcAd26.Mos2ENV.

The results are expressed as spot forming cells (SFC) per $10^6$ splenocytes, and the data is plotted in FIG. 10. The results demonstrated that all rcAd26 vectors tested produced immune responses in Balb/c mice to their respective peptide pools.

Example 11

Mouse Immunogenicity and Infectivity of Lyophilized rcAd26.Mos1Env

The effect of lyophilizing rcAd26.Mos1Env replicating recombinant adenovirus vector according to the invention on mouse immunogenicity and infectivity was tested. Two batches of rcAd26.Mos1Env were lyophilized using different buffers. A sample of each of the lyophilized batches, labeled Lyo#2 and Lyo#3, was reconstituted in phosphate buffered saline and filtered through a 0.22 um sterile filter. The virus particle concentration (vp) was determined by spectrophotometry and the vp/PFU results were calculated as shown below in Table 2.

TABLE 2

| vp/PFU Results for rcAd26.Mos1ENV vector | |
|---|---|
| Test Material | Vp/PFU |
| Non-lyophilized | 39 |
| Lyophilized powder - Lyo #2 | 39 |
| Lyophilized powder - Lyo #3 | 24 |

Balb/c mice (n=4) were immunized by IM injection with $10^8$ or $10^9$ vp of either reconstituted Lyo #2 or reconstituted Lyo #3 rcAd26.Mos1Env vector. As a control, a non-lyophilized batch of rcAd26.Mos1Env was tested. 28 days after immunization, the mice were sacrificed and the splenocytes were assessed by IFN-γ ELISPOT using overlapping HIV-1 envelope peptide pools matching the HIV-1 Env sequences in the rcAd26.Mos1Env construct, as well as other HIV-1 envelope peptide pools.

The mosaic peptide pool Mos1Env (split into two subpools: Mos1Env1 and Mos1 Env2) consisted of peptides 15 amino acids in length that overlap by 11 amino acids covering the entire amino acid sequence of the mosaic Env protein, Mos1ENV (SEQ ID NO: 48). The potential T-cell epitope (PTE) envelope peptide pools (HIV PTE Env, split into three subpools: HIV PTE Env1, HIV PTE Env2, HIV PTE Env3), obtained from the National Institutes of Health, consisted of peptides of 15 amino acids in length containing naturally occurring 9 amino acid sequences that are potential T cell determinants, captured in an unbiased manner. The PTE peptide panel is designed to permit expression of the most frequent potential T cell epitopes (PTE) embedded in the sequence of circulating HIV-1 strains of HIV-1 worldwide. The IFN-γ ELISPOT assays were performed in the same manner as described above in Example 7, and the results are shown in FIG. 11A. HIV-1 Clade C envelope and Mos1HIVEnv binding antibody ELISA's were performed prior to dosing and 28 days after immunization to determine induction of antibodies. The results are shown in FIG. 11B.

The results of the ELISPOT and ELISA assays indicate that lyophilized and reconstituted rcAd26.Mos1Env remains infectious. Accordingly, the ability of the rcAd26.Mos1Env vector to induce an immune response is not affected by lyophilization of the vector.

Example 12

Comparison of In Vivo Replication of Replication Incompetent Ad26 Adenovirus Vector to In Vivo Replication of Replication Competent rcAd26 Adenovirus Vector in Mice In vivo replication of replication-incompetent Ad26 recombinant adenovirus vector (Ad26.Mos1Env) was compared to that of replication-competent rcAd26 recombinant adenovirus vector (rcAd26.Mos1Env) in mice by immunizing Balb/c mice (n=4) with $10^{10}$ vp by intramuscular (IM) injection (50 μl/quadricep) or intra-nasally (IN) (25 μl/nostril). The replication incompetent Ad26.Mos1Env vectors contained an E1 deletion (see FIG. 1 for schematic diagram of replication incompetent recombinant Ad26 vector).

Serum, rectal and oral swabs were collected from the immunized mice at days (d) 0 (wk0), 7 (wk1), 14 (wk2), 21 (wk3) and 28 (wk4). RT-PCR was performed on the samples to determine viral shedding. Primers were directed to the hexon region of Ad26, in particular the hypervariable regions were targeted to prevent cross reactivity with other serotypes. Primers were used in combination with a Taqman probe. The primers used were Ad26.RT.fwd 5'-TGCT-TACTTTGACGTCCCTG-3' (SEQ ID NO: 86) and Ad26.RT.rev 5'-ACTGTTATCTGAAGTTCCTGGC-3' (SEQ ID NO: 87). The probe used was Ad26.RT probe 5'-TTGTATTCTTCCCCACTACCACCTGC-3' (SEQ ID NO: 88). The results of the RT-PCR are shown in FIG. 12, and are reported as copies/mL. Control samples were spiked with $5.04 \times 10^6$ copies/ml plasmid DNA. The sensitivity of the assay is 1000 copies/mL. The results indicate that there was no evidence of viral shedding.

ELISAs were also performed on the collected serum samples at all time points (days 0, 7, 14, 21, and 28) to determine HIV Clade C Envelope (FIG. 13A) and Mosaic Env (FIG. 13B) binding antibody titers. The results indicate that both replication-incompetent Ad26.Mos1Env and replication-competent rcAd26.Mos1Env induced HIV-1 Clade C envelope and Mosaic envelope binding antibody titers.

At day 28, the splenocytes were harvested and IFNγELISPOT was performed to determine immunogenicity in the same manner as described in Examples 6 and 10 (FIG. 14). The peptide pools tested for each regimen (i.e., vector and administration route) were Mos1 Env, Mos2 Env, PTE Env 1, PTE Env 2, and PTE Env 3. Results are reported as spot forming cells (SFC) per $10^6$ splenocytes.

Although no safety data was collected, it was noted that all of the mice in all groups appeared healthy and well over the course of the study. No adverse effects in mood or physical appearance were observed.

The results of the ELISA and ELISPOT experiments show that both replication-competent rcAd26.Mos1Env and replication-incompetent Ad26.Mos1Env recombinant adenovirus vectors were immunogenic in mice. The HIV specific antibody responses were similar for the replicating and non-replicating vectors given either by IM or IN administration (FIGS. 13A and 13B). The T-cell responses were much greater when the vectors were given by IM administration (FIG. 14). RT-PCR results indicated that there was no evidence of replication of vectors in mice, as expected because there is a species barrier for adenoviruses.

Example 13 rcAd26.SIVgag Immunogenicity and Replication in Non-Human Primates

Non-human primates Indian-origin rhesus monkeys (*Macaca* Mulatta) (N=3/group) were immunized by intramuscular (IM) injection with $10^{11}$ vp with replication-competent Ad26-SIVGag vector (containing the E1 coding region) and replication-incompetent Ad26-SIVGag vector (lacking the E1 coding region) at weeks 0 and 24. IFNγ-ELISPOT was performed at weeks 0, 2, 24, 26, and 32 to determine immune response using a Gag peptide pool (obtained from the National Institutes of Health) consisting of 15 amino acid peptides overlapping by 11 amino acids, covering the entire Gag sequence. RT-PCR on serum was done at weeks −1, 1, 4, 6, 8, 10, 12 and 16 to look at virus replication as described above in Example 12. The RT-PCR and IFNγ-ELISPOT assays were performed as described above in Examples 6 and 10-11, and the results are shown in FIGS. 15A and 15B.

The results demonstrate that both replication-competent and replication-incompetent Ad26.SIVGag vectors are immunogenic in non-human primates. There was no evidence by RT-PCR that the replication-competent vector replicates in non-human primates. As with the experiments described in Example 12 above in mice, and demonstrated by Example 7 (FIG. 7B), it was expected that the adenovirus vectors would not replicate in non-human primates due to a species barrier.

Example 14

Cloning of Ad35 Adaptor Plasmid Lacking a Transgene (pAdApt35BSU.E1atg.Empty) with E1 Coding Region after Transgene Cassette The empty Ad35 recombinant vector, pAdApt35BSU.E1atg.Empty was constructed as shown in FIG. 16A. The pAdApt35BSU.E1atg.Empty vector contains the E1 coding region after the transgene cassette. "Empty" denotes that the vector does not contain a heterologous nucleic acid sequence or transgene, however any heterologous nucleic acid sequence of interest can be inserted into the multiple cloning site of the transgene cassette of the pAdApt35BSU.E1atg.Empty vector under control of the CMV promoter and upstream of the E1 coding region. For example, a nucleic acid sequence encoding the mosaic antigen Mos1-HIVEnv can be cloned into the multiple cloning site of the transgene cassette of pAdApt35BSU.E1atg.Empty to obtain the Ad35 recombinant vector pAdApt35BSU.E1atg. Mos1-HIVEnv (SEQ ID NO: 84), with the Mos1-HIVEnv gene located before the E1 coding region.

Production of "PCR Fragment A" and "PCR Fragment B"

Two PCRs were performed to clone the E1 region after the transgene cassette. The first PCR was to amplify the transgene cassette from the pAdApt35BSU, and was performed using a forward primer that overlaps with the existing NdeI site in the CMV promoter and a reverse primer designed to contain a MluI site that overlaps with the polyA region. The forward primer used was AdApt35BSU.NdeI.fwd having the sequence 5'-GTGTAT-CATATGCCAAGTACGCCC-3' (SEQ ID NO: 89), and the reverse primer used was AdApt35BSU.MluI.rev having the sequence 5-CGATCACGCGTATCTAGACATGATAAGA-TACATTGATG-3' (SEQ ID NO: 90). PCR fragment A was obtained from this reaction. See the schematic labeled "pAdApt35BSU PCR Fragment A" of FIG. 16A.

The second PCR was to amplify the E1 coding region from the wild-type adenovirus vector genome ("Ad35 WT"), and was performed using a forward primer designed to contain a MluI site that starts at nucleotide 464 of the Ad35 WT sequence. The reverse primer was designed to overlap with the existing AleI site in pIX region. The forward primer used was Ad35WT.464.MluI.fwd having the sequence 5'-CACAGACGCGTCTGATCGCTAGGGTATT-TATACCTC-3' (SEQ ID NO: 91), and the reverse primer used was Ad35WT.AleI.rev having the sequence 5'-GGAG-GACACAAGGGTGTCTCCAAA-3' (SEQ ID NO: 92). PCR fragment B was obtained from this reaction. See the schematic labeled "Ad35 WT PCR Fragment B" of FIG. 16A.

Cloning of pAdapt35BSU.E1atg.Empty (E1 Region after Transgene Cassette)

PCR fragment A was digested with NdeI and MluI. PCR fragment B was digested with MluI and AleI. pAdApt35BSU.Empty was digested with NdeI and AleI. Digestions were gel purified and ligated together in a triple ligation resulting in pAdApt35BSU.E1atg.Empty.

Example 15

Cloning of Ad35 Adaptor Plasmid Lacking a Transgene (pAdApt35BSU.Empty) with E1 Coding Region Before Transgene Cassette The empty Ad35 recombinant vector, pAdApt35BSU.E1btg.Empty (SEQ ID NO: 26) was constructed as shown in FIG. 16B. The pAdApt35BSU.E1btg.Empty vector contains the E1 coding region before the transgene cassette. "Empty" denotes that the vector does not contain a heterologous nucleic acid sequence or transgene, however any heterologous nucleic acid sequence of interest can be inserted into the multiple cloning site of the transgene cassette of the pAdApt35BSU.E1btg.Empty vector under control of the CMV promoter and downstream of the E1 coding region. For example, a nucleic acid sequence encoding the mosaic antigen Mos1-HIVEnv can be cloned into the multiple cloning site of the transgene cassette of pAdApt35BSU.E1btg.Empty to obtain the Ad35 recombinant vector pAdApt35BSU.E1btg. Mos1-HIVEnv (SEQ ID NO: 85), with the Mos1-HIVEnv gene located after the E1 coding region.

Mutation of PacI Site in E1 Gene

The Ad35 Wild Type E1 coding region contains a PacI restriction enzyme site. To inactivate the PacI site, site-directed mutagenesis was performed. The PacI site was inactivated by changing one base pair from a T to a C using rcAd35.Elmut.fwd 5'-GTTTTATTTTAATCAAGGGAAAT-GCCA-3' (SEQ ID NO: 64) as forward primer, rcAd35.Elmut.rev 5'-TGGCATTTCCCTTGAT-TAAAATAAAAC-3' (SEQ ID NO: 65) was used as reverse primer, and pAdApt35BSU.E1.atg.Empty as template (obtained from Example 14) in a PCR covering the entire plasmid. After completion of the PCR, the PCR mix was digested with DpnI enzyme to remove the pAdApt35BSU.E1.atg.Empty template DNA. A small aliquot of the digested PCR mix was transformed into E. coli and clones containing the mutated PacI site were screened by restriction enzyme analysis and sequencing.

Cloning of pAdApt35BSU.E1btg.Empty (E1 Region Before Transgene Cassette)

To clone the E1 region before the transgene cassette, a PCR was performed using pAdApt35BSU.E1atg.Empty as template. The forward primer used was located at the start of the E1 region right after the polyA sequence (nt464 in Ad35 WT), and the reverse primer is located at the end of the E1 region before the pIX (nt3483 in Ad35 WT). Both forward and reverse primer had AvrII sites designed in them. The sequences of the primers were as follows: 35BSU.E1btg.AvrII.fwd 5'-ATAACACCTAGGCT-CATCGCTAGGGTATTTATACCTC-3' (SEQ ID NO: 82) and 35BSU.E1btg.AvrII.rev 5'-ATAACACCTAGGT-TAGTCAGTTTCTTCTCCACTGGAT-3' (SEQ ID NO: 83).

After digesting both the PCR product as well as pAdApt35BSU with AvrII, the PCR product and pAdApt35BSU were ligated together resulting in pAdAPt35BSU.E1btg.Empty that also contained the mutated PacI site in the E1 coding region. Screening of the clones was done by restriction enzyme analysis and sequencing.

Example 16

Cloning of Ad35 Cosmid Vector (pWe/Ad35.pIX-rITR.dE3.dE3.35orf6)

Cloning of Full Cosmid pWe/Ad35.pIX-rITR.dE3.dE3.35orf6 Vector (SEQ ID NO: 25).

A PCR was done to obtain the pWe cosmid backbone with a NotI site on each end using the following primer pair: forward primer, pWe.Nottfwd 5'-AATTTAGCGGCCG-CATCGTCCATTCCGACAGCATCGC-3' (SEQ ID NO: 66); and reverse primer, pWe.NotI.rev 5'-GAAGCATTTC-CACTCATGTCG (SEQ ID NO: 67). The 5' NotI site was designed in the primer. Both the pWe/Ad35.pIX-EcoRV and pBr/Ad35.dE3.dE4.35orf6 plasmids were digested with NotI and RsrII and gel purified (see Vogels et al., Replication-deficient human adenovirus type 35 vectors for gene transfer and vaccination: efficient human cell infection and bypass of preexisting adenovirus immunity J. Virology (2003) 77(15) 8263-71 for a description of both plasmids).

A three point ligation was done to obtain the full length pWe/Ad35.pIX-rITR.dE3.dE4.35orf6 cosmid vector (SEQ ID NO: 25), which was screened by digestions and sequencing.

In this Example, E1 was cloned both before and after the transgene cassette. It was observed that for the rcAd35 vectors, when E1 is placed downstream of the transgene cassette, there was some instability of the rcAd35 vector, while when E1 is placed upstream of the transgene cassette, this instability was not seen.

Accordingly, in a preferred embodiment of the invention, the heterologous nucleic acid sequence is located between the left ITR and the 5'-end of the functional E1 coding region, i.e., the functional E1 coding region is placed upstream of the heterologous nucleic acid sequence.

Example 17

Clinical Study of the Safety and Immunogenicity of Oral Replicating Recombinant Ad26 Vector Vaccine for HIV-1 in Uninfected Human Adults Replicating recombinant rcAd26.MOS1.HIVEnv vaccine vector is tested for safety and immunogenicity against HIV-1 in adult humans uninfected with HIV-1 when administered as a single oral dose in a randomized, controlled, double-blind phase 1 clinical trial. Objectives of the study include evaluating the safety and tolerability of the vaccine, determining viral shedding in rectal and oropharyngeal secretions, and evaluating humoral and cellular immune responses elicited by four increasing dosages of the vaccine vector.

The study population includes healthy men and women aged 18-40 years old. The vaccine is formulated as an enteric-coated capsule for oral administration. Study participants are divided into four groups, with each receiving a different dosage of the rcAd26.MOS1.HIVEnv vaccine: $10^8$ viral particles ("vp")/placebo capsule, $10^9$ vp/placebo capsule, $10^{10}$ vp/placebo capsule, or $10^{11}$ vp/placebo capsule. Study participants receiving placebo are administered a sucrose-containing capsule. Since the vaccine is replication competent, study participants are housed in an isolation unit beginning two days prior to administration of the vaccine, and continuing until at least nine days post-vaccination. The study lasts for approximately twelve months.

Rectal and throat swabs are obtained from the study participants to evaluate viral shedding. In particular, the rectal and throat swabs are analyzed for the presence of rcAd26.MOS1.HIVEnv by PCR and adenovirus culture. Real-time (rt)-PCR is performed for both the Ad26 vector and Env insert to allow for quantification of vector and insert, and to evaluate the stability of the vaccine. Adenovirus culture is performed to assess the presence of infectious virus. Serotyping is further be performed on positive cultures to confirm that the virus is rcAd26.MOS1.HIVEnv.

Blood samples are obtained from each of the study participants at various time points after immunization to assess HIV-associated immunogenicity, including assessment of cellular immune and humoral immune response. Blood samples are assayed for the magnitude of antibody binding to HIV-1 Env as quantified by enzyme-linked immunosorbent assay (ELISA), the magnitude of neutralizing antibodies against HIV-1 as quantified by virus neutralization assay, and the magnitude of HIV-1 specific T-lymphocyte responses as quantified by IFN-γ ELISPOT. Blood samples can also be used for exploratory DNA and RNA micro-array and deep-sequencing assays.

Additional immunogenicity assessments of systemic and mucosal responses can include HIV-1 specific antibody-dependent cell-mediated cytotoxicity (ADCC) and cell-mediated viral inhibition (ADCVI) assays, measurement of Ad26-specific antibodies (e.g., ADCC, ADCVI, etc.), intracellular cytokine staining (ICS) assays, flow cytometry of CD4+ and CD8+ T cell-mediated inhibition of HIV-1, proliferative capacity of T lymphocytes, B cell repertoire analysis, gene expression profiling, and eptitope mapping.

Additionally, rectal mucosal secretions are collected from the study participants with rectal wicks for evaluation of potential mucosal immunity to HIV-1 Env and Ad26. Such studies can include measurement of Ad26 and HIV-1 specific antibodies by ELISA, and antibody epitope mapping to Env peptides by linear peptide microarray.

The possibility of transmission of the rcAd26.MOS1.HIVEnv to volunteers' household contacts, i.e., an individual who shares the same residence as the study participant, is evaluated. Household contacts of the study participants are contacted on a weekly basis to assess for the presence of illness that may be related to transmission of the vaccine vector.

Throughout the course of the study, participants are also monitored for the occurrence of any adverse events.

REFERENCES

1. Gurwith, M., et al., Safety and immunogenicity of an oral, replicating adenovirus serotype 4 vector vaccine for H5N1 influenza: a randomised, double-blind, placebo-controlled, phase 1 study. *Lancet Infect Dis*, 2013. 13(3): p. 238-50.
2. Centers for Disease, Control, and Prevention, Vital signs: HIV prevention through care and treatment—United States. *MMWR Morb Mortal Wkly Rep*, 2011. 60(47): p. 1618-23.
3. Centlivre, M., et al., In HIV-1 pathogenesis the die is cast during primary infection. *AIDS*, 2007. 21(1): p. 1-11.
4. Wawer, M. J., et al., Rates of HIV-1 transmission per coital act, by stage of HIV-1 infection, in Rakai, Uganda. *J Infect Dis*, 2005. 191(9): p. 1403-9.
5. Flynn, N. M., et al., Placebo-controlled phase 3 trial of a recombinant glycoprotein 120 vaccine to prevent HIV-1 infection. *J Infect Dis*, 2005. 191(5): p. 654-65.
6. Pitisuttithum, P., et al., Randomized, double-blind, placebo-controlled efficacy trial of a bivalent recombinant glycoprotein 120 HIV-1 vaccine among injection drug users in Bangkok, Thailand. *J Infect Dis*, 2006. 194(12): p. 1661-71.
7. Gray, G. E., et al., Safety and efficacy of the HVTN 503/Phambili study of a Glade-B-based HIV-1 vaccine in South Africa: a double-blind, randomised, placebo-controlled test-of-concept phase 2b study. *Lancet Infect Dis*, 2011. 11(7): p. 507-15.
8. Buchbinder, S. P., et al., Efficacy assessment of a cell-mediated immunity HIV-1 vaccine (the Step Study): a double-blind, randomised, placebo-controlled, test-of-concept trial. *Lancet*, 2008. 372(9653): p. 1881-93.
9. Rerks-Ngarm, S., et al., Vaccination with ALVAC and AIDSVAX to prevent HIV-1 infection in Thailand. *N Engl J Med*, 2009. 361(23): p. 2209-20.
10. McElrath, M. J., et al., HIV-1 vaccine-induced immunity in the test-of-concept Step Study: a case-cohort analysis. *Lancet*, 2008. 372(9653): p. 1894-905.

11. Abbink, P., et al., Comparative seroprevalence and immunogenicity of six rare serotype recombinant adenovirus vaccine vectors from subgroups B and D. *J Virol,* 2007. 81(9): p. 4654-63.
12. Vogels, R., et al., Replication-deficient human adenovirus type 35 vectors for gene transfer and vaccination: efficient human cell infection and bypass of preexisting adenovirus immunity. *J Virol,* 2003. 77(15): p. 8263-71.
13. Farina, S. F., et al., Replication-defective vector based on a chimpanzee adenovirus. *J Virol,* 2001. 75(23): p. 11603-13.
14. Barouch, D. H., et al., International seroepidemiology of adenovirus serotypes 5, 26, 35, and 48 in pediatric and adult populations. *Vaccine,* 2011. 29: p. 5203-5209.
15. Mast, T. C., et al., International epidemiology of human pre-existing adenovirus (Ad) type-5, type-6, type-26 and type-36 neutralizing antibodies: correlates of high Ad5 titers and implications for potential HIV vaccine trials. *Vaccine,* 2010. 28(4): p. 950-7.
16. Chen, H., et al., Adenovirus-based vaccines: comparison of vectors from three species of adenoviridae. *J Virol,* 2010. 84(20): p. 10522-32.
17. Thorner, A. R., et al., Age dependence of adenovirus-specific neutralizing antibody titers in individuals from sub-Saharan Africa. *J Clin Microbiol,* 2006. 44(10): p. 3781-3.
18. Sprangers, M. C., et al., Quantifying adenovirus-neutralizing antibodies by luciferase transgene detection: addressing preexisting immunity to vaccine and gene therapy vectors. *J Clin Microbiol,* 2003. 41(11): p. 5046-52.
19. Waddington, S. N., et al., Adenovirus serotype 5 hexon mediates liver gene transfer. *Cell,* 2008. 132(3): p. 397-409.
20. Liu, J., et al., Magnitude and phenotype of cellular immune responses elicited by recombinant adenovirus vectors and heterologous prime-boost regimens in rhesus monkeys. *J Virol,* 2008. 82(10): p. 4844-52.
21. Liu, J., et al., Immune control of an SIV challenge by a T-cell-based vaccine in rhesus monkeys. *Nature,* 2009. 457(7225): p. 87-91.
22. Lore, K., et al., Myeloid and plasmacytoid dendritic cells are susceptible to recombinant adenovirus vectors and stimulate polyfunctional memory T cell responses. *J Immunol,* 2007. 179(3): p. 1721-9.
23. unpublished, Barouch. et al.
24. Barouch et al., in *AIDS Vaccine.* 2009. Paris, France.
25. Kuschner, R. A., et al., A phase 3, randomized, double-blind, placebo-controlled study of the safety and efficacy of the live, oral adenovirus type 4 and type 7 vaccine, in U.S. military recruits. *Vaccine,* 2013. 31(28): p. 2963-71.
26. Masopust, D. and L. J. Picker, Hidden memories: frontline memory T cells and early pathogen interception. *J Immunol,* 2012. 188(12): p. 5811-7.
27. Bell, J. A., et al., Illness and microbial experiences of nursery children at junior village. *American Journal of Hygiene,* 1961. 74: p. 267-292.
28. Rhee, E. G. and D. H. Barouch, Adenoviruses, in *Principles and Practice of Infectious Diseases,* G. L. Mandell, J. E. Bennett, and R. Dolin, Editors. 2010, Elsevier: Philadelphia, Pa.
29. Brandt, C. D., et al., Infections in 18,000 infants and children in a controlled study of respiratory tract disease. I. Adenovirus pathogenicity in relation to serologic type and illness syndrome. *Am J Epidemiol,* 1969. 90(6): p. 484-500.
30. Fox, J. P., et al., The virus watch program: a continuing surveillance of viral infections in metropolitan New York families. VI. Observations of adenovirus infections: virus excretion patterns, antibody response, efficiency of surveillance, patterns of infections, and relation to illness. *Am J Epidemiol,* 1969. 89(1): p. 25-50.
31. Fox, J. P., C. E. Hall, and M. K. Cooney, The Seattle Virus Watch. VII. Observations of adenovirus infections. *Am J Epidemiol,* 1977. 105(4): p. 362-86.
32. Noel, J., et al., Identification of adenoviruses in faeces from patients with diarrhoea at the Hospitals for Sick Children, London, 1989-1992. *J Med Virol,* 1994. 43(1): p. 84-90.
33. Faden, H., et al., Pediatric adenovirus infection: relationship of clinical spectrum, seasonal distribution, and serotype. Clin Pediatr (Phila), 2011. 50(6): p. 483-7.
34. Abbas, K. Z., et al., Temporal changes in respiratory adenovirus serotypes circulating in the greater Toronto area, Ontario, during December 2008 to April 2010. *Virol J,* 2013. 10: p. 15.
35. Diarrhea: Why children are still dying and what can be done, 2009, The United Nations Chidlren's Fund (UNICEF)/World Health Organization (WHO): New York, N.Y.
36. Ramani, S. and G. Kang, Viruses causing childhood diarrhoea in the developing world. *Curr Opin Infect Dis,* 2009. 22(5): p. 477-82.
37. Kotloff, K. L., et al., Burden and aetiology of diarrhoeal disease in infants and young children in developing countries (the Global Enteric Multicenter Study, GEMS): a prospective, case-control study. *Lancet,* 2013. 382 (9888): p. 209-22.
38. Magwalivha, M., et al., High prevalence of species D human adenoviruses in fecal specimens from Urban Kenyan children with diarrhea. *J Med Virol,* 2010. 82(1): p. 77-84.
39. Liu, L. Y., et al., [Investigation of adenovirus infection in hospitalized children with diarrhea during 2010 in Beijing, China]. Zhonghua Er Ke Za Zhi, 2012. 50(6): p. 450-4.
40. Ouyang, Y., et al., Etiology and epidemiology of viral diarrhea in children under the age of five hospitalized in Tianjin, China. *Arch Virol,* 2012. 157(5): p. 881-7.
41. Lee, J. I., et al., Detection and molecular characterization of adenoviruses in Korean children hospitalized with acute gastroenteritis. *Microbiol Immunol,* 2012. 56(8): p. 523-8.
42. Espinola, E. E., et al., Genetic diversity of human adenovirus in hospitalized children with severe acute lower respiratory infections in Paraguay. *J Clin Virol,* 2012. 53(4): p. 367-9.
43. Mast, T. C., et al., International epidemiology of human pre-existing adenovirus (Ad) type-5, type-6, type-26 and type-36 neutralizing antibodies: correlates of high Ad5 titers and implications for potential HIV vaccine trials. *Vaccine,* 2010. 28: p. 950-957.
44. Kasel, J. A., et al., Conjunctivitis and enteric infection with adenovirus types 26 and 27: responses to primary, secondary and reciprocal cross-challenges. *Am J Hyg,* 1963. 77: p. 265-82.45. Hierholzer, J. C., et al., Adenoviruses from patients with AIDS: a plethora of serotypes and a description of five new serotypes of subgenus D (types 43-47). *J Infect Dis,* 1988. 158(4): p. 804-13.
46. Khoo, S. H., et al., Adenovirus infections in human immunodeficiency virus-positive patients: clinical features and molecular epidemiology. *J Infect Dis,* 1995. 172(3): p. 629-37.

47. Curlin, M. E., et al., Frequent detection of human adenovirus from the lower gastrointestinal tract in men who have sex with men. *PLoS One*, 2010. 5(6): p. e11321.
48. Dubberke, E. R., et al., Acute meningoencephalitis caused by adenovirus serotype 26. *J Neurovirol*, 2006. 12(3): p. 235-40.
49. Koneru, B., et al., Adenoviral infections in pediatric liver transplant recipients. *JAMA*, 1987. 258(4): p. 489-92.
50. Venard, V., et al., Genotyping of adenoviruses isolated in an outbreak in a bone marrow transplant unit shows that diverse strains are involved. *J Hosp Infect*, 2000. 44(1): p. 71-4.
51. Al Qurashi, Y. M., M. Guiver, and R. J. Cooper, Sequence typing of adenovirus from samples from hematological stem cell transplant recipients. *J Med Virol*, 2011. 83(11): p. 1951-8.
52. Janes, H., et al., MRKAd5 HIV-1 Gag/Pol/Nef vaccine-induced T-cell responses inadequately predict distance of breakthrough HIV-1 sequences to the vaccine or viral load. *PLoS One*, 2012. 7(8): p. e43396.
53. Fischer, W., et al., Polyvalent vaccines for optimal coverage of potential T-cell epitopes in global HIV-1 variants. *Nat Med*, 2007. 13(1): p. 100-6.
54. Barouch, D. H., et al., Mosaic HIV-1 vaccines expand the breadth and depth of cellular immune responses in rhesus monkeys. *Nat Med*, 2010. 16(3): p. 319-23.
55. Santra, S., et al., Mosaic vaccines elicit CD8+ T lymphocyte responses that confer enhanced immune coverage of diverse HIV strains in monkeys. *Nat Med*, 2010. 16(3): p. 324-8.
56. Li, Q., et al., Visualizing antigen-specific and infected cells in situ predicts outcomes in early viral infection. *Science*, 2009. 323(5922): p. 1726-9.
57. Baden, L. R., et al., First-in-human evaluation of the safety and immunogenicity of a recombinant adenovirus serotype 26 HIV-1 Env vaccine (IPCAVD 001). *J Infect Dis*, 2013. 207(2): p. 240-7.
58. Barouch, D. H., et al., Characterization of humoral and cellular immune responses elicited by a recombinant adenovirus serotype 26 HIV-1 Env vaccine in healthy adults (IPCAVD 001). *J Infect Dis*, 2013. 207(2): p. 248-56.
59. Alexander, J. et al., Pre-clinical evaluation of a replication-competent recombinant adenovirus serotype 4 vaccine expressing influenza H5 hemagglutinin. *PloS one* 7:e31177.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

We claim:

1. A replicating recombinant adenovirus vector, comprising a recombinant human adenovirus serotype 26 genome having:
   (a) a promoter operably linked to a heterologous nucleic acid sequence;
   (b) a functional E1 coding region that is sufficient for viral replication;
   (c) a deletion in the E3 coding region; and
   (d) a deletion in the E4 coding region, provided that E4 open reading frame 6/7 is not deleted.

2. The replicating recombinant adenovirus vector of claim 1, wherein the heterologous nucleic acid sequence is located between left inverted terminal repeat (ITR) and 5'-end of the functional E1 coding region.

3. The replicating recombinant adenovirus vector of claim 1, wherein the heterologous nucleic acid sequence encodes an immunogenic polypeptide.

4. The replicating recombinant adenovirus vector of claim 1, wherein the heterologous nucleic acid sequence encodes an HIV antigen.

5. The replicating recombinant adenovirus vector of claim 1, wherein the heterologous nucleic acid sequence encodes a mosaic HIV antigen.

6. The replicating recombinant adenovirus vector of claim 1, wherein the heterologous nucleic acid sequence encodes a polypeptide comprising the amino acid sequence of SEQ ID NO: 48 or SEQ ID NO: 50.

7. The replicating recombinant adenovirus vector of claim 1, wherein the vector is lyophilized.

8. A replicating recombinant adenovirus vector comprising a recombinant human adenovirus serotype 26 genome having:
   (a) a promoter operably linked to a heterologous nucleic acid sequence encoding the amino acid sequence of SEQ ID NO: 48 or SEQ ID NO: 50;
   (b) a functional E1 coding region that is sufficient for viral replication encoding the amino acid sequences of SEQ ID NOs: 14-16;
   (c) a partially deleted E3 coding region consisting of the nucleotide sequence encoding the amino acid sequence of SEQ ID NO: 6; and
   (d) a partially deleted E4 coding region consisting of the nucleotide sequence encoding the amino acid sequence of SEQ ID NO: 22.

9. The replicating recombinant adenovirus vector of claim 8, wherein the heterologous nucleic acid sequence is located between left ITR and 5'-end of the functional E1 coding region.

10. The replicating recombinant adenovirus vector of claim 9, wherein,
    (a) the promoter is CMV promoter having the nucleotide sequence of SEQ ID NO: 51, and the heterologous nucleic acid sequence comprises the nucleotide sequence of SEQ ID NO: 47 or SEQ ID NO: 49;
    (b) the functional E1 coding region comprises the nucleotide sequence of SEQ ID NO: 13;
    (c) the partially deleted E3 coding region consists of the nucleotide sequence of SEQ ID NO: 5; and
    (d) the partially deleted E4 coding region consists of the nucleotide sequence of SEQ ID NO: 23.

11. A composition comprising the replicating recombinant adenovirus vector of claim 1 and a pharmaceutically acceptable carrier.

12. The composition of claim 11, being formulated for oral administration to a subject.

13. The composition of claim 12, being an enteric-coated capsule.

14. A method of producing a replicating adenovirus particle, comprising:
introducing the replicating recombinant adenovirus vector of claim 1 into a cell under conditions sufficient for replication of the recombinant adenovirus genome and packaging of the adenovirus particle in the cell; and collecting the adenovirus particle.

15. A method of producing an immune response in a subject, comprising: administering to the subject an immunogenically effective amount of the composition according to claim 11.

16. The method of claim 15, wherein the composition is orally administered to the subject.

17. A method of producing an immune response in a human subject against an HIV infection, comprising: orally administering to the subject an immunogenically effective amount of a composition comprising a pharmaceutically acceptable carrier and a replicating recombinant adenovirus vector comprising a recombinant human adenovirus serotype 26 genome having:
(a) a promoter operably linked to a heterologous nucleic acid sequence encoding the amino acid sequence of SEQ ID NO: 48 or SEQ ID NO: 50;
(b) a functional E1 coding region that is sufficient for viral replication encoding the amino acid sequences of SEQ ID NOs: 14-16;
(c) a partially deleted E3 coding region consisting of the nucleotide sequence encoding the amino acid sequence of SEQ ID NO: 6; and
(d) a partially deleted E4 coding region consisting of the nucleotide sequence encoding the amino acid sequence of SEQ ID NO: 22,
wherein the heterologous nucleic acid sequence is located between left ITR and 5'-end of the functional E1 coding region.

18. The method of claim 17, wherein
(a) the promoter is CMV promoter having the nucleotide sequence of SEQ ID NO: 51 and the heterologous nucleic acid sequence comprises the nucleotide sequence of SEQ ID NO: 47 or SEQ ID NO: 49;
(b) the functional E1 coding region comprises the nucleotide sequence of SEQ ID NO: 13;
(c) the partially deleted E3 coding region consists of the nucleotide sequence of SEQ ID NO: 5; and
(d) the partially deleted E4 coding region consists of the nucleotide sequence of SEQ ID NO: 23.

19. The replicating recombinant adenovirus vector of claim 1, comprising a partially deleted E3 coding region, wherein all nucleic acid sequence of the E3 coding region with the exception of nucleic acid sequence encoding the E3 12.5K protein product is deleted.

20. The replicating recombinant adenovirus of claim 19, wherein a replicative capacity of the vector is attenuated by at least about 80-fold, as compared to a replicative capacity of a wild-type human adenovirus serotype 26, and the attenuation is measured in vitro in non-complementing human A549 cells or human HuTu80 cells.

* * * * *

SEQUENCE LISTING

```
<160> NUMBER OF SEQ ID NOS: 93

<210> SEQ ID NO 1
<211> LENGTH: 35152
<212> TYPE: DNA
<213> ORGANISM: Adenovirus Serotype 26

<400> SEQUENCE: 1
catcatcaat aatatacccc acaaagtaaa caaaagttaa tatgcaaatg agcttttgaa      60
ttttaacggt tttggggcgg agccaacgct gattggacga gaaacggtga tgcaaatgac     120
gtcacgacgc acggctaacg gtcgccgcgg aggcgtggcc tagcccggaa gcaagtcgcg     180
gggctgatga cgtataaaaa agcggacttt agacccggaa acggccgatt ttcccgcggc     240
cacgcccgga tatgaggtaa ttctgggcgg atgcaagtga aattaggtca ttttggcgcg     300
aaaactgaat gaggaagtga aaagcgaaaa ataccggtcc ctcccagggc ggaatattta     360
ccgagggccg agagactttg accgattacg tggggtttc gattgcggtg ttttttcgc      420 gaatttccgc gtccgtgtca aagtccggtg tttatgtcac agatcagctg atccgcaggg     480
tatttaaacc agtcgagtcc gtcaagaggc cactcttgag tgccagcgag tagagatttc     540
tctgagctcc gctcccagag accgagaaaa atgagacacc tgcgcctcct gccttcaact     600
gtgcccggtg agctggctgt gcttatgctg gaggactttg tggatacagt attggaggac     660
gaactgcatc caagtccgtt cgagctggga cccacacttc aggatctcta tgatctggag     720
gtagatgccc atgatgacga ccctaacgag gaggctgtga atttaatatt tccagaatct     780
atgattcttc aggctgacat agccaacgaa tctactccac ttcatacacc gactctgtca     840 cccataccctg aattggaaga ggaggacgaa ctagacctcc ggtgttatga ggaaggtttt     900
cctcccagcg attcagagga tgaacggggt gagcagacca tggctctgat ctcagactat     960
gcttgtgtga ttgtggagga acaagtagtg attgaaaatt ctaccgagcc agtggagggc    1020
tgtagaaaat gccagtacca ccgggataag tctggagacc cgaacgcatc atgcgctttg    1080
```

```
tgctatatga aacagacttt cagctttatt tacagtaagt ggagtgaatg tgagagaggc    1140
tgagtgctta acacatcact gtgtattgct tgaacagctg tgctaagtgt ggtttatttt    1200
tgtttctagg tccggtgtca gaggatgagt catcaccctc agaagaagac cacccgtctc    1260
cccctgatct cacagatgac acgcccctgc aagtgcacag acccacccca gtcagagcca    1320
gtggcgagag gcgagcagct gttgaaaaaa ttgaggactt gttacatgac atgggtgggg    1380
atgaaccttt ggacctgagc ttgaaacgcc caggaactaa ggcgcagctg cgcttagtca    1440
tgtgtaaata aagttgtaca ataaaagtat atgtgacgca tgcaaggtgt ggtttatgac    1500
tcatgggcgg ggcttagtcc tatataagtg gcaacacctg ggcactgggc acagaccttc    1560
agggagttcc tgatggatgt gtggactatc cttgcagact ttagcaagac acgccggctt    1620
gtagaggata gttcagacgg gtgctccggg ttctggagac actggtttgg aactcctcta    1680
tctcgcctgg tgtacacagt aagaaggat tataaagagg aatttgaaaa tattttttgct    1740 gactgctctg gcctgctaga ttctctgaat cttggccacc agtcccttt ccaggaaagg    1800 gtactccaca gccttgattt ttccagccca gggcgcacta cagccgggt tgcttttgtg    1860 gttttttctgg ttgacaaatg gagccaggac acccaactga gcaggggcta catcctggac    1920
ttcgcagcca tgcacctgtg gagggcctgg atcaggcagc ggggacagag aatcttgaat    1980
tactggcttc tacagccagc agctccgggt cttcttcgtc tacacagaca acatccatg    2040 ttggaggaag aaatgaggca ggccatggac gagaacccga ggagcggcct ggaccctccg    2100
tcggaagagg agctggattg aatcaggtat ccagcctgta cccagagctt agcaaggtgc    2160
tgacatccat ggccagggga gttaagaggg agaggagcga tgggggtaat accgggatga    2220
tgaccgagct gacggccagc ctgatgaatc ggaagcgccc agagcgcctt acctggtacg    2280
agctacagca ggagtgcagg gatgagttgg gcctgatgca ggataaatat ggcctggagc    2340
agataaaaac ccattggttg aacccagatg aggattggga ggaggctatt aagaagtatg    2400
ccaagatagc cctgcgccca gattgcaagt acatagtgac caagaccgtg aatatcagac    2460
atgcctgcta catctcgggg aacggggcag aggtggtcat cgataccctg gacaaggccg    2520
ccttcaggtg ttgcatgatg ggaatgagag caggagtgat gaatatgaat tccatgatct    2580
tcatgaacat gaagttcaat ggagagaagt ttaatggggt gctgttcatg ccaacagcc    2640 acatgaccct gcatggctgc agtttcttcg gcttcaacaa tatgtgcgca gaggtctggg    2700
gcgcttccaa gatcagggga tgtaagtttt atggctgctg gatgggcgtg gtcggaagac    2760
ccaagagcga gatgtctgtg aagcagtgtg tgtttgagaa atgctacctg ggagtctcta    2820
ccgagggcaa tgctagagtg agacactgct cttccctgga gacgggctgc ttctgcctgg    2880
tgaagggcac agcctctctg aagcataata tggtgaaggg ctgcacggat gagcgcatgt    2940
acaacatgct gacctgcgat tcgggggtct gccatatcct gaagaacatc catgtgacct    3000
cccaccccag aaagaagtgg ccagtgtttg agaataacct gctgatcaag tgccatatgc    3060
acctgggagc cagaagggc accttccagc cgtaccagtg caactttagc cagaccaagc    3120
tgctgttgga gaacgatgcc ttctccaggg tgaacctgaa cggcatcttt gacatggatg    3180
tctcggtgta caagatcctg agatacgatg agaccaagtc cagggtgcgc gcttgcgagt    3240 gcggggcag acacaccagg atgcagccag tggccctgga tgtgaccgag gagctgagac    3300
cagaccacct ggtgatggcc tgtaccggga ccgagttcag ctccagtggg gaggatacag    3360
attagaggta ggtttgagta gtgggcgtgg ctaaggtgac tataaggcg ggtgtcttac    3420 gagggtctttt ttgcttttct gcagacatca tgaacgggac tggcggggcc ttcgaagggg    3480
```

```
ggcttttag  cccttatttg  acaacccgcc  tgccgggatg  ggccggagtt  cgtcagaatg  3540
tgatgggatc  gacggtggat  gggcgcccag  tgcttccagc  aaattcctcg  accatgacct  3600
acgcgaccgt  ggggaactcg  tcgctcgaca  gcaccgccgc  agccgcggca  gccgcagccg  3660
ccatgacagc  gacgagactg  gcctcgagct  acatgcccag  cagcggtagt  agcccctctg  3720
tgcccagttc  catcatcgcc  gaggagaaac  tgctggccct  gctggccgag  ctggaagccc  3780
tgagccgcca  gctggccgcc  ctgacccagc  aggtgtccga  gctccgcgaa  cagcagcagc  3840
agcaaaataa  atgattcaat  aaacacagat  tctgattcaa  acagcaaagc  atctttatta  3900
tttatttttt  cgcgcgcggt  aggccctggt  ccacctctcc  cgatcattga  gagtgcggtg  3960
gattttttcc  aggacccggt  agaggtggga  ttggatgttg  aggtacatgg  gcatgagccc  4020
gtcccgtggg  tggaggtagc  accactgcat  ggcctcgtgc  tctggggtcg  tgttgtagat  4080
gatccagtca  tagcaggggc  gctgggcgtg  gtgctggatg  atgtccttga  ggaggagact  4140
gatggccacg  gggagcccct  tggtgtaggt  gttggcaaaa  cggttgagct  gggagggatg  4200
catgcggggg  gagatgatgt  gcagtttggc  ctggatcttg  aggttggcga  tgttgccacc  4260
cagatcccgc  cggggggttca  tgttgtgcag  gaccaccaga  acggtgtagc  ccgtgcactt  4320
ggggaacttg  tcatgcaact  tggaagggaa  tgcgtggaag  aatttggaga  cgcccttgtg  4380
cccgcccagg  ttttccatgc  actcatccat  gatgatggca  atgggcccgt  gggctgcggc  4440
tttggcaaag  acgtttctgg  ggtcagagac  atcgtaatta  tgctcctggg  tgagatcatc  4500
ataagacatt  ttaatgaatt  tggggcgag  ggtgccagat  tggggacga  tggttccctc  4560
gggccccggg  gcgaagttcc  cctcgcagat  ctgcatctcc  caggctttca  tctcggaggg  4620
ggggatcatg  tccacctgcg  gggcgatgaa  aaaacggtt  tccggggcgg  gggtgatgag  4680
ctgcgaggag  agcaggtttc  tcaacagctg  ggacttgccg  cacccggtcg  ggccgtagat  4740
gaccccgatg  acgggttgca  ggtggtagtt  caaggacatg  cagctgccgt  cgtcccggag  4800
gagggggggcc  acctcgttga  gcttgtctct  gacttggagg  ttttcccgga  cgagctcgcc  4860
gaggaggcgg  tccccgccca  gcgagagaag  ctcttgcagg  gaagcaaagt  ttttcagggg  4920
cttgagcccg  tcggccatgg  gcatcttggc  gagggtctgc  gagaggagct  ccaggcggtc  4980
ccagagctcg  gtgacgtgct  ctacggcatc  tcgatccagc  agacttcctc  gtttcggggg  5040
ttgggacgac  tgcgactgta  gggcacgaga  cgatgggcgt  ccagcgcggc  cagcgtcatg  5100
tccttccagg  gtctcagggt  ccgcgtgagg  gtggtctccg  tcacggtgaa  ggggtgggcc  5160
gcgggctggg  cgcttgcaag  ggtgcgcttg  agactcatcc  tgctggtgct  gaaacgggca  5220
cggtcttcgc  cctgcgcgtc  ggcgagatag  cagttgacca  tgagctcgta  gttgagggcc  5280
tcggcggcgt  ggcccttggc  gcggagcttg  cccttggaag  agcgcccgca  ggcgggacag  5340
aggagggatt  gcagggcgta  gagcttgggc  gcgagaaaga  cggactcggg  ggcgaaggcg  5400
tccgctccgc  agtgggcgca  gacgtctcg  cactcgacta  gccaggtgag  ctcgggctgc  5460
tcggggtcaa  aaaccagttt  tccccccgttc  tttttgatgc  gcttcttacc  tcgcgtctcc  5520
atgagtctgt  gtccgcgctc  ggtgacaaac  aggctgtctg  tgtccccgta  gacggacttg  5580
atgggcctgt  cctgcagggg  cgtcccgcgg  tcctcctcgt  agagaaactc  agaccactct  5640
gagacgaagg  cgcgcgtcca  cgccaagaca  aaggaggcca  cgtgcgaggg  gtagcggtcg  5700
ttgtccacca  gggggtccac  cttttccacg  gtatgcaggc  acatgtcccc  ctcctccgca  5760
tccaagaagg  tgattggctt  gtaggtgtag  gccacgtgac  ctgggggttcc  cgacgggggg  5820
```

```
gtataaaagg gggcgggtct gtgctcgtcc tcactctctt ccgcgtcgct gtccacgagc    5880
gccagctgtt ggggtaggta ttccctctca agagcgggca tgacctcggc actcaggttg    5940
tcagtttcta gaaacgagga ggatttgatg tgggcctgcc ctgccgcgat gcttttagg     6000 agactttcat ccatctggtc agaaaagact attttttat tgtcaagctt ggtggcgaag     6060
gagccataga gggcgtttga gagaagcttg gcgatggatc tcatggtctg attttgtca    6120 cggtcggcgc gctccttggc cgcgatgttg agctggacat attcgcgcgc gacacacttc    6180
cattcgggga agacggtggt gcgctcgtcg ggcacgatcc tgacgcgcca ccgcggtta    6240 tgcagggtga ccaggtccac gctggtggcc acctcgccgc gcagggggctc gttggtccag    6300 cagagtctgc cgcccttgcg cgagcagaac gggggcagca catcaagcag atgctcgtca    6360
ggggggtccg catcgatggt gaagatgccc ggacagagtt ccttgtcaaa ataatcgatt    6420
tttgaggatg catcgtccaa ggccatctgc cactcgcggg cggccagcgc tcgctcgtag    6480
gggttgaggg gcggaccccca aggcatggga tgcgtgaggg cggaggcgta catgccgcag    6540
atgtcataga catagatggg ctccgagagg atgccgatgt aggtgggata gcagcgcccc    6600
ccgcggatgc ttgcgcgcac gtagtcatac aactcgtgcg aggggccaa gaaggcgggg     6660 ccgagattgg tgcgctgggg ctgctcggcg cggaagacga tctggcgaaa gatggcgtgc    6720
gagttggagg agatggtggg ccgttggaag atgttaaagt gggcgtgagg caggcggacc    6780
gagtcgcgga tgaagtgcgc gtaggagtct tgcagcttgg cgacgagctc ggcggtgacg    6840
aggacgtcca tggcgcagta gtccagcgtt tcgcggatga tgtcataact cgcctctcct    6900
ttcttctccc acagctcgcg gttgagggcg tattcctcgt catccttcca gtactcccgg    6960
agcgggaatc ctcgatcgtc cgcacggtaa gagcccagca tgtagaaatg gttcacggcc    7020 ttgtaggac agcagcccctt ctccacgggg agggcgtaag cttgagcggc cttgcggagc    7080
gaggtgtgcg tcagggcaaa ggtgtccctg accatgactt tcaagaactg gtacttgaag    7140
tccgagtcgt cgcagccgcc gtgctcccag agctcgaaat cggtgcgctt cttcgagagg    7200
gggttaggca gagcgaaagt gacgtcattg aagagaatct tgcctgcccg cggcatgaaa    7260
ttgcgggtga tgcggaaagg gcccgggacg gaggctcggt tgttgatgac ctgggcggcg    7320
aggacgatct cgtcaaagcc gttgatgttg tgcccgacga tgtagagttc catgaatcgc    7380
gggcggcctt tgatgtgcgg cagcttttg agctcctcgt aggtgaggtc ctcggggcat    7440
tgcaggccgt gctgctcgag cgcccactcc tggagatgtg ggttggcttg catgaaggaa    7500
gcccagagct cgcgggccat gagggtctgg agctcgtcgc gaaagaggcg gaactgctgg    7560
cccacggcca tcttttctgg ggtgacgcag tagaaggtga gggggtcccg ctcccagcga    7620
tcccagcgta aacgcacggc gagatcgcga gcgagggcga ccagctctgg gtccccggag    7680
aatttcatga ccagcatgaa ggggacgagc tgcttgccga aggaccccat ccaggtgtag    7740
gtttctacat cgtaggtgac aaagagccgc tccgtgcgag gatgagagcc gattgggaag    7800
aactggattt cctgccacca gttggacgag tggctgttga tgtgatgaaa gtagaaatcc    7860
cgccggcgaa ccgagcactc gtgctgatgc ttgtaaaagc gtccgcagta ctcgcagcgc    7920
tgcacgggct gtacctcatc cacgagatac acagcgcgtc ccttgaggag gaacttcagg    7980
agtggcggcc ctggctggtg gttttcatgt tcgcctgcgt gggactcacc ctggggctcc    8040
tcgaggacgg agaggctgac gagcccgcgc gggagccagg tccagatctc ggcgcggcgg    8100
gggcggagag cgaagacgag ggcgcgcagt tgggagctgt ccatggtgtc gcggagatcc    8160
aggtccgggg gcagggttct gaggttgacc tcgtagaggc gggtgagggc gtgcttgaga    8220
```

```
tgcagatggt acttgatttc tacgggtgag ttggtggtcg tgtccacgca ttgcatgagc    8280
ccgtagctgc gcggggccac gaccgtgccg cggtgcgctt ttagaagcgg tgtcgcggac    8340
gcgctcccgg cggcagcggc ggttccggcc ccgcgggcag gggcggcaga ggcacgtcgg    8400
cgtggcgctc gggcaggtcc cggtgctgcg ccctgagagc gctggcgtgc gcgacgacgc    8460
ggcggttgac atcctggatc tgccgcctct gcgtgaagac cacgggcccc gtgactttga    8520
acctgaaaga cagttcaaca gaatcaatct ctgcgtcatt gacggcggcc tgacgcagga    8580
tctcttgcac gtcgcccgag ttgtcctggt aggcgatctc ggacatgaac tgttcgatct    8640
cctcctcctg gagatcgccg cggcccgcgc gctccacggt ggcggcgagg tcattggaga    8700
tgcgacccat gagctgcgag aaggcgccca ggccgctctc gttccagacg cggctgtaga    8760
ccacgtcccc gtcggcgtcg cgcgcgcgca tgaccacctg cgcgaggttg agctccacgt    8820
gccgcgcaaa gacggcgtag ttgcgcaggc gctggaagag gtagttgagg gtggtggcga    8880
tgtgctcggt gacgaagaag tacatgatcc agcggcgcag gggcatctcg ctgatgtcgc    8940
cgatggcttc cagcctttcc atggcctcgt agaagtccac ggcgaagttg aaaaactggg    9000
cgttgcgggc cgagaccgtg agctcgtctt ccaggagccg gatgagttcg gcgatggtgg    9060
cgcgcacctc gcgctcgaaa tccccggggg cctcctcctc ttcctcttct tccatgacga    9120
cctcttcttc tatttcttcc tctggggcg gtggtggtgg cggggccga cgacgacggc    9180 gacgcaccgg gagacggtcg acgaagcgct cgatcatctc cccgcggcgg cgacgcatgg    9240
tttcggtgac ggcgcgaccc cgttcgcgag gacgcagcgt gaagacgccg ccggtcatct    9300
cccggtaatg gggcgggtcc ccattgggca gcgatagggc gctgacgatg catcttatca    9360
attgcggtgt aggggacgtg agcgcgtcga gatcgaccgg atcggagaat ctttcgagga    9420
aagcgtctag ccaatcgcag tcgcaaggta agctcaaaca cgtagcagcc ctgcggacgc    9480
tgttagaatt gcggttgctg atgatgtaat tgaagtaggc gttttgtgagg cggcggatgg    9540 tggcgaggag gaccaggtcc ttgggtccag cttgctggat gcggagccgc tcggccatgc    9600
cccaggcctg gccctgacac cggctcaggt tcttgtagta gtcatgcatg agcctctcaa    9660
tgtcatcact ggctgaggcg gagtcttcca tgcgggtgac cccgacgccc ctgagcggct    9720
gcacgagcgc caggtcggcg acgacgcgct cggcgaggat ggcctgttgc acgcgggtga    9780
gggtgtcctg gaagtcgtcc atgtcgacga agcggtgata ggccccggtg ttgatggtgt    9840
aggtgcagtt ggccatgagc gaccagttga cggtctgcag gcctggctgc acgacctcgg    9900
agtacctgag ccgcgagaag gcgcgcgagt cgaagacgta gtcgttgcag gtgcgcacga    9960
ggtactggta tccgactagg aagtgcggcg gcggctggcg gtagagcggc cagcgctggg    10020
tggccggcgc gcccggggcc aggtcctcga gcatgaggcg gtggtagccg tagaggtagc    10080
gggacatcca ggtgatgccg gcggcggtgg tggaggcgcg cgggaactcg cggacgcggt    10140
tccagatgtt gcgcagcggc aggaaatagt ccatggtcgg cacggtctgg ccggtgagac    10200
gcgcgcagtc attgacgctc tagaggcaaa aacgaaagcg gttgagcggg ctcttcctcc    10260
gtagcctggc ggaacgcaaa cgggttaggc cgcgtgtgta ccccggttcg agtcccctcg    10320
aatcaggctg gagccgcgac taacgtggta ttggcactcc cgtctcgacc cgagcccgat    10380
agccgccagg atacggcgga gagcccttt tgccggccga gtgggtcgc tagacttgaa    10440 agcgaccgaa aaccctgccg ggtagtggct cgcgcccgta gtctggagaa gcatcgccag    10500
ggttgagtcg cggcagaacc cggttcgagg acggccgcgg cgagcgggac ttggtcaccc    10560
```

```
cgccgatata aagacccaca gccagccgac ttctccagtt acgggagcga gcccccttt     10620
ttcttttgc  cagatgcatc ccgtcctgcg ccaaatgcgt cccacccccc ggcgaccac     10680
cgcgaccgcg gccgtagcag gcgccggcgc tagccagcca ccacagacag agatggactt    10740
ggaagagggc gaaggctgg  caagactggg ggcgccgtcc ccggagcgac atccccgcgt    10800
gcagctgcag aaggacgtgc gcccggcgta cgtgcctacg cagaacctgt tcagggaccg    10860
cagcggggag gagcccgagg agatgcgcga ctgccggttt cgggcgggca gggagctgcg    10920
cgagggcctg gaccgccagc gcgtgctgcg cgacgaggat ttcgagccga acgagcagac    10980
ggggatcagc cccgcacgcg cgcacgtggc ggcagccaac ctggtgacgg cctacgagca    11040
gacggtgaag caggagcgca acttccaaaa gagtttcaac aaccacgtgc gcaccctgat    11100
cgcgcgcgag gaggtggccc tgggcctgat gcacctgtgg gacctggcgg aggccatcgt    11160
gcagaacccg gacagcaagc ctctgacggc gcagctgttc ctggtggtgc agcacagcag    11220
ggacaacgag gcgttcaggg aggcgctgct gaacatcgcc gagcccgagg gtcgctggct    11280
gctggagctg attaacatct tgcagagcat cgtagtgcag gagcgcagcc tgagcctggc    11340
cgagaaggtg gcggcgatca actactcggt gctgagcctg ggcaagtttt acgcgcgcaa    11400
gatttacaag acgccgtacg tgcccataga caaggaggtg aagatagaca gcttttacat    11460
gcgcatggcg ctcaaggtgc tgacgctgag cgacgacctg ggcgtgtacc gcaacgaccg    11520
catccacaag gccgtgagca cgagccggcg gcgcgagctg agcgaccgcg agctgatgct    11580
gagtctgcgc cgggcgctgg tagggggcgc cgccggcggc gaggagtcct acttcgacat    11640
gggtgcggac ctgcattggc agccgagccg gcgcgccttg gaggccgcct acggttcaga    11700
ggacttggat gaggaagagg aagaggagga ggatgcaccc gctgcggggt actgacgcct    11760
ccgtgatgtg tttttagatg tcccagcaag ccccggaccc cgccataagg gcggcgctgc    11820
aaagccagcc gtccggtcta gcatcggacg actgggaggc cgcgatgcaa cgcatcatgg    11880
ccctgacgac ccgcaacccc gagtccttta gacaacagcc gcaggccaac agactctcgg    11940
ccattctgga ggcggtggtc ccctctcgga ccaaccccac gcacgagaag gtgctggcga    12000
tcgtgaacgc gctggcggag aacaaggcca tccgtcccga cgaggccggg ctggtgtaca    12060
acgccctgct ggagcgcgtg ggccgctaca acagcacgaa cgtgcagtcc aacctggatc    12120
ggctggtgac ggacgtgcgc gaggccgtgg cgcagcgcga gcggttcaag aacgagggcc    12180
tgggctcgct ggtggcgctg aacgccttcc tggcgacgca gccggcgaac gtgccgcgcg    12240
ggcaggacga ttacaccaac tttatcagcg cgctgcggct gatggtgacc gaggtgcccc    12300
agagcgaggt gtaccagtct ggcccggact acttttttcca gacgagccgg cagggcttgc    12360
agacggtgaa cctgagccag gctttcaaga atctgcgcgg gctgtggggc gtgcaggcgc    12420
ccgtgggcga ccggtcaacg gtgagcagct tgctgacgcc caactcgcgg ctgctgctgc    12480
tgctgatcgc gcccttcacc gacagcggca gcgtgaaccg caactcgtac ctgggccatc    12540
tgctgacgct gtaccgcgag gccataggcc aggcgcaggt ggacgagcag accttccagg    12600
agatcactag cgtgagccgc gcgctggggc agaacgacac cgacagtctg agggccaccc    12660
tgaacttttt gctgaccaat agacagcaga agatcccggc gcagtacgca ctgtcggccg    12720
aggaggaaag gattctgaga tatgtgcagc agagcgtagg gctgttcctg atgcaggagg    12780
gtgccacccc cagcgccgcg ctggacatga ccgcgcgcaa catggaacct agcatgtacg    12840
ccgccaaccg gccgttcatc aataagctga tggactactt gcaccgcgcg gcggccatga    12900
acacggacta ctttaccaac gccatcctga accccgcactg gctcccgccg ccggggttct    12960
```

```
acacgggcga gtacgacatg cccgaccccα acgacgggtt cctgtgggac gacgtggaca   13020
gcgcggtgtt ctcgccgacc tttcaaaagc gccaggaggc gccgccgagc gagggcgcgg   13080
tggggaggag cccctttcct agcttaggga gtttgcatag cttgccgggc tcggtgaaca   13140
gcggcagggt gagccggccg cgcttgctgg gcgaggacga gtacctgaac gactcgctgc   13200
tgcagccgcc gcgggccaag aacgccatgg ccaataacgg gatagagagt ctggtggaca   13260
aactgaaccg ctggaagacc tacgctcagg accataggga cgcgcccgcg ccgcggcgac   13320
agcgccacga ccggcagcgg ggcctggtgt gggacgacga ggactcggcc gacgatagca   13380
gcgtgttgga cttgggcggg agcggtgggg tcaacccgtt cgcgcatctg cagcccaaac   13440
tggggcgacg gatgttttga atgaaataaa actcaccaag gccatagcgt gcgttctctt   13500
ccttgttaga gatgaggcgc gcggtggtgt cttcctctcc tcctccctcg tacgagagcg   13560
tgatggcgca ggcgacccctg gaggttccgt tgtgcctcc gcggtatatg ctcctacgg   13620
agggcagaaa cagcattcgt tactcggagc tggctccgca gtacgacacc actcgcgtgt   13680
acttggtgga caacaagtcg gcggacatcg cttccctgaa ctaccaaaac gaccacagca   13740
acttcctgac cacggtggtg cagaacaacg atttcacccc cgccgaggcc agcacgcaga   13800
cgataaattt tgacgagcgg tcgcggtggg gcggtgatct gaagaccatt ctgcacacta   13860
acatgcccaa tgtgaacgag tacatgttca ccagcaagtt taaggcgcgg gtgatggtgt   13920
ctaggaagca tccagagggg gtagttgaaa cagatttgag tcaggataag cttgaatatg   13980
agtggtttga gtttaccctg cccgagggaa acttttccga gaccatgacc atagacctga   14040
tgaacaacgc catcttggaa aactacttgc aagtggggcg gcagaatggc gtgctggaga   14100
gcgatatcgg agtcaagttt gacagcagaa atttcaagct gggctgggac ccggtgacca   14160
agctggtgat gccaggggtc tacacctacg aggccttcca cccggacgtg gtgctgctgc   14220
cgggctgcgg ggtggacttc accgagagcc gcctgagcaa cctcctgggc attcgcaaga   14280
agcaaccttt ccaagagggc ttcagaatca tgtatgagga tctagaaggt ggcaacatcc   14340
ccgccctcct tgatgtgccc aagtacttgg aaagcaagaa gaaagttgaa gacgaaacta   14400
aaaatgcagc tgcggccaca gccgatacaa ccactagggg tgatacattt gcaactccag   14460
cgcaagagac agcagctgat aagaaggtag aagtcttgcc cattgaaaag gatgagagtg   14520
gtagaagtta caacctgatc cagggggaccc acgacacgct gtaccgcagt tggtacctgt   14580
cctatacctα cggggacccc gagaagggg tgcagtcgtg gacgctgctc accaccccgg   14640
acgttacctg cggcgcggag caagtctact ggtcactgcc ggacctcatg caagaccccg   14700
tcaccttccg ctccacccag caagtcagca actacccgt ggtcggcgcc gagctcatgc   14760
ccttccgcgc caagagcttt tacaacgacc tcgccgtcta ctcccagctc atccgcagct   14820
acacctccct cacccacgtc ttcaaccgct tccccgacaa ccagatcctc tgccgcccgc   14880
ccgcgcccac catcaccacc gtcagtgaaa acgtgcctgc tctcacagat cacgggacgc   14940
taccgctgcg cagcagtatc cgcggagtcc agcgagtgac cgtcactgac gcccgtcgcc   15000
gcacctgtcc ctacgtctac aaggccctgg gcatagtcgc gccgcgcgtg ctttccagtc   15060
gcaccttcta aaaaaatgtc tattctcatc tcgcccagca ataacaccgg ctgggtctt   15120
actagaccca gcaccatgta cggaggagcc aagaagcgct cccagcagca cccgtccgc   15180
gtccgcggcc acttccgcgc tccctgggc gcatacaagc gcgggcggac ttccaccgcc   15240
gccgtgcgca ccaccgtcga cgacgtcatc gactcggtgg tcgccgacgc gcgcaactat   15300
```

```
accccccgccc cctccaccgt ggacgcggtc atcgacagcg tggtggccga cgcgcgcgac    15360
tatgccagac gcaagagccg gcggcgacgg atcgccaggc gccaccggag cacgcccgcc    15420
atgcgcgccg cccgggctct gctgcgccgc gccagacgca cgggccgccg gccatgatg    15480 cgagccgcgc gccgcgctgc cactgcaccc accccccgcag gcaggactcg cagacgagcg    15540
gccgccgccg ccgctgcggc catctctagc atgaccagac ccaggcgcgg aaacgtgtac    15600
tgggtgcgcg actccgtcac gggcgtgcgc gtgcccgtgc gcacccgtcc tcctcgtccc    15660
tgatctaatg cttgtgtcct cccccgcaag cgacgatgtc aaagcgcaaa atcaaggagg    15720
agatgctcca ggtcgtcgcc ccggagattt acggaccacc ccaggcggac cagaaacccc    15780
gcaaaatcaa gcgggttaaa aaaaaggatg aggtggacga gggggcagta gagtttgtgc    15840
gcgagttcgc tccgcggcgg cgcgtaaatt ggaaggggcg cagggtgcag cgcgtgttgc    15900
ggcccggcac ggcggtggtg ttcacgcccg gcgagcggtc ctcggtcagg agcaagcgta    15960
gctatgacga ggtgtacggc gacgacgaca tcctggacca ggcggcggag cgggcgggcg    16020
agttcgccta cgggaagcgg tcgcgcgaag aggagctgat ctcgctgccg ctggacgaaa    16080
gcaaccccac gccgagcctg aagcccgtga ccctgcagca ggtgctgccc caggcggtgc    16140
tgctgccgag ccgcggggtc aagcgcgagg gcgagagcat gtacccgacc atgcagatca    16200
tggtgcccaa gcgccggcgc gtggaggacg tgctggacac cgtgaaaatg gatgtggagc    16260
ccgaggtcaa ggtgcgcccc atcaagcagg tggcgccggg cctgggcgtg caaaccgtgg    16320
acattcagat ccccaccgac atggatgtcg acaaaaaacc ctcgaccagc atcgaggtgc    16380
aaaccgaccc ctggctccca gcctccaccg ctaccgtctc cacttctacc gccgccacgg    16440
ctaccgagcc tcccaggagg cgaagatggg gcgccgccag ccggctgatg cccaactacg    16500
tgttgcatcc ttccatcatc ccgacgccgg gctaccgcgg caccccggtac tacgccagcc    16560 gccggcgccc agccagcaaa cgccgccgcc gcaccgccac ccgccgccgt ctggccccccg    16620 cccgcgtgcg ccgcgtgacc acgcgccggg gccgctcgct cgttctgccc accgtgcgct    16680
accaccccag catcctttaa tccgtgtgct gtgatactgt tgcagagaga tggctctcac    16740
ttgccgcctg cgcatccccg tcccgaatta ccgaggaaga tcccgccgca ggagaggcat    16800
ggcaggcagc ggcctgaacc gccgccggcg gcgggccatg cgcaggcgcc tgagtggcgg    16860 cttctctgccc gcgctcatcc ccataatcgc gcggccatt ggcacgatcc cgggcatagc    16920
ttccgttgcg ctgcaggcgt cgcagcgccg ttgatgtgcg aataaagcct ctttagactc    16980
tgacacacct ggtcctgtat attttttagaa tggaagacat caattttgcg tccctggctc    17040
cgcggcacgg cacgcggccg ttcatgggca cctggaacga gatcggcacc agccagctga    17100
acggggcgcg cttcaattgg agcagtgtct ggagcgggct taaaaatttc ggctcgacgc    17160
tccggaccta tgggaacaag gcctggaata gtagcacggg gcagttgttg agggaaaagc    17220
tcaaagacca gaacttccag cagaaggtgg tggacgggct ggcctcgggc attaacgggg    17280
tggtggacat cgcgaaccag gccgtgcagc gcgagataaa cagccgcctg acccgcgac    17340 cgcccacggt ggtggagatg gaagatgcaa ctcttccgcc gcccaagggc gagaagcggc    17400 gcggccgca gcggaggag acgatcctgc aggtggacga gccgccctcg tacgaggagg    17460
ccgtcaaggc cggcatgccc accacgcgca tcatcgcgcc gctggccacg ggtgtaatga    17520
aacccgccac ccttgacctg cctccaccac ccgcgcccgc tccaccgaag gcaactccgg    17580
ttgtgcaggc cccccggtg gcgaccgccg tgcgccgcgt cccgcccgc cgccaggccc    17640 agaactggca gagcacgctg cacagtatcg tgggcctggg agtgaaaagt ctgaagcgcc    17700
```

```
gccgatgcta ttgagagaga ggaaagagga cactaaaggg agagcttaac ttgtatgtgc    17760
cttaccgcca gagaacgcgc gaagatggcc accccctcga tgatgccgca gtgggcgtac    17820
atgcacatcg ccgggcagga cgcctcggag tacctgagcc cgggtctggt gcagtttgcc    17880
cgcgccaccg acacgtactt cagcctgggc aacaagttta ggaaccccac ggtggccccg    17940
acccacgatg tgaccacgga ccggtcccag cgtctgacgc tgcgcttcgt gcccgtggat    18000
cgcgaggaca ccacgtactc gtacaaggcg cgcttcactc tggccgtggg cgacaaccgg    18060
gtgctagaca tggccagcac ttactttgac atccgcggcg tcctggaccg cggtcccagc    18120
ttcaaaccct actcgggcac ggcctacaac agcctggctc ccaagggtgc ccccaatccc    18180
agtcagtggg aaacaaaaga aaagcaagga actactggag gagtgcagca agaaaaagat    18240
gtcacaaaaa catttggtgt ggctgccacc ggcggaatta atataacaaa ccagggtctg    18300
ttactaggaa ctgacgaaac cgctgagaat ggcaaaaaag acatttatgc agacaagact    18360
ttccagccag aacctcaagt tggagaagaa aactggcagg aaaatgaagc cttctatgga    18420
ggaagggctc ttaaaaagga cactaaaatg aaaccatgct atggatcttt tgctagacct    18480
actaatgaga aggaggtca ggcaaagttc aaaccagtta atgaaggaga acaacctaaa    18540
gatctggata tagattttgc ttactttgac gtccctggcg gaagtcctcc agcaggtggt    18600
agtggggaag aatacaaagc agatataatt ttgtacactg aaaatgttaa tcttgaaaca    18660
ccagacactc atgtggttta caagccagga acttcagata cagttcaga aatcaatctg    18720 gttcagcagt ccatgccaaa cagacccaac tacattggct ttagggacaa cttttgtaggt    18780 ctcatgtatt acaacagcac cggaaatatg ggtgtgctgg ctggtcaggc ttctcagttg    18840
aacgctgtgg tcgacttgca agacagaaac accgagttat cttaccagct attgctagat    18900
tctctgggtg acagaaccag atactttagc atgtggaact ctgcggtgga cagttacgat    18960
ccagatgtca ggatcattga aaatcacggt gtggaagatg aacttccaaa ctattgcttc    19020
ccattgaatg gcactggaac caattccact tatcaaggtg taaagattac aaatggtaat    19080
gatggtgctg aagaaagtga gtgggagaaa gacgatgcaa tttctagaca aaaccaaatc    19140
tgcaagggca atgtctacgc catggagatc aacctgcagg ccaacctgtg gaagagtttt    19200
ctgtactcga acgtggccct gtacctgccc gactcctaca agtacacgcc ggccaacgtc    19260
aagctgcccg ccaacaccaa cacctacgag tacatgaacg gccgcgtggt agcccctcg    19320 ctggtggacg cctacatcaa catcggcgcc cgctggtcgt tggaccccat ggacaacgtc    19380 aacccttca accaccaccg caatgcgggc ctgcgctacc gctccatgct gctgggcaac    19440
ggccgctacg tgcccttcca catccaagtg ccccaaaagt tctttgccat caagaacctg    19500
ctcctgctcc cgggctccta cacctacgag tggaacttcc gcaaggacgt caacatgatc    19560
ctgcagagtt ccctcggcaa cgacctgcgc gtcgacggcg cctccgtccg cttcgacagc    19620
gtcaacctat acgccacttt cttccccatg gcgcacaaca ccgcttcaac cttggaagcc    19680
atgctgcgca acgacaccaa cgaccagtcc ttcaacgact acctctcggc cgccaacatg    19740
ctctacccca tcccggccaa ggccaccaac gtgcccatct ccatcccatc gcgcaactgg    19800
gccgccttcc gcggctggag tttcacccgg ctcaagacca aggaaactcc ttccctcggc    19860
tcgggtttcg accccactt tgtctactcg ggctccatcc cctacctcga cgggaccttc    19920
tacctcaacc acaccttcaa gaaggtctcc atcatgttcg actcctcggt cagctggccc    19980
ggcaacgacc ggctgctcac gccgaacgag ttcgagatca agcgcagcgt cgacggggag    20040
```

```
ggctacaacg tggcccaatg caacatgacc aaggactggt tcctcgtcca gatgctctcc   20100
cactacaaca tcggctacca gggcttccac gtgcccgagg gctacaagga ccgcatgtac   20160
tccttcttcc gcaacttcca gcccatgagc aggcaggtgg tcgatgagat caactacaag   20220
gactacaagg ccgtcaccct gcccttccag cacaataact cgggcttcac cggctacctc   20280
gcacccacca tgcgccaggg gcagccctac cccgccaact tcccctaccc gctcatcggt   20340
cagacagccg tgccctccgt cacccagaaa aagttcctct gcgacagggt catgtggcgc   20400
atccccttct ccagcaactt catgtccatg ggcgccctca ccgacctggg tcagaacatg   20460
ctctacgcca actcggccca cgcgctcgac atgaccttcg aggtggaccc catggatgag   20520 cccacccctcc tctatcttct cttcgaagtt ttcgacgtgg tcagagtaca ccagccgcac   20580
cgcggcgtca tcgaggccgt ctacctgcgc acgcccttct ccgccggcaa cgccaccacc   20640
taagcatgag cggctccagc gaacgagagc tcgcggccat cgtgcgcgac ctgggctgcg   20700
ggccctactt tttgggcacc cacgacaagc gcttcccggg cttttctcgcc ggcgacaagc   20760 tggcctgcgc catcgtcaac acggccgcc gcgagaccgg aggcgtgcac tggctcgcct   20820
tcggctggaa cccgcgctcg cgcacctgct acatgttcga cccctttggg ttctcggacc   20880
gccggctcaa gcagatttac agcttcgagt acgaggccat gctgcgccgc agcgccctgg   20940
cctcctcgcc cgaccgctgt ctcagcctcg agcagtccac tcagaccgtg caggggcccg   21000
actccgccgc ctgcggactc ttctgttgca tgttcttgca tgccttcgtg cactggcccg   21060
accgacccat ggacggaaac cccaccatga acttgctgac gggggtgccc aacggcatgc   21120
tacaatcgcc acaggtgctg cccaccctca ggcgcaacca ggaggaactc taccgcttcc   21180
tcgcgcgcca ctccccttac tttcgctccc accgcgccgc catcgaacac gccaccgctt   21240
ttgacaaaat gaaacaactg cgtgtatctc aataaacagc acttttattt tacatgcact   21300
ggagtatatg caagttattt aaaagtcgaa ggggttctcg cgctcgtcgt tgtgcgccgc   21360 gctgggagg ccacgttgc ggtactggta cttgggctgc cacttgaact cggggatcac   21420
cagtttgggc actggggtct cggggaaggt ctcgctccac atgcgccggc tcatctgcag   21480
ggcgcccagc atgtccgggg cggagatctt gaaatcgcag ttggggccgg tgctctgcgc   21540
gcgcgagttg cggtacacgg ggttgcagca ctggaacacc atcagactgg ggtacttcac   21600
actagccagc acgctcttgt cgctgatctg atccttgtcc agatcctcgg cgttgctcag   21660
gccgaacggg gtcatcttgc acagctggcg tcccaggaag ggcacgctct gaggcttgtg   21720
gttacactcg cagtgcacgg gcatcagcat catccccgcg ccgcgctgca tattcgggta   21780
gagggccttg acaaaggccg cgatctgctt gaaagcttgc tgggccttgg cccccctcgct   21840 gaaaaacagg ccgcagctct tcccgctgaa ctggttattc ccacacccgg catcctgcac   21900
gcagcagcgc gcgtcatggc tggtcagttg caccacgctc cgtccccagc ggttctgggt   21960
caccttagcc ttgctgggct gctccttcaa cgcgcgctgc ccgttctcgc tggtcacatc   22020
catctccacc acgtggtcct tgtggatcat catcgtcccg tgcagacact tgagctggcc   22080
ttccacctcg gtgcagccgt gatcccacag ggcgcaaccg gtgcactccc agttcttgtg   22140
cgcaatcccg ctgtggctga agatgtaacc ttgcaacatg cggcccatga tggtgctaaa   22200
tgctttctgg gtggtgaagg tcagttgcat cccgcgggcc tcctcgttca tccaggtctg   22260
gcacatcttc tggaagatct cggtctgctc gggcatgagc ttgtaagcat cgcgcaggcc   22320
gctgtcgacg cggtagcgtt ccatcagcac gttcatggta tccatgccct tctcccagga   22380
cgagaccaga ggcagactca gagggttgcg tacgttcagg acaccggggg tcgcgggctc   22440
```

```
gacgatgcgt tttccgtcct tgccttcctt caatagaacc ggcggctggc tgaatcccac   22500
tcccacgatc acggcatctt cctggggcat ctcttcgtcg gggtctacct tggtcacatg   22560
cttggtcttt ctggcttgct tcttttttgg agggctgtcc acggggagca cgtcctcctc   22620
ggaagacccg gagcccaccc gctgatactt tcggcgcttg gtgggcagag gaggtggcgg   22680 cgagggctc ctctcctgct ccggcggata gcgcgccgac ccgtggcccc ggggcggagt    22740
ggcctctcgg cccatgaacc ggcgcacgtc ctgactgccg ccggccattg tttcctaggg   22800
gaagatggag gagcagccgc gtaagcagga gcaggaggag gacttaacca cccacgagca   22860
acccaaaatc gagcaggacc tgggcttcga agagccggct cgtctagaac ccccacagga   22920
tgaacaggag cacgagcaag acgcaggcca ggaggagacc gacgctgggc tcgagcatgg   22980
ctacctggga ggagaggagg atgtgctgct gaaacacctg cagcgccagt ccctcatcct   23040
ccgggacgcc ctggccgacc ggagcgaaac ccccctcagc gtcgaggagc tgtgtcgggc   23100
ctacgagctc aacctcttct cgccgcgcgt acccccccaaa cgccagccca acggcacctg   23160
cgagcccaac ccgcgtctca acttctatcc cgtctttgcg gtccccgaag ccctcgccac   23220
ctatcacatc ttttttcaaga accaaaagat ccccgtctcc tgccgcgcca accgcaccag   23280
cgccgacgcg ctcctcgctt tggggcccgg cgcgcgcata cctgatatcg cttccctgga   23340
agaggtgccc aagatcttcg aagggctcgg tcgggacgag acgcgcgcgg cgaacgctct   23400
gaaagaaaca gcagaggaag agggtcacac tagcgccctg gtagagttgg aaggcgacaa   23460
cgccaggctg gccgtgctca agcgcagcgt cgagcttacc cacttcgcct accccgccgt   23520
caacctcccg cccaaggtca tgcgtcgcat catggatcag ctcatcatgc cccacatcga   23580
ggccctcgat gaaagtcagg agcagcgccc cgaggacgcc cggccgtgg tcagcgacga    23640 gatgctcgcg cgctggctcg ggacccgcga ccccaggct ttggaacagc ggcgcaaact    23700
catgctggcc gtggtcctgg tcacccttga gctcgaatgc atgcgccgct ttttcagcga   23760 cccccgagacc ctgcgcaagg tcgaggagac cctgcactac actttcaggc acggtttcgt   23820
caggcaggcc tgcaagatct ccaacgtgga gctgaccaac ctggtctcct gcctggggat   23880
cctgcacgag aaccgcctgg gccagaccgt gctccactct accctgaagg gcgaggcgcg   23940
gcgggactat gtccgcgact gcgtctttct ctttctctgc cacacatggc aagcggccat   24000
gggcgtgtgg cagcagtgtc tcgaggacga gaacctaaag gagctggaca gcttcttgc    24060 tagaaaacctt aaaaagctgt ggacgggctt cgacgagcgc accgtcgcct cggacctggc  24120
cgagatcgtc ttccccgagc gcctgagaca gacgctgaaa ggcgggctgc ccgacttcat   24180
gagccagagc atgttgcaaa actaccgcac tttcattctt gagcgatcag gcatcctgcc   24240
cgccacctgc aacgccttcc cctccgactt tgtaccgctg agctaccgcg agtgtcccccc  24300 gccgctgtgg agccactgct acctcttgca gctggccaac tacatcgcct accactcgga   24360
cgtgatcgag gacgtgagcg gcgaggggct gctcgagtgc cactgtcgct gcaacctgtg   24420 ctcccccgcat cgctccctgg tctgcaaccc ccagctcctg agcgagaccc aggtcatcgg   24480
taccttcgag ctgcaaggtc cgcaggagtc caccgctccg ctgaaactca cgccggggtt   24540
gtggacttcc gcgtacctgc gcaaatttgt acccgaagac taccacgccc atgagataaa   24600
gttctttgag gaccaatcgc gtccgcagca cgcggatctc acggcctgcg tcatcaccca   24660
gggcgcgatc ctcgcccaat tgcacgccat ccaaaaatcc cgccaagagt tcttctgaa    24720 aaagggtaga ggggtctacc tggaccccca gacgggcgag gtgctcaacc cgggtctccc   24780
```

-continued

```
ccagcatgcc gaggaagaag caggagccgc tagtggagga gatggaagaa gaatgggaca    24840
gccaggcaga ggaggacgaa tgggaggagg agacagagga ggaagaattg aagaggtgg     24900
aagaggagca ggcaacagag cagcccgtcg ccgcaccatc cgcgccggca gccccgccgg    24960
tcacggatac aacctccgct ccggtcaagc ctcctcgtag atgggatcaa gtgaagggtg    25020
acggtaagca cgagcggcag ggctaccgat catggagggc ccacaaagcc gcgatcatcg    25080
cctgcttgca agactgcggg gggaacatcg ctttcgcccg ccgctacctg ctcttccacc    25140
gcggggtgaa catccccgc aacgtgttgc attactaccg tcaccttcac agctaagaaa     25200
aagcaagtca aaggagtcgc cggaggagga ggaggaggcc tgaggatcgc ggcgaacgag    25260
cccttgacca ccagggagct gaggaaccgg atcttcccca ctctttatgc cattttttcag  25320
cagagtcgag gtcagcagca agagctcaaa gtaaaaaacc ggtctctgcg ctcgctcacc   25380
cgcagttgct tgtaccacaa aaacgaagat cagctgcagc gcactctcga agacgccgag   25440
gctctgttcc acaagtactg cgcgctcact cttaaagact aaggcgcgcc caccccggaaa  25500
aaaggcggga attacctcat cgccaccatg agcaaggaga ttcccacccc ttacatgtgg   25560
agctatcagc cccaaatggg cctggccgcg ggcgcctccc aggactactc cacccgcatg   25620
aactggctca gtgccggccc ctcgatgatc tcacgggtca acggggtccg cagtcatcga   25680
aaccagatat tgttggagca ggcggcggtc acctccacgc ccagggcaaa gctcaacccg   25740
cgtaattggc cctccaccct ggtgtatcag gaaatccccg gccgactac cgtactactt    25800
ccgcgtgacg cactggccga agtccgcatg actaactcag gtgtccagct ggccggcggc   25860
gcttcccggt gccgctccg cccacaatcg ggtataaaaa ccctggtgat ccgaggcaga    25920
ggcacacagc tcaacgacga gttggtgagc tcttcgatcg gtctgcgacc ggacggagtg   25980
ttccaactag ccggagccgg gagatcctcc ttcactccca accaggccta cctgaccttg   26040
cagagcagct cttcggagcc tcgctccgga ggcatcggaa ccctccagtt tgtggaggag   26100
tttgtgccct cggtctactt caaccccttc tcgggatcgc caggcctcta cccgacgag    26160
ttcataccga acttcgacgc agtgagagaa gcggtggacg gctacgactg aatgtcccat   26220
ggtgactcgc ctgagctcgc tcggttgagg catctggacc actgccgccg cctgcgctgc   26280
ttcgcccggg agagctgcgg actcatctac tttgagtttc ccgaggagca ccccaacggc   26340
cctgcacacg gagtgcggat caccgtagag ggcaccaccg agtctcacct ggtcaggttc   26400
ttcacccagc aacccttcct ggtcgagcgg gaccggggcg ccaccaccta caccgtctac   26460
tgcatctgtc caaccccgaa gttgcatgag aattttttgtt gtactctttg tggtgagttt  26520
aataaaagct aaactcttgc aatactctgg accttgtcgt cgtcaactca acgagaccgt   26580
ctacctcacc aaccagactg aggtaaaact cacctgcaga ccacacaaga cctatatcat   26640
ctggttcttc gagaacacct catttgcagt ctccaacact cactgcaacg acggtgttga   26700
acttcccaac aaccttttcca gtggactgag ttacgataca catagagcta agctcgtcct  26760
ctacaatcct tttgtagagg gaacctacca gtgccagagc ggaccttgta ctcacacctt   26820
ccatttggtg aacgtcacca gcagcagcaa cagctcagaa actaaccttc cttctgatac   26880
taacaaacct cgtttcggag gtgagctaag gcttcccccct tctgaggagg gggttagccc  26940
atacgaagtg gtcgggtatt tgattttagg ggtggtcctg ggtgggtgca tagcggtgct   27000
agctcagctg ccttgctggg tggaaatcaa aatctttata tgctgggtca gatattgtgg   27060
ggaggaacca tgaaggggct tttgctgatt atccttttca tggtgggggg tgtactgtca   27120
tgccacgaac agccacgatg taacatcacc acaggcaatc atatgagcag agagtgcact   27180
```

```
gtagtcatca aatgcgagca cgactgccca ctaaacatta cattcaagaa taacaccatg  27240
ggaaatgtat gggtgggttt ctgggaacca ggagatgagc agaactacac ggtcactgtc  27300
catggtagca atggaaatca cactttcggt ttcaaattca tttttgaagt catgtgtgat  27360
atcacactgc atgtggctag acttcatggc ttgtggcccc ctaccaagga gaacatggtt  27420
gggttttctt tggcttttgt gatcatggcc tgcttgatgt caggtctgct ggtaggggct  27480
ttagtgtggt tcctgaagcg caagcctagg tacggaaatg aagaaaagga aaaattgcta  27540
taatcttttt cttttcaca gaaccatgaa tgctttgacc agtgtcgtgc tgctctctct  27600
tcttgtagct tttagtaatg gggaagctga aactgtagtt gtaaatgtta aatctggtac  27660
aaaccacacc cttgaaggtc ctagaaaaac tccagttcag tggtatgggg gtgctaactt  27720
tgacatgttt tgcaatggct ctaaaataca tcacaatgaa ttgaatcaca cttgctctat  27780
tcagaacata actcttacat tcataaacag aacacatcat ggaacatact atggttttgg  27840
ctctgacaat caaaattcaa aagtgtatca tgtcagagta gatgtagagc ctcctagacc  27900
ccgtgctact ttggctcctc ctcaggacat aactattaag tatggctcaa atagaacatt  27960
gcagggccca agtgttactc cagttagttg gtatgatggt gaaggaaatc ggttttgcga  28020
tggcgataaa attgatcata cagaaattaa tcacacttgc aatgctcaaa accttacttt  28080
gctgtttgtg aatgaaacac atgaaagaac atattatgga attagtggtg attggaaaca  28140
gcgaaatgag tatgatgtta ctgttacaaa gacacaatta aatattaaaa atttgggcca  28200
acgcaaaact gatgaaaacc ataaaaatgg aatgcatcag aaagtcgaac aaaatcctga  28260
aactaagaaa gaacagaagc cttcaaaaag acctagacaa aaaacattgc aaactacaat  28320
tcaggttatg attcctattg gaactaatta tactttagtg gggccttcgc caccagtgag  28380
ctggcatact acaaaaaatg gcttaacaga actctgtaat ggaaacccta ttttaagaca  28440
cacttgtgat gggcaaaata ttacacttat taatgttaat gctacatttg aggctgatta  28500
ctatggctcg aacaataaga gtgaatcaaa acactacaga gtcaaggttt tcaaagaaag  28560
aaaagatcag gcactattat tcagaccgct tactaccaaa ggaagcatga tcattactac  28620
tgaaaatcaa aactttgaat tacaacaagg tgacaatcaa gatgatgaca aaattccatc  28680
aactactgtg gcaatcgtgg tgggtgtgat tgcgggcttt gtgactctga tcattgtctt  28740
catatgctac atctgctgcc gcaagcgtcc caggtcatac aatcatatgg tagacccact  28800
actcagcttc tcttactgaa actcagtcac tctcatttca gaaccatgaa ggctttcaca  28860
gcttgcgttc tgattagcat agtcacactt agtgcagctg aagctaaatg ctttcatact  28920
tataacttaa ctagagggga aaatattaca ttagcaggtg ctggcttaaa cacaacatgg  28980
gaagcatatc acaatggatg gaaacaagtt tgtccatgga atgacggtcg ctatgtgtgc  29040
gttggaaaca gcagtaccat aactaatctt acagttgtag ctaatgcaaa tttatcatca  29100
actgttaaat ttagagctga agtttatac attggaacag atggatatga agcaatcca  29160
tcatgctttt atactatcaa tgtaattgag cttccaacca ccagatcgcc aactaccacc  29220
acggtcagta caactactga gaccacaact cacactacac agttagacac tacagtgcag  29280
aatagtactg tattggttag gtatttgtta agggaggaaa gtactactga acagacagag  29340
gctacctcaa gcgccttcag cagcacttca aatttaactt cgcttgcttg gactaatgaa  29400
accggagtat cattgatgca tggccagcct tactcaggtt tggatattca aattactttt  29460
ctggttgtct gtgggatctt tattcttgtg gttcttctgt actttgtctg ctgcaaagcc  29520
```

```
agagaaaaat ctaggcggcc catctacagg ccagtaatcg gggaacctca gccactccaa    29580
gtggatggag gcttaaggaa tcttcttttc tcttttacag tatggtgatc agccatgatt    29640
cctaggttct tcctatttaa catcctcttc tgtctcttca acgtgtgcgc tgccttcgcg    29700
gccgtctcgc acgcctcacc cgactgtctc gggcccttcc ccacctacct cctctttgcc    29760
ctgctcacct gcacctgcgt ctgcagcatt gtctgcctgg tcatcacctt cctgcagctc    29820
atcgactggt gctgcgcgcg ctacaattac ctgcatcata gtcccgaata cagggacgag    29880
aacgtagcca gaatcttaag gctcatatga ccatgcagac tctgctcata ctgctatccc    29940
tcctatcccc tacctcgcc acttctgctg attactctaa atgcaaattc gcggacatat     30000
ggaatttctt agactgctat caggagaaaa ttgacatgcc ctcctattac ttggtgattg    30060
tgggaatagt tatggtctgc tcctgcactt tctttgccat catgatctac ccctgttttg    30120
atctcggctg gaactctgtt gaagcattca catacacact agaaagcagt tcactagcct    30180
ccacgccacc acccacaccg cctccccgca gaaatcagtt tcccatgatt cagtacttag    30240
aagagccccc tccccgaccc ccttccactg ttagctactt tcacataacc ggcggcgatg    30300
actgaccacc acctggacct cgagatggac ggccaggcct ccgagcagcg catcctgcaa    30360
ctgcgcgtcc gtcagcagca ggagcgtgcc gccaaggagc tcctcgatgc catcaacatc    30420
caccagtgca agaagggcat cttctgcctg gtcaaacagg caaagatcac ctacgagctc    30480
gtgtccggcg gcaagcagca tcgcctcgcc tatgagctgc cccagcagaa gcagaagttc    30540
acctgcatgg tgggcgtcaa ccccatagtc atcacccagc agtcgggcga gaccagcggc    30600
tgcatccact gctcctgcga aagccccgag tgcatctact ccctgctcaa gacccttgc    30660 ggactccgcg acctcctccc catgaactga tgttgattaa agcccaaaa accaatcagc     30720 cccttccccc atttccccat cccccaatta ctcataaaaa ataaatcatt ggaattaatc    30780
attcaataaa gatcacttac ttgaaatctg aaagtatgtc tctggtgtag ttgttcagca    30840
gcacctcggt accctcctcc cagctctggt actccagtcc ccggcgggcg gcgaacttcc    30900
tccacacctt gaaagggatg tcaaattcct ggtccacaat tttcattgtc ttccctctca    30960
gatggcaaag aggctccggg tggaagatga cttcaacccc gtctaccct atggctacgc     31020 gcggaatcag aatatcccct tcctcactcc cccctttgtc tcctccgatg gattcaaaaa    31080 cttccccccct ggggtcctgt cacttaaact ggctgatcca atcaccatca acaatgggga    31140
tgtctcactt aaggtgggag ggggacttgc tgtagagcaa cagactggta acctaagcgt    31200
aaaccctgat gcaccttgc aagttgcaag tgataagcta cagcttgctc tggctcctcc     31260
attcgaggtc agagatggaa agcttgcttt aaaggcaggt aatggattaa aagtactaga    31320
taattccatt actggattga ctggattatt gaatacactt gtggtattaa ctggaagggg    31380
aataggaacg gaggaattaa aaaatgacga tggtgtaaca aacaaaggag tcggcttgcg    31440
tgtaagactt ggagatgacg gcgggctgac atttgataaa aagggtgatt tagtagcctg    31500
gaataaaaaa gatgacaggc gcaccctgtg gacaacccct gacacatctc caaattgcaa    31560
aatgagtaca gaaaaggatt ctaaacttac gttgacactt acaaagtgtg gaagtcaggt    31620
tctgggaaat gtatctttac ttgcagttac aggtgaatat catcaaatga ctgctactac    31680
aaagaaggat gtaaaaatat ctttactatt tgatgagaat ggaattctat taccatcttc    31740
gtcccttagc aaagattatt ggaattacag aagtgatgat tctattgtat ctcaaaaata    31800
taataatgca gttccattca tgccaaacct gacagcttat ccaaaaccaa gcgctcaaaa    31860
tgcaaaaaac tattcaagaa ctaaaatcat aagtaatgtc tacttaggtg ctcttaccta    31920
```

```
ccaacctgta attatcacta ttgcatttaa tcaggaaact gaaaatggat gtgcttattc   31980
tataacattt accttcactt ggcaaaaaga ctattctgcc caacagtttg atgttacatc   32040
ttttaccttc tcatatctta cccaagagaa caaagacaaa gactaataaa atgttttgaa   32100
ctgaatttat gaatctttat ttattttac accagcacgg gtagtcagtt tcccaccacc    32160
agcccatttc acagtgtaaa caattctctc agcacgggtg gccttaaata gggaaatgtt   32220
ctgattagtg cgggaactgg acttggggtc tataatccac acagtttcct ggcgagccaa   32280 acggggtcg gtgattgaga tgaagccgtc ctctgaaaag tcatccaagc gggcctcaca    32340
gtccaaggtc acagtctggt ggaatgagaa gaacgcacag attcatactc ggaaaacagg   32400
atgggtctgt gcctctccat cagcgccctc aacagtcttt gccgccgggg ctcggtgcgg   32460
ctgctgcaga tgggatcggg atcgcaagtc tctctgacta tgatcoccac agccttcagc   32520 aacagtctcc tggtgcgtcg ggcacagcac cgcatcctga tctctgccat gttctcacag   32580
taagtgcagc acataatcac catgttattc agcagcccat aattcagggc gctccaacca   32640
aagctcatgt tggggatgat ggaacccacg tgaccatcgt accagatgcg gcagtatatc   32700
aggtgcctgc ccctcatgaa cacactgccc atatacatga tctctttggg catgtttctg   32760
ttcacaatct gccggtacca tgggaatcgc tggttgaaca tgcacccgta aatgactctc    32820
ctgaaccaca cggccagcat ggtgcctccc gcccgacact gcagggatcc cggggctgaa   32880
cagtggcaat gcaggatcca gcgctcgtac ccgctcacca tctgagctct caccaagtcc   32940
agggtagcgg ggcacaggca cactgacata catctttta aaattttat ttcctctggg     33000 gtcaggatca tatcccaggg gactggaaac tcttggagca gggtaaagcc agcagcacat   33060
ggtaatccac ggacagaact tacattatga taatctgcat gatcacaatc gggcaacagg   33120
gggtgttgtt cagttagtga ggccctagtc tcctcctcac atcgtggtaa acgggccctg   33180
cggtaaggat gatggcggag cgagctcgac tgttcctcgg tggacattga aatggattct   33240
cttgcgtacc ttgtcgtact tctgccagca gaaagtggct cgggaacagc agatacctt    33300 cctcctgctg tccttccgct gctgacgctc agtcatccaa ctgaagtaca gccattcccg   33360
caggttctcc agcagctcct gtgcatctga tgaaacaaaa gtcccgtcga tgcggattcc   33420
ccttaaaaca tcagccagga cattgtaggc catcccaatc cagttaatgc atcctgatct   33480
atcatgaaga ggaggtgggg gaagaactgg aagaaccatt tttattccaa gcggtctcga   33540
aggacgataa agtgcaagtc acgcaggtga cagcgttccc cgccgctgtg ctggtggaaa   33600
cagacagcca ggtcaaaacc cactctattt tcaaggtgct cgactgtggc ttcgagcagt   33660
ggctctacgc gtacatccag cataagaatc acattaaagg ctggacctcc atcgatttca   33720
tcaatcatca ggttacactc attccaccatc cccaggtaat tctcattttt ccagccttgg   33780
attatttcta caaattgttg gtgtaagtcc actccgcaca tgtggaaaag ttcccacagc   33840 gcccctcca ctttcataat caggcagacc ttcatattag aaacagatcc tgctgctcca    33900
ccacctgcag cgtgttcaaa acaacaagat tcaatgaggt tctgccctct gccctcagct   33960
cacgtctcag cgtcagctgc aaaaagtcac tcaagtcctc agccactaca gctgacaatt   34020
cagagccagg gctaagcgtg ggactggcaa gcgtgagtga gtactttaat gctccaaagc   34080
tagcacccaa aaactgcatg ctggaataag ctctctttgt gtcaccggtg atgccttcca   34140
ataggtgagt gataaagcga ggtagttttt ctttaatcat ttgagtaata gaaaagtcct   34200
ctaaataagt cactaggacc ccaggaacca caatgtggta gctgacagcg tgtcgctcaa   34260
```

| | |
|---|---:|
| gcatggttag tagagatgag agtctgaaaa acagaaagca tgcactaaac cagagttgcc | 34320 |
| agtctcactg aaggaaaaat cactctctcc agcagcaaag tgcccactgg gtggccctct | 34380 |
| cggacataca aaaatcgatc cgtgtggtta aagagcagca cagttagctc ctgtcttctc | 34440 |
| ccagcaaaga tcacatcgga ctgggttagt atgcccctgg aatggtagtc attcaaggcc | 34500 |
| ataaatctgc cttggtagcc attaggaatc agcacgctca ctctcaagtg aaccaaaacc | 34560 |
| accccatgcg gaggaatgtg gaaagattct gggcaaaaaa aggtatatct attgctagtc | 34620 |
| ccttcctgga cgggagcaat ccctccaggg ctatctatga aagcatacag agattcagcc | 34680 |
| atagctcagc ccgcttacca gtagacagag agcacagcag tacaagcgcc aacagcagcg | 34740 |
| actgactacc cactgaccca gctccctatt taaaggcacc ttacactgac gtaatgacca | 34800 |
| aaggtctaaa aaccccgcca aaaaacaca cacgccctgg gtgttttttcg cgaaaacact | 34860 |
| tccgcgttct cacttcctcg tatcgatttc gtgactcaac ttccgggttc ccacgttacg | 34920 |
| tcacttctgc ccttacatgt aactcagccg tagggcgcca tcttgcccac gtccaaaatg | 34980 |
| gcttccatgt ccggccacgc ctccgcgcg accgttagcc gtgcgtcgtg acgtcatttg | 35040 |
| catcaccgtt tctcgtccaa tcagcgttgg ctccgcccca aaaccgttaa aattcaaaag | 35100 |
| ctcatttgca tattaacttt tgtttacttt gtggggtata ttattgatga tg | 35152 |

<210> SEQ ID NO 2
<211> LENGTH: 34126
<212> TYPE: DNA
<213> ORGANISM: Artificial Sequence
<220> FEATURE:
<223> OTHER INFORMATION: pWe/Ad26.pIX-rITR.dE3.dE4.26orf6

<400> SEQUENCE: 2

| | |
|---|---:|
| gtaggtattc cctctcaaga gcgggcatga cctcggcact caggttgtca gtttctagaa | 60 |
| acgaggagga tttgatgtgg gcctgccctg ccgcgatgct ttttaggaga ctttcatcca | 120 |
| tctggtcaga aaagactatt tttttattgt caagcttggt ggcgaaggag ccatagaggg | 180 |
| cgtttgagag aagcttggcg atggatctca tggtctgatt tttgtcacgg tcggcgcgct | 240 |
| ccttggccgc gatgttgagc tggacatatt cgcgcgcgac acacttccat tcggggaaga | 300 |
| cggtggtgcg ctcgtcgggc acgatcctga cgcgccagcc gcggttatgc agggtgacca | 360 |
| ggtccacgct ggtggccacc tcgccgcgca gggctcgtt ggtccagcag agtctgccgc | 420 |
| ccttgcgcga gcagaacggg ggcagcacat caagcagatg ctcgtcaggg gggtccgcat | 480 |
| cgatggtgaa gatgcccgga cagagttcct tgtcaaaata atcgattttt gaggatgcat | 540 |
| cgtccaaggc catctgccac tcgcgggcgg ccagcgctcg ctcgtagggg ttgaggggcg | 600 |
| gaccccaagg catgggatgc gtgagggcgg aggcgtacat gccgcagatg tcatagacat | 660 |
| agatgggctc cgagaggatg ccgatgtagg tgggatagca gcgcccccg cggatgcttg | 720 |
| cgcgcacgta gtcatacaac tcgtgcgagg gggccaagaa ggcggggccg agattggtgc | 780 |
| gctgggggctg ctcggcgcgg aagacgatct ggcgaaagat ggcgtgcgag ttggaggaga | 840 |
| tggtgggccg ttggaagatg ttaaagtggg cgtgaggcag gcggaccgag tcgcggatga | 900 |
| agtgcgcgta ggagtcttgc agcttggcga cgagctcggc ggtgacgagg acgtccatgg | 960 |
| cgcagtagtc cagcgtttcg cggatgatgt cataactcgc ctctcctttc ttctcccaca | 1020 |
| gctcgcggtt gagggcgtat tcctcgtcat ccttccagta ctcccggagc gggaatcctc | 1080 |
| gatcgtccgc acggtaagag cccagcatgt agaaatggtt cacggccttg tagggacagc | 1140 |
| agcccttctc cacggggagg gcgtaagctt gagcggcctt gcggagcgag gtgtgcgtca | 1200 |

```
gggcaaaggt gtccctgacc atgactttca agaactggta cttgaagtcc gagtcgtcgc   1260
agccgccgtg ctcccagagc tcgaaatcgg tgcgcttctt cgagaggggg ttaggcagag   1320
cgaaagtgac gtcattgaag agaatcttgc ctgcccgcgg catgaaattg cgggtgatgc   1380
ggaaagggcc cgggacggag gctcggttgt tgatgacctg ggcggcgagg acgatctcgt   1440
caaagccgtt gatgttgtgc ccgacgatgt agagttccat gaatcgcggg cggcctttga   1500
tgtgcggcag cttttgagc tcctcgtagg tgaggtcctc ggggcattgc aggccgtgct   1560
gctcgagcgc ccactcctgg agatgtgggt tggcttgcat gaaggaagcc cagagctcgc   1620
gggccatgag ggtctggagc tcgtcgcgaa agaggcggaa ctgctggccc acggccatct   1680
tttctggggt gacgcagtag aaggtgaggg ggtcccgctc ccagcgatcc cagcgtaaac   1740
gcacggcgag atcgcgagcg agggcgacca gctctgggtc cccggagaat tcatgacca    1800 gcatgaaggg gacgagctgc ttgccgaagg accccatcca ggtgtaggtt tctacatcgt   1860
aggtgacaaa gagccgctcc gtgcgaggat gagagccgat tgggaagaac tggatttcct   1920
gccaccagtt ggacgagtgg ctgttgatgt gatgaaagta gaaatcccgc cggcgaaccg   1980
agcactcgtg ctgatgcttg taaaagcgtc cgcagtactc gcagcgctgc acgggctgta   2040
cctcatccac gagatacaca gcgcgtccct tgaggaggaa cttcaggagt ggcggccctg   2100
gctggtggtt ttcatgttcg cctgcgtggg actcaccctg gggctcctcg aggacgagaa   2160
ggctgacgag cccgcgcggg agccaggtcc agatctcggc gcggcggggg cggagagcga   2220
agacgagggc gcgcagttgg gagctgtcca tggtgtcgcg gagatccagg tccggggca   2280 gggttctgag gttgacctcg tagaggcggg tgagggcgtg cttgagatgc agatggtact   2340
tgatttctac gggtgagttg gtggtcgtgt ccacgcattg catgagcccg tagctgcgcg   2400
gggccacgac cgtgccgcgg tgcgctttta gaagcggtgt cgcggacgcg ctcccggcgg   2460
cagcggcggt tccggccccg cgggcagggg cggcagaggc acgtcggcgt ggcgctcggg   2520
caggtcccgg tgctgcgccc tgagagcgct ggcgtgcgcg acgacgcggc ggttgacatc   2580
ctggatctgc cgcctctgcg tgaagaccac gggcccgtg actttgaacc tgaaagacag   2640
ttcaacagaa tcaatctctg cgtcattgac ggcggcctga cgcaggatct cttgcacgtc   2700
gcccgagttg tcctggtagg cgatctcgga catgaactgt tcgatctcct cctcctggag   2760
atcgccgcgg cccgcgcgct ccacggtggc ggcgaggtca ttggagatgc gacccatgag   2820
ctgcgagaag gcgcccaggc cgctctcgtt ccagacgcgg ctgtagacca cgtccccgtc   2880
ggcgtcgcgc gcgcgcatga ccacctgcgc gaggttgagc tccacgtgcc gcgcaaagac   2940
ggcgtagttg cgcaggcgct ggaagaggta gttgagggtg gtggcgatgt gctcggtgac   3000
gaagaagtac atgatccagc ggcgcagggg catctcgctg atgtcgccga tggcttccag   3060
cctttccatg gcctcgtaga agtccacggc gaagttgaaa aactgggcgt tgcgggccga   3120
gaccgtgagc tcgtcttcca ggagccggat gagttcggcg atggtggcgc gcacctcgcg   3180
ctcgaaatcc ccgggggcct cctcctcttc ctcttcttcc atgacgacct cttcttctat   3240
ttcttcctct gggggcggtg gtggtggcgg gggccgacga cgacggcgac gcaccgggag   3300 acgtcgacg aagcgctcga tcatctcccc gcggcggcga cgcatggttt cggtgacggc   3360
gcgaccccgt tcgcgaggac gcagcgtgaa gacgccgccg gtcatctccc ggtaatgggg   3420
cgggtcccca ttgggcagcg ataggcgct gacgatgcat cttatcaatt gcggtgtagg   3480
ggacgtgagc gcgtcgagat cgaccggatc ggagaatctt tcgaggaaag cgtctagcca   3540
```

-continued

```
atcgcagtcg caaggtaagc tcaaacacgt agcagccctg cggacgctgt tagaattgcg    3600
gttgctgatg atgtaattga agtaggcgtt tttgaggcgg cggatggtgg cgaggaggac    3660
caggtccttg ggtccagctt gctggatgcg gagccgctcg gccatgcccc aggcctggcc    3720
ctgacaccgg ctcaggttct tgtagtagtc atgcatgagc ctctcaatgt catcactggc    3780
tgaggcggag tcttccatgc gggtgacccc gacgcccctg agcggctgca cgagcgccag    3840
gtcggcgacg acgcgctcgg cgaggatggc ctgttgcacg cgggtgaggg tgtcctggaa    3900
gtcgtccatg tcgacgaagc ggtgataggc cccggtgttg atggtgtagg tgcagttggc    3960
catgagcgac cagttgacgg tctgcaggcc tggctcacg acctcggagt acctgagccg     4020
cgagaaggcg cgcgagtcga agacgtagtc gttgcaggtg cgcacgaggt actggtatcc    4080
gactaggaag tgcggcggcg gctggcggta gagcggccag cgctgggtgg ccggcgcgcc    4140
cggggccagg tcctcgagca tgaggcggtg gtagccgtag aggtagcggg acatccaggt    4200
gatgccggcg gcggtggtgg aggcgcgcgg gaactcgcgg acgcggttcc agatgttgcg    4260
cagcggcagg aaatagtcca tggtcggcac ggtctggccg gtgagacgcg cgcagtcatt    4320
gacgctctag aggcaaaaac gaaagcggtt gagcgggctc ttcctccgta gcctggcgga    4380
acgcaaacgg gttaggccgc gtgtgtaccc cggttcgagt cccctcgaat caggctggag    4440
ccgcgactaa cgtggtattg gcactcccgt ctcgacccga gcccgatagc cgccaggata    4500
cggcggagag cccttttgc cggccgagtg gggtcgctag acttgaaagc gaccgaaaac     4560
cctgccgggt agtggctcgc gcccgtagtc tggagaagca tcgccagggt tgagtcgcgg    4620
cagaacccgg ttcgaggacg gccgcggcga gcgggacttg gtcaccccgc cgatataaag    4680
acccacagcc agccgacttc tccagttacg ggagcgagcc cccttttttc tttttgccag    4740
atgcatcccg tcctgcgcca aatgcgtccc accccccggg cgaccaccgc gaccgcggcc    4800
gtagcaggcg ccggcgctag ccagccacca cagacagaga tggacttgga agagggcgaa    4860
gggctggcaa gactggggc gccgtccccg gagcgacatc cccgcgtgca gctgcagaag     4920
gacgtgcgcc cggcgtacgt gcctacgcag aacctgttca gggaccgcag cggggaggag    4980
cccgaggaga tgcgcgactg ccggtttcgg gcgggcaggg agctgcgcga gggcctggac    5040
cgccagcgcg tgctgcgcga cgaggatttc gagccgaacg agcagacggg gatcagcccc    5100
gcacgcgcgc acgtggcggc agccaacctg gtgacggcct acgagcagac ggtgaagcag    5160
gagcgcaact tccaaaagag tttcaacaac cacgtgcgca ccctgatcgc gcgcgaggag    5220
gtggccctgg gcctgatgca cctgtgggac ctggcggagg ccatcgtgca gaacccggac    5280
agcaagcctc tgacggcgca gctgttcctg gtggtgcagc acagcaggga caacgaggcg    5340
ttcagggagg cgctgctgaa catcgccgag cccgagggtc gctggctgct ggagctgatt    5400
aacatcttgc agagcatcgt agtgcaggag cgcagcctga gcctggccga aaggtggcg     5460 gcgatcaact actcggtgct gagcctgggc aagttttacg cgcgcaagat ttacaagacg    5520
ccgtacgtgc ccatagacaa ggaggtgaag atagacagct tttacatgcg catggcgctc    5580
aaggtgctga cgctgagcga cgacctgggc gtgtaccgca acgaccgcat ccacaaggcc    5640
gtgagcacga gccggcggcg cgagctgagc gaccgcgagc tgatgctgag tctgcgccgg    5700
gcgctggtag ggggcgccgc cggcggcgag gagtcctact tcgacatggg tgcggacctg    5760
cattggcagc cgagccggcg cgccttggag gccgcctacg gttcagagga cttggatgag    5820
gaagaggaag aggaggagga tgcacccgct gcggggtact gacgcctccg tgatgtgttt    5880
ttagatgtcc cagcaagccc cggaccccgc cataagggcg gcgctgcaaa gccagccgtc    5940
```

```
cggtctagca tcggacgact gggaggccgc gatgcaacgc atcatggccc tgacgacccg     6000
caaccccgag tcctttagac aacagccgca ggccaacaga ctctcggcca ttctggaggc     6060
ggtggtcccc tctcggacca accccacgca cgagaaggtg ctggcgatcg tgaacgcgct     6120
ggcggagaac aaggccatcc gtcccgacga ggccgggctg tgtacaacg ccctgctgga     6180 gcgcgtgggc cgctacaaca gcacgaacgt gcagtccaac ctggatcggc tggtgacgga     6240
cgtgcgcgag gccgtggcgc agcgcgagcg gttcaagaac gagggcctgg gctcgctggt     6300
ggcgctgaac gccttcctgg cgacgcagcc ggcgaacgtg ccgcgcgggc aggacgatta     6360
caccaacttt atcagcgcgc tgcggctgat ggtgaccgag gtgccccaga gcgaggtgta     6420
ccagtctggc ccggactact tttccagac gagccggcag ggcttgcaga cggtgaacct     6480
gagccaggct ttcaagaatc tgcgcgggct gtggggcgtg caggcgcccg tgggcgaccg     6540
gtcaacggtg agcagcttgc tgacgcccaa ctcgcggctg ctgctgctgc tgatcgcgcc     6600
cttcaccgac agcggcagcg tgaaccgcaa ctcgtacctg ggccatctgc tgacgctgta     6660
ccgcgaggcc ataggccagg cgcaggtgga cgagcagacc ttccaggaga tcactagcgt     6720
gagccgcgcg ctggggcaga acgacaccga cagtctgagg gccaccctga acttttttgct     6780 gaccaataga cagcagaaga tcccggcgca gtacgcactg tcggccgagg aggaaaggat     6840
tctgagatat gtgcagcaga gcgtagggct gttcctgatg caggagggtg ccaccccag     6900 cgccgcgctg gacatgaccg cgcgcaacat ggaacctagc atgtacgccg ccaaccggcc     6960
gttcatcaat aagctgatgg actacttgca ccgcgcggcg gccatgaaca cggactactt     7020
taccaacgcc atcctgaacc cgcactggct cccgccgccg gggttctaca cgggcgagta     7080
cgacatgccc gaccccaacg acgggttcct gtgggacgac gtggacagcg cggtgttctc     7140
gccgaccttt caaaagcgcc aggaggcgcc gccgagcgag ggcgcggtgg ggaggagccc     7200 cttcctagc ttagggagtt tgcatagctt gccgggctcg gtgaacagcg gcagggtgag     7260
ccggccgcgc ttgctgggcg aggacgagta cctgaacgac tcgctgctgc agccgccgcg     7320
ggccaagaac gccatggcca ataacgggat agagagtctg gtggacaaac tgaaccgctg     7380
gaagacctac gctcaggacc atagggacgc gcccgcgccg cggcgacagc gccacgaccg     7440
gcagcggggc ctggtgtggg acgacgagga ctcggccgac gatagcagcg tgttggactt     7500
gggcgggagc ggtggggtca acccgttcgc gcatctgcag cccaaactgg ggcgacggat     7560
gttttgaatg aaataaaact caccaaggcc atagcgtgcg ttctcttcct tgttagagat     7620
gaggcgcgcg gtggtgtctt cctctcctcc tccctcgtac gagagcgtga tggcgcaggc     7680
gaccctggag gttccgtttg tgcctccgcg gtatatggct cctacggagg gcagaaacag     7740
cattcgttac tcggagctgg ctccgcagta cgacaccact cgcgtgtact ggtggacaa     7800 caagtcggcg gacatcgctt ccctgaacta ccaaaacgac cacagcaact tcctgaccac     7860
ggtggtgcag aacaacgatt tcacccccgc cgaggccagc acgcagacga taaattttga     7920
cgagcggtcg cggtggggcg tgatctgaa gaccattctg cacactaaca tgcccaatgt     7980
gaacgagtac atgttcacca gcaagtttaa ggcgcgggtg atggtgtcta ggaagcatcc     8040 agaggggta gttgaaacag atttgagtca ggataagctt gaatatgagt ggtttgagtt     8100
taccctgccc gagggaaact tttccgagac catgaccata gacctgatga caacgccat     8160 cttggaaaac tacttgcaag tggggcggca gaatggcgtg ctggagagcg atatcggagt     8220
caagtttgac agcagaaatt tcaagctggg ctggacccg gtgaccaagc tggtgatgcc     8280
```

```
agggtctac acctacgagg ccttccaccc ggacgtggtg ctgctgccgg gctgcgggt      8340
ggacttcacc gagagccgcc tgagcaacct cctgggcatt cgcaagaagc aacctttcca   8400
agagggcttc agaatcatgt atgaggatct agaaggtggc aacatccccg ccctccttga   8460
tgtgcccaag tacttggaaa gcaagaagaa agttgaagac gaaactaaaa atgcagctgc   8520
ggccacagcc gatacaacca ctaggggtga tacatttgca actccagcgc aagagacagc   8580
agctgataag aaggtagaag tcttgcccat tgaaaaggat gagagtggta aagttacaa    8640
cctgatccag gggacccacg acacgctgta ccgcagttgg tacctgtcct atacctacgg   8700
ggaccccgag aaggggggtgc agtcgtggac gctgctcacc accccggacg ttacctgcgg   8760
cgcggagcaa gtctactggt cactgccgga cctcatgcaa gaccccgtca ccttccgctc   8820
cacccagcaa gtcagcaact accccgtggt cggcgccgag ctcatgccct ccgcgccaa    8880
gagcttttac aacgacctcg ccgtctactc ccagctcatc cgcagctaca cctccctcac   8940
ccacgtcttc aaccgcttcc ccgacaacca gatcctctgc cgcccgcccg cgcccaccat   9000
caccaccgtc agtgaaaacg tgcctgctct cacagatcac gggacgctac cgctgcgcag   9060
cagtatccgc ggagtccagc gagtgaccgt cactgacgcc cgtcgccgca cctgtcccta   9120
cgtctacaag gccctgggca tagtcgcgcc gcgcgtgctt ccagtcgca ccttctaaaa    9180
aaatgtctat tctcatctcg cccagcaata acaccggctg gggtcttact agacccagca   9240
ccatgtacgg aggagccaag aagcgctccc agcagcaccc cgtccgcgtc cgcggccact   9300
tccgcgctcc ctggggcgca tacaagcgcg gcggacttc accgccgcc gtgcgcacca    9360
ccgtcgacga cgtcatcgac tcggtggtcg ccgacgcgcg caactatacc cccgcccct    9420
ccaccgtgga cgcggtcatc gacagcgtgg tggccgacgc gcgcgactat gccagacgca   9480
agagccggcg gcgacggatc gccaggcgcc accgagcac gcccgccatg cgcgccgccc    9540
gggctctgct gcgccgcgcc agacgcacgg gccgccgggc catgatgcga ccgcgcgcc    9600
gcgctgccac tgcacccacc cccgcaggca ggactcgcag acgagcggcc gccgccgccg   9660
ctgcggccat ctctagcatg accagaccca ggcgcggaaa cgtgtactgg gtgcgcgact   9720
ccgtcacggg cgtgcgcgtg cccgtgcgca cccgtcctcc tcgtccctga tctaatgctt   9780
gtgtcctccc ccgcaagcga cgatgtcaaa gcgcaaaatc aaggaggaga tgctccaggt   9840
cgtcgccccg gagatttacg gaccacccca ggcggaccag aaaccccgca aaatcaagcg   9900
ggttaaaaaa aaggatgagg tggacgaggg ggcagtagag tttgtgcgcg agttcgctcc   9960
gcggcggcgc gtaaattgga agggggcgcag ggtgcagcgc gtgttgcggc ccggcacggc  10020
ggtggtgttc acgcccggcg agcggtcctc ggtcaggagc aagcgtagct atgacgaggt  10080
gtacggcgac gacgacatcc tggaccaggc ggcggagcgg gcgggcgagt cgcctacgg    10140
gaagcggtcg cgcgaagagg agctgatctc gctgccgctg gacgaaagca ccccacgcc    10200
gagcctgaag cccgtgaccc tgcagcaggt gctgccccag gcggtgctgc tgccgagccg   10260
cgggggtcaag cgcgagggcg agagcatgta cccgaccatg cagatcatgg tgcccaagcg  10320
ccggcgcgtg gaggacgtgc tggacaccgt gaaaatggat gtggagcccg aggtcaaggt   10380
gcgccccatc aagcaggtgg cgccgggcct gggcgtgcaa accgtggaca ttcagatccc   10440
caccgacatg gatgtcgaca aaaaaccctc gaccagcatc gaggtgcaaa ccgaccctg    10500
gctcccagcc tccaccgcta ccgtctccac ttctaccgcc gccacggcta ccgagcctcc   10560
caggaggcga agatggggcg ccgccagccg gctgatgccc aactacgtgt tgcatccttc   10620
catcatcccg acgccgggct accgcggcac ccggtactac gccagccgcc ggcgcccagc   10680
```

```
cagcaaacgc cgccgccgca ccgccacccg ccgccgtctg gccccgccc gcgtgcgccg    10740 cgtgaccacg cgccggggcc gctcgctcgt tctgcccacc gtgcgctacc accccagcat    10800
cctttaatcc gtgtgctgtg atactgttgc agagagatgg ctctcacttg ccgcctgcgc    10860
atccccgtcc cgaattaccg aggaagatcc cgccgcagga gaggcatggc aggcagcggc    10920
ctgaaccgcc gccggcggcg ggccatgcgc aggcgcctga gtggcggctt tctgcccgcg    10980
ctcatcccca taatcgccgc ggccattggc acgatcccgg gcatagcttc cgttgcgctg    11040
caggcgtcgc agcgccgttg atgtgcgaat aaagcctctt tagactctga cacacctggt    11100
cctgtatatt tttagaatgg aagacatcaa ttttgcgtcc ctggctccgc ggcacggcac    11160
gcggccgttc atgggcacct ggaacgagat cggcaccagc cagctgaacg ggggcgcctt    11220
caattggagc agtgtctgga gcgggcttaa aaatttcggc tcgacgctcc ggacctatgg    11280
gaacaaggcc tggaatagta gcacggggca gttgttgagg gaaaagctca agaccagaa    11340 cttccagcag aaggtggtgg acgggctggc ctcgggcatt aacggggtgg tggacatcgc    11400
gaaccaggcc gtgcagcgcg agataaacag ccgcctggac ccgcgaccgc ccacggtggt    11460
ggagatggaa gatgcaactc ttccgccgcc caagggcgag aagcggccgc ggcccgacgc    11520
ggaggagacg atcctgcagg tggacgagcc gccctcgtac gaggaggccg tcaaggccgg    11580
catgcccacc acgcgcatca tcgcgccgct ggccacgggt gtaatgaaac ccgccaccct    11640
tgacctgcct ccaccacccg cgcccgctcc accgaaggca actccggttg tgcaggcccc    11700
cccggtggcg accgccgtgc gccgcgtccc cgcccgccgc caggcccaga actggcagag    11760
cacgctgcac agtatcgtgg gcctgggagt gaaaagtctg aagcgccgcc gatgctattg    11820
agagagagga aagaggacac taaagggaga gcttaacttg tatgtgcctt accgccagag    11880
aacgcgcgaa gatggccacc ccctcgatga tgccgcagtg ggcgtacatg cacatcgccg    11940
ggcaggacgc ctcggagtac ctgagcccgg gtctggtgca gtttgcccgc gccaccgaca    12000
cgtacttcag cctgggcaac aagtttagga accccacggt ggccccgacc cacgatgtga    12060
ccacggaccg gtcccagcgt ctgacgctgc gcttcgtgcc cgtggatcgc gaggacacca    12120
cgtactcgta caaggcgcgc ttcactctgg ccgtgggcga caaccgggtg ctagacatgg    12180
ccagcactta ctttgacatc cgcggcgtcc tggaccgcgg tcccagcttc aaaccctact    12240
cgggcacggc ctacaacagc ctggctccca agggtgcccc caatcccagt cagtgggaaa    12300
caaaagaaaa gcaaggaact actggaggag tgcagcaaga aaagatgtc acaaaaacat    12360 ttggtgtggc tgccaccggc ggaattaata taacaaacca gggtctgtta ctaggaactg    12420
acgaaaccgc tgagaatggc aaaaaagaca tttatgcaga caagactttc agccagaac    12480 ctcaagttgg agaagaaaac tggcaggaaa atgaagcctt ctatggagga agggctctta    12540
aaaaggacac taaaatgaaa ccatgctatg atcttttgc tagacctact aatgagaaag    12600
gaggtcaggc aaagttcaaa ccagttaatg aaggagaaca acctaaagat ctggatatag    12660
attttgctta ctttgacgtc cctggcggaa gtcctccagc aggtggtagt ggggaagaat    12720
acaaagcaga tataattttg tacactgaaa atgttaatct tgaaacacca gacactcatg    12780
tggtttacaa gccaggaact tcagataaca gttcagaaat caatctggtt cagcagtcca    12840
tgccaaacag acccaactac attggcttta gggacaactt tgtaggtctc atgtattaca    12900
acagcaccgg aaatatgggt gtgctggctg tcaggcttc tcagttgaac gctgtggtcg    12960
acttgcaaga cagaaacacc gagttatctt accagctatt gctagattct ctgggtgaca    13020
```

```
gaaccagata ctttagcatg tggaactctg cggtggacag ttacgatcca gatgtcagga   13080
tcattgaaaa tcacggtgtg gaagatgaac ttccaaacta ttgcttccca ttgaatggca   13140
ctggaaccaa ttccacttat caaggtgtaa agattacaaa tggtaatgat ggtgctgaag   13200
aaagtgagtg ggagaaagac gatgcaattt ctagacaaaa ccaaatctgc aagggcaatg   13260
tctacgccat ggagatcaac ctgcaggcca acctgtggaa gagttttctg tactcgaacg   13320
tggccctgta cctgcccgac tcctacaagt acacgccggc caacgtcaag ctgcccgcca   13380
acaccaacac ctacgagtac atgaacggcc gcgtggtagc cccctcgctg gtggacgcct   13440
acatcaacat cggcgcccgc tggtcgttgg accccatgga caacgtcaac cccttcaacc   13500
accaccgcaa tgcgggcctg cgctaccgct ccatgctgct gggcaacggc cgctacgtgc   13560
ccttccacat ccaagtgccc caaaagttct ttgccatcaa gaacctgctc ctgctcccgg   13620
gctcctacac ctacgagtgg aacttccgca aggacgtcaa catgatcctg cagagttccc   13680
tcggcaacga cctgcgcgtc gacgcgcct ccgtccgctt cgacagcgtc aacctatacg   13740
ccactttctt ccccatggcg cacaacaccg cttcaacctt ggaagccatg ctgcgcaacg   13800
acaccaacga ccagtccttc aacgactacc tctcggccgc caacatgctc taccccatcc   13860
cggccaaggc caccaacgtg cccatctcca tcccatcgcg caactgggcc gccttccgcg   13920
gctggagttt cacccggctc aagaccaagg aaactccttc cctcggctcg ggtttcgacc   13980
cctactttgt ctactcgggc tccatcccct acctcgacgg gaccttctac ctcaaccaca   14040
ccttcaagaa ggtctccatc atgttcgact cctcggtcag ctggcccggc aacgaccggc   14100
tgctcacgcc gaacgagttc gagatcaagc gcagcgtcga cggggagggc tacaacgtgg   14160
cccaatgcaa catgaccaag gactggttcc tcgtccagat gctctcccac tacaacatcg   14220
gctaccaggg cttccacgtg cccgagggct acaaggaccg catgtactcc ttcttccgca   14280
acttccagcc catgagcagg caggtggtcg atgagatcaa ctacaaggac tacaaggccg   14340
tcaccctgcc cttccagcac aataactcgg gcttcaccgg ctacctcgca cccaccatgc   14400
gccaggggca gccctacccc gccaacttcc cctacccgct catcggtcag acagccgtgc   14460
cctccgtcac ccagaaaaag ttcctctgcg acagggtcat gtggcgcatc cccttctcca   14520
gcaacttcat gtccatgggc gccctcaccg acctgggtca gaacatgctc tacgccaact   14580
cggcccacgc gctcgacatg accttcgagg tggaccccat ggatgagccc accctcctct   14640
atcttctctt cgaagttttc gacgtggtca gagtacacca gccgcaccgc ggcgtcatcg   14700
aggccgtcta cctgcgcacg cccttctccg ccggcaacgc caccacctaa gcatgagcgg   14760
ctccagcgaa cgagagctcg cggccatcgt gcgcgacctg ggctgcgggc cctactttt   14820 gggcacccac gacaagcgct tcccgggctt tctcgccggc gacaagctgg cctgcgccat   14880
cgtcaacacg gccggccgcg agaccggagg cgtgcactgg ctcgccttcg gctggaaccc   14940
gcgctcgcgc acctgctaca tgttcgaccc ctttgggttc tcggaccgcc ggctcaagca   15000
gatttacagc ttcgagtacg aggccatgct gcgccgcagc ccctggcct cctcgcccga   15060 ccgctgtctc agcctcgagc agtccactca gaccgtgcag gggcccgact ccgccgcctg   15120
cggactcttc tgttgcatgt tcttgcatgc cttcgtgcac tggcccgacc gacccatgga   15180
cggaaacccc accatgaact tgctgacggg ggtgcccaac ggcatgctac aatcgccaca   15240
ggtgctgccc accctcaggc gcaaccagga ggaactctac cgcttcctcg cgcgccactc   15300
cccttacttt cgctccccacc gcgccgccat cgaacacgcc accgcttttg acaaaatgaa   15360
acaactgcgt gtatctcaat aaacagcact tttatttac atgcactgga gtatatgcaa   15420
```

```
gttatttaaa agtcgaaggg gttctcgcgc tcgtcgttgt gcgccgcgct ggggagggcc    15480
acgttgcggt actggtactt gggctgccac ttgaactcgg ggatcaccag tttgggcact    15540
ggggtctcgg ggaaggtctc gctccacatg cgccggctca tctgcagggc gcccagcatg    15600
tccggggcgg agatcttgaa atcgcagttg gggccggtgc tctgcgcgcg cgagttgcgg    15660
tacacggggt tgcagcactg gaacaccatc agactggggt acttcacact agccagcacg    15720
ctcttgtcgc tgatctgatc cttgtccaga tcctcggcgt tgctcaggcc gaacgggtc     15780 atcttgcaca gctggcgtcc caggaagggc acgctctgag gcttgtggtt acactcgcag    15840
tgcacgggca tcagcatcat ccccgcgccg cgctgcatat tcgggtagag ggccttgaca    15900
aaggccgcga tctgcttgaa agcttgctgg gccttggccc cctcgctgaa aaacaggccg    15960
cagctcttcc cgctgaactg gttattccca cacccggcat cctgcacgca gcagcgcgcg    16020
tcatggctgg tcagttgcac cacgctccgt ccccagcggt tctgggtcac cttagccttg    16080
ctgggctgct ccttcaacgc gcgctgcccg ttctcgctgg tcacatccat ctccaccacg    16140
tggtccttgt ggatcatcat cgtcccgtgc agacacttga gctggccttc cacctcggtg    16200
cagccgtgat cccacagggc gcaaccggtg cactcccagt tcttgtgcgc aatcccgctg    16260
tggctgaaga tgtaaccttg caacatgcgg cccatgatgg tgctaaatgc tttctgggtg    16320
gtgaaggtca gttgcatccc gcgggcctcc tcgttcatcc aggtctggca catcttctgg    16380
aagatctcgg tctgctcggg catgagcttg taagcatcgc gcaggccgct gtcgacgcgg    16440
tagcgttcca tcagcacgtt catggtatcc atgcccttct cccaggacga gaccagaggc    16500
agactcagag ggttgcgtac gttcaggaca ccggggtcg cgggctcgac gatgcgtttt     16560
ccgtccttgc cttccttcaa tagaaccggc ggctggctga atcccactcc cacgatcacg    16620
gcatcttcct ggggcatctc ttcgtcgggg tctaccttgg tcacatgctt ggtctttctg    16680
gcttgcttct tttttggagg gctgtccacg gggagcacgt cctcctcgga agacccggag    16740
cccacccgct gatactttcg gcgcttggtg ggcagaggag gtggcggcga ggggctcctc    16800
tcctgctccg gcggatagcg cgccgacccg tggccccggg gcggagtggc ctctcggccc    16860
atgaaccggc gcacgtcctg actgccgccg gccattgttt cctaggggaa gatggaggag    16920
cagccgcgta agcaggagca ggaggaggac ttaaccaccc acgagcaacc caaaatcgag    16980
caggacctgg gcttcgaaga gccggctcgt ctagaacccc cacaggatga acaggagcac    17040
gagcaagacg caggccagga ggagaccgac gctgggctcg agcatggcta cctgggagga    17100
gaggaggatg tgctgctgaa acacctgcag cgccagtccc tcatcctccg ggacgccctg    17160
gccgaccgga gcgaaacccc cctcagcgtc gaggagctgt gtcgggccta cgagctcaac    17220
ctcttctcgc cgcgcgtacc ccccaaacgc cagcccaacg gcacctgcga gcccaacccg    17280
cgtctcaact tctatcccgt ctttgcggtc cccgaagccc tcgccaccta tcacatcttt    17340
ttcaagaacc aaaagatccc cgtctcctgc cgcgccaacc gcaccagcgc cgacgcgctc    17400
ctcgctttgg ggcccggcgc gcgcatacct gatatcgctt ccctggaaga ggtgcccaag    17460
atcttcgaag ggctcggtcg ggacgagacg cgcgcggcga acgctctgaa agaaacagca    17520
gaggaagagg gtcacactag cgccctggta gagttggaag gcgacaacgc caggctggcc    17580
gtgctcaagc gcagcgtcga gcttacccac ttcgcctacc ccgccgtcaa cctcccgccc    17640
aaggtcatgc gtcgcatcat ggatcagctc atcatgcccc acatcgaggc cctcgatgaa    17700
agtcaggagc agcgccccga ggacgcccgg cccgtggtca gcgacgagat gctcgcgcgc    17760
```

```
tggctcggga cccgcgaccc ccaggctttg aacagcggc gcaaactcat gctggccgtg   17820
gtcctggtca cccttgagct cgaatgcatg cgccgctttt tcagcgaccc cgagaccctg   17880
cgcaaggtcg aggagaccct gcactacact ttcaggcacg gtttcgtcag gcaggcctgc   17940
aagatctcca acgtggagct gaccaacctg gtctcctgcc tggggatcct gcacgagaac   18000
cgcctgggcc agaccgtgct ccactctacc ctgaagggcg aggcgcggcg ggactatgtc   18060
cgcgactgcg tctttctctt tctctgccac acatggcaag cggccatggg cgtgtggcag   18120
cagtgtctcg aggacgagaa cctaaaggag ctggacaagc ttcttgctag aaaccttaaa   18180
aagctgtgga cgggcttcga cgagcgcacc gtcgcctcgg acctggccga gatcgtcttc   18240
cccgagcgcc tgagacagac gctgaaaggc gggctgcccg acttcatgag ccagagcatg   18300
ttgcaaaact accgcacttt cattcttgag cgatcaggca tcctgcccgc cacctgcaac   18360
gccttcccct ccgactttgt accgctgagc taccgcgagt gtccccgcc gctgtggagc   18420 cactgctacc tcttgcagct ggccaactac atcgcctacc actcggacgt gatcgaggac   18480
gtgagcggcg aggggctgct cgagtgccac tgtcgctgca acctgtgctc cccgcatcgc   18540
tccctggtct gcaaccccca gctcctgagc gagacccagg tcatcggtac cttcgagctg   18600
caaggtccgc aggagtccac cgctccgctg aaactcacgc cggggttgtg gacttccgcg   18660
tacctgcgca aatttgtacc gaagactac cacgcccatg agataaagtt cttttgaggac   18720 caatcgcgtc cgcagcacgc ggatctcacg gcctgcgtca tcacccaggg cgcgatcctc   18780
gcccaattgc acgccatcca aaaatcccgc caagagtttc ttctgaaaaa gggtagaggg   18840
gtctacctgg accccagac gggcgaggtg ctcaacccgg tctccccca gcatgccgag   18900 gaagaagcag gagccgctag tggaggagat ggaagaagaa tgggacagcc aggcagagga   18960
ggacgaatgg gaggaggaga cagaggagga agaattggaa gaggtggaag aggagcaggc   19020
aacagagcag cccgtcgccg caccatccgc gccggcagcc ccgccggtca cggatacaac   19080
ctccgctccg gtcaagcctc ctcgtagatg ggatcaagtg aagggtgacg gtaagcacga   19140
gcggcagggc taccgatcat ggagggccca caaagccgcg atcatcgcct gcttgcaaga   19200 ctgcggggg aacatcgctt tcgcccgccg ctacctgctc ttccaccgcg gggtgaacat   19260
cccccgcaac gtgttgcatt actaccgtca ccttcacagc taagaaaaag caagtcaaag   19320
gagtcgccgg aggaggagga ggaggcctga ggatcgcggc gaacgagccc ttgaccacca   19380
gggagctgag gaaccggatc ttccccactc tttatgccat ttttcagcag agtcgaggtc   19440
agcagcaaga gctcaaagta aaaaaccggt ctctgcgctc gctcacccgc agttgcttgt   19500
accacaaaaa cgaagatcag ctgcagcgca ctctcgaaga cgccgaggct ctgttccaca   19560
agtactgcgc gctcactctt aaagactaag gcgcgcccac ccggaaaaaa ggcgggaatt   19620
acctcatcgc caccatgagc aaggagattc ccacccctta catgtggagc tatcagcccc   19680
aaatgggcct ggccgcgggc gcctcccagg actactccac ccgcatgaac tggctcagtg   19740
ccggcccctc gatgatctca cgggtcaacg gggtccgcag tcatcgaaac cagatattgt   19800
tggagcaggc ggcggtcacc tccacgccca gggcaaagct caacccgcgt aattggccct   19860
ccaccctggt gtatcaggaa atccccgggc cgactaccgt actacttccg cgtgacgcac   19920
tggccgaagt ccgcatgact aactcaggtg tccagctggc cggcggcgct tcccggtgcc   19980
cgctccgccc acaatcgggt ataaaaaccc tggtgatccg aggcagaggc acacagctca   20040
acgacgagtt ggtgagctct tcgatcggtc tgcgaccgga cggagtgttc caactagccg   20100
gagccgggag atcctccttc actcccaacc aggcctacct gaccttgcag agcagctctt   20160
```

```
cggagcctcg ctccggaggc atcggaaccc tccagtttgt ggaggagttt gtgccctcgg   20220
tctacttcaa cccctcctcg ggatcgccag gcctctaccc ggacgagttc ataccgaact   20280
tcgacgcagt gagagaagcg gtggacggct acgactgaat gtcccatggt gactcggctg   20340
agctcgctcg gttgaggcat ctggaccact gccgccgcct gcgctgcttc gcccgggaga   20400
gctgcggact catctacttt gagtttcccg aggagcaccc caacggccct gcacacggag   20460
tgcggatcac cgtagagggc accaccgagt ctcacctggt caggttcttc acccagcaac   20520
ccttcctggt cgagcgggac cggggcgcca ccacctacac cgtctactgc atctgtccaa   20580
ccccgaagtt gcatgagaat ttttgttgta ctctttgtgg tgagtttaat aaaagctaaa   20640
ctcttgcaat actctggacc ttgtcgtcgt caactcaacg agaccgtcta cctcaccaac   20700
cagactgagg taaaactcac ctgcagacca cacaagacct atatcatctg gttcttcgag   20760
aacacctcat ttgcagtctc caacactcac tgcactagtc catgaactga tgttgattaa   20820
aagcccaaaa accaatcagc cccttccccc atttccccat cccccaatta ctcataaaaa   20880
ataaatcatt ggaattaatc attcaataaa gatcacttac ttgaaatctg aaagtatgtc   20940
tctggtgtag ttgttcagca gcacctcggt accctcctcc cagctctggt actccagtcc   21000
ccggcgggcg gcgaacttcc tccacacctt gaaagggatg tcaaattcct ggtccacaat   21060
tttcattgtc ttccctctca gatggcaaag aggctccggg tggaagatga cttcaacccc   21120
gtctacccct atggctacgc gcggaatcag aatatcccct tcctcactcc ccccttttgtc   21180 tcctccgatg gattcaaaaa cttcccccct ggggtcctgt cacttaaact ggctgatcca   21240
atcaccatca acaatgggga tgtctcactt aaggtgggag ggggacttgc tgtagagcaa   21300
cagactggta acctaagcgt aaaccctgat gcacccttgc aagttgcaag tgataagcta   21360
cagcttgctc tggctcctcc attcgaggtc agagatggaa agcttgcttt aaaggcaggt   21420
aatggattaa aagtactaga taattccatt actggattga ctggattatt gaatacactt   21480
gtggtattaa ctggaagggg aataggaacg gaggaattaa aaaatgacga tggtgtaaca   21540
aacaaaggag tcggcttgcg tgtaagactt ggagatgacg gcgggctgac atttgataaa   21600
aagggtgatt tagtagcctg gaataaaaaa gatgacaggc gcaccctgtg gacaacccct   21660
gacacatctc caaattgcaa aatgagtaca gaaaaggatt ctaaacttac gttgacactt   21720
acaaagtgtg gaagtcaggt tctgggaaat gtatctttac ttgcagttac aggtgaatat   21780
catcaaatga ctgctactac aaagaaggat gtaaaaatat cttactatt tgatgagaat   21840 ggaattctat taccatcttc gtcccttagc aaagattatt ggaattacag aagtgatgat   21900
tctattgtat ctcaaaaata taatatgca gttccattca tgccaaacct gacagcttat   21960
ccaaaaccaa gcgctcaaaa tgcaaaaaac tattcaagaa ctaaaatcat aagtaatgtc   22020
tacttaggtg ctcttaccta ccaacctgta attatcacta ttgcatttaa tcaggaaact   22080
gaaaatggat gtgcttattc tataacattt accttcactt ggcaaaaaga ctattctgcc   22140
caacagtttg atgttacatc ttttaccttc tcatatctta cccaagagaa caaagacaaa   22200
gactaataaa atgttttgaa ctgaatttat gaatctttat ttattttttac accagcacgg   22260 gtagtcagtt tcccaccacc agcccatttc acagtgtaaa caattctctc agcacgggtg   22320
gccttaaata gggaaatgtt ctgattagtg cgggaactgg acttggggtc tataatccac   22380
acagtttcct ggcgagccaa acgggggtcg gtgattgaga tgaagccgtc ctctgaaaag   22440
tcatccaagc gggcctcaca gtccaaggtc acagtctggt ggaatgagaa gaacgcacag   22500
```

```
attcatactc ggaaaacagg atgggtctgt gcctctccat cagcgccctc aacagtcttt   22560
gccgccgggg ctcggtgcgg ctgctgcaga tgggatcggg atcgcaagtc tctctgacta   22620
tgatccccac agccttcagc aacagtctcc tggtgcgtcg ggcacagcac cgcatcctga   22680
tctctgccat gttctcacag taagtgcagc acataatcac catgttattc agcagcccat   22740
aattcagggc gctccaacca aagctcatgt tggggatgat ggaacccacg tgaccatcgt   22800
accagatgcg gcagtatatc aggtgcctgc ccctcatgaa cacactgccc atatacatga   22860
tctctttggg catgtttctg ttcacaatct gccggtacca tgggaatcgc tggttgaaca   22920
tgcacccgta aatgactctc ctgaaccaca cggccagcat ggtgcctccc gcccgacact   22980
gcagggatcc cggggctgaa cagtggcaat gcaggatcca gcgctcgtac ccgctcacca   23040
tctgagctct caccaagtcc agggtagcgg ggcacaggca cactgacata catctttta   23100
aaattttat ttcctctggg gtcaggatca tatcccaggg gactggaaac tcttggagca   23160
gggtaaagcc agcagcacat ggtaatccac ggacagaact tacattatga taatctgcat   23220
gatcacaatc gggcaacagg gggtgttgtt cagttagtga ggccctagtc tcctcctcac   23280
atcgtggtaa acgggccctg cggtaaggat gatggcggag cgagctcgac tgttcctcgg   23340
tggacattga aatggattct cttgcgtacc ttgtcgtact acgcgtagct cagcccgctt   23400
accagtagac agagagcaca gcagtacaag cgccaacagc agcgactgac tacccactga   23460
cccagctccc tatttaaagg caccttacac tgacgtaatg accaaaggtc taaaaacccc   23520
gccaaaaaaa cacacacgcc ctgggtgttt ttcgcgaaaa cacttccgcg ttctcacttc   23580
ctcgtatcga tttcgtgact caacttccgg gttcccacgt tacgtcactt ctgcccttac   23640
atgtaactca gccgtagggc gccatcttgc ccacgtccaa aatggcttcc atgtccggcc   23700
acgcctccgc ggcgaccgtt agccgtgcgt cgtgacgtca tttgcatcac cgtttctcgt   23760
ccaatcagcg ttggctccgc cccaaaaccg ttaaaattca aaagctcatt tgcatattaa   23820
cttttgttta ctttgtgggg tatattattg atgatgttaa ttaagacaat tcttgaagac   23880
gaaagggcct cgtgatacgc ctattttat aggttaatgt catgataata atggtttctt   23940
agacgtcagg tggcacttttt cggggaaatg tgcgcggaac ccctatttgt ttattttct   24000
aaatacattc aaatatgtat ccgctcatga gacaataacc ctgataaatg cttcaataat   24060
attgaaaaag gaagagtatg agtattcaac atttccgtgt cgcccttatt cccttttttg   24120
cggcattttg ccttcctgtt tttgctcacc cagaaacgct ggtgaaagta aaagatgctg   24180
aagatcagtt gggtgcacga gtgggttaca tcgaactgga tctcaacagc ggtaagatcc   24240
ttgagagttt tcgccccgaa gaacgttttc caatgatgag cacttttaaa gttctgctat   24300
gtggcgcggt attatcccgt gttgacgccg ggcaagagca actcggtcgc cgcatacact   24360
attctcagaa tgacttggtt gagtactcac cagtcacaga aaagcatctt acggatggca   24420
tgacagtaag agaattatgc agtgctgcca taaccatgag tgataacact gcggccaact   24480
tacttctgac aacgatcgga ggaccgaagg agctaaccgc ttttttgcac aacatggggg   24540
atcatgtaac tcgccttgat cgttgggaac cggagctgaa tgaagccata ccaaacgacg   24600
agcgtgacac cacgatgcct gcagcaatgg caacaacgtt gcgcaaacta ttaactggcg   24660
aactacttac tctagcttcc cggcaacaat taatagactg gatggaggcg gataaagttg   24720
caggaccact tctgcgctcg gcccttccgg ctggctggtt tattgctgat aaatctggag   24780
ccggtgagcg tgggtctcgc ggtatcattg cagcactggg gccagatggt aagccctccc   24840
gtatcgtagt tatctacacg acggggagtc aggcaactat ggatgaacga aatagacaga   24900
```

```
tcgctgagat aggtgcctca ctgattaagc attggtaact gtcagaccaa gtttactcat    24960
atatacttta gattgattta aaacttcatt tttaatttaa aaggatctag gtgaagatcc    25020
tttttgataa tctcatgacc aaaatccctt aacgtgagtt ttcgttccac tgagcgtcag    25080
accccgtaga aagatcaaa ggatcttctt gagatccttt ttttctgcgc gtaatctgct    25140
gcttgcaaac aaaaaaacca ccgctaccag cggtggtttg tttgccggat caagagctac    25200
caactctttt tccgaaggta actggcttca gcagagcgca gataccaaat actgtccttc    25260
tagtgtagcc gtagttaggc caccacttca agaactctgt agcaccgcct acatacctcg    25320
ctctgctaat cctgttacca gtggctgctg ccagtggcga taagtcgtgt cttacccggt    25380
tggactcaag acgatagtta ccggataagg cgcagcggtc gggctgaacg gggggttcgt    25440
gcacacagcc cagcttggag cgaacgacct acaccgaact gagataccta cagcgtgagc    25500
tatgagaaag cgccacgctt cccgaaggga gaaaggcgga caggtatccg gtaagcggca    25560
gggtcggaac aggagagcgc acgagggagc ttccaggggg aaacgcctgg tatctttata    25620
gtcctgtcgg gtttcgccac ctctgacttg agcgtcgatt tttgtgatgc tcgtcagggg    25680
ggcggagcct atggaaaaac gccagcaacg cggcctttttt acggttcctg gccttttgct    25740
ggccttttgc tggccttttg ctcacatgtt ctttcctgcg ttatcccctg attctgtgga    25800
taaccgtatt accgcctttg agtgagctga taccgctcgc cgcagccgaa cgaccgagcg    25860
cagcgagtca gtgagcgagg aagcggaaga gcgctgactt ccgcgtttcc agactttacg    25920
aaacacggaa accgaagacc attcatgttg ttgctcaggt cgcagacgtt ttgcagcagc    25980
agtcgcttca cgttcgctcg cgtatcggtg attcattctg ctaaccagta aggcaacccc    26040
gccagcctag ccgggtcctc aacgacagga gcacgatcat gcgcacccgt cagatccaga    26100
catgataaga tacattgatg agtttggaca aaccacaact agaatgcagt gaaaaaaatg    26160
ctttatttgt gaaatttgtg atgctattgc tttatttgta accattataa gctgcaataa    26220
acaagttaac aacaacaatt gcattcattt tatgtttcag gttcaggggg aggtgtggga    26280
ggttttttaa agcaagtaaa acctctacaa atgtggtatg gctgattatg atctctagtc    26340
aaggcactat acatcaaata ttccttatta acccctttac aaattaaaaa gctaaaggta    26400
cacaattttt gagcatagtt attaatagca gacactctat gcctgtgtgg agtaagaaaa    26460
aacagtatgt tatgattata actgttatgc ctacttataa aggttacaga atattttttcc    26520 ataattttct tgtatagcag tgcagctttt tcctttgtgg tgtaaatagc aaagcaagca    26580
agagttctat tactaaacac agcatgactc aaaaaactta gcaattctga aggaaagtcc    26640
ttggggtctt ctacctttct cttcttttt ggaggagtag aatgttgaga gtcagcagta    26700
gcctcatcat cactagatgg catttcttct gagcaaaaca ggttttcctc attaaaggca    26760
ttccaccact gctcccattc atcagttcca taggttggaa tctaaaatac acaaacaatt    26820
agaatcagta gttaacaca ttatacactt aaaaatttta tatttacctt agagctttaa    26880
atctctgtag gtagtttgtc caattatgtc acaccacaga agtaaggttc cttcacaaag    26940
atccggacca aagcggccat cgtgcctccc cactcctgca gttcggggc atggatgcgc    27000 ggatagccgc tgctggtttc ctggatgccg acggatttgc actgccggta gaactccgcg    27060
aggtcgtcca gcctcaggca gcagctgaac caactcgcga ggggatcgag cccggggtgg    27120
gcgaagaact ccagcatgag atcccccgcg tggaggatca tccagccggc gtccggaaa    27180 acgattccga agcccaacct ttcatagaag gcggcggtgg aatcgaaatc tcgtgatggc    27240
```

```
aggttgggcg tcgcttggtc ggtcatttcg aaccccagag tcccgctcag aagaactcgt  27300
caagaaggcg atagaaggcg atgcgctgcg aatcgggagc ggcgataccg taaagcacga  27360
ggaagcggtc agcccattcg ccgccaagct cttcagcaat atcacgggta gccaacgcta  27420
tgtcctgata gcggtccgcc acacccagcc ggccacagtc gatgaatcca gaaaagcggc  27480
cattttccac catgatattc ggcaagcagg catcgccatg ggtcacgacg agatcctcgc  27540
cgtcgggcat gcgcgccttg agcctggcga acagttcggc tggcgcgagc ccctgatgct  27600
cttcgtccag atcatcctga tcgacaagac cggcttccat ccgagtacgt gctcgctcga  27660
tgcgatgttt cgcttggtgg tcgaatgggc aggtagccgg atcaagcgta tgcagccgcc  27720
gcattgcatc agccatgatg gatactttct cggcaggagc aaggtgagat gacaggagat  27780
cctgccccgg cacttcgccc aatagcagcc agtcccttcc cgcttcagtg acaacgtcga  27840
gcacagctgc gcaaggaacg cccgtcgtgg ccagccacga tagccgcgct gcctcgtcct  27900
gcagttcatt cagggcaccg gacaggtcgg tcttgacaaa agaaccggg cgcccctgcg   27960
ctgacagccg gaacacggcg gcatcagagc agccgattgt ctgttgtgcc cagtcatagc  28020
cgaatagcct ctccacccaa gcggccggag aacctgcgtg caatccatct tgttcaatca  28080
tgcgaaacga tcctcatcct gtctcttgat cagatcttga tccctgcgc catcagatcc   28140
ttggcggcaa gaaagccatc cagtttactt tgcagggctt cccaacctta ccagagggcg  28200
ccccagctgg caattccggt tcgcttgctg tccataaaac cgcccagtct agctatcgcc  28260
atgtaagccc actgcaagct acctgctttc tctttgcgct tgcgttttcc cttgtccaga  28320
tagcccagta gctgacattc atccggggtc agcaccgttt ctgcggactg gctttctacg  28380
tgttccgctt cctttagcag cccttgcgcc ctgagtgctt gcggcagcgt gaagcttttt  28440
gcaaaagcct aggcctccaa aaaagcctcc tcactactc tggaatagct cagaggccga   28500
ggcggcctcg gcctctgcat aaataaaaaa aattagtcag ccatggggcg gagaatgggc  28560
ggaactgggc ggagttaggg gcgggatggg cggagttagg ggcggactga tggttgctga  28620
ctaattgaga tgcatgcttt gcatacttct gcctgctggg gagcctgggg acttccaca   28680
cctggttgct gactaattga gatgcatgct ttgcatactt ctgcctgctg gggagcctgg  28740
ggactttcca caccctaact gacacacatt ccacagccgg atctgcagga cccaacgctg  28800
cccgagatgc gccgcgtgcg gctgctggag atggcggacg cgatggatat gttctgccaa  28860
gggttggttt gcgcattcac agttctccgc aagaattgat tggctccaat tcttggagtg  28920
gtgaatccgt tagcgaggtg ccgccggctt ccattcaggt cgaggtggcc cggctccatg  28980
caccgcgacg caacgcgggg aggcagacaa ggtatagggc ggcgcctaca atccatgcca  29040
acccgttcca tgtgctcgcc gaggcggcat aaatcgccgt gacgatcagc ggtccaatga  29100
tcgaagttag gctggtaaga gccgcgagcg atccttgaag ctgtccctga tggtcgtcat  29160
ctacctgcct ggacagcatg gcctgcaacg cgggcatccc gatgccgccg aagcgagaa   29220
gaatcataat ggggaaggcc atccagcctc gcgtcgcgaa cgccagcaag acgtagccca  29280
gcgcgtcggc cgccatgccg gcgataatgg cctgcttctc gccgaaacgt ttggtggcgg  29340
gaccagtgac gaaggcttga gcgagggcgt gcaagattcc gaataccgca agcgacaggc  29400
cgatcatcgt cgcgctccag cgaaagcggt cctcgccgaa aatgacccag agcgctgccg  29460
gcacctgtcc tacgagttgc atgataaaga agacagtcat aagtgcggcg acgatagtca  29520
tgccccgcgc ccaccggaag gagctgactg ggttgaaggc tctcaagggc atcggtcgac  29580
gctctccctt atgcgactcc tgcattagga agcagcccag tagtaggttg aggccgttga  29640
```

```
gcaccgccgc cgcaaggaat ggtgcatgca aggagatggc gcccaacagt cccccggcca   29700
cggggcctgc caccatacco acgccgaaac aagcgctcat gagcccgaag tggcgagccc   29760
gatcttcccc atcggtgatg tcggcgatat aggcgccagc aaccgcacct gtggcgccgg   29820
tgatgccggc cacgatgcgt ccggcgtaga ggatcttggc agtcacagca tgcgcatatc   29880
catgcttcga ccatgcgctc acaaagtagg tgaatgcgca atgtagtacc cacatcgtca   29940
tcgctttcca ctgctctcgc gaataaagat ggaaaatcaa tctcatggta atagtccatg   30000
aaaatccttg tattcataaa tcctccaggt agctatatgc aaattgaaac aaaagagatg   30060
gtgatctttc taagagatga tggaatctcc cttcagtatc ccgatggtca atgcgctgga   30120
tatgggatag atgggaatat gctgattttt atgggacaga gttgcgaact gttcccaact   30180
aaaatcattt tgcacgatca gcgcactacg aactttaccc acaaatagtc aggtaatgaa   30240
tcctgatata aagacaggtt gataaatcag tcttctacgc gcatcgcacg cgcacaccgt   30300
agaaagtctt tcagttgtga gcctgggcaa accgttaact ttcggcggct ttgctgtgcg   30360
acaggctcac gtctaaaagg aaataaatca tgggtcataa aattatcacg ttgtccggcg   30420
cggcgacgga tgttctgtat gcgctgtttt tccgtggcgc gttgctgtct ggtgatctgc   30480
cttctaaatc tggcacagcc gaattgcgcg agcttggttt tgctgaaacc agacacacag   30540
caactgaata ccagaaagaa aatcacttta cctttctgac atcagaaggg cagaaatttg   30600
ccgttgaaca cctggtcaat acgcgttttg gtgagcagca atattgcgct tcgatgacgc   30660
ttggcgttga gattgatacc tctgctgcac aaaaggcaat cgacgagctg gaccagcgca   30720
ttcgtgacac cgtctccttc gaacttattc gcaatggagt gtcattcatc aaggacgccg   30780
ctatcgcaaa tggtgctatc cacgcagcgg caatcgaaac acctcagccg gtgaccaata   30840
tctacaacat cagccttggt atccagcgtg atgagccagc gcagaacaag gtaaccgtca   30900
gtgccgataa gttcaaagtt aaacctggtg ttgataccaa cattgaaacg ttgatcgaaa   30960
acgcgctgaa aaacgctgct gaatgtgcgg cgctggatgt cacaaagcaa atggcagcag   31020
acaagaaagc gatggatgaa ctggcttcct atgtccgcac ggccatcatg atggaatgtt   31080
tccccggtgg tgttatctgg cagcagtgcc gtcgatagta tgcaattgat aattattatc   31140
atttgcgggt cctttccggc gatccgcctt gttacggggc ggcgacctcg cgggttttcg   31200
ctatttatga aaattttccg gtttaaggcg tttccgttct tcttcgtcat aacttaatgt   31260
ttttatttaa ataccctct gaaaagaaag gaaacgacag gtgctgaaag cgagcttttt   31320
ggcctctgtc gtttccttc tctgttttg tccgtggaat gaacaatgga agtcaacaaa   31380
aagcagctgg ctgacatttt cggtgcgagt atccgtacca ttcagaactg caggaacag   31440 ggaatgcccg ttctgcgagg cggtggcaag ggtaatgagg tgctttatga ctctgccgcc   31500
gtcataaaat ggtatgccga aagggatgct gaaattgaga acgaaaagct gcgccgggag   31560
gttgaagaac tgcggcaggc cagcgaggca gatccacagg acgggtgtgg tcgccatgat   31620
cgcgtagtcg atagtggctc caagtagcga agcgagcagg actgggcggc ggccaaagcg   31680
gtcggacagt gctccgagaa cgggtgcgca tagaaattgc atcaacgcat atagcgctag   31740
cagcacgcca tagtgactgg cgatgctgtc ggaatggacg atatcccgca agaggcccgg   31800
cagtaccggc ataaccaagc ctatgcctac agcatccagg gtgacggtgc cgaggatgac   31860
gatgagcgca ttgttagatt tcatacacgg tgcctgactg cgttagcaat ttaactgtga   31920
taaactaccg cattaaagct tatcgatgat aagcggtcaa acatgagaat tgcggttaat   31980
```

```
taatgctggc cctgctggcc gagctggaag ccctgagccg ccagctggcc gccctgaccc   32040
agcaggtgtc cgagctccgc gaacagcagc agcagcaaaa taaatgattc aataaacaca   32100
gattctgatt caaacagcaa agcatcttta ttatttattt tttcgcgcgc ggtaggccct   32160
ggtccacctc tcccgatcat tgagagtgcg gtggattttt tccaggaccc ggtagaggtg   32220
ggattggatg ttgaggtaca tgggcatgag cccgtcccgt gggtggaggt agcaccactg   32280
catggcctcg tgctctgggg tcgtgttgta gatgatccag tcatagcagg ggcgctgggc   32340
gtggtgctgg atgatgtcct tgaggaggag actgatggcc acggggagcc ccttggtgta   32400
ggtgttggca aaacggttga gctgggaggg atgcatgcgg ggggagatga tgtgcagttt   32460
ggcctggatc ttgaggttgg cgatgttgcc acccagatcc cgccgggggt tcatgttgtg   32520
caggaccacc agaacggtgt agcccgtgca cttggggaac ttgtcatgca acttggaagg   32580
gaatgcgtgg aagaatttgg gacgcccctt gtgcccgccc aggttttcca tgcactcatc   32640
catgatgatg gcaatgggcc cgtgggctgc ggctttggca aagacgtttc tggggtcaga   32700
gacatcgtaa ttatgctcct gggtgagatc atcataagac atttttaatga atttggggcg   32760 gagggtgcca gattggggga cgatggttcc ctcgggcccc ggggcgaagt tcccctcgca   32820
gatctgcatc tcccaggctt tcatctcgga ggggggatc atgtccacct gcggggcgat   32880
gaaaaaaacg gtttccgggg cggggtgat gagctgcgag gagagcaggt ttctcaacag   32940
ctgggacttg ccgcacccgg tcgggccgta gatgaccccg atgacgggtt gcaggtggta   33000
gttcaaggac atgcagctgc cgtcgtcccg gaggagggg gccacctcgt tgagcttgtc   33060
tctgacttgg aggttttccc ggacgagctc gccgaggagg cggtccccgc ccagcgagag   33120
aagctcttgc agggaagcaa agttttttcag gggcttgagc ccgtcggcca tgggcatctt   33180
ggcgagggtc tgcgagagga gctccaggcg gtcccagagc tcggtgacgt gctctacggc   33240
atctcgatcc agcagacttc ctcgtttcgg gggttgggac gactgcgact gtagggcacg   33300
agacgatggg cgtccagcgc ggccagcgtc atgtccttcc agggtctcag ggtccgcgtg   33360
agggtggtct ccgtcacggt gaaggggtgg gccgcgggct gggcgcttgc aagggtgcgc   33420
ttgagactca tcctgctggt gctgaaacgg gcacggtctt cgccctgcgc gtcggcgaga   33480
tagcagttga ccatgagctc gtagttgagg gcctcggcgg cgtggccctt ggcgcggagc   33540
ttgcccttgg aagagcgccc gcaggcggga cagaggaggg attgcagggc gtagagcttg   33600
ggcgcgagaa agacggactc gggggcgaag gcgtccgctc cgcagtgggc gcagacggtc   33660
tcgcactcga ctagccaggt gagctcgggc tgctcggggt caaaaaccag ttttccccccg   33720 ttctttttga tgcgcttctt acctcgcgtc tccatgagtc tgtgtccgcg ctcggtgaca   33780
aacaggctgt ctgtgtcccc gtagacggac ttgatgggcc tgtcctgcag gggcgtcccg   33840
cggtcctcct cgtagagaaa ctcagaccac tctgagacga aggcgcgcgt ccacgccaag   33900
acaaaggagg ccacgtgcga ggggtagcgg tcgttgtcca ccaggggggtc cacctttttcc   33960 acggtatgca ggcacatgtc cccctcctcc gcatccaaga aggtgattgg cttgtaggtg   34020
taggccacgt gacctggggt tcccgacggg ggggtataaa aggggggcggg tctgtgctcg   34080 tcctcactct cttccgcgtc gctgtccacg agcgccagct gttggg                 34126
```

<210> SEQ ID NO 3
<211> LENGTH: 9071
<212> TYPE: DNA
<213> ORGANISM: Artificial Sequence
<220> FEATURE:
<223> OTHER INFORMATION: pAdApt26.E1atg.Empty

<400> SEQUENCE: 3

```
aaagtaaaca aaagttaata tgcaaatgag cttttgaatt ttaacggttt tggggcggag      60
ccaacgctga ttggacgaga aacggtgatg caaatgacgt cacgacgcac ggctaacggt     120
cgccgcggag gcgtggccta gcccggaagc aagtcgcggg gctgatgacg tataaaaaag     180
cggactttag acccggaaac ggccgatttt cccgcggcca cgcccggata tgaggtaatt     240
ctgggcggat gcaagtgaaa ttaggtcatt ttggcgcgaa aactgaatga ggaagtgaaa     300
agcgaaaaat accggtccct cccagggcgg aatatttacc gagggccgag agactttgac     360
cgattacgtg ggggtttcga ttgcggtgtt tttttcgcga atttccgcgt ccgtgtcaaa     420
gtccggtgtt tatgtcacag atcagctgac ctaggtggtc aatattggcc attagccata     480
ttattcattg gttatatagc ataaatcaat attggctatt ggccattgca tacgttgtat     540
ccatatcata atatgtacat ttatattggc tcatgtccaa cattaccgcc atgttgacat     600
tgattattga ctagttatta atagtaatca attacgggt cattagttca tagcccatat      660
atggagttcc gcgttacata acttacggta aatggcccgc ctggctgacc gcccaacgac     720
ccccgcccat tgacgtcaat aatgacgtat gttcccatag taacgccaat agggactttc     780
cattgacgtc aatgggtgga gtatttacgg taaactgccc acttggcagt acatcaagtg     840
tatcatatgc caagtacgcc ccctattgac gtcaatgacg gtaaatggcc cgcctggcat     900
tatgcccagt acatgacctt atgggacttt cctacttggc agtacatcta cgtattagtc     960
atcgctatta ccatggtgat gcggttttgg cagtacatca atgggcgtgg atagcggttt    1020
gactcacggg gatttccaag tctccacccc attgacgtca atgggagttt gttttggcac    1080
caaaatcaac gggactttcc aaaatgtcgt aacaactccg ccccattgac gcaaatgggc    1140
ggtaggcgtg tacggtggga ggtctatata agcagagctc gtttagtgaa ccgtcagatc    1200
gcctggagac gccatccacg ctgttttgac ctccatagaa gacaccggga ccgatccagc    1260
ctccgcggcc gggaacggtg cattggaagc ttggtaccgg tgaattcgct agcgttaacg    1320
gatcctctag acgagatccg aacttgttta ttgcagctta taatggttac aaataaagca    1380
atagcatcac aaatttcaca ataaagcat ttttttcact gcattctagt tgtggtttgt     1440
ccaaactcat caatgtatct tatcatgtct agatacgcgt atcagctgat ccgcagggta    1500
tttaaaccag tcgagtccgt caagaggcca ctcttgagtg ccagcgagta gagatttctc    1560
tgagctccgc tcccagagac cgagaaaaat gagacacctg cgcctcctgc cttcaactgt    1620
gcccggtgag ctggctgtgc ttatgctgga ggactttgtg gatacagtat tggaggacga    1680
actgcatcca gtccgttcg agctgggacc cacacttcag gatctctatg atctggaggt     1740
agatgcccat gatgacgacc taacgagga ggctgtgaat ttaatatttc cagaatctat     1800
gattcttcag gctgacatag ccaacgaatc tactccactt catacaccga ctctgtcacc    1860
catacctgaa ttggaagagg aggacgaact agacctccgg tgttatgagg aaggttttcc    1920
tcccagcgat tcagaggatg aacggggtga gcagaccatg gctctgatct cagactatgc    1980
ttgtgtgatt gtggaggaac aagtagtgat tgaaaattct accgagccag tggagggctg    2040
tagaaaatgc cagtaccacc gggataagtc tggagacccg aacgcatcat gcgctttgtg    2100
ctatatgaaa cagactttca gctttattta cagtaagtgg agtgaatgtg agagaggctg    2160
agtgcttaac acatcactgt gtattgcttg aacagctgtg ctaagtgtgg tttattttg     2220
tttctaggtc cggtgtcaga ggatgagtca tcaccctcag aagaagacca cccgtctccc    2280
```

```
cctgatctca cagatgacac gcccctgcaa gtgcacagac ccaccccagt cagagccagt    2340
ggcgagaggc gagcagctgt tgaaaaaatt gaggacttgt tacatgacat gggtggggat    2400
gaacctttgg acctgagctt gaaacgcccc aggaactagg cgcagctgcg cttagtcatg    2460
tgtaaataaa gttgtacaat aaaagtatat gtgacgcatg caaggtgtgg tttatgactc    2520
atgggcgggg cttagtccta tataagtggc aacacctggg cactgggcac agaccttcag    2580
ggagttcctg atggatgtgt ggactatcct tgcagacttt agcaagacac gccggcttgt    2640
agaggatagt tcagacgggt gctccggggtt ctggagacac tggtttggaa ctcctctatc    2700
tcgcctggtg tacacagtta agaaggatta taaagaggaa tttgaaaata tttttgctga    2760
ctgctctggc ctgctagatt tctgaatct tggccaccag tcccttttcc aggaaagggt    2820
actccacagc cttgattttt ccagcccagg gcgcactaca gccggggttg cttttgtggt    2880
ttttctggtt gacaaatgga gccaggacac ccaactgagc aggggctaca tcctggactt    2940
cgcagccatg cacctgtgga gggcctggat caggcagcgg ggacagagaa tcttgaatta    3000
ctggcttcta cagccagcag ctccgggtct tcttcgtcta cacagacaaa catccatgtt    3060
ggaggaagaa atgaggcagg ccatggacga gaacccgagg agcggcctgg accctccgtc    3120
ggaagaggag ctggattgaa tcaggtatcc agcctgtacc cagagcttag caaggtgctg    3180
acatccatgg ccaggggagt taagaggag aggagcgatg ggggtaatac cgggatgatg    3240
accgagctga cggccagcct gatgaatcgg aagcgcccag agcgccttac ctggtacgag    3300
ctacagcagg agtgcaggga tgagttgggc ctgatgcagg ataaatatgg cctggagcag    3360
ataaaaaccc attggttgaa cccagatgag gattgggagg aggctattaa gaagtatgcc    3420
aagatagccc tgcgcccaga ttgcaagtac atagtgacca agaccgtgaa tatcagacat    3480
gcctgctaca tctcggggaa cggggcagag gtggtcatcg ataccctgga caaggccgcc    3540
ttcaggtgtt gcatgatggg aatgagagca ggagtgatga atatgaattc catgatcttc    3600
atgaacatga agttcaatgg agagaagttt aatggggtgc tgttcatggc caacagccac    3660
atgaccctgc atggctgcag tttcttcggc ttcaacaata tgtgcgcaga ggtctggggc    3720
gcttccaaga tcagggggatg taagttttat ggctgctgga tgggcgtggt cggaagaccc    3780
aagagcgaga tgtctgtgaa gcagtgtgtg tttgagaaat gctacctggg agtctctacc    3840
gagggcaatg ctagagtgag acactgctct tccctggaga cgggctgctt ctgcctggtg    3900
aagggcacag cctctctgaa gcataatatg gtgaagggct gcacggatga gcgcatgtac    3960
aacatgctga cctgcgattc gggggtctgc catatcctga gaacatcca tgtgacctcc    4020 caccccagaa agaagtggcc agtgtttgag aataacctgc tgatcaagtg ccatatgcac    4080
ctgggagcca aaggggcac cttccagccg taccagtgca actttagcca gaccaagctg    4140
ctgttggaga cgatgccctt ctccagggtg aacctgaacg gcatctttga catggatgtc    4200
tcggtgtaca agatcctgag atacgatgag accaagtcca gggtgcgcgc ttgcgagtgc    4260
gggggcagac acaccaggat gcagccagtg gccctgatg tgaccgagga gctgagacca    4320
gaccacctgg tgatggcctg taccgggacc gagttcagct ccagtgggga ggatacagat    4380
tagaggtagg tttgagtagt gggcgtggct aaggtgacta taaaggcggg tgtcttacga    4440
gggtcttttt gctttttctgc agacatcatg aacgggactg gcggggcctt cgaaggggggg    4500 cttttttagcc cttatttgac aacccgcctg ccgggatggg ccggagttcg tcagaatgtg    4560
atgggatcga cggtggatgg gcgcccagtg cttccagcaa attcctcgac catgacctac    4620
gcgaccgtgg ggaactcgtc gctcgacagc accgccgcag ccgcggcagc cgcagccgcc    4680
```

```
atgacagcga cgagactggc ctcgagctac atgcccagca gcggtagtag cccctctgtg    4740
cccagttcca tcatcgccga ggagaaactg ctggccctgc tggccgagct ggaagccctg    4800
agccgccagc tggccgccct gacccagcag gtgtccgagc tccgcgaaca gcagcagcag    4860
caaaataaat gattcaataa acacagattc tgattcaaac agcaaagcat ctttattatt    4920
tattttttcg cgcgcggtag gccctggtcc acctctcccg atcattgaga gtgcggtgga    4980 tttttttccag gacccggtag aggtgggatt ggatgttgag gtacatgggc atgagcccgt    5040
cccgtgggtg gaggtagcac cactgcatgg cctcgtgctc tggggtcgtg ttgtagatga    5100
tccagtcata gcaggggcgc tgggcgtggt gctggatgat gtccttgagg aggagactga    5160
tggccacggg gagccccttg gtgtaggtgt tggcaaaacg gttgagctgg gagggatgca    5220
tgcgggggga gatgatgtgc agtttggcct ggatcttgag gttggcgatg ttgccaccca    5280
gatcccgccg ggggttcatg ttgtgcagga ccaccagaac ggtgtagccc gtgcacttgg    5340
ggaacttgtc atgcaacttg gaagggaatg cgtggaagaa tttggagacg cccttgtgcc    5400
cgcccaggtt ttccatgcac tcatccatga tgatggcaat gggcccgtgg gctgcggctt    5460
tggcaaagac gtttctgggg tcagagacat cgtaattatg ctcctgggtg agatcatcat    5520
aagacatttt aatgaatttg gggcggaggg tgccagattg ggggacgatg gttccctcgg    5580
gccccggggc gaagttcccc tcgcagatct gcatctccca ggctttcatc tcggaggggg    5640
ggatcatgtc cacctgcggg gcgatgaaaa aaacggtttc cggggcgggg gtgatgagct    5700
gcgaggagag caggtttctc aacagctggg acttgccgca cccggtcggg ccgtagatga    5760
ccccgatgac ggggttgcagg tggtagttca aggacatgca gctgccgtcg tcccggagga    5820 gggggggccac ctcgttgagc ttgtctctga cttggaggtt ttcccggacg agctcgccga    5880
ggaggcggtc cccgcccagc gagagaagct cttgcaggga agcaaagttt ttcagggggct    5940 tgagcccgtc ggccatgggc atcttggcga gggtctgcga gaggagctcc aggcggtccc    6000
agagctcggt gacgtgctct acggcatctc gatccagcag acttcctcgt ttcggggggtt    6060 gggacgactg cgactgtagg gcacgagacg atgggcgtcc agcgcggcca gcgtcatgtc    6120
cttccagggt ctcagggtcc gcgtgagggt ggtctccgtc acggtgaagg ggtgggccgc    6180
gggctgggcg cttgcaaggg tgcgcttgag actcatcctg ctggtgctga acgggcacg    6240 gtcttcgccc tgcgcgtcgg cgagatagca gttgaccatg agctcgtagt tgagggcctc    6300
ggcggcgtgg cccttggcgc ggagcttgcc cttggaagag cgcccgcagg cgggacagag    6360
gagggattgc agggcgtaga gcttgggcgc gagaaagacg gactcggggg cgaaggcgtc    6420
cgctccgcag tgggcgcaga cggtctcgca ctcgactagc caggtgagct cgggctgctc    6480
ggggtcaaaa accagttttc ccccgttctt tttgatgcgc ttcttacctc gcgtctccat    6540
gagtctgtgt ccgcgctcgg tgacaaacag gctgtctgtg tccccgtaga cggacttgat    6600
gggcctgtcc tgcaggggcg tcccgcggtc ctcctcgtag agaaactcag accactctga    6660
gacgaaggcg cgcgtccacg ccaagacaaa ggaggccacg tgcgaggggt agcggtcgtt    6720
gtccaccagg gggtccacct tttccacggt atgcaggcac atgtccccct cctccgcatc    6780
caagaaggtg attggcttgt aggtgtaggc cacgtgacct ggggttcccg acgggggggt    6840
ataaaagggg gcgggtctgt gctcgtcctc actctcttcc gcgtcgctgt ccacgagcgc    6900
cagctgttgg ggtaggtatt ccctctcaag attaattaat tcgaacccat aatacccata    6960
atagctgttt gccatcgacg cgaggctgga tggccttccc cattatgatt cttctcgctt    7020
```

```
ccggcggcat cgggatgccc gcgttgcagg ccatgctgtc caggcaggta gatgacgacc    7080
atcagggaca gcttcaagga tcgctcgcgg ctcttaccag cccagcaaaa ggccaggaac    7140
cgtaaaaagg ccgcgttgct ggcgttttc catagctcc gccccctga cgagcatcac     7200
aaaaatcgac gctcaagtca gaggtggcga acccgacag gactataaag ataccaggcg    7260
tttccccctg gaagctccct cgtgcgctct cctgttccga ccctgccgct taccggatac    7320
ctgtccgcct ttctcccttc gggaagcgtg gcgctttctc atagctcacg ctgtaggtat    7380
ctcagttcgg tgtaggtcgt tcgctccaag ctgggctgtg tgcacgaacc ccccgttcag   7440
cccgaccgct gcgccttatc cggtaactat cgtcttgagt ccaacccggt aagcacgac    7500
ttatcgccac tggcagcagc cactggtaac aggattagca gagcgaggta tgtaggcggt    7560
gctacagagt tcttgaagtg gtggcctaac tacggctaca ctagaaggac agtatttggt    7620
atctgcgctc tgctgaagcc agttaccttc ggaaaaagag ttggtagctc ttgatccggc    7680
aaacaaacca ccgctggtag cggtggtttt tttgtttgca agcagcagat tacgcgcaga    7740
aaaaaaggat ctcaagaaga tcctttgatc ttttctacgg ggtctgacgc tcagtggaac    7800
gaaaactcac gttaagggat tttggtcatg agattatcaa aaaggatctt cacctagatc    7860
ctttttaaatt aaaaatgaag ttttaaatca atctaaagta tatatgagta aacttggtct    7920
gacagttacc aatgcttaat cagtgaggca cctatctcag cgatctgtct atttcgttca    7980
tccatagttg cctgactccc cgtcgtgtag ataactacga tacggggagg g cttaccatct   8040
ggccccagtg ctgcaatgat accgcgagac ccacgctcac cggctccaga tttatcagca    8100
ataaccagc cagccggaag ggccgagcgc agaagtggtc ctgcaacttt atccgcctcc    8160
atccagtcta ttaattgttg ccgggaagct agagtaagta gttcgccagt taatagtttg    8220
cgcaacgttg ttgccattgc tgcaggcatc gtggtgtcac gctcgtcgtt tggtatggct    8280
tcattcagct ccggttccca acgatcaagg cgagttacat gatccccat gttgtgcaaa    8340
aaagcggtta gctccttcgg tcctccgatc gttgtcagaa gtaagttggc cgcagtgtta    8400
tcactcatgg ttatggcagc actgcataat tctcttactg tcatgccatc cgtaagatgc    8460
ttttctgtga ctggtgagta ctcaaccaag tcattctgag aatagtgtat gcggcgaccg    8520
agttgctctt gcccggcgtc aacacgggat aataccgcgc cacatagcag aactttaaaa    8580
gtgctcatca ttggaaaacg ttcttcgggg cgaaaactct caaggatctt accgctgttg    8640
agatccagtt cgatgtaacc cactcgtgca cccaactgat cttcagcatc ttttactttc    8700
accagcgttt ctgggtgagc aaaaacagga aggcaaaatg ccgcaaaaaa gggaataagg    8760
gcgacacgga aatgttgaat actcatactc ttcctttttc aatattattg aagcatttat    8820
cagggttatt gtctcatgag cggatacata tttgaatgta tttagaaaaa taaacaaata    8880
ggggttccgc gcacatttcc ccgaaaagtg ccacctgacg tctaagaaac cattattatc    8940
atgacattaa cctataaaaa taggcgtatc acgaggccct ttcgtcttca agaattggtc    9000
gatggcaaac agctattatg ggtattatgg gttcgaatta attaatcgac atcatcaata    9060
atataccccca c                                                       9071
```

<210> SEQ ID NO 4
<211> LENGTH: 4479
<212> TYPE: DNA
<213> ORGANISM: Adenovirus Serotype 26

<400> SEQUENCE: 4

```
atgtcccatg gtgactcggc tgagctcgct cggttgaggc atctggacca ctgccgccgc    60
```

| | |
|---|---|
| ctgcgctgct tcgcccggga gagctgcgga ctcatctact ttgagtttcc cgaggagcac | 120 |
| cccaacggcc ctgcacacgg agtgcggatc accgtagagg gcaccaccga gtctcacctg | 180 |
| gtcaggttct tcacccagca acccttcctg gtcgagcggg accggggcgc caccacctac | 240 |
| accgtctact gcatctgtcc aaccccgaag ttgcatgaga ttttttgttg tactctttgt | 300 |
| ggtgagttta ataaaagcta aactcttgca atactctgga ccttgtcgtc gtcaactcaa | 360 |
| cgagaccgtc tacctcacca accagactga ggtaaaactc acctgcagac cacacaagac | 420 |
| ctatatcatc tggttcttcg agaacacctc atttgcagtc tccaacactc actgcaacga | 480 |
| cggtgttgaa cttcccaaca acctttccag tggactgagt tacgatacac atagagctaa | 540 |
| gctcgtcctc tacaatcctt ttgtagaggg aacctaccag tgccagagcg accttgtac | 600 |
| tcacaccttc catttggtga acgtcaccag cagcagcaac agctcagaaa ctaaccttcc | 660 |
| ttctgatact aacaaacctc gtttcggagg tgagctaagg cttcccccctt ctgaggaggg | 720 |
| ggttagccca tacgaagtgg tcgggtattt gattttaggg gtggtcctgg gtgggtgcat | 780 |
| agcggtgcta gctcagctgc cttgctgggt ggaaatcaaa atctttatat gctgggtcag | 840 |
| atattgtggg gaggaaccat gaaggggctt ttgctgatta tccttttcat ggtgggggt | 900 |
| gtactgtcat gccacgaaca gccacgatgt aacatcacca caggcaatca tatgagcaga | 960 |
| gagtgcactg tagtcatcaa atgcgagcac gactgcccac taaacattac attcaagaat | 1020 |
| aacaccatgg gaaatgtatg ggtgggttc tgggaaccag gagatgagca gaactacacg | 1080 |
| gtcactgtcc atggtagcaa tggaaatcac actttcggtt tcaaattcat tttttgaagtc | 1140 |
| atgtgtgata tcacactgca tgtggctaga cttcatggct tgtggccccc taccaaggag | 1200 |
| aacatggttg ggttttcttt ggcttttgtg atcatggcct gcttgatgtc aggtctgctg | 1260 |
| gtagggggctt tagtgtggtt cctgaagcgc aagcctaggt acggaaatga agaaaaggaa | 1320 |
| aaattgctat aatctttttc tttttcacag aaccatgaat gctttgacca gtgtcgtgct | 1380 |
| gctctctctt cttgtagctt ttagtaatgg ggaagctgaa actgtagttg taaatgttaa | 1440 |
| atctggtaca aaccacaccc ttgaaggtcc tagaaaaact ccagttcagt ggtatggggg | 1500 |
| tgctaacttt gacatgtttt gcaatggctc taaaatacat cacaatgaat tgaatcacac | 1560 |
| ttgctctatt cagaacataa ctcttacatt cataaacaga acacatcatg gaacatacta | 1620 |
| tggttttggc tctgacaatc aaaattcaaa agtgtatcat gtcagagtag atgtagagcc | 1680 |
| tcctagaccc cgtgctactt tggctcctcc tcaggacata actattaagt atggctcaaa | 1740 |
| tagaacattg cagggcccaa gtgttactcc agttagttgg tatgatggtg aaggaaatcg | 1800 |
| gttttgcgat ggcgataaaa ttgatcatac agaaattaat cacacttgca atgctcaaaa | 1860 |
| ccttactttg ctgtttgtga atgaaacaca tgaaagaaca tattatggaa ttagtggtga | 1920 |
| ttggaaacag cgaaatgagt atgatgttac tgttacaaag acacaattaa atattaaaaa | 1980 |
| tttgggccaa cgcaaaactg atgaaaacca taaaaatgga atgcatcaga agtcgaaca | 2040 |
| aaatcctgaa actaagaaag aacagaagcc ttcaaaaaga cctagacaaa aacattgca | 2100 |
| aactacaatt caggttatga ttcctattgg aactaattat actttagtgg ggccttcgcc | 2160 |
| accagtgagc tggcatacta caaaaaatgg cttaacagaa ctctgtaatg aaaccctat | 2220 |
| tttaagacac acttgtgatg gcaaaatat tacacttatt aatgttaatg ctacatttga | 2280 |
| ggctgattac tatggctcga acaataagag tgaatcaaaa cactacagag tcaaggtttt | 2340 |
| caaagaaaga aaagatcagg cactattatt cagaccgctt actaccaaag gaagcatgat | 2400 |

```
cattactact gaaaatcaaa actttgaatt acaacaaggt gacaatcaag atgatgacaa      2460
aattccatca actactgtgg caatcgtggt gggtgtgatt gcgggctttg tgactctgat      2520
cattgtcttc atatgctaca tctgctgccg caagcgtccc aggtcataca atcatatggt      2580
agacccacta ctcagcttct cttactgaaa ctcagtcact ctcatttcag aaccatgaag      2640
gctttcacag cttgcgttct gattagcata gtcacactta gtgcagctga agctaaatgc      2700
tttcatactt ataacttaac tagaggggaa aatattacat tagcaggtgc tggcttaaac      2760
acaacatggg aagcatatca caatggatgg aaacaagttt gtccatggaa tgacggtcgc      2820
tatgtgtgcg ttggaaacag cagtaccata actaatctta cagttgtagc taatgcaaat      2880
ttatcatcaa ctgttaaatt tagagctgaa agtttataca ttggaacaga tggatatgaa      2940
agcaatccat catgctttta tactatcaat gtaattgagc ttccaaccac cagatcgcca      3000
actaccacca cggtcagtac aactactgag accacaactc acactacaca gttagacact      3060
acagtgcaga atagtactgt attggttagg tatttgttaa gggaggaaag tactactgaa      3120
cagacagagg ctacctcaag cgccttcagc agcacttcaa atttaacttc gcttgcttgg      3180
actaatgaaa ccggagtatc attgatgcat ggccagcctt actcaggttt ggatattcaa      3240
attacttttc tggttgtctg tgggatcttt attcttgtgg ttcttctgta ctttgtctgc      3300
tgcaaagcca gagaaaaatc taggcggccc atctacaggc cagtaatcgg ggaacctcag      3360
ccactccaag tggatggagg cttaaggaat cttcttttct cttttacagt atggtgatca      3420
gccatgattc ctaggttctt cctatttaac atcctcttct gtctcttcaa cgtgtgcgct      3480
gccttcgcgg ccgtctcgca cgcctcaccc gactgtctcg ggcccttccc cacctacctc      3540
ctctttgccc tgctcacctg cacctgcgtc tgcagcattg tctgcctggt catcaccttc      3600
ctgcagctca tcgactggtg ctgcgcgcgc tacaattacc tgcatcatag tcccgaatac      3660
agggacgaga acgtagccag aatcttaagg ctcatatgac catgcagact ctgctcatac      3720
tgctatccct cctatcccct accctcgcca cttctgctga ttactctaaa tgcaaattcg      3780
cggacatatg gaatttctta gactgctatc aggagaaaat tgacatgccc tcctattact      3840
tggtgattgt gggaatagtt atggtctgct cctgcacttt cttttgccatc atgatctacc      3900 cctgttttga tctcggctgg aactctgttg aagcattcac atacacacta gaaagcagtt      3960
cactagcctc cacgccacca cccacaccgc ctccccgcag aaatcagttt ccatgattc       4020 agtacttaga agagccccct ccccgacccc cttccactgt tagctacttt cacataaccg      4080
gcggcgatga ctgaccacca cctggacctc gagatggacg gccaggcctc cgagcagcgc      4140
atcctgcaac tgcgcgtccg tcagcagcag gagcgtgccg ccaaggagct cctcgatgcc      4200
atcaacatcc accagtgcaa gaagggcatc ttctgcctgg tcaaacaggc aaagatcacc      4260
tacgagctcg tgtccggcgg caagcagcat cgcctcgcct atgagctgcc ccagcagaag      4320
cagaagttca cctgcatggt gggcgtcaac cccatagtca tcacccagca gtcgggcgag      4380
accagcggct gcatccactg ctcctgcgaa agccccgagt gcatctactc cctgctcaag      4440 acccttttgcg gactccgcga cctcctcccc atgaactga                             4479
```

<210> SEQ ID NO 5
<211> LENGTH: 318
<212> TYPE: DNA
<213> ORGANISM: Adenovirus Serotype 26

<400> SEQUENCE: 5

```
atgtcccatg gtgactcggc tgagctcgct cggttgaggc atctggacca ctgccgccgc       60
```

-continued

```
ctgcgctgct tcgcccggga gagctgcgga ctcatctact ttgagtttcc cgaggagcac    120
cccaacggcc ctgcacacgg agtgcggatc accgtagagg gcaccaccga gtctcacctg    180
gtcaggttct tcacccagca accctcctg gtcgagcggg accggggcgc caccacctac     240
accgtctact gcatctgtcc aaccccgaag ttgcatgaga ttttgttg tactctttgt      300 ggtgagttta ataaaagc                                                  318
```

<210> SEQ ID NO 6
<211> LENGTH: 106
<212> TYPE: PRT
<213> ORGANISM: Adenovirus Serotype 26

<400> SEQUENCE: 6

```
Met Ser His Gly Asp Ser Ala Glu Leu Ala Arg Leu Arg His Leu Asp
1               5                   10                  15

His Cys Arg Arg Leu Arg Cys Phe Ala Arg Glu Ser Cys Gly Leu Ile
            20                  25                  30

Tyr Phe Glu Phe Pro Glu His Pro Asn Gly Pro Ala His Gly Val
        35                  40                  45

Arg Ile Thr Val Glu Gly Thr Thr Glu Ser His Leu Val Arg Phe Phe
    50                  55                  60

Thr Gln Gln Pro Phe Leu Val Glu Arg Asp Arg Gly Ala Thr Thr Tyr
65                  70                  75                  80

Thr Val Tyr Cys Ile Cys Pro Thr Pro Lys Leu His Glu Asn Phe Cys
                85                  90                  95

Cys Thr Leu Cys Gly Glu Phe Asn Lys Ser
            100                 105
```

<210> SEQ ID NO 7
<211> LENGTH: 195
<212> TYPE: PRT
<213> ORGANISM: Adenovirus Serotype 26

<400> SEQUENCE: 7

```
Met Arg Ile Phe Val Val Leu Phe Val Val Ser Leu Ile Lys Ala Lys
1               5                   10                  15

Leu Leu Gln Tyr Ser Gly Pro Cys Arg Arg Gln Leu Asn Glu Thr Val
            20                  25                  30

Tyr Leu Thr Asn Gln Thr Glu Val Lys Leu Thr Cys Arg Pro His Lys
        35                  40                  45

Thr Tyr Ile Ile Trp Phe Phe Glu Asn Thr Ser Phe Ala Val Ser Asn
    50                  55                  60

Thr His Cys Asn Asp Gly Val Glu Leu Pro Asn Asn Leu Ser Ser Gly
65                  70                  75                  80

Leu Ser Tyr Asp Thr His Arg Ala Lys Leu Val Leu Tyr Asn Pro Phe
                85                  90                  95

Val Glu Gly Thr Tyr Gln Cys Gln Ser Gly Pro Cys Thr His Thr Phe
            100                 105                 110

His Leu Val Asn Val Thr Ser Ser Asn Ser Glu Thr Asn Leu
        115                 120                 125

Pro Ser Asp Thr Asn Lys Pro Arg Phe Gly Gly Glu Leu Arg Leu Pro
    130                 135                 140

Pro Ser Glu Glu Gly Val Ser Pro Tyr Glu Val Gly Tyr Leu Ile
145                 150                 155                 160

Leu Gly Val Val Leu Gly Gly Cys Ile Ala Val Leu Ala Gln Leu Pro
```

```
                    165                 170                 175
Cys Trp Val Glu Ile Lys Ile Phe Ile Cys Trp Val Arg Tyr Cys Gly
            180                 185                 190
Glu Glu Pro
        195
```

<210> SEQ ID NO 8
<211> LENGTH: 167
<212> TYPE: PRT
<213> ORGANISM: Adenovirus Serotype 26

<400> SEQUENCE: 8

```
Met Leu Gly Gln Ile Leu Trp Gly Gly Thr Met Lys Gly Leu Leu Leu
1               5                   10                  15

Ile Ile Leu Phe Met Val Gly Gly Val Leu Ser Cys His Glu Gln Pro
            20                  25                  30

Arg Cys Asn Ile Thr Thr Gly Asn His Met Ser Arg Glu Cys Thr Val
        35                  40                  45

Val Ile Lys Cys Glu His Asp Cys Pro Leu Asn Ile Thr Phe Lys Asn
    50                  55                  60

Asn Thr Met Gly Asn Val Trp Val Gly Phe Trp Glu Pro Gly Asp Glu
65                  70                  75                  80

Gln Asn Tyr Thr Val Thr Val His Gly Ser Asn Gly Asn His Thr Phe
                85                  90                  95

Gly Phe Lys Phe Ile Phe Glu Val Met Cys Asp Ile Thr Leu His Val
            100                 105                 110

Ala Arg Leu His Gly Leu Trp Pro Pro Thr Lys Glu Asn Met Val Gly
        115                 120                 125

Phe Ser Leu Ala Phe Val Ile Met Ala Cys Leu Met Ser Gly Leu Leu
    130                 135                 140

Val Gly Ala Leu Val Trp Phe Leu Lys Arg Lys Pro Arg Tyr Gly Asn
145                 150                 155                 160

Glu Glu Lys Glu Lys Leu Leu
                165
```

<210> SEQ ID NO 9
<211> LENGTH: 433
<212> TYPE: PRT
<213> ORGANISM: Adenovirus Serotype 26

<400> SEQUENCE: 9

```
Met Lys Lys Arg Lys Asn Cys Tyr Asn Leu Phe Leu Phe His Arg Thr
1               5                   10                  15

Met Asn Ala Leu Thr Ser Val Val Leu Leu Ser Leu Leu Val Ala Phe
            20                  25                  30

Ser Asn Gly Glu Ala Glu Thr Val Val Asn Val Lys Ser Gly Thr
        35                  40                  45

Asn His Thr Leu Glu Gly Pro Arg Lys Thr Pro Val Gln Trp Tyr Gly
    50                  55                  60

Gly Ala Asn Phe Asp Met Phe Cys Asn Gly Ser Lys Ile His His Asn
65                  70                  75                  80

Glu Leu Asn His Thr Cys Ser Ile Gln Asn Ile Thr Leu Thr Phe Ile
                85                  90                  95

Asn Arg Thr His His Gly Thr Tyr Tyr Gly Phe Gly Ser Asp Asn Gln
            100                 105                 110

Asn Ser Lys Val Tyr His Val Arg Val Asp Val Glu Pro Pro Arg Pro
```

```
                  115                 120                 125
Arg Ala Thr Leu Ala Pro Pro Gln Asp Ile Thr Ile Lys Tyr Gly Ser
        130                 135                 140

Asn Arg Thr Leu Gln Gly Pro Ser Val Thr Pro Val Ser Trp Tyr Asp
145                 150                 155                 160

Gly Glu Gly Asn Arg Phe Cys Asp Gly Asp Lys Ile Asp His Thr Glu
                165                 170                 175

Ile Asn His Thr Cys Asn Ala Gln Asn Leu Thr Leu Leu Phe Val Asn
            180                 185                 190

Glu Thr His Glu Arg Thr Tyr Tyr Gly Ile Ser Gly Asp Trp Lys Gln
        195                 200                 205

Arg Asn Glu Tyr Asp Val Thr Val Thr Lys Thr Gln Leu Asn Ile Lys
    210                 215                 220

Asn Leu Gly Gln Arg Lys Thr Asp Glu Asn His Lys Asn Gly Met His
225                 230                 235                 240

Gln Lys Val Glu Gln Asn Pro Glu Thr Lys Lys Glu Gln Lys Pro Ser
                245                 250                 255

Lys Arg Pro Arg Gln Lys Thr Leu Gln Thr Thr Ile Gln Val Met Ile
            260                 265                 270

Pro Ile Gly Thr Asn Tyr Thr Leu Val Gly Pro Ser Pro Pro Val Ser
        275                 280                 285

Trp His Thr Thr Lys Asn Gly Leu Thr Glu Leu Cys Asn Gly Asn Pro
    290                 295                 300

Ile Leu Arg His Thr Cys Asp Gly Gln Asn Ile Thr Leu Ile Asn Val
305                 310                 315                 320

Asn Ala Thr Phe Glu Ala Asp Tyr Tyr Gly Ser Asn Asn Lys Ser Glu
                325                 330                 335

Ser Lys His Tyr Arg Val Lys Val Phe Lys Glu Arg Lys Asp Gln Ala
            340                 345                 350

Leu Leu Phe Arg Pro Leu Thr Thr Lys Gly Ser Met Ile Ile Thr Thr
        355                 360                 365

Glu Asn Gln Asn Phe Glu Leu Gln Gln Gly Asp Asn Gln Asp Asp Asp
    370                 375                 380

Lys Ile Pro Ser Thr Thr Val Ala Ile Val Val Gly Val Ile Ala Gly
385                 390                 395                 400

Phe Val Thr Leu Ile Ile Val Phe Ile Cys Tyr Ile Cys Cys Arg Lys
                405                 410                 415

Arg Pro Arg Ser Tyr Asn His Met Val Asp Pro Leu Leu Ser Phe Ser
            420                 425                 430

Tyr

<210> SEQ ID NO 10
<211> LENGTH: 294
<212> TYPE: PRT
<213> ORGANISM: Adenovirus Serotype 26

<400> SEQUENCE: 10

Met Leu His Leu Leu Pro Gln Ala Ser Gln Val Ile Gln Ser Tyr Gly
1               5                   10                  15

Arg Pro Thr Thr Gln Leu Leu Leu Lys Leu Ser His Ser His Phe
                20                  25                  30

Arg Thr Met Lys Ala Phe Thr Ala Cys Val Leu Ile Ser Ile Val Thr
            35                  40                  45

Leu Ser Ala Ala Glu Ala Lys Cys Phe His Thr Tyr Asn Leu Thr Arg
```

Gly Glu Asn Ile Thr Leu Ala Gly Ala Gly Leu Asn Thr Thr Trp Glu
65                  70                  75                  80

Ala Tyr His Asn Gly Trp Lys Gln Val Cys Pro Trp Asn Asp Gly Arg
                85                  90                  95

Tyr Val Cys Val Gly Asn Ser Ser Thr Ile Thr Asn Leu Thr Val Val
            100                 105                 110

Ala Asn Ala Asn Leu Ser Ser Thr Val Lys Phe Arg Ala Glu Ser Leu
        115                 120                 125

Tyr Ile Gly Thr Asp Gly Tyr Glu Ser Asn Pro Ser Cys Phe Tyr Thr
    130                 135                 140

Ile Asn Val Ile Glu Leu Pro Thr Thr Arg Ser Pro Thr Thr Thr Thr
145                 150                 155                 160

Val Ser Thr Thr Thr Glu Thr Thr Thr His Thr Thr Gln Leu Asp Thr
                165                 170                 175

Thr Val Gln Asn Ser Thr Val Leu Val Arg Tyr Leu Leu Arg Glu Glu
            180                 185                 190

Ser Thr Thr Glu Gln Thr Glu Ala Thr Ser Ser Ala Phe Ser Ser Thr
        195                 200                 205

Ser Asn Leu Thr Ser Leu Ala Trp Thr Asn Glu Thr Gly Val Ser Leu
    210                 215                 220

Met His Gly Gln Pro Tyr Ser Gly Leu Asp Ile Gln Ile Thr Phe Leu
225                 230                 235                 240

Val Val Cys Gly Ile Phe Ile Leu Val Val Leu Leu Tyr Phe Val Cys
                245                 250                 255

Cys Lys Ala Arg Glu Lys Ser Arg Arg Pro Ile Tyr Arg Pro Val Ile
            260                 265                 270

Gly Glu Pro Gln Pro Leu Gln Val Asp Gly Gly Leu Arg Asn Leu Leu
        275                 280                 285

Phe Ser Phe Thr Val Trp
    290

<210> SEQ ID NO 11
<211> LENGTH: 132
<212> TYPE: PRT
<213> ORGANISM: Adenovirus Serotype 26

<400> SEQUENCE: 11

Met Thr Met Gln Thr Leu Leu Ile Leu Leu Ser Leu Ser Pro Thr
1               5                   10                  15

Leu Ala Thr Ser Ala Asp Tyr Ser Lys Cys Lys Phe Ala Asp Ile Trp
            20                  25                  30

Asn Phe Leu Asp Cys Tyr Gln Glu Lys Ile Asp Met Pro Ser Tyr Tyr
        35                  40                  45

Leu Val Ile Val Gly Ile Val Met Val Cys Ser Cys Thr Phe Phe Ala
    50                  55                  60

Ile Met Ile Tyr Pro Cys Phe Asp Leu Gly Trp Asn Ser Val Glu Ala
65                  70                  75                  80

Phe Thr Tyr Thr Leu Glu Ser Ser Ser Leu Ala Ser Thr Pro Pro Pro
                85                  90                  95

Thr Pro Pro Pro Arg Arg Asn Gln Phe Pro Met Ile Gln Tyr Leu Glu
            100                 105                 110

Glu Pro Pro Pro Arg Pro Pro Ser Thr Val Ser Tyr Phe His Ile Thr
        115                 120                 125

Gly Gly Asp Asp
    130

<210> SEQ ID NO 12
<211> LENGTH: 130
<212> TYPE: PRT
<213> ORGANISM: Adenovirus Serotype 26

<400> SEQUENCE: 12

Met Thr Asp His His Leu Asp Leu Glu Met Asp Gly Gln Ala Ser Glu
1               5                   10                  15

Gln Arg Ile Leu Gln Leu Arg Val Arg Gln Gln Glu Arg Ala Ala
            20                  25                  30

Lys Glu Leu Leu Asp Ala Ile Asn Ile His Gln Cys Lys Lys Gly Ile
                35                  40                  45

Phe Cys Leu Val Lys Gln Ala Lys Ile Thr Tyr Glu Leu Val Ser Gly
    50                  55                  60

Gly Lys Gln His Arg Leu Ala Tyr Glu Leu Pro Gln Gln Lys Gln Lys
65                  70                  75                  80

Phe Thr Cys Met Val Gly Val Asn Pro Ile Val Ile Thr Gln Gln Ser
                85                  90                  95

Gly Glu Thr Ser Gly Cys Ile His Cys Ser Cys Glu Ser Pro Glu Cys
            100                 105                 110

Ile Tyr Ser Leu Leu Lys Thr Leu Cys Gly Leu Arg Asp Leu Leu Pro
        115                 120                 125

Met Asn
    130

<210> SEQ ID NO 13
<211> LENGTH: 2792
<212> TYPE: DNA
<213> ORGANISM: Adenovirus Serotype 26

<400> SEQUENCE: 13
atgagacacc tgcgcctcct gccttcaact gtgcccggtg agctggctgt gcttatgctg      60
gaggactttg tggatacagt attggaggac gaactgcatc aagtccgtt cgagctggga     120 cccacacttc aggatctcta tgatctggag gtagatgccc atgatgacga ccctaacgag     180
gaggctgtga atttaatatt tccagaatct atgattcttc aggctgacat agccaacgaa     240
tctactccac ttcatacacc gactctgtca cccatacctg aattggaaga ggaggacgaa     300
ctagacctcc ggtgttatga ggaaggtttt cctcccagcg attcagagga tgaacggggt     360
gagcagacca tggctctgat ctcagactat gcttgtgtga ttgtggagga acaagtagtg     420
attgaaaatt ctaccgagcc agtggagggc tgtagaaaat gccagtacca ccgggataag     480
tctggagacc cgaacgcatc atgcgctttg tgctatatga acagactttt cagctttatt     540
tacagtaagt ggagtgaatg tgagagaggc tgagtgctta acacatcact gtgtattgct     600
tgaacagctg tgctaagtgt ggtttatttt tgtttctagg tccggtgtca gaggatgagt     660
catcaccctc agaagaagac cacccgtctc cccctgatct cacagatgac acgcccctgc     720
aagtgcacag accccaccca gtcagagcca gtggcgagag cgagcagct gttgaaaaaa     780 ttgaggactt gttacatgac atgggtgggg atgaacctttt ggacctgagc ttgaaacgcc     840
ccaggaacta gcgcagctg cgcttagtca tgtgtaaata agttgtaca ataaaagtat     900 atgtgacgca tgcaaggtgt ggtttatgac tcatgggcgg ggcttagtcc tatataagtg     960
gcaacacctg ggcactgggc acagaccttc agggagttcc tgatggatgt gtggactatc    1020

```
cttgcagact ttagcaagac acgccggctt gtagaggata gttcagacgg gtgctccggg    1080
ttctggagac actggtttgg aactcctcta tctcgcctgg tgtacacagt taagaaggat    1140
tataaagagg aatttgaaaa tattttgct gactgctctg gcctgctaga ttctctgaat     1200
cttggccacc agtcccttt ccaggaaagg gtactccaca gccttgattt ttccagccca     1260
gggcgcacta cagccggggt tgcttttgtg gttttctgg ttgacaaatg gagccaggac     1320
acccaactga gcaggggcta catcctggac ttcgcagcca tgcacctgtg agggcctgg     1380 atcaggcagc ggggacagag aatcttgaat tactggcttc tacagccagc agctccgggt    1440
cttcttcgtc tacacagaca acatccatg ttggaggaag aaatgaggca ggccatggac     1500
gagaacccga ggagcggcct ggaccctccg tcggaagagg agctggattg aatcaggtat    1560
ccagcctgta cccagagctt agcaaggtgc tgacatccat ggccagggga gttaagaggg    1620
agaggagcga tgggggtaat accgggatga tgaccgagct gacggccagc ctgatgaatc    1680
ggaagcgccc agagcgcctt acctggtacg agctacagca ggagtgcagg gatgagttgg    1740
gcctgatgca ggataaatat ggcctggagc agataaaaac ccattggttg aacccagatg    1800
aggattggga ggaggctatt aagaagtatg ccaagatagc cctgcgccca gattgcaagt    1860
acatagtgac caagaccgtg aatatcagac atgcctgcta catctcgggg aacggggcag    1920
aggtggtcat cgatacctg gacaaggccg ccttcaggtg ttgcatgatg ggaatgagag     1980
caggagtgat gaatatgaat tccatgatct tcatgaacat gaagttcaat ggagagaagt    2040
ttaatggggt gctgttcatg gccaacagcc acatgaccct gcatggctgc agtttcttcg    2100
gcttcaacaa tatgtgcgca gaggtctggg gcgcttccaa gatcagggga tgtaagtttt    2160
atggctgctg gatgggcgtg gtcggaagac ccaagagcga gatgtctgtg aagcagtgtg    2220
tgtttgagaa atgctacctg ggagtctcta ccgagggcaa tgctagagtg agacactgct    2280
cttccctgga gacgggctgc ttctgcctgg tgaaggcac agcctctctg aagcataata    2340
tggtgaaggg ctgcacggat gagcgcatgt acaacatgct gacctgcgat tcgggggtct    2400
gccatatcct gaagaacatc catgtgacct cccaccccag aaagaagtgg ccagtgtttg    2460
agaataacct gctgatcaag tgccatatgc acctgggagc cagaagggc accttccagc     2520 cgtaccagtg caactttagc cagaccaagc tgctgttgga gaacgatgcc ttctccaggg    2580
tgaacctgaa cggcatcttt gacatggatg tctcggtgta caagatcctg agatacgatg    2640
agaccaagtc cagggtgcgc gcttgcgagt gcggggcag acacaccagg atgcagccag     2700
tggccctgga tgtgaccgag gagctgagac cagaccacct ggtgatggcc tgtaccggga    2760
ccgagttcag ctccagtggg gaggatacag at                                  2792
```

<210> SEQ ID NO 14
<211> LENGTH: 190
<212> TYPE: PRT
<213> ORGANISM: Adenovirus Serotype 26

<400> SEQUENCE: 14

```
Met Arg His Leu Arg Leu Leu Pro Ser Thr Val Pro Gly Glu Leu Ala
1               5                   10                  15

Val Leu Met Leu Glu Asp Phe Val Asp Thr Val Leu Glu Asp Glu Leu
            20                  25                  30

His Pro Ser Pro Phe Glu Leu Gly Pro Thr Leu Gln Asp Leu Tyr Asp
        35                  40                  45

Leu Glu Val Asp Ala His Asp Asp Asp Pro Asn Glu Glu Ala Val Asn
```

```
                50                  55                  60
Leu Ile Phe Pro Glu Ser Met Ile Leu Gln Ala Asp Ile Ala Asn Glu
 65                  70                  75                  80

Ser Thr Pro Leu His Thr Pro Thr Leu Ser Pro Ile Pro Glu Leu Glu
                 85                  90                  95

Glu Glu Asp Glu Leu Asp Leu Arg Cys Tyr Glu Gly Phe Pro Pro
                100                 105                 110

Ser Asp Ser Glu Asp Glu Arg Gly Gln Thr Met Ala Leu Ile Ser
                115                 120                 125

Asp Tyr Ala Cys Val Ile Val Glu Gln Val Val Ile Glu Asn Ser
            130                 135                 140

Thr Glu Pro Val Glu Gly Cys Arg Lys Cys Gln Tyr His Arg Asp Lys
145                 150                 155                 160

Ser Gly Asp Pro Asn Ala Ser Cys Ala Leu Cys Tyr Met Lys Gln Thr
                165                 170                 175

Phe Ser Phe Ile Tyr Ser Lys Trp Ser Glu Cys Glu Arg Gly
                180                 185                 190

<210> SEQ ID NO 15
<211> LENGTH: 182
<212> TYPE: PRT
<213> ORGANISM: Adenovirus Serotype 26

<400> SEQUENCE: 15

Met Asp Val Trp Thr Ile Leu Ala Asp Phe Ser Lys Thr Arg Arg Leu
  1               5                  10                  15

Val Glu Asp Ser Ser Asp Gly Cys Ser Gly Phe Trp Arg His Trp Phe
                 20                  25                  30

Gly Thr Pro Leu Ser Arg Leu Val Tyr Thr Val Lys Lys Asp Tyr Lys
             35                  40                  45

Glu Glu Phe Glu Asn Ile Phe Ala Asp Cys Ser Gly Leu Leu Asp Ser
         50                  55                  60

Leu Asn Leu Gly His Gln Ser Leu Phe Gln Glu Arg Val Leu His Ser
 65                  70                  75                  80

Leu Asp Phe Ser Ser Pro Gly Arg Thr Thr Ala Gly Val Ala Phe Val
                 85                  90                  95

Val Phe Leu Val Asp Lys Trp Ser Gln Asp Thr Gln Leu Ser Arg Gly
                100                 105                 110

Tyr Ile Leu Asp Phe Ala Ala Met His Leu Trp Arg Ala Trp Ile Arg
            115                 120                 125

Gln Arg Gly Gln Arg Ile Leu Asn Tyr Trp Leu Leu Gln Pro Ala Ala
        130                 135                 140

Pro Gly Leu Leu Arg Leu His Arg Gln Thr Ser Met Leu Glu Glu Glu
145                 150                 155                 160

Met Arg Gln Ala Met Asp Glu Asn Pro Arg Ser Gly Leu Asp Pro Pro
                165                 170                 175

Ser Glu Glu Glu Leu Asp
                180

<210> SEQ ID NO 16
<211> LENGTH: 495
<212> TYPE: PRT
<213> ORGANISM: Adenovirus Serotype 26

<400> SEQUENCE: 16

Met Glu Pro Gly His Pro Thr Glu Gln Gly Leu His Pro Gly Leu Arg
```

-continued

```
1               5                   10                  15
Ser His Ala Pro Val Glu Gly Leu Asp Gln Ala Ala Gly Thr Glu Asn
                20                  25                  30

Leu Glu Leu Leu Ala Ser Thr Ala Ser Ser Gly Ser Ser Ser Ser Ser
                35                  40                  45

Thr Gln Thr Asn Ile His Val Gly Gly Arg Asn Glu Ala Gly His Gly
                50                  55                  60

Arg Glu Pro Glu Glu Arg Pro Gly Pro Ser Val Gly Arg Gly Ala Gly
 65                 70                  75                  80

Leu Asn Gln Val Ser Ser Leu Tyr Pro Glu Leu Ser Lys Val Leu Thr
                    85                  90                  95

Ser Met Ala Arg Gly Val Lys Arg Glu Arg Ser Asp Gly Gly Asn Thr
                100                 105                 110

Gly Met Met Thr Glu Leu Thr Ala Ser Leu Met Asn Arg Lys Arg Pro
                115                 120                 125

Glu Arg Leu Thr Trp Tyr Glu Leu Gln Gln Glu Cys Arg Asp Glu Leu
                130                 135                 140

Gly Leu Met Gln Asp Lys Tyr Gly Leu Glu Gln Ile Lys Thr His Trp
145                 150                 155                 160

Leu Asn Pro Asp Glu Asp Trp Glu Glu Ala Ile Lys Tyr Ala Lys
                    165                 170                 175

Ile Ala Leu Arg Pro Asp Cys Lys Tyr Ile Val Thr Lys Thr Val Asn
                180                 185                 190

Ile Arg His Ala Cys Tyr Ile Ser Gly Asn Gly Ala Glu Val Val Ile
                195                 200                 205

Asp Thr Leu Asp Lys Ala Ala Phe Arg Cys Cys Met Met Gly Met Arg
                210                 215                 220

Ala Gly Val Met Asn Met Asn Ser Met Ile Phe Met Asn Met Lys Phe
225                 230                 235                 240

Asn Gly Glu Lys Phe Asn Gly Val Leu Phe Met Ala Asn Ser His Met
                245                 250                 255

Thr Leu His Gly Cys Ser Phe Phe Gly Phe Asn Asn Met Cys Ala Glu
                260                 265                 270

Val Trp Gly Ala Ser Lys Ile Arg Gly Cys Lys Phe Tyr Gly Cys Trp
                275                 280                 285

Met Gly Val Val Gly Arg Pro Lys Ser Glu Met Ser Val Lys Gln Cys
                290                 295                 300

Val Phe Glu Lys Cys Tyr Leu Gly Val Ser Thr Glu Gly Asn Ala Arg
305                 310                 315                 320

Val Arg His Cys Ser Ser Leu Glu Thr Gly Cys Phe Cys Leu Val Lys
                325                 330                 335

Gly Thr Ala Ser Leu Lys His Asn Met Val Lys Gly Cys Thr Asp Glu
                340                 345                 350

Arg Met Tyr Asn Met Leu Thr Cys Asp Ser Gly Val Cys His Ile Leu
                355                 360                 365

Lys Asn Ile His Val Thr Ser His Pro Arg Lys Lys Trp Pro Val Phe
                370                 375                 380

Glu Asn Asn Leu Leu Ile Lys Cys His Met His Leu Gly Ala Arg Arg
385                 390                 395                 400

Gly Thr Phe Gln Pro Tyr Gln Cys Asn Phe Ser Gln Thr Lys Leu Leu
                405                 410                 415

Leu Glu Asn Asp Ala Phe Ser Arg Val Asn Leu Asn Gly Ile Phe Asp
                420                 425                 430
```

Met Asp Val Ser Val Tyr Lys Ile Leu Arg Tyr Asp Glu Thr Lys Ser
          435                 440                 445

Arg Val Arg Ala Cys Glu Cys Gly Gly Arg His Thr Arg Met Gln Pro
    450                 455                 460

Val Ala Leu Asp Val Thr Glu Glu Leu Arg Pro Asp His Leu Val Met
465                 470                 475                 480

Ala Cys Thr Gly Thr Glu Phe Ser Ser Ser Gly Glu Asp Thr Asp
                485                 490                 495

<210> SEQ ID NO 17
<211> LENGTH: 2334
<212> TYPE: DNA
<213> ORGANISM: Adenovirus Serotype 26

<400> SEQUENCE: 17
tcacagtctg gtggaatgag aagaacgcac agattcatac tcggaaaaca ggatgggtct    60
gtgcctctcc atcagcgccc tcaacagtct ttgccgccgg gctcggtgc ggctgctgca    120 gatgggatcg ggatcgcaag tctctctgac tatgatcccc acagccttca gcaacagtct    180
cctggtgcgt cgggcacagc accgcatcct gatctctgcc atgttctcac agtaagtgca    240
gcacataatc accatgttat tcagcagccc ataattcagg gcgctccaac caaagctcat    300
gttgggattg atggaaccca cgtgaccatc gtaccagatg cggcagtata tcaggtgcct    360
gcccctcatg aacacactgc ccatatacat gatctctttg gcatgttttc tgttcacaat    420
ctgccggtac catgggaatc gctggttgaa catgcacccg taaatgactc tcctgaacca    480
cacggccagc atggtgcctc cgcccgacac tgcagggat cccggggctg aacagtggca    540
atgcaggatc cagcgctcgt acccgctcac catctgagct ctcaccaagt ccagggtagc    600
ggggcacagg cacactgaca tacatctttt taaaattttt atttcctctg ggtcaggat    660 catatcccag gggactggaa actcttggag cagggtaaag ccagcagcac atggtaatcc    720
acggacagaa cttacattat gataatctgc atgatcacaa tcgggcaaca gggggtgttg    780
ttcagttagt gaggccctag tctcctcctc acatcgtggt aaacgggccc tgcggtaagg    840
atgatggcgg agcgagctcg actgttcctc ggtggacatt gaaatggatt ctcttgcgta    900
ccttgtcgta cttctgccag cagaaagtgg ctcgggaaca gcagatacct ttcctcctgc    960
tgtccttccg ctgctgacgc tcagtcatcc aactgaagta cagccattcc cgcaggttct    1020
ccagcagctc ctgtgcatct gatgaaacaa aagtcccgtc gatgcggatt cccctaaaa    1080 catcagccag acattgtag gccatcccaa tccagttaat gcatcctgat ctatcatgaa    1140
gaggaggtgg gggaagaact ggaagaacca ttttttattcc aagcggtctc gaaggacgat    1200
aaagtgcaag tcacgcaggt gacagcgttc cccgccgctg tgctggtgga acagacagc    1260 caggtcaaaa cccactctat tttcaaggtg ctcgactgtg gcttcgagca gtggctctac    1320
gcgtacatcc agcataagaa tcacattaaa ggctggacct ccatcgattt catcaatcat    1380
caggttacac tcattcacca tccccaggta attctcattt ttccagcctt ggattatttc    1440
tacaaattgt tggtgtaagt ccactccgca catgtggaaa agttcccaca gcgcccctc    1500 cactttcata atcaggcaga ccttcatatt agaaacagat cctgctgctc cacccactgc    1560
agcgtgttca aaacaacaag attcaatgag gttctgccct ctgccctcag ctcacgtctc    1620
agcgtcagct gcaaaaagtc actcaagtcc tcagccacta cagctgacaa ttcagagcca    1680
gggctaagcg tgggactggc aagcgtgagt gagtacttta atgctccaaa gctagcaccc    1740

-continued

```
aaaaactgca tgctggaata agctctcttt gtgtcaccgg tgatgccttc caataggtga    1800
gtgataaagc gaggtagttt ttctttaatc atttgagtaa tagaaaagtc ctctaaataa    1860
gtcactagga ccccaggaac cacaatgtgg tagctgacag cgtgtcgctc aagcatggtt    1920
agtagagatg agagtctgaa aaacagaaag catgcactaa accagagttg ccagtctcac    1980
tgaaggaaaa atcactctct ccagcagcaa agtgcccact gggtggccct ctcggacata    2040
caaaaatcga tccgtgtggt taaagagcag cacagttagc tcctgtcttc tcccagcaaa    2100
gatcacatcg gactgggtta gtatgcccct ggaatggtag tcattcaagg ccataaatct    2160
gccttggtag ccattaggaa tcagcacgct cactctcaag tgaaccaaaa ccaccccatg    2220
cggaggaatg tggaaagatt ctgggcaaaa aaggtatat ctattgctag tcccttcctg    2280
gacgggagca atccctccag ggctatctat gaaagcatac agagattcag ccat           2334
```

<210> SEQ ID NO 18
<211> LENGTH: 125
<212> TYPE: PRT
<213> ORGANISM: Adenovirus Serotype 26

<400> SEQUENCE: 18

Met Ala Glu Ser Leu Tyr Ala Phe Ile Asp Ser Pro Gly Gly Ile Ala
1               5                   10                  15

Pro Val Gln Glu Gly Thr Ser Asn Arg Tyr Thr Phe Phe Cys Pro Glu
            20                  25                  30

Ser Phe His Ile Pro Pro His Gly Val Val Leu Val His Leu Arg Val
        35                  40                  45

Ser Val Leu Ile Pro Asn Gly Tyr Gln Gly Arg Phe Met Ala Leu Asn
    50                  55                  60

Asp Tyr His Ser Arg Gly Ile Leu Thr Gln Ser Asp Val Ile Phe Ala
65                  70                  75                  80

Gly Arg Arg Gln Glu Leu Thr Val Leu Leu Phe Asn His Thr Asp Arg
                85                  90                  95

Phe Leu Tyr Val Arg Glu Gly His Pro Val Gly Thr Leu Leu Leu Glu
            100                 105                 110

Arg Val Ile Phe Pro Ser Val Arg Leu Ala Thr Leu Val
        115                 120                 125

<210> SEQ ID NO 19
<211> LENGTH: 130
<212> TYPE: PRT
<213> ORGANISM: Adenovirus Serotype 26

<400> SEQUENCE: 19

Met Leu Glu Arg His Ala Val Ser Tyr His Ile Val Val Pro Gly Val
1               5                   10                  15

Leu Val Thr Tyr Leu Glu Asp Phe Ser Ile Thr Gln Met Ile Lys Glu
            20                  25                  30

Lys Leu Pro Arg Phe Ile Thr His Leu Leu Gly Ile Thr Gly Asp
        35                  40                  45

Thr Lys Arg Ala Tyr Ser Ser Met Gln Phe Leu Gly Ala Ser Phe Gly
    50                  55                  60

Ala Leu Lys Tyr Ser Leu Thr Leu Ala Ser Pro Thr Leu Ser Pro Gly
65                  70                  75                  80

Ser Glu Leu Ser Ala Val Val Ala Glu Asp Leu Ser Asp Phe Leu Gln
                85                  90                  95

Leu Thr Leu Arg Arg Glu Leu Arg Ala Glu Gly Arg Thr Ser Leu Asn

```
            100                 105                 110

Leu Val Val Leu Asn Thr Leu Gln Val Val Glu Gln Gln Asp Leu Phe
        115                 120                 125

Leu Ile
    130

<210> SEQ ID NO 20
<211> LENGTH: 130
<212> TYPE: PRT
<213> ORGANISM: Adenovirus Serotype 26

<400> SEQUENCE: 20

Met Leu Glu Arg His Ala Val Ser Tyr His Ile Val Pro Gly Val
1               5                   10                  15

Leu Val Thr Tyr Leu Glu Asp Phe Ser Ile Thr Gln Met Ile Lys Glu
            20                  25                  30

Lys Leu Pro Arg Phe Ile Thr His Leu Leu Glu Gly Ile Thr Gly Asp
        35                  40                  45

Thr Lys Arg Ala Tyr Ser Ser Met Gln Phe Leu Gly Ala Ser Phe Gly
    50                  55                  60

Ala Leu Lys Tyr Ser Leu Thr Leu Ala Ser Pro Thr Leu Ser Pro Gly
65                  70                  75                  80

Ser Glu Leu Ser Ala Val Val Ala Glu Asp Leu Ser Asp Phe Leu Gln
                85                  90                  95

Leu Thr Leu Arg Arg Glu Leu Arg Ala Glu Gly Arg Thr Ser Leu Asn
            100                 105                 110

Leu Val Val Leu Asn Thr Leu Gln Val Val Glu Gln Gln Asp Leu Phe
        115                 120                 125

Leu Ile
    130

<210> SEQ ID NO 21
<211> LENGTH: 120
<212> TYPE: PRT
<213> ORGANISM: Adenovirus Serotype 26

<400> SEQUENCE: 21

Met Val Leu Pro Val Leu Pro Pro Pro Leu His Asp Arg Ser Gly
1               5                   10                  15

Cys Ile Asn Trp Ile Gly Met Ala Tyr Asn Val Leu Ala Asp Val Leu
            20                  25                  30

Arg Gly Ile Arg Ile Asp Gly Thr Phe Val Ser Ser Asp Ala Gln Glu
        35                  40                  45

Leu Leu Glu Asn Leu Arg Glu Trp Leu Tyr Phe Ser Trp Met Thr Glu
    50                  55                  60

Arg Gln Gln Arg Lys Asp Ser Arg Arg Lys Gly Ile Cys Cys Ser Arg
65                  70                  75                  80

Ala Thr Phe Cys Trp Gln Lys Tyr Asp Lys Val Arg Lys Arg Ile His
                85                  90                  95

Phe Asn Val His Arg Gly Thr Val Glu Leu Ala Pro Pro Ser Ser Leu
            100                 105                 110

Pro Gln Gly Pro Phe Thr Thr Met
        115                 120

<210> SEQ ID NO 22
<211> LENGTH: 292
<212> TYPE: PRT
```

<213> ORGANISM: Adenovirus Serotype 26

<400> SEQUENCE: 22

```
Met Ser Thr Glu Glu Gln Ser Ser Leu Arg His His Pro Tyr Arg
1               5                   10                  15

Arg Ala Arg Leu Pro Arg Cys Glu Glu Thr Arg Ala Ser Leu Thr
                20                  25                  30

Glu Gln His Pro Leu Leu Pro Asp Cys Asp His Ala Asp Tyr His Asn
            35                  40                  45

Val Ser Ser Val Arg Gly Leu Pro Cys Ala Ala Gly Phe Thr Leu Leu
    50                  55                  60

Gln Glu Phe Pro Val Pro Trp Asp Met Ile Leu Thr Pro Glu Glu Ile
65                  70                  75                  80

Lys Ile Leu Lys Arg Cys Met Ser Val Cys Leu Cys Pro Ala Thr Leu
                85                  90                  95

Asp Leu Val Arg Ala Gln Met Val Ser Gly Tyr Glu Arg Trp Ile Leu
            100                 105                 110

His Cys His Cys Ser Ala Pro Gly Ser Leu Gln Cys Arg Ala Gly Gly
        115                 120                 125

Thr Met Leu Ala Val Trp Phe Arg Arg Val Ile Tyr Gly Cys Met Phe
    130                 135                 140

Asn Gln Arg Phe Pro Trp Tyr Arg Gln Ile Val Asn Arg Asn Met Pro
145                 150                 155                 160

Lys Glu Ile Met Tyr Met Gly Ser Val Phe Met Arg Gly Arg His Leu
                165                 170                 175

Ile Tyr Cys Arg Ile Trp Tyr Asp Gly His Val Gly Ser Ile Ile Pro
            180                 185                 190

Asn Met Ser Phe Gly Trp Ser Ala Leu Asn Tyr Gly Leu Leu Asn Asn
        195                 200                 205

Met Val Ile Met Cys Cys Thr Tyr Cys Glu Asn Met Ala Glu Ile Arg
    210                 215                 220

Met Arg Cys Cys Ala Arg Arg Thr Arg Arg Leu Leu Leu Lys Ala Val
225                 230                 235                 240

Gly Ile Ile Val Arg Glu Thr Cys Asp Pro Asp Pro Ile Cys Ser Ser
                245                 250                 255

Arg Thr Glu Pro Arg Arg Gln Arg Leu Leu Arg Ala Leu Met Glu Arg
            260                 265                 270

His Arg Pro Ile Leu Phe Ser Glu Tyr Glu Ser Val Arg Ser Ser His
        275                 280                 285

Ser Thr Arg Leu
    290
```

<210> SEQ ID NO 23
<211> LENGTH: 876
<212> TYPE: DNA
<213> ORGANISM: Adenovirus Serotype 26

<400> SEQUENCE: 23

```
cagtctggtg gaatgagaag aacgcacaga ttcatactcg gaaaacagga tgggtctgtg     60
cctctccatc agcgccctca acagtctttg ccgccggggc tcggtgcggc tgctgcagat    120
gggatcggga tcgcaagtct ctctgactat gatccccaca gccttcagca acagtctcct    180
ggtgcgtcgg gcacagcacc gcatcctgat ctctgccatg ttctcacagt aagtgcagca    240
cataatcacc atgttattca gcagcccata attcagggcg ctccaaccaa agctcatgtt    300
```

-continued

| | |
|---|---|
| ggggatgatg gaacccacgt gaccatcgta ccagatgcgg cagtatatca ggtgcctgcc | 360 |
| cctcatgaac acactgccca tatacatgat ctctttgggc atgtttctgt tcacaatctg | 420 |
| ccggtaccat gggaatcgct ggttgaacat gcacccgtaa atgactctcc tgaaccacac | 480 |
| ggccagcatg gtgcctcccg cccgacactg cagggatccc ggggctgaac agtggcaatg | 540 |
| caggatccag cgctcgtacc cgctcaccat ctgagctctc accaagtcca gggtagcggg | 600 |
| gcacaggcac actgacatac atcttttaa aattttatt tcctctgggg tcaggatcat | 660 |
| atcccagggg actggaaact cttggagcag ggtaaagcca gcagcacatg gtaatccacg | 720 |
| gacagaactt acattatgat aatctgcatg atcacaatcg gcaacaggg ggtgttgttc | 780 |
| agttagtgag gccctagtct cctcctcaca tcgtggtaaa cgggccctgc ggtaaggatg | 840 |
| atggcggagc gagctcgact gttcctcggt ggacat | 876 |

<210> SEQ ID NO 24
<211> LENGTH: 34794
<212> TYPE: DNA
<213> ORGANISM: Adenovirus Serotype 35

<400> SEQUENCE: 24

| | |
|---|---|
| catcatcaat aatataccct atagatggaa tggtgccaat atgtaaatga ggtgatttta | 60 |
| aaaagtgtgg gccgtgtggt gattggctgt ggggttaacg gttaaagggg gcggcgcggc | 120 |
| cgtgggaaaa tgacgtttta tgggggtgga gttttttgc aagttgtcgc gggaaatgtt | 180 |
| acgcataaaa aggcttcttt tctcacggaa ctacttagtt ttcccacggt atttaacagg | 240 |
| aaatgaggta gttttgaccg gatgcaagtg aaaattgctg attttcgcgc gaaaactgaa | 300 |
| tgaggaagtg tttttctgaa taatgtggta tttatggcag ggtggagtat tgttcaggg | 360 |
| ccaggtagac tttgacccat tacgtggagg tttcgattac cgtgtttttt acctgaattt | 420 |
| ccgcgtaccg tgtcaaagtc ttctgttttt acgtaggtgt cagctgatcg ctagggtatt | 480 |
| tatacctcag ggtttgtgtc aagaggccac tcttgagtgc cagcgagaag agttttctcc | 540 |
| tctgcgccgg cagtttaata ataaaaaaat gagagatttg cgatttctgc ctcaggaaat | 600 |
| aatctctgct gagactggaa atgaaatatt ggagcttgtg gtgcacgccc tgatgggaga | 660 |
| cgatccggag ccacctgtgc agcttttga gcctcctacg cttcaggaac tgtatgattt | 720 |
| agaggtagag ggatcggagg attctaatga ggaagctgtg aatggctttt ttaccgattc | 780 |
| tatgctttta gctgctaatg aaggattaga attagatccg cctttggaca cttcaatac | 840 |
| tccagggggtg attgtggaaa gcggtacagg tgtaagaaaa ttacctgatt tgagttccgt | 900 |
| ggactgtgat ttgcactgct atgaagacgg gttcctccg agtgatgagg aggaccatga | 960 |
| aaaggagcag tccatgcaga ctgcagcggg tgagggagtg aaggctgcca atgttggttt | 1020 |
| tcagttggat tgcccggagc ttcctggaca tggctgtaag tcttgtgaat tcacaggaa | 1080 |
| aaatactgga gtaaaggaac tgttatgttc gctttgttat atgagaacgc actgccactt | 1140 |
| tatttacagt aagtgtgttt aagttaaaat ttaaggaat atgctgtttt tcacatgtat | 1200 |
| attgagtgtg agttttgtgc ttcttattat aggtcctgtg tctgatgctg atgaatcacc | 1260 |
| atctcctgat tctactacct cacctcctga tattcaagca cctgttcctg tggacgtgcg | 1320 |
| caagcccatt cctgtgaagc ttaagcctgg gaaacgtcca gcagtggaga acttgagga | 1380 |
| cttgttacag ggtggggacg gacctttgga cttgagtaca cggaaacgtc caagacaata | 1440 |
| agtgttccat atccgtgttt acttaaggtg acgtcaatat ttgtgtgaga gtgcaatgta | 1500 |
| ataaaaatat gttaactgtt cactggtttt tattgctttt tgggcgggga ctcaggtata | 1560 |

```
taagtagaag cagacctgtg tggttagctc ataggagctg gctttcatcc atggaggttt    1620
gggccatttt ggaagacctt aggaagacta ggcaactgtt agagagcgct tcggacggag    1680
tctccggttt ttggagattc tggttcgcta gtgaattagc tagggtagtt tttaggataa    1740
aacaggacta taaacaagaa tttgaaaagt tgttggtaga ttgcccagga cttttttgaag   1800 ctcttaattt gggccatcag gttcacttta aagaaaaagt tttatcagtt ttagactttt    1860
caaccccagg tagaactgct gctgctgtgg cttttcttac ttttatatta gataaatgga    1920
tcccgcagac tcatttcagc aggggatacg ttttggattt catagccaca gcattgtgga    1980
gaacatggaa ggttcgcaag atgaggacaa tcttaggtta ctggccagtg cagccttttgg   2040 gtgtagcggg aatcctgagg catccaccgg tcatgccagc ggttctggag gaggaacagc    2100
aagaggacaa cccgagagcc ggcctggacc ctccagtgga ggaggcggag tagctgactt    2160
gtctcctgaa ctgcaacggg tgcttactgg atctacgtcc actggacggg ataggggcgt    2220
taagagggag agggcatcca gtggtactga tgctagatct gagttggctt taagtttaat    2280
gagtcgcaga cgtcctgaaa ccatttggtg gcatgaggtt cagaaagagg aagggatga    2340 agtttctgta ttgcaggaga aatattcact ggaacaggtg aaaacatgtt ggttggagcc    2400
agaggatgat tgggaggtgg ccattaaaaa ttatgccaag atagctttga ggcctgataa    2460
acagtataag atcagtagac ggattaatat ccggaatgct tgttacatat ctggaaatgg    2520
ggctgaggtg gtaatagata ctcaagacaa gacagttatt agatgctgca tgatggatat    2580
gtggcctgga gtagtcggta tggaagcagt cacttttgta aatgttaagt ttaggggaga    2640
tggttataat ggaatagtgt ttatggccaa taccaaactt atattgcatg gttgtagctt    2700
ttttggtttc aacaatacct gtgtagatgc ctggggacag gttagtgtac ggggtgtag    2760 tttctatgcg tgttggattg ccacagctgg cagaaccaag agtcaattgt ctctgaagaa    2820
atgcatattc caaagatgta acctgggcat tctgaatgaa ggcgaagcaa gggtccgtca    2880
ctgcgcttct acagatactg gatgttttat tttaattaag ggaaatgcca gcgtaaagca    2940
taacatgatt tgtggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgttga ccaagtgcac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tctttgacat gaacacgcaa atctggaaga tcctgaggta    3240
tgatgatacg agatcgaggg tgcgcgcatg cgaatgcgga ggcaagcatg ccaggttcca    3300
gccggtgtgt gtagatgtga ccgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gacatgagtg gaaatgcttc ttttaagggg ggagtcttca gcccttatct gacagggcgt    3540
ctcccatcct gggcaggagt tcgtcagaat gttatgggat ctactgtgga tggaagaccc    3600
gttcaacccg ccaattcttc aacgctgacc tatgctactt taagttcttc acctttggac    3660
gcagctgcag ccgctgccgc cgcctctgtc gccgctaaca ctgtgcttgg aatgggttac    3720
tatggaagca tcgtggctaa ttccacttcc tctaataacc cttctacact gactcaggac    3780
aagttacttg tccttttggc ccagctggag gctttgaccc aacgtctggg tgaacttcct   3840
cagcaggtgg ccgagttgcg agtacaaact gagtctgctg tcggcacggc aaagtctaaa    3900
```

```
taaaaaaaat tccagaatca atgaataaat aaacgagctt gttgttgatt taaaatcaag    3960
tgtttttatt tcattttttcg cgcacggtat gccctggacc accgatctcg atcattgaga   4020
actcggtgga ttttttccag aatcctatag aggtgggatt gaatgtttag atacatgggc   4080
attaggccgt ctttggggtg gagatagctc cattgaaggg attcatgctc cggggtagtg   4140
ttgtaaatca cccagtcata acaaggtcgc agtgcatggt gttgcacaat atcttttaga   4200
agtaggctga ttgccacaga taagcccttg gtgtaggtgt ttacaaaccg gttgagctgg   4260
gaggggtgca ttcgaggtga aattatgtgc attttggatt ggattttaa gttggcaata    4320
ttgccgccaa gatcccgtct tgggttcatg ttatgaagga ctaccaagac ggtgtatccg   4380
gtacatttag gaaatttatc gtgcagcttg gatggaaaag cgtggaaaaa tttggagaca   4440
cccttgtgtc ctccgagatt ttccatgcac tcatccatga taatagcaat ggggccgtgg   4500
gcagcggcgc gggcaaacac gttccgtggg tctgacacat catagttatg ttcctgagtt   4560
aaatcatcat aagccatttt aatgaatttg gggcggagcg taccagattg ggtatgaat    4620
gttccttcgg gccccggagc atagttcccc tcacagattt gcatttccca agctttcagt   4680
tctgagggtg gaatcatgtc cacctggggg gctatgaaga acaccgtttc ggggggcgggg  4740
gtgattagtt gggatgatag caagtttctg agcaattgag atttgccaca tccggtgggg   4800
ccataaataa ttccgattac aggttgcagg tggtagttta gggaacggca actgccgtct   4860
tctcgaagca agggggccac ctcgttcatc atttcccctta catgcatatt ttcccgcacc   4920
aaatccatta ggaggcgctc tcctcctagt gatagaagtt cttgtagtga ggaaaagttt   4980
ttcagcggtt ttagaccgtc agccatgggc attttggaaa gagtttgctg caaaagttct   5040
agtctgttcc acagttcagt gatgtgttct atggcatctc gatccagcag acctcctcgt   5100
ttcgcgggtt tggacggctc ctggagtagg gtatgagacg atgggcgtcc agcgctgcca   5160
gggttcggtc cttccagggt ctcagtgttc gagtcagggt tgtttccgtc acagtgaagg   5220
ggtgtgcgcc tgcttgggcg cttgccaggg tgcgcttcag actcattctg ctggtggaga   5280
acttctgtcg cttggcgccc tgtatgtcgg ccaagtagca gtttaccatg agttcgtagt   5340
tgagcgcctc ggctgcgtgg cctttggcgc ggagcttacc tttggaagtt ttcttgcata   5400
ccgggcagta taggcatttc agcgcataca gcttgggcgc aaggaaaatg gattctgggg   5460
agtatgcatc cgcgccgcag gaggcgcaaa cagtttcaca ttccaccagc caggttaaat   5520
ccggttcatt ggggtcaaaa acaagttttc cgccatattt tttgatgcgt ttcttacctt    5580
tggtctccat aagttcgtgt cctcgttgag tgacaaacag gctgtccgta tctccgtaga   5640
ctgattttac aggcctcttc tccagtggag tgcctcggtc ttcttcgtac aggaactctg   5700
accactctga tacaaaggcg cgcgtccagg ccagcacaaa ggaggctatg tgggaggggt   5760
agcgatcgtt gtcaaccagg gggtccacct tttccaaagt atgcaaacac atgtcaccct   5820
cttcaacatc caggaatgtg attggcttgt aggtgtattt cacgtgacct ggggtccccg   5880
ctgggggggt ataaaagggg gcggttcttt gctcttcctc actgtcttcc ggatcgctgt   5940
ccaggaacgt cagctgttgg ggtaggtatt ccctctcgaa ggcgggcatg acctctgcac   6000
tcaggttgtc agtttctaag aacgaggagg atttgatatt gacagtgccg gttgagatgc   6060
ctttcatgag gttttcgtcc atttggtcag aaaacacaat ttttttattg tcaagtttgg   6120
tggcaaatga tccatacagg gcgttggata aagtttggc aatggatcgc atggtttggt    6180
tcttttcctt gtccgcgcgc tctttggcgg cgatgttgag ttggacatac tcgcgtgcca   6240
ggcacttcca ttcggggaag atagttgtta attcatctgg cacgattctc acttgccacc   6300
```

```
ctcgattatg caaggtaatt aaatccacac tggtggccac ctcgcctcga aggggttcat   6360
tggtccaaca gagcctacct cctttcctag aacagaaagg gggaagtggg tctagcataa   6420
gttcatcggg agggtctgca tccatggtaa agattcccgg aagtaaatcc ttatcaaaat   6480
agctgatggg agtggggtca tctaaggcca tttgccattc tcgagctgcc agtgcgcgct   6540
catatgggtt aaggggactg ccccagggca tgggatgggt gagagcagag gcatacatgc   6600
cacagatgtc atagacgtag atgggatcct caaagatgcc tatgtaggtt ggatagcatc   6660 gccccctct gatacttgct cgcacatagt catatagttc atgtgatggc gctagcagcc    6720
ccggacccaa gttggtgcga ttgggttttt ctgttctgta gacgatctgg cgaaagatgg   6780
cgtgagaatt ggaagagatg gtgggtcttt gaaaaatgtt gaaatgggca tgaggtagac   6840
ctacagagtc tctgacaaag tgggcataag attcttgaag cttggttacc agttcggcgg   6900
tgacaagtac gtctagggcg cagtagtcaa gtgtttcttg aatgatgtca taacctggtt   6960
ggtttttctt tcccacagt tcgcggttga aaggtattc ttcgcgatcc ttccagtact     7020
cttctagcgg aaacccgtct ttgtctgcac ggtaagatcc tagcatgtag aactgattaa   7080
ctgccttgta agggcagcag cccttctcta cgggtagaga gtatgcttga gcagttttc    7140 gtagcgaagc gtgagtaagg gcaaaggtgt ctctgaccat gactttgaga aattggtatt   7200
tgaagtccat gtcgtcacag gctccctgtt cccagagttg gaagtctacc cgtttcttgt   7260
aggcggggtt gggcaaagcg aaagtaacat cattgaagag aatcttaccg gctctgggca   7320
taaaattgcg agtgatgcgg aaaggctgtg gtacttccgc tcgattgttg atcacctggg   7380
cagctaggac gatttcgtcg aaaccgttga tgttgtgtcc tacgatgtat aattctatga   7440
aacgcggcgt gcctctgacg tgaggtagct tactgagctc atcaaaggtt aggtctgtgg   7500
ggtcagataa ggcgtagtgt tcgagagccc attcgtgcag gtgaggattt gcatgtagga   7560
atgatgacca aagatctacc gccagtgctg tttgtaactg gtcccgatac tgacgaaaat   7620
gccggccaat tgccattttt tctggagtga cacagtagaa ggttctgggg tcttgttgcc   7680
atcgatccca cttgagtta atggctagat cgtgggccat gttgacgaga cgctcttctc    7740
ctgagagttt catgaccagc atgaaaggaa ctagttgttt gccaaaggat cccatccagg   7800
tgtaagtttc cacatcgtag gtcaggaaga gtctttctgt gcgaggatga gagccgatcg   7860
ggaagaactg gatttcctgc caccagttgg aggattggct gttgatgtga tggaagtaga   7920
agtttctgcg gcgcgccgag cattcgtgtt tgtgcttgta cagacggccg cagtagtcgc   7980
agcgttgcac gggttgtatc tcgtgaatga gctgtacctg gcttcccttg acgagaaatt   8040
tcagtgggaa gccgaggcct ggcgattgta tctcgtgctc ttctatattc gctgtatcgg   8100
cctgttcatc ttctgtttcg atggtggtca tgctgacgag ccccgcgggg aggcaagtcc   8160
agacctcggc gcgggagggg cggagctgaa ggacgagagc gcgcaggctg gagctgtcca   8220
gagtcctgag acgctgcgga ctcaggttag taggtaggga cagaagatta acttgcatga   8280
tcttttccag ggcgtgcggg aggttcagat ggtacttgat ttccacaggt tcgtttgtag   8340
agacgtcaat ggcttgcagg gttccgtgtc ctttgggcgc cactaccgta cctttgtttt   8400
ttcttttgat cggtggtggc tctccttgctt cttgcatgct cagaagcggt gacgggacg    8460 cgcgccgggc ggcagcggtt gttccggacc cgggggcatg gctggtagtg gcacgtcggc   8520
gccgcgcacg ggcaggttct ggtattgcgc tctgagaaga cttgcgtgcg ccaccacgcg   8580
tcgattgacg tcttgtatct gacgtctctg ggtgaaagct accggccccg tgagcttgaa   8640
```

```
cctgaaagag agttcaacag aatcaatttc ggtatcgtta acggcagctt gtctcagtat    8700
ttcttgtacg tcaccagagt tgtcctggta ggcgatctcc gccatgaact gctcgatttc    8760
ttcctcctga agatctccgc gacccgctct ttcgacggtg gccgcgaggt cattggagat    8820
acggcccatg agttgggaga atgcattcat gcccgcctcg ttccagacgc ggctgtaaac    8880
cacggccccc tcggagtctc ttgcgcgcat caccacctga gcgaggttaa gctccacgtg    8940
tctggttaag accgcatagt tgcataggcg ctgaaaaagg tagttgagtg tggtggcaat    9000
gtgttcggcg acgaagaaat acatgatcca tcgtctcagc ggcatttcgc taacatcgcc    9060
cagagcttcc aagcgctcca tggcctcgta gaagtccacg gcaaaattaa aaaactggga    9120
gtttcgcgcg gacacggtca attcctcctc gagaagacgg atgagttcgg ctatggtggc    9180
ccgtacttcg cgttcgaagg ctcccgggat ctcttcttcc tcttctatct cttcttccac    9240
taacatctct tcttcgtctt caggcggggg cggagggggc acgcggcgac gtcgacggcg    9300
cacgggcaaa cggtcgatga atcgttcaat gacctctccg cggcggcggc gcatggtttc    9360
agtgacggcg cggccgttct cgcgcggtcg cagagtaaaa acaccgccgc gcatctcctt    9420
aaagtggtga ctgggaggtt ctccgtttgg gagggagagg gcgctgatta tacattttat    9480
taattggccc gtagggactg cgcgcagaga tctgatcgtg tcaagatcca cgggatctga    9540
aaacctttcg acgaaagcgt ctaaccagtc acagtcacaa ggtaggctga gtacggcttc    9600
ttgtgggcgg gggtggttat gtgttcggtc tgggtcttct gtttcttctt catctcggga    9660
aggtgagacg atgctgctgg tgatgaaatt aaagtaggca gttctaagac ggcggatggt    9720
ggcgaggagc accaggtctt tgggtccggc ttgctggata cgcaggcgat tggccattcc    9780
ccaagcatta tcctgacatc tagcaagatc tttgtagtag tcttgcatga gccgttctac    9840
gggcacttct tcctcacccg ttctgccatg catacgtgtg agtccaaatc cgcgcattgg    9900
ttgtaccagt gccaagtcag ctacgactct ttcggcgagg atggcttgct gtacttgggt    9960
aagggtggct tgaaagtcat caaaatccac aaagcggtgg taagcccctg tattaatggt   10020
gtaagcacag ttggccatga ctgaccagtt aactgtctgg tgaccagggc gcacgagctc   10080
ggtgtattta aggcgcgaat aggcgcgggt gtcaaagatg taatcgttgc aggtgcgcac   10140
cagatactgg taccctataa gaaaatgcgg cggtggttgg cggtagagag gccatcgttc   10200
tgtagctgga gcgccagggg cgaggtcttc aacataagg cggtgatagc cgtagatgta   10260
cctggacatc caggtgattc ctgcggcggt agtagaagcc cgaggaaact cgcgtacgcg   10320
gttccaaatg ttgcgtagcg gcatgaagta gttcattgta ggcacggttt gaccagtgag   10380
gcgcgcgcag tcattgatgc tctatagaca cggagaaaat gaaagcgttc agcgactcga   10440
ctccgtagcc tggaggaacg tgaacgggtt gggtcgcggt gtaccccggt tcgagacttg   10500
tactcgagcc ggccggagcc gcggctaacg tggtattggc actcccgtct cgacccagcc   10560
tacaaaaatc caggatacgg aatcgagtcg ttttgctggt ttccgaatgg cagggaagtg   10620
agtcctattt ttttttttt ttgccgctca gaatgcatcc cgtgctgcga cagatgcgcc   10680
cccaacaaca gccccctcg cagcagcagc agcagcaacc acaaaaggct gtccctgcaa   10740
ctactgcaac tgccgccgtg agcggtgcgg gacagcccgc ctatgatctg gacttggaag   10800
agggcgaagg actggcacgt ctaggtgcgc cttcgcccga gcggcatccg cgagttcaac   10860
tgaaaaaaga ttctcgcgag gcgtatgtgc cccaacagaa cctatttaga gacagaagcg   10920
gcgaggagcc ggaggagatg cgagcttccc gctttaacgc gggtcgtgag ctgcgtcacg   10980
gtttggaccg aagacgagtg ttgcgagacg aggatttcga agttgatgaa gtgacaggga   11040
```

```
tcagtcctgc cagggcacac gtggctgcag ccaaccttgt atcggcttac gagcagacag   11100
taaaggaaga gcgtaacttc caaaagtctt ttaataatca tgtgcgaacc ctgattgccc   11160
gcgaagaagt taccccttggt ttgatgcatt tgtgggattt gatggaagct atcattcaga   11220
accctactag caaacctctg accgcccagc tgtttctggt ggtgcaacac agcagagaca   11280
atgaggcttt cagagaggcg ctgctgaaca tcaccgaacc cgaggggaga tggttgtatg   11340
atcttatcaa cattctacag agtatcatag tgcaggagcg gagcctgggc ctggccgaga   11400
aggtagctgc catcaattac tcggttttga gcttgggaaa atattacgct cgcaaaatct   11460
acaagactcc atacgttccc atagacaagg aggtgaagat agatgggttc acatgcgca   11520 tgacgctcaa ggtcttgacc ctgagcgatg atcttgggt gtatcgcaat gacagaatgc   11580
atcgcgcggt tagcgccagc aggaggcgcg agttaagcga cagggaactg atgcacagtt   11640
tgcaaagagc tctgactgga gctggaaccg agggtgagaa ttacttcgac atgggagctg   11700
acttgcagtg gcagcctaat cgcagggctc tgagcgccgc gacggcagga tgtgagcttc   11760
cttacataga agaggcggat gaaggcgagg aggaagaggg cgagtacttg gaagactgat   11820
ggcacaaccc gtgttttttg ctagatggaa cagcaagcac cggatcccgc aatgcgggcg   11880
gcgctgcaga gccagccgtc cggcattaac tcctcggacg attggaccca ggccatgcaa   11940
cgtatcatgg cgttgacgac tcgcaaccc gaagcctta gacagcaacc ccaggccaac   12000
cgtctatcgg ccatcatgga agctgtagtg ccttcccgat ctaatcccac tcatgagaag   12060
gtcctggcca tcgtgaacgc gttggtggag aacaaagcta ttcgtccaga tgaggccgga   12120
ctggtataca acgctctctt agaacgcgtg gctcgctaca acagtagcaa tgtgcaaacc   12180
aatttggacc gtatgataac agatgtacgc gaagccgtgt ctcagcgcga aaggttccag   12240
cgtgatgcca acctgggttc gctggtggcg ttaaatgctt tcttgagtac tcagcctgct   12300
aatgtgccgc gtggtcaaca ggattatact aacttttaa gtgctttgag actgatggta   12360
tcagaagtac ctcagagcga agtgtatcag tccggtcctg attacttctt tcagactagc   12420
agacagggct tgcagacggt aaatctgagc caagctttta aaaaccttaa aggtttgtgg   12480
ggagtgcatg ccccggtagg agaaagagca accgtgtcta gcttgttaac tccgaactcc   12540
cgcctgttat tactgttggt agctcctttc accgacagcg gtagcatcga ccgtaattcc   12600
tatttgggtt acctactaaa cctgtatcgc gaagccatag gcaaagtca ggtggacgag   12660 cagacctatc aagaaattac ccaagtcagt cgcgctttgg gacaggaaga cactggcagt   12720
ttggaagcca ctctgaactt cttgcttacc aatcggtctc aaaagatccc tcctcaatat   12780
gctcttactg cggaggagga gaggatcctt agatatgtgc agcagagcgt gggattgttt   12840
ctgatgcaag aggggcaac tccgactgca gcactggaca tgacagcgcg aaatatggag   12900
cccagcatgt atgccagtaa ccgaccttc attaacaaac tgctggacta cttgcacaga   12960
gctgccgcta tgaactctga ttatttcacc aatgccatct aaacccgca ctggctgccc   13020 ccacctggtt tctacacggg cgaatatgac atgcccgacc ctaatgacgg atttctgtgg   13080
gacgacgtgg acagcgatgt tttttcacct ctttctgatc atcgcacgtg gaaaaaggaa   13140
ggcggtgata gaatgcattc ttctgcatcg ctgtccgggg tcatgggtgc taccgcggct   13200
gagcccgagt ctgcaagtcc ttttcctagt ctaccctttt ctctacacag tgtacgtagc   13260
agcgaagtgg gtagaataag tcgcccgagt ttaatgggcg aagaggagta cctaaacgat   13320
tccttgctca gaccggcaag agaaaaaaat ttcccaaaca atggaataga aagtttggtg   13380
```

```
gataaaatga gtagatggaa gacttatgct caggatcaca gagacgagcc tgggatcatg    13440
gggactacaa gtagagcgag ccgtagacgc cagcgccatg acagacagag gggtcttgtg    13500
tgggacgatg aggattcggc cgatgatagc agcgtgttgg acttgggtgg gagaggaagg    13560
ggcaacccgt ttgctcattt gcgccctcgc ttgggtggta tgttgtgaaa aaaataaaa     13620 aagaaaaact caccaaggcc atggcgacga gcgtacgttc gttcttcttt attatctgtg    13680
tctagtataa tgaggcgagt cgtgctaggc ggagcgtgg tgtatccgga gggtcctcct     13740
ccttcgtacg agagcgtgat gcagcagcag caggcgacgg cggtgatgca atccccactg    13800
gaggctccct ttgtgcctcc gcgatacctg gcacctacgg agggcagaaa cagcattcgt    13860
tactcggaac tggcacctca gtacgatacc accaggttgt atctggtgga caacaagtcg    13920
gcggacattg cttctctgaa ctatcagaat gaccacagca acttcttgac cacggtggtg    13980
cagaacaatg actttacccc tacggaagcc agcacccaga ccattaactt tgatgaacga    14040
tcgcggtggg gcggtcagct aaagaccatc atgcatacta acatgccaaa cgtgaacgag    14100
tatatgttta gtaacaagtt caaagcgcgt gtgatggtgt ccagaaaacc tcccgacggt    14160
gctgcagttg gggatactta tgatcacaag caggatattt tggaatatga gtggttcgag    14220
tttactttgc cagaaggcaa cttttcagtt actatgacta ttgatttgat gaacaatgcc    14280
atcatagata attacttgaa agtgggtaga cagaatggag tgcttgaaag tgacattggt    14340
gttaagttcg acaccaggaa cttcaagctg ggatgggatc ccgaaaccaa gttgatcatg    14400
cctggagtgt atacgtatga agccttccat cctgacattg tcttactgcc tggctgcgga    14460
gtggatttta ccgagagtcg tttgagcaac cttcttggta tcagaaaaaa acagccattt    14520
caagagggtt ttaagatttt gtatgaagat ttagaaggtg gtaatattcc ggccctcttg    14580
gatgtagatg cctatgagaa cagtaagaaa gaacaaaaag ccaaaataga agctgctaca    14640
gctgctgcag aagctaaggc aaacatagtt gccagcgact ctacaagggt tgctaacgct    14700
ggagaggtca gaggagacaa ttttgcgcca cacctgttc cgactgcaga atcattattg     14760
gccgatgtgt ctgaaggaac ggacgtgaaa ctcactattc aacctgtaga aaagatagt     14820 aagaatagaa gctataatgt gttggaagac aaaatcaaca cagcctatcg cagttggtat    14880 cttttcgtaca attatggcga tcccgaaaaa ggagtgcgtt cctggacatt gctcaccacc    14940
tcagatgtca cctgcggagc agagcaggtt tactggtcgc ttccagacat gatgaaggat    15000
cctgtcactt tccgctccac tagacaagtc agtaactacc ctgtggtggg tgcagagctt    15060
atgcccgtct tctcaaagag cttctacaac gaacaagctg tgtactccca gcagctccgc    15120
cagtccacct cgcttacgca cgtcttcaac cgctttcctg agaaccagat tttaatccgt    15180 ccgcggcgc ccaccattac caccgtcagt gaaaacgttc ctgctctcac agatcacggg      15240
accctgccgt tgcgcagcag tatccgggga gtccaacgtg tgaccgttac tgacgccaga    15300
cgccgcacct gtccctacgt gtacaaggca ctgggcatag tcgcaccgcg cgtccttca    15360 agccgcactt tctaaaaaaa aaatgtccat tcttatctcg cccagtaata acaccggttg    15420
gggtctgcgc gctccaagca agatgtacgg aggcgcacgc aaacgttcta cccaacatcc    15480
cgtgcgtgtt cgcggacatt ttcgcgctcc atggggtgcc ctcaagggcc gcactcgcgt    15540
tcgaaccacc gtcgatgatg taatcgatca ggtggttgcc gacgcccgta attatactcc    15600
tactgcgcct acatctactg tggatgcagt tattgacagt gtagtggctg acgctcgcaa    15660
ctatgctcga cgtaagagcc ggcgaaggcg cattgccaga cgccaccgag ctaccactgc    15720
catgcgagcc gcaagagctc tgctacgaag agctagacgc gtggggcgaa gagccatgct    15780
```

```
tagggcggcc agacgtgcag cttcgggcgc cagcgccggc aggtcccgca ggcaagcagc   15840
cgctgtcgca gcggcgacta ttgccgacat ggcccaatcg cgaagaggca atgtatactg   15900
ggtgcgtgac gctgccaccg gtcaacgtgt acccgtgcgc acccgtcccc ctcgcactta   15960
gaagatactg agcagtctcc gatgttgtgt cccagcggcg aggatgtcca agcgcaaata   16020
caaggaagaa atgctgcagg ttatcgcacc tgaagtctac ggccaaccgt gaaggatga    16080 aaaaaaaccc cgcaaaatca agcgggttaa aaaggacaaa aaagaagagg aagatggcga   16140
tgatgggctg gcggagtttg tgcgcgagtt tgccccacgg cgacgcgtgc aatggcgtgg   16200
gcgcaaagtt cgacatgtgt tgagacctgg aacttcggtg gtctttacac ccggcgagcg   16260
ttcaagcgct acttttaagc gttcctatga tgaggtgtac ggggatgatg atattcttga   16320
gcaggcggct gaccgattag gcgagtttgc ttatggcaag cgtagtagaa taacttccaa   16380
ggatgagaca gtgtcaatac ccttggatca tggaaatccc accctagtc  ttaaaccggt   16440 cactttgcag caagtgttac ccgtaactcc gcgaacaggg gttaaacgcg aaggtgaaga   16500
tttgtatccc actatgcaac tgatggtacc caaacgccag aagttggagg acgttttgga   16560
gaaagtaaaa gtggatccag atattcaacc tgaggttaaa gtgagaccca ttaagcaggt   16620
agcgcctggt ctgggggtac aaactgtaga cattaagatt cccactgaaa gtatggaagt   16680
gcaaactgaa cccgcaaagc ctactgccac ctccactgaa gtgcaaacgg atccatggat   16740
gcccatgcct attacaactg acgccgccgg tcccactcga agatcccgac gaaagtacgg   16800
tccagcaagt ctgttgatgc ccaattatgt tgtacaccca tctattattc ctactcctgg   16860
ttaccgaggc actcgctact atcgcagccg aaacagtacc tcccgccgtc gccgcaagac   16920
acctgcaaat cgcagtcgtc gccgtagacg cacaagcaaa ccgactcccg cgcccctggt   16980
gcggcaagtg taccgcaatg gtagtgcgga acctttgaca ctgccgcgtg cgcgttacca   17040
tccgagtatc atcacttaat caatgttgcc gctgcctcct tgcagatatg gccctcactt   17100
gtcgccttcg cgttcccatc actggttacc gaggaagaaa ctcgcgccgt agaagaggga   17160
tgttgggacg cggaatgcga cgctacaggc gacggcgtgc tatccgcaag caattgcggg   17220
gtggtttttt accagcctta attccaatta tcgctgctgc aattggcgcg ataccaggca   17280
tagcttccgt ggcggttcag gcctcgcaac gacattgaca ttggaaaaaa aacgtataaa   17340
taaaaaaaaa tacaatggac tctgacactc ctggtcctgt gactatgttt tcttagagat   17400
ggaagacatc aattttttcat ccttggctcc gcgacacggc acgaagccgt acatgggcac   17460
ctggagcgac atcggcacga gccaactgaa cgggggcgcc ttcaattgga gcagtatctg   17520
gagcgggctt aaaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaaccca  ggtgaaatgc aagtggagga   17760
agaaattcct ccgccagaaa aacgaggcga caagcgtccg cgtcccgatt ggaagagac   17820 gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttggatttgc cccctccccc tgctgctact gctgtacccg cttctaagcc   18000
tgtcgctgcc ccgaaaccag tcgccgtagc caggtcacgt cccgggggcg ctcctcgtcc   18060
aaatgcgcac tggcaaaata ctctgaacag catcgtgggt ctaggcgtgc aaagtgtaaa   18120
```

```
acgccgtcgc tgcttttaat taaatatgga gtagcgctta acttgcctat ctgtgtatat    18180
gtgtcattac acgccgtcac agcagcagag gaaaaaagga agaggtcgtg cgtcgacgct    18240
gagttacttt caagatggcc acccatcga tgctgcccca atgggcatac atgcacatcg    18300
ccggacagga tgcttcggag tacctgagtc cgggtctggt gcagttcgcc cgcgccacag    18360
acacctactt caatctggga aataagttta gaaatcccac cgtagcgccg acccacgatg    18420
tgaccaccga ccgtagccag cggctcatgt tgcgcttcgt gcccgttgac cgggaggaca    18480
atacatactc ttacaaagtg cggtacaccc tggccgtggg cgacaacaga gtgctggata    18540
tggccagcac gttctttgac attaggggcg tgttggacag aggtcccagt ttcaaaccct    18600
attctggtac ggcttacaac tctctggctc ctaaaggcgc tccaaatgca tctcaatgga    18660
ttgcaaaagg cgtaccaact gcagcagccg caggcaatgg tgaagaagaa catgaaacag    18720
aggagaaaac tgctacttac acttttgcca atgctcctgt aaaagccgag gctcaaatta    18780
caaaagaggg cttaccaata ggtttggaga tttcagctga aaacgaatct aaacccatct    18840
atgcagataa actttatcag ccagaacctc aagtgggaga tgaaacttgg actgacctag    18900
acggaaaaac cgaagagtat ggaggcaggg ctctaaagcc tactactaac atgaaaccct    18960
gttacgggtc ctatgcgaag cctactaatt taaaaggtgg tcaggcaaaa ccgaaaaact    19020
cggaaccgtc gagtgaaaaa attgaatatg atattgacat ggaatttttt gataactcat    19080
cgcaaagaac aaacttcagt cctaaaattg tcatgtatgc agaaaatgta ggtttggaaa    19140
cgccagacac tcatgtagtg tacaaacctg gaacagaaga cacaagttcc gaagctaatt    19200
tgggacaaca gtctatgccc aacagaccca actacattgg cttcagagat aactttattg    19260
gactcatgta ctataacagt actggtaaca tgggggtgct ggctggtcaa cgtctcagt    19320
taaatgcagt ggttgacttg caggacagaa acacagaact ttcttaccaa ctcttgcttg    19380
actctctggg cgacagaacc agatacttta gcatgtggaa tcaggctgtg gacagttatg    19440
atcctgatgt acgtgttatt gaaaatcatg gtgtggaaga tgaacttccc aactattgtt    19500
ttccactgga cggcataggt gttccaacaa ccagttacaa atcaatagtt ccaaatggag    19560
aagataataa taattggaaa gaacctgaag taaatggaac aagtgagatc ggacagggta    19620
atttgtttgc catggaaatt aaccttcaag ccaatctatg gcgaagtttc ctttattcca    19680
atgtggctct gtatctccca gactcgtaca aatacacccc gtccaatgtc actcttccag    19740
aaaacaaaaa cacctacgac tacatgaacg ggcgggtggt gccgccatct ctagtagaca    19800
cctatgtgaa cattggtgcc aggtggtctc tggatgccat ggacaatgtc aacccattca    19860
accaccaccg taacgctggc ttgcgttacc gatctatgct tctgggtaac ggacgttatg    19920
tgccttttcca catacaagtg cctcaaaaat tcttcgctgt taaaaacctg ctgcttctcc    19980
caggctccta cacttatgag tggaaccttta ggaaggatgt gaacatggtt ctacagagtt    20040
ccctcggtaa cgacctgcgg gtagatggcg ccagcatcag tttcacgagc atcaacctct    20100
atgctacttt tttccccatg gctcacaaca ccgcttccac ccttgaagcc atgctgcgga    20160
atgacaccaa tgatcagtca ttcaacgact acctatctgc agctaacatg ctctaccccca    20220
ttcctgccaa tgcaaccaat attcccattt ccattccttc tcgcaactgg gcggctttca    20280
gaggctggtc atttaccaga ctgaaaacca agaaactcc ctctttgggg tctggatttg    20340
accctactt tgtctattct ggttctattc cctacctgga tggtaccttc tacctgaacc    20400
acactttta gaaggtttcc atcatgtttg actcttcagt gagctggcct ggaaatgaca    20460
ggttactatc tcctaacgaa tttgaaataa agcgcactgt ggatggcgaa ggctacaacg    20520
```

```
tagcccaatg caacatgacc aaagactggt tcttggtaca gatgctcgcc aactacaaca  20580
tcggctatca gggcttctac attccagaag gatacaaaga tcgcatgtat tcatttttca  20640
gaaacttcca gcccatgagc aggcaggtgg ttgatgaggt caattacaaa gacttcaagg  20700
ccgtcgccat accctaccaa cacaacaact ctggctttgt gggttacatg gctccgacca  20760
tgcgccaagg tcaaccctat cccgctaact atccctatcc actcattgga caactgccg   20820
taaatagtgt tacgcagaaa aagttcttgt gtgacagaac catgtggcgc ataccgttct  20880
cgagcaactt catgtctatg ggggccctta cagacttggg acagaatatg ctctatgcca  20940
actcagctca tgctctggac atgacctttg aggtggatcc catggatgag cccaccctgc  21000
tttatcttct cttcgaagtt ttcgacgtgg tcagagtgca tcagccacac cgcggcatca  21060
tcgaggcagt ctacctgcgt acaccgttct cggccggtaa cgctaccacg taagaagctt  21120
cttgcttctt gcaaatagca gctgcaacca tggcctgcgg atcccaaaac ggctccagcg  21180
agcaagagct cagagccatt gtccaagacc tgggttgcgg accctatttt ttgggaacct  21240
acgataagcg cttcccgggg ttcatggccc ccgataagct cgcctgtgcc attgtaaata  21300
cggccggacg tgagacgggg ggagagcact ggttggcttt cggttggaac ccacgttcta  21360
acacctgcta cctttttgat ccttttggat tctcggatga tcgtctcaaa cagatttacc  21420
agtttgaata tgagggtctc ctgcgccgca gcgctcttgc taccaaggac cgctgtatta  21480
cgctggaaaa atctacccag accgtgcagg gcccccgttc tgccgcctgc ggacttttct  21540
gctgcatgtt ccttcacgcc tttgtgcact ggcctgaccg tcccatggac ggaaacccca  21600
ccatgaaatt gctaactgga gtgccaaaca acatgcttca ttctcctaaa gtccagccca  21660
ccctgtgtga caatcaaaaa gcactctacc attttcttaa tacccattcg ccttattttc  21720
gctctcatcg tacacacatc gaaagggcca ctgcgttcga ccgtatggat gttcaataat  21780
gactcatgta aacaacgtgt tcaataaaca tcactttatt tttttacatg tatcaaggct  21840
ctggattact tatttattta caagtcgaat gggttctgac gagaatcaga atgacccgca  21900
ggcagtgata cgttgcggaa ctgatacttg ggttgccact tgaattcggg aatcaccaac  21960
ttgggaaccg gtatatcggg caggatgtca ctccacagct ttctggtcag ctgcaaagct  22020
ccaagcaggt caggagccga aatcttgaaa tcacaattag gaccagtgct ctgagcgcga  22080
gagttgcggt acaccggatt gcagcactga aacaccatca gcgacggatg tctcacgctt  22140
gccagcacgg tgggatctgc aatcatgccc acatccagat cttcagcatt ggcaatgctg  22200
aacgggtca tcttgcaggt ctgcctaccc atggcgggca cccaattagg cttgtggttg  22260
caatcgcagt gcaggggat cagtatcatc ttggcctgat cctgtctgat tcctggatac  22320
acggctctca tgaaagcatc atattgcttg aaagcctgct gggctttact accctcggga  22380
taaaacatcc cgcaggacct gctcgaaaac tggttagcct gcacagccgg catcattcac  22440
acagcagcgg gcgtcattgt tggctatttg caccacactt ctgccccagc ggttttgggt  22500
gattttggtt cgctcgggat tctcctttaa ggctcgttgt ccgttctcgc tggccacatc  22560
catctcgata atctgctcct tctgaatcat aatattgcca tgcaggcact tcagcttgcc  22620
ctcataatca ttgcagccat gaggccacaa cgcacagcct gtacattccc aattatggtg  22680
ggcgatctga gaaaagaat gtatcattcc ctgcagaaat cttcccatca tcgtgctcag  22740
tgtcttgtga ctagtgaaag ttaactggat gcctcggtgc tcttcgttta cgtactggtg  22800
acagatgcgc ttgtattgtt cgtgttgctc aggcattagt ttaaaacagg ttctaagttc  22860
```

```
gttatccagc ctgtacttct ccatcagcag acacatcact tccatgcctt tctcccaagc   22920
agacaccagg ggcaagctaa tcggattctt aacagtgcag gcagcagctc ctttagccag   22980
agggtcatct ttagcgatct tctcaatgct tcttttgcca tccttctcaa cgatgcgcac   23040
gggcgggtag ctgaaaccca ctgctacaag ttgcgcctct tctctttctt cttcgctgtc   23100
ttgactgatg tcttgcatgg ggatatgttt ggtcttcctt ggcttctttt tgggggtat    23160 cggaggagga ggactgtcgc tccgttccgg agacagggag gattgtgacg tttcgctcac   23220
cattaccaac tgactgtcgg tagaagaacc tgacccaca cggcgacagg tgttttctt     23280 cgggggcaga ggtggaggcg attgcgaagg gctgcggtcc gacctggaag gcggatgact   23340
ggcagaaccc cttccgcgtt cggggtgtg ctccctgtgg cggtcgctta actgatttcc    23400
ttcgcggctg gccattgtgt tctcctaggc agagaaacaa cagacatgga aactcagcca   23460 tgctgtcaa catcgccacg agtgccatca catctcgtcc tcagcgacga ggaaaaggag    23520
cagagcttaa gcattccacc gcccagtcct gccaccacct ctaccctaga agataaggag   23580
gtcgacgcat ctcatgacat gcagaataaa aaagcgaaag agtctgagac agacatcgag   23640
caagacccgg gctatgtgac accggtggaa cacgaggaag agttgaaacg cttttctagag  23700 agagaggatg aaaactgccc aaaacagcga gcagataact atcaccaaga tgctggaaat   23760
agggatcaga acaccgacta cctcataggg cttgacgggg aagacgcgct ccttaaacat   23820
ctagcaagac agtcgctcat agtcaaggat gcattattgg acagaactga agtgcccatc   23880
agtgtggaag agctcagctg cgcctacgag cttaacctttt tttcacctcg tactccccc    23940 aaacgtcagc caaacggcac ctgcgagcca aatcctcgct taaacttttta tccagctttt   24000 gctgtgccag aagtactggc tacctatcac atcttttta aaaatcaaaa aattccagtc    24060
tcctgccgcg ctaatcgcac ccgcgccgat gccctactca atctgggacc tggttcacgc   24120
ttacctgata tagcttcctt ggaagaggtt ccaaagatct tcgagggtct gggcaataat   24180
gagactcggg ccgcaaatgc tctgcaaaag ggagaaaatg gcatggatga gcatcacagc   24240
gttctggtgg aattggaagg cgataatgcc agactcgcag tactcaagcg aagcgtcgag   24300
gtcacacact tcgcatatcc cgctgtcaac ctgccccta aagtcatgac ggcggtcatg     24360
gaccagttac tcattaagcg cgcaagtccc cttttcagaag acatgcatga cccagatgcc   24420
tgtgatgagg gtaaaccagt ggtcagtgat gagcagctaa cccgatggct gggcaccgac   24480
tctccccggg atttggaaga gcgtcgcaag cttatgatgg ccgtggtgct ggttaccgta   24540
gaactagagt gtctccgacg tttctttacc gattcagaaa ccttgcgcaa actcgaagag   24600
aatctgcact acacttttag acacggcttt gtgcggcagg catgcaagat atctaacgtg   24660
gaactcacca acctggtttc ctacatgggt attctgcatg agaatcgcct aggacaaagc   24720
gtgctgcaca gcacccttaa gggggaagcc cgccgtgatt acatccgcga ttgtgtctat   24780
ctctacctgt gccacacgtg gcaaaccggc atgggtgtat ggcagcaatg tttagaagaa   24840
cagaacttga aagagcttga caagctctta cagaaatctc ttaaggttct gtggacaggg   24900
ttcgacgagc gcaccgtcgc ttccgacctg gcagacctca tcttcccaga gcgtctcagg   24960
gttactttgc gaaacggatt gcctgacttt atgagccaga gcatgcttaa caattttcgc   25020
tctttcatcc tggaacgctc cggtatcctg cccgccacct gctgcgcact gccctccgac   25080
tttgtgcctc tcacctaccg cgagtgcccc ccgccgctat ggagtcactg ctacctgttc   25140
cgtctggcca actatctctc ctaccactcg gatgtgatcg aggatgtgag cggagacggc   25200
ttgctggagt gccactgccg ctgcaatctg tgcacgcccc accggtccct agcttgcaac   25260
```

```
ccccagttga tgagcgaaac ccagataata ggcacctttg aattgcaagg ccccagcagc   25320
caaggcgatg ggtcttctcc tgggcaaagt ttaaaactga ccccgggact gtggacctcc   25380
gcctacttgc gcaagtttgc tccggaagat taccacccct atgaaatcaa gttctatgag   25440
gaccaatcac agcctccaaa ggccgaactt tcggcttgcg tcatcaccca gggggcaatt   25500
ctggcccaat tgcaagccat ccaaaaatcc cgccaagaat ttctactgaa aaagggtaag   25560
ggggtctacc ttgaccccca gaccggcgag gaactcaaca caaggttccc tcaggatgtc   25620
ccaacgacga gaaaacaaga agttgaaggt gcagccgccg ccccagaag atatggagga    25680 agattgggac agtcaggcag aggaggcgga ggaggacagt ctggaggaca gtctggagga   25740
agacagtttg gaggaggaaa acgaggaggc agaggaggtg gaagaagtaa ccgccgacaa   25800
acagttatcc tcggctgcgg agacaagcaa cagcgctacc atctccgctc cgagtcgagg   25860
aacccggcgg cgtcccagca gtagatggga cgagaccgga cgcttcccga acccaaccag   25920
cgcttccaag accggtaaga aggatcggca gggatacaag tcctggcggg ggcataagaa   25980
tgccatcatc tcctgcttgc atgagtgcgg gggcaacata tccttcacgc ggcgctactt   26040
gctattccac catggggtga actttccgcg caatgttttg cattactacc gtcacctcca   26100
cagcccctac tatagccagc aaatcccgac agtctcgaca gataaagaca gcggcggcga   26160
cctccaacag aaaaccagca gcggcagtta gaaaatacac aacaagtgca gcaacaggag   26220
gattaaagat tacagccaac gagccagcgc aaacccgaga gttaagaaat cggatctttc   26280
caaccctgta tgccatcttc cagcagagtc ggggtcaaga gcaggaactg aaaataaaaa   26340
accgatctct gcgttcgctc accagaagtt gtttgtatca caagagcgaa gatcaacttc   26400
agcgcactct cgaggacgcc gaggctctct tcaacaagta ctgcgcgctg actcttaaag   26460
agtaggcagc gaccgcgctt attcaaaaaa ggcgggaatt acatcatcct cgacatgagt   26520
aaagaaattc ccacgcctta catgtggagt tatcaacccc aaatgggatt ggcagcaggc   26580
gcctcccagg actactccac ccgcatgaat tggctcagcg ccgggccttc tatgatttct   26640
cgagttaatg atatacgcgc ctaccgaaac caaatacttt tggaacagtc agctcttacc   26700
accacgcccc gccaacacct taatcccaga aattggcccg ccgccctagt gtaccaggaa   26760
agtcccgctc ccaccactgt attacttcct cgagacgccc aggccgaagt ccaaatgact   26820
aatgcaggtg cgcagttagc tggcggctcc accctatgtc gtcacaggcc tcggcataat   26880
ataaaacgcc tgatgatcag aggccgaggt atccagctca acgacgagtc ggtgagctct   26940
ccgcttggtc tacgaccaga cggaatcttt cagattgccg gctgcgggag atcttccttc   27000
acccctcgtc aggctgttct gactttggaa agttcgtctt cgcaaccccg ctcgggcgga   27060
atcgggaccg ttcaatttgt agaggagttt actccctctg tctacttcaa cccttctcc    27120 ggatctcctg ggcactaccc ggacgagttc ataccgaact tcgacgcgat tagcgagtca   27180
gtggacggct acgattgatg tctggtgacg cggctgagct atctcggctg cgacatctag   27240
accactgccg ccgctttcgc tgctttgccc gggaacttat tgagttcatc tacttcgaac   27300
tccccaagga tcaccctcaa ggtccggccc acggagtgcg gattactatc gaaggcaaaa   27360
tagactctcg cctgcaacga atttctccc agcggcccgt gctgatcgag cgagaccagg    27420
gaaacaccac ggtttccatc tactgcattt gtaatcaccc cggattgcat gaaagccttt   27480
gctgtcttat gtgtactgag tttaataaaa actgaattaa gactctccta cggactgccg   27540
cttcttcaac ccggatttta caaccagaag aacaaaactt ttcctgtcgt ccaggactct   27600
```

```
gttaacttca cctttcctac tcacaaacta gaagctcaac gactacaccg cttttccaga   27660
agcattttcc ctactaatac tactttcaaa accggaggtg agctccacgg tctccctaca   27720
gaaaacccct tgggtggaagc gggccttgta gtactaggaa ttcttgcggg tgggcttgtg   27780
attattcttt gctacctata cacaccttgc ttcactttcc tagtggtgtt gtggtattgg   27840
tttaaaaaat ggggcccata ctagtcttgc ttgttttact ttcgcttttg gaaccgggtt   27900
ctgccaatta cgatccatgt ctagactttg acccagaaaa ctgcacactt acttttgcac   27960
ccgacacaag ccgcatctgt ggagttctta ttaagtgcgg atgggaatgc aggtccgttg   28020
aaattacaca caataacaaa acctggaaca ataccttatc caccacatgg gagccaggag   28080
ttcccgagtg gtacactgtc tctgtccgag gtcctgacgg ttccatccgc attagtaaca   28140
acactttcat tttttctgaa atgtgcgatc tggccatgtt catgagcaaa cagtattctc   28200
tatggcctcc tagcaaggac aacatcgtaa cgttctccat tgcttattgc ttgtgcgctt   28260
gccttcttac tgctttactg tgcgtatgca tacacctgct tgtaaccact cgcatcaaaa   28320
acgccaataa caaagaaaaa atgccttaac ctctttctgt ttacagacat ggcttctctt   28380
acatctctca tatttgtcag cattgtcact gccgctcacg gacaaacagt cgtctctatc   28440
ccactaggac ataattacac tctcatagga cccccaatca cttcagaggt catctggacc   28500
aaactgggaa gcgttgatta ctttgatata atctgtaaca aaacaaaacc aataatagta   28560
acttgcaaca tacaaaatct tacattgatt aatgttagca aagtttacag cggttactat   28620
tatggttatg acagatacag tagtcaatat agaaattact tggttcgtgt tacccagttg   28680
aaaaccacga aaatgccaaa tatggcaaag attcgatccg atgacaattc tctagaaact   28740
tttacatctc ccaccacacc cgacgaaaaa aacatcccag attcaatgat tgcaattgtt   28800
gcagcggtgg cagtggtgat ggcactaata ataatatgca tgctttata tgcttgtcgc   28860 tacaaaaagt ttcatcctaa aaaacaagat ctcctactaa ggcttaacat ttaatttctt   28920
tttatacagc catggtttcc actaccacat tccttatgct tactagtctc gcaactctga   28980
cttctgctcg ctcacaccct actgtaacta taggctcaaa ctgcacacta aaaggacctc   29040
aaggtggtca tgtcttttgg tggagaatat atgacaatgg atggtttaca aaaccatgtg   29100
accaacctgg tagatttttc tgcaacggca gagacctaac cattatcaac gtgacagcaa   29160
atgacaaagg cttctattat ggaaccgact ataaaagtag tttagattat aacattattg   29220
tactgccatc taccactcca ccaccccgca caactacttt ctctagcagc agtgtcgcta   29280
acaatacaat ttccaatcca acctttgccg cgcttttaaa acgcactgtg ataattcta   29340 caacttcaca tacaacaatt tccacttcaa caatcagcat catcgctgca gtgacaattg   29400
gaatatctat tcttgttttt accataacct actacgcctg ctgctataga aaagacaaac   29460
ataaaggtga tccattactt agatttgata tttaatttgt tctttttttt tatttacagt   29520
atggtgaaca ccaatcatgg tacctagaaa tttcttcttc accatactca tctgtgcttt   29580
taatgtttgc gctactttca cagcagtagc cacagcaacc ccagactgta taggagcatt   29640
tgcttcctat gcactttttg cttttgttac ttgcatctgc gtatgtagca tagtctgcct   29700
ggttattaat ttttttccaac ttctagactg gatccttgtg cgaattgcct acctgcgcca   29760
ccatcccgaa taccgcaacc aaaatatcgc ggcacttctt agactcatct aaaaccatgc   29820
aggctatact accaatattt ttgcttctat tgcttcccta cgctgtctca accccagctg   29880
cctatagtac tccaccagaa cacctagaaa atgcaaatt ccaacaaccg tggtcatttc   29940
ttgcttgcta tcgagaaaaa tcagaaatcc ccccaaattt aataatgatt gctggaataa   30000
```

-continued

```
ttaatataat ctgttgcacc ataatttcat ttttgatata cccccctattt gattttggct   30060 ggaatgctcc caatgcacat gatcatccac aagacccaga ggaacacatt cccccacaaa   30120
acatgcaaca tccaatagcg ctaatagatt acgaaagtga accacaaccc ccactactcc   30180
ctgctattag ttacttcaac ctaaccggcg gagatgactg aaacactcac cacctccaat   30240
tccgccgagg atctgctcga tatggacggc cgcgtctcag aacaacgact tgcccaacta   30300
cgcatccgcc agcagcagga acgcgtggcc aaagagctca gagatgtcat ccaaattcac   30360
caatgcaaaa aaggcatatt ctgtttggta aaacaagcca agatatccta cgagatcacc   30420
gctactgacc atcgcctctc ttacgaactt ggcccccaac gacaaaaatt tacctgcatg   30480
gtgggaatca accccatagt tatcacccaa caaagtggag atactaaggg ttgcattcac   30540
tgttcctgcg attccatcga gtgcacctac accctgctga agaccctatg cggcctaaga   30600
gacctgctac caatgaatta aaaaaaaatg attaataaaa aatcacttac ttgaaatcag   30660
caataaggtc tctgttgaaa ttttctccca gcagcacctc acttccctct tcccaactct   30720
ggtattctaa accccgttca gcggcatact ttctccatac tttaaagggg atgtcaaatt   30780
ttagctcctc tcctgtaccc acaatcttca tgtctttctt cccagatgac caagagagtc   30840
cggctcagtg actccttcaa ccctgtctac ccctatgaag atgaaagcac ctcccaacac   30900 ccctttata acccagggtt tatttcccca aatggcttca cacaaagccc agacggagtt   30960
cttactttaa aatgtttaac cccactaaca accacaggcg gatctctaca gctaaaagtg   31020 ggaggggggac ttacagtgga tgacactgat ggtaccttac aagaaaacat acgtgctaca   31080
gcacccatta ctaaaaataa tcactctgta gaactatcca ttggaaatgg attagaaact   31140
caaaacaata aactatgtgc caaattggga aatgggttaa aatttaacaa cggtgacatt   31200
tgtataaagg atagtattaa caccttatgg actggaataa accctccacc taactgtcaa   31260
attgtggaaa acactaatac aaatgatggc aaacttactt tagtattagt aaaaaatgga   31320
gggcttgtta atggctacgt gtctctagtt ggtgtatcag acactgtgaa ccaaatgttc   31380
acacaaaaga cagcaaacat ccaattaaga ttatattttg actcttctgg aaatctatta   31440
actgaggaat cagacttaaa aattccactt aaaaataaat cttctacagc gaccagtgaa   31500
actgtagcca gcagcaaagc ctttatgcca agtactacag cttatcccctt caacaccact   31560 actagggata gtgaaaacta cattcatgga atatgttact acatgactag ttatgataga   31620
agtctatttc ccttgaacat ttctataatg ctaaacagcc gtatgatttc ttccaatgtt   31680
gcctatgcca tacaatttga atggaatcta aatgcaagtg aatctccaga aagcaacata   31740
gctacgctga ccacatcccc ctttttcttt tcttacatta cagaagacga caactaaaat   31800
aaagtttaag tgtttttatt taaaatcaca aaattcgagt agttattttg cctccacctt   31860
cccatttgac agaatacacc aatctctccc cacgcacagc tgttaaacat ttggatacca   31920
ttagagatag acattgtttt agattccaca ttccaaacag tttcagagcg agccaatctg   31980
gggtcagtga tagataaaaa tccatcgcga tagtcttttta aagcgctttc acagtccaac   32040
tgctgcggat gcgactccgg agtttggatc acggtcatct ggaagaagaa cgatgggaat   32100
cataatccga aaacggtatc ggacgattgt gtctcatcaa acccacaagc agccgctgtc   32160
tgcgtcgctc cgtgcgactg ctgtttatgg gatcagggtc cacagtttcc tgaagcatga   32220
ttttaatagc ccttaacatc aactttctgg tgcgatgcgc gcagcaacgc attctgattt   32280
cactcaaatc tttgcagtag gtacaacaca ttattacaat attgtttaat aaaccataat   32340
```

```
taaaagcgct ccagccaaaa ctcatatctg atataatcgc ccctgcatga ccatcatacc   32400
aaagtttaat ataaattaaa tgacgttccc tcaaaaacac actacccaca tacatgatct   32460
cttttggcat gtgcatatta acaatctgtc tgtaccatgg acaacgttgg ttaatcatgc   32520
aacccaatat aaccttccgg aaccacactg ccaacaccgc tcccccagcc atgcattgaa   32580
gtgaaccctg ctgattacaa tgacaatgaa gaacccaatt ctctcgaccg tgaatcactt   32640
gagaatgaaa aatatctata gtggcacaac atagacataa atgcatgcat cttctcataa   32700
tttttaactc ctcaggattt agaaacatat cccagggaat aggaagctct tgcagaacag   32760
taaagctggc agaacaagga agaccacgaa cacaacttac actatgcata gtcatagtat   32820
cacaatctgg caacagcggg tggtcttcag tcatagaagc tcgggtttca ttttcctcac   32880
aacgtggtaa ctgggctctg gtgtaagggt gatgtctggc gcatgatgtc gagcgtgcgc   32940
gcaaccttgt cataatggag ttgcttcctg acattctcgt attttgtata gcaaaacgcg   33000
gccctggcag aacacactct tcttcgcctt ctatcctgcc gcttagcgtg ttccgtgtga   33060
tagttcaagt acagccacac tcttaagttg gtcaaaagaa tgctggcttc agttgtaatc   33120
aaaactccat cgcatctaat tgttctgagg aaatcatcca cggtagcata tgcaaatccc   33180
aaccaagcaa tgcaactgga ttgcgtttca agcaggagag gagagggaag agacggaaga   33240
accatgttaa ttttttattcc aaacgatctc gcagtacttc aaattgtaga tcgcgcagat   33300
ggcatctctc gcccccactg tgttggtgaa aaagcacagc taaatcaaaa gaatgcgat   33360 tttcaaggtg ctcaacggtg gcttccaaca aagcctccac gcgcacatcc aagaacaaaa   33420
gaataccaaa agaaggagca ttttctaact cctcaatcat catattacat tcctgcacca   33480
ttcccagata attttcagct ttccagcctt gaattattcg tgtcagttct tgtggtaaat   33540
ccaatccaca cattacaaac aggtcccgga gggcgccctc caccaccatt cttaaacaca   33600
ccctcataat gacaaaatat cttgctcctg tgtcacctgt agcgaattga gaatggcaac   33660
atcaattgac atgcccttgg ctctaagttc ttctttaagt tctagttgta aaaactctct   33720
catattatca ccaaactgct tagccagaag ccccccggga acaagagcag gggacgctac   33780
agtgcagtac aagcgcagac ctccccaatt ggctccagca aaaacaagat tggaataagc   33840
atattgggaa ccaccagtaa tatcatcgaa gttgctggaa atataatcag gcagagtttc   33900
ttgtagaaat tgaataaaag aaaaatttgc caaaaaaaca ttcaaaacct ctgggatgca   33960
aatgcaatag gttaccgcgc tgcgctccaa cattgttagt tttgaattag tctgcaaaaa   34020
taaaaaaaaa acaagcgtca tatcatagta gcctgacgaa caggtggata aatcagtctt   34080
tccatcacaa gacaagccac agggtctcca gctcgaccct cgtaaaacct gtcatcgtga   34140
ttaaacaaca gcaccgaaag ttcctcgcgg tgaccagcat gaataagtct tgatgaagca   34200
tacaatccag acatgttagc atcagttaag gagaaaaaac agccaacata gcctttgggt   34260
ataattatgc ttaatcgtaa gtatagcaaa gccaccctc gcggatacaa agtaaaaggc   34320
acaggagaat aaaaaatata attatttctc tgctgctgtt taggcaacgt cgcccccggt   34380
ccctctaaat acacatacaa agcctcatca gccatggctt accagagaaa gtacagcggg   34440
cacacaaacc acaagctcta aagtcactct ccaacctctc cacaatatat atacacaagc   34500
cctaaactga cgtaatggga ctaaagtgta aaaaatcccg ccaaacccaa cacacacccc   34560
gaaactgcgt caccagggaa aagtacagtt tcacttccgc aatcccaaca agcgtcactt   34620 cctcttttctc acggtacgtc acatcccatt aacttacaac gtcatttcc cacggccgcg   34680 ccgccccttt taaccgttaa ccccacagcc aatcaccaca cggcccacac tttttaaaat   34740
```

```
                                                       -continued cacctcattt acatattggc accattccat ctataaggta tattattgat gatg    34794

<210> SEQ ID NO 25
<211> LENGTH: 35133
<212> TYPE: DNA
<213> ORGANISM: Artificial Sequence
<220> FEATURE:
<223> OTHER INFORMATION: pWe/Ad35.pIX-rITR.dE3.dE4.35orf6 cosmid vector

<400> SEQUENCE: 25
ggccgcatcg tccattccga cagcatcgcc agtcactatg gcgtgctgct agcgctatat      60
gcgttgatgc aatttctatg cgcacccgtt ctcggagcac tgtccgaccg ctttggccgc    120
cgcccagtcc tgctcgcttc gctacttgga gccactatcg actacgcgat catggcgacc    180
acacccgtcc tgtggatctg cctcgctggc ctgccgcagt tcttcaacct cccggcgcag    240
cttttcgttc tcaatttcag catccctttc ggcataccat tttatgacgg cggcagagtc    300
ataaagcacc tcattaccct tgccaccgcc tcgcagaacg ggcattccct gttcctgcca    360
gttctgaatg gtacggatac tcgcaccgaa aatgtcagcc agctgctttt tgttgacttc    420
cattgttcat tccacggaca aaaacagaga aggaaacga cagaggccaa aaagctcgct    480
ttcagcacct gtcgtttcct ttcttttcag agggtatttt aaataaaaac attaagttat    540
gacgaagaag aacggaaacg ccttaaaccg gaaaattttc ataaatagcg aaaacccgcg    600
aggtcgccgc cccgtaacaa ggcggatcgc cggaaaggac ccgcaaatga taataattat    660
caattgcata ctatcgacgg cactgctgcc agataacacc accggggaaa cattccatca    720
tgatggccgt gcggacatag gaagccagtt catccatcgc tttcttgtct gctgccattt    780
gctttgtgac atccagcgcc gcacattcag cagcgttttt cagcgcgttt tcgatcaacg    840
tttcaatgtt ggtatcaaca ccaggtttaa ctttgaactt atcggcactg acggttacct    900
tgttctgcgc tggctcatca cgctggatac caaggctgat gttgtagata ttggtcaccg    960
gctgaggtgt ttcgattgcc gctgcgtgga tagcaccatt tgcgatagcg gcgtccttga   1020
tgaatgacac tccattgcga ataagttcga aggagacggt gtcacgaatg cgctggtcca   1080
gctcgtcgat tgccttttgt gcagcagagg tatcaatctc aacgccaagc gtcatcgaag   1140
cgcaatattg ctgctcacca aaacgcgtat tgaccaggtg ttcaacggca aatttctgcc   1200
cttctgatgt cagaaaggta aagtgatttt ctttctggta ttcagttgct gtgtgtctgg   1260
tttcagcaaa accaagctcg cgcaattcgg ctgtgccaga tttagaaggc agatcaccag   1320
acagcaacgc gccacggaaa aacagcgcat acagaacatc cgtcgccgcg ccggacaacg   1380
tgataatttt atgacccatg atttatttcc ttttagacgt gagcctgtcg cacagcaaag   1440
ccgccgaaag ttaacggttt gcccaggctc acaactgaaa gactttctac ggtgtgcgcg   1500
tgcgatgcgc gtagaagact gatttatcaa cctgtcttta tatcaggatt cattacctga   1560
ctatttgtgg gtaaagttcg tagtgcgctg atcgtgcaaa atgattttag ttgggaacag   1620
ttcgcaactc tgtcccataa aaatcagcat attcccatct atcccatatc cagcgcattg   1680
accatcggga tactgaaggg agattccatc atctcttaga aagatcacca tctcttttgt   1740
ttcaatttgc atatagctac ctggaggatt tatgaataca aggattttca tggactatta   1800
ccatgagatt gattttccat ctttattcgc gagagcagtg gaaagcgatg acgatgtggg   1860
tactacattg cgcattcacc tactttgtga gcgcatggtc gaagcatgga tatgcgcatg   1920
ctgtgactgc caagatcctc tacgccggac gcatcgtggc cggcatcacc ggcgccacag   1980
```

```
gtgcggttgc tggcgcctat atcgccgaca tcaccgatgg ggaagatcgg gctcgccact    2040
tcgggctcat gagcgcttgt ttcggcgtgg gtatggtggc aggccccgtg gccgggggac    2100
tgttgggcgc catctccttg catgcaccat tccttgcggc ggcggtgctc aacggcctca    2160
acctactact gggctgcttc ctaatgcagg agtcgcataa gggagagcgt cgaccgatgc    2220
ccttgagagc cttcaaccca gtcagctcct tccggtgggc gcggggcatg actatcgtcg    2280
ccgcacttat gactgtcttc tttatcatgc aactcgtagg acaggtgccg gcagcgctct    2340
gggtcatttt cggcgaggac cgctttcgct ggagcgcgac gatgatcggc ctgtcgcttg    2400
cggtattcgg aatcttgcac gccctcgctc aagccttcgt cactggtccc gccaccaaac    2460
gtttcggcga gaagcaggcc attatcgccg gcatggcggc cgacgcgctg gctacgtct    2520
tgctggcgtt cgcgacgcga ggctggatgg ccttccccat tatgattctt ctcgcttccg    2580
gcggcatcgg gatgcccgcg ttgcaggcca tgctgtccag gcaggtagat gacgaccatc    2640
agggacagct tcaaggatcg ctcgcggctc ttaccagcct aacttcgatc attggaccgc    2700
tgatcgtcac ggcgatttat gccgcctcgg cgagcacatg gaacgggttg gcatggattg    2760
taggcgccgc cctataccct gtctgcctcc ccgcgttgcg tcgcggtgca tggagccggg    2820
ccacctcgac ctgaatggaa gccggcggca cctcgctaac ggattcacca ctccaagaat    2880
tggagccaat caattcttgc ggagaactgt gaatgcgcaa accaacccct ggcagaacat    2940
atccatcgcg tccgccatct ccagcagccg cacgcggcgc atctcgggca gcgttgggtc    3000
ctgcagatcc ggctgtggaa tgtgtgtcag ttagggtgtg gaaagtcccc aggctcccca    3060
gcaggcagaa gtatgcaaag catgcatctc aattagtcag caaccaggtg tggaaagtcc    3120
ccaggctccc cagcaggcag aagtatgcaa agcatgcatc tcaattagtc agcaaccata    3180
gtcccgcccc taactccgcc catcccgccc ctaactccgc ccagttccgc ccattctccg    3240
ccccatggct gactaatttt ttttattat gcagaggccg aggccgcctc ggcctctgag    3300
ctattccaga agtagtgagg aggcttttt ggaggcctag gcttttgcaa aaagcttcac    3360
gctgccgcaa gcactcaggg cgcaagggct gctaaggaa gcggaacacg tagaaagcca    3420
gtccgcagaa acgtgctga ccccggatga atgtcagcta ctgggctatc tggacaaggg    3480
aaaacgcaag cgcaaagaga aagcaggtag cttgcagtgg gcttacatgg cgatagctag    3540
actgggcggt tttatggaca gcaagcgaac cggaattgcc agctgggcg ccctctggta    3600
aggttgggaa gccctgcaaa gtaaactgga tggctttctt gccgccaagg atctgatggc    3660
gcagggatc aagatctgat caagagacag gatgaggatc gtttcgcatg attgaacaag    3720
atggattgca cgcaggttct ccggccgctt gggtggagag gctattcggc tatgactggg    3780
cacaacagac aatcggctgc tctgatgccg ccgtgttccg gctgtcagcg caggggcgcc    3840
cggttctttt tgtcaagacc gacctgtccg gtgccctgaa tgaactgcag gacgaggcag    3900
cgcggctatc gtggctggcc acgacgggcg ttccttgcgc agctgtgctc gacgttgtca    3960
ctgaagcggg aagggactgg ctgctattgg gcgaagtgcc ggggcaggat ctcctgtcat    4020
ctcaccttgc tcctgccgag aaagtatcca tcatggctga tgcaatgcgg cggctgcata    4080
cgcttgatcc ggctacctgc ccattcgacc accaagcgaa acatcgcatc gagcgagcac    4140
gtactcggat ggaagccggt cttgtcgatc aggatgatct ggacgaagag catcagggc    4200
tcgcgccagc cgaactgttc gccaggctca aggcgcgcat gcccgacggc gaggatctcg    4260
tcgtgaccca tggcgatgcc tgcttgccga atatcatggt ggaaaatggc cgcttttctg    4320
gattcatcga ctgtggccgg ctgggtgtgg cggaccgcta tcaggacata gcgttggcta    4380
```

| | |
|---|---|
| cccgtgatat tgctgaagag cttggcggcg aatgggctga ccgcttcctc gtgctttacg | 4440 |
| gtatcgccgc tcccgattcg cagcgcatcg ccttctatcg ccttcttgac gagttcttct | 4500 |
| gagcgggact ctggggttcg aaatgaccga ccaagcgacg cccaacctgc catcacgaga | 4560 |
| tttcgattcc accgccgcct tctatgaaag gttgggcttc ggaatcgttt tccgggacgc | 4620 |
| cggctggatg atcctccagc gcgggatct catgctggag ttcttcgccc accccgggct | 4680 |
| cgatcccctc gcgagttggt tcagctgctg cctgaggctg gacgacctcg cggagttcta | 4740 |
| ccggcagtgc aaatccgtcg gcatccagga aaccagcagc ggctatccgc gcatccatgc | 4800 |
| ccccgaactg caggagtggg gaggcacgat ggccgctttg gtccggatct ttgtgaagga | 4860 |
| accttacttc tgtggtgtga cataattgga caaactacct acagagattt aaagctctaa | 4920 |
| ggtaaatata aaattttttaa gtgtataatg tgttaaacta ctgattctaa ttgtttgtgt | 4980 |
| attttagatt ccaacctatg gaactgatga atgggagcag tggtggaatg cctttaatga | 5040 |
| ggaaaacctg ttttgctcag aagaaatgcc atcagtgat gatgaggcta ctgctgactc | 5100 |
| tcaacattct actcctccaa aaaagaagag aaaggtagaa gaccccaagg actttccttc | 5160 |
| agaattgcta agtttttga gtcatgctgt gtttagtaat agaactcttg cttgctttgc | 5220 |
| tatttacacc acaaaggaaa aagctgcact gctatacaag aaaattatgg aaaaatattc | 5280 |
| tgtaaccttt ataagtaggc ataacagtta aatcataac atactgtttt tcttactcc | 5340 |
| acacaggcat agagtgtctg ctattaataa ctatgctcaa aaattgtgta cctttagctt | 5400 |
| tttaatttgt aaaggggtta ataaggaata tttgatgtat agtgccttga ctagagatca | 5460 |
| taatcagcca taccacattt gtagaggttt tacttgcttt aaaaaacctc ccacacctcc | 5520 |
| ccctgaacct gaaacataaa atgaatgcaa ttgttgttgt taacttgttt attgcagctt | 5580 |
| ataatggtta caaataaagc aatagcatca caaatttcac aaataaagca ttttttttcac | 5640 |
| tgcattctag ttgtggtttg tccaaactca tcaatgtatc ttatcatgtc tggatctgac | 5700 |
| gggtgcgcat gatcgtgctc ctgtcgttga ggacccggct aggctggcgg ggttgcctta | 5760 |
| ctggttagca gaatgaatca ccgatacgcg agcgaacgtg aagcgactgc tgctgcaaaa | 5820 |
| cgtctgcgac ctgagcaaca acatgaatgg tcttcggttt ccgtgtttcg taaagtctgg | 5880 |
| aaacgcggaa gtcagcgctc ttccgcttcc tcgctcactg actcgctgcg ctcggtcgtt | 5940 |
| cggctgcggc gagcggtatc agctcactca aaggcggtaa tacggttatc cacagaatca | 6000 |
| ggggataacg caggaaagaa catgtgagca aaaggccagc aaaaggccag caaaaggcca | 6060 |
| ggaaccgtaa aaaggccgcg ttgctggcgt ttttccatag gctccgcccc cctgacgagc | 6120 |
| atcacaaaaa tcgacgctca agtcagaggt ggcgaaaccc gacaggacta taaagatacc | 6180 |
| aggcgtttcc ccctggaagc tccctcgtgc gctctcctgt tccgaccctg ccgcttaccg | 6240 |
| gatacctgtc cgcctttctc ccttcgggaa gcgtggcgct ttctcatagc tcacgctgta | 6300 |
| ggtatctcag ttcggtgtag gtcgttcgct ccaagctggg ctgtgtgcac gaaccccccg | 6360 |
| ttcagcccga ccgctgcgcc ttatccggta actatcgtct tgagtccaac ccggtaagac | 6420 |
| acgacttatc gccactggca gcagccactg gtaacaggat tagcagagcg aggtatgtag | 6480 |
| gcggtgctac agagttcttg aagtggtggc ctaactacgg ctacactaga aggacagtat | 6540 |
| ttggtatctg cgctctgctg aagccagtta ccttcggaaa aagagttggt agctcttgat | 6600 |
| ccggcaaaca aaccaccgct ggtagcggtg gtttttttgt ttgcaagcag cagattacgc | 6660 |
| gcagaaaaaa aggatctcaa gaagatcctt tgatcttttc tacggggtct gacgctcagt | 6720 |

```
ggaacgaaaa ctcacgttaa gggattttgg tcatgagatt atcaaaaagg atcttcacct      6780 agatccttt  aaattaaaaa tgaagtttta aatcaatcta aagtatatat gagtaaactt      6840
ggtctgacag ttaccaatgc ttaatcagtg aggcacctat ctcagcgatc tgtctatttc      6900
gttcatccat agttgcctga ctccccgtcg tgtagataac tacgatacgg gagggcttac      6960
catctggccc cagtgctgca atgataccgc gagacccacg ctcaccggct ccagatttat      7020
cagcaataaa ccagccagcc ggaagggccg agcgcagaag tggtcctgca actttatccg      7080
cctccatcca gtctattaat tgttgccggg aagctagagt aagtagttcg ccagttaata      7140
gtttgcgcaa cgttgttgcc attgctgcag gcatcgtggt gtcacgctcg tcgtttggta      7200
tggcttcatt cagctccggt tcccaacgat caaggcgagt tacatgatcc cccatgttgt      7260
gcaaaaaagc ggttagctcc ttcggtcctc cgatcgttgt cagaagtaag ttggccgcag      7320
tgttatcact catggttatg gcagcactgc ataattctct tactgtcatg ccatccgtaa      7380 gatgctttc  tgtgactggt gagtactcaa ccaagtcatt ctgagaatag tgtatgcggc      7440
gaccgagttg ctcttgcccg cgtcaacac  ggataatac  cgcgccacat agcagaactt      7500
taaaagtgct catcattgga aaacgttctt cggggcgaaa actctcaagg atcttaccgc      7560
tgttgagatc cagttcgatg taacccactc gtgcacccaa ctgatcttca gcatctttta      7620
ctttcaccag cgtttctggg tgagcaaaaa caggaaggca aaatgccgca aaaagggaa       7680 taagggcgac acgaaatgt  tgaatactca tactcttcct ttttcaatat tattgaagca      7740
tttatcaggg ttattgtctc atgagcggat acatatttga atgtatttag aaaaataaac      7800
aaataggggt tccgcgcaca tttccccgaa aagtgccacc tgacgtctaa gaaaccatta      7860
ttatcatgac attaacctat aaaaataggc gtatcacgag gcccttcgt  cttcaagaat      7920 tcgcggccgc gacatgagtg gaaatgcttc ttttaagggg ggagtcttca gcccttatct      7980
gacagggcgt ctcccatcct gggcaggagt tcgtcagaat gttatgggat ctactgtgga      8040
tggaagaccc gttcaacccg ccaattcttc aacgctgacc tatgctactt taagttcttc      8100
acctttggac gcagctgcag ccgctgccgc cgcctctgtc gccgctaaca ctgtgcttgg      8160
aatgggttac tatggaagca tcgtggctaa ttccacttcc tctaataacc cttctacact      8220
gactcaggac aagttacttg tccttttggc ccagctggag gctttgaccc aacgtctggg      8280
tgaactttct cagcaggtgg ccgagttgcg agtacaaact gagtctgctg tcggcacggc      8340
aaagtctaaa taaaaaaaat tccagaatca atgaataaat aaacgagctt gttgttgatt      8400
taaaatcaag tgtttttatt tcattttcg  cgcacggtat gccctggacc accgatctcg      8460
atcattgaga actcggtgga ttttttccag aatcctatag aggtgggatt gaatgtttag      8520 atacatggc  attaggccgt ctttggggtg gagatagctc cattgaaggg attcatgctc      8580
cggggtagtg ttgtaaatca cccagtcata acaaggtcgc agtgcatggt gttgcacaat      8640
atcttttaga agtaggctga ttgccacaga taagcccttg gtgtaggtgt ttacaaaccg      8700
gttgagctgg gagggtgca  ttcgaggtga aattatgtgc attttggatt ggattttaa      8760 gttggcaata ttgccgccaa gatcccgtct tgggttcatg ttatgaagga ctaccaagac      8820
ggtgtatccg gtacatttag gaaatttatc gtgcagcttg gatggaaaag cgtggaaaaa      8880
tttggagaca cccttgtgtc ctccgagatt ttccatgcac tcatccatga  aatagcaat      8940 ggggccgtgg gcagcggcgc gggcaaacac gttccgtggg tctgacacat catagttatg      9000
ttcctgagtt aaatcatcat aagccatttt aatgaatttg gggcggagcg taccagattg      9060
gggtatgaat gttccttcgg gccccggagc atagttcccc tcacagattt gcatttccca      9120
```

```
agctttcagt tctgagggtg gaatcatgtc cacctggggg gctatgaaga acaccgtttc   9180
gggggcgggg gtgattagtt gggatgatag caagtttctg agcaattgag atttgccaca   9240
tccggtgggg ccataaataa ttccgattac aggttgcagg tggtagttta gggaacggca   9300
actgccgtct tctcgaagca aggggccac ctcgttcatc atttccctta catgcatatt    9360
ttcccgcacc aaatccatta ggaggcgctc tcctcctagt gatagaagtt cttgtagtga   9420
ggaaaagttt ttcagcggtt ttagaccgtc agccatgggc attttggaaa gagtttgctg   9480
caaaagttct agtctgttcc acagttcagt gatgtgttct atggcatctc gatccagcag   9540
acctcctcgt ttcgcgggtt tggacggctc ctggagtagg gtatgagacg atgggcgtcc   9600
agcgctgcca gggttcggtc cttccagggt ctcagtgttc gagtcagggt tgtttccgtc   9660
acagtgaagg ggtgtgcgcc tgcttgggcg cttgccaggg tgcgcttcag actcattctg   9720
ctggtggaga acttctgtcg cttggcgccc tgtatgtcgg ccaagtagca gtttaccatg   9780
agttcgtagt tgagcgcctc ggctgcgtgg ccttttggcgc ggagcttacc tttggaagtt   9840
ttcttgcata ccgggcagta taggcatttc agcgcataca gcttgggcgc aaggaaaatg   9900
gattctgggg agtatgcatc cgcgccgcag gaggcgcaaa cagtttcaca ttccaccagc   9960
caggttaaat ccggttcatt ggggtcaaaa acaagttttc cgccatattt tttgatgcgt  10020
ttcttacctt tggtctccat aagttcgtgt cctcgttgag tgacaaacag gctgtccgta  10080
tctccgtaga ctgattttac aggcctcttc tccagtggag tgcctcggtc ttcttcgtac  10140
aggaactctg accactctga tacaaaggcg cgcgtccagg ccagcacaaa ggaggctatg  10200
tgggaggggt agcgatcgtt gtcaaccagg gggtccacct tttccaaagt atgcaaacac  10260
atgtcaccct cttcaacatc caggaatgtg attggcttgt aggtgtattt cacgtgacct  10320
ggggtccccg ctggggggt ataaaagggg gcggttcttt gctcttcctc actgtcttcc   10380
ggatcgctgt ccaggaacgt cagctgttgg ggtaggtatt ccctctcgaa ggcgggcatg  10440
acctctgcac tcaggttgtc agtttctaag aacgaggagg atttgatatt gacagtgccg  10500
gttgagatgc ctttcatgag gttttcgtcc atttggtcag aaaacacaat ttttttattg   10560
tcaagtttgg tggcaaatga tccatacagg gcgttggata aaagtttggc aatggatcgc   10620
atggtttggt tcttttcctt gtccgcgcgc tctttggcgg cgatgttgag ttggacatac   10680
tcgcgtgcca ggcacttcca ttcggggaag atagttgtta attcatctgg cacgattctc   10740
acttgccacc ctcgattatg caaggtaatt aaatccacac tggtggccac ctcgcctcga  10800
aggggttcat tggtccaaca gagcctacct cctttcctag aacagaaagg gggaagtggg  10860
tctagcataa gttcatcggg agggtctgca tccatggtaa agattcccgg aagtaaatcc   10920
ttatcaaaat agctgatggg agtggggtca tctaaggcca tttgccattc tcgagctgcc   10980
agtgcgcgct catatgggtt aaggggactg ccccagggca tgggatgggt gagagcagag   11040
gcatacatgc cacagatgtc atagacgtag atgggatcct caaagatgcc tatgtaggtt   11100
ggatagcatc gccccctct gatacttgct cgcacatagt catatagttc atgtgatggc    11160
gctagcagcc ccggacccaa gttggtgcga ttgggttttt ctgttctgta gacgatctgg   11220
cgaaagatgg cgtgagaatt ggaagagatg gtgggtcttt gaaaaatgtt gaatgggca    11280
tgaggtagac ctacagagtc tctgacaaag tgggcataag attcttgaag cttggttacc   11340
agttcggcgg tgacaagtac gtctagggcg cagtagtcaa gtgtttcttg aatgatgtca   11400
taacctggtt ggttttttctt ttcccacagt tcgcggttga gaaggtattc ttcgcgatcc  11460
```

| | |
|---|---|
| ttccagtact cttctagcgg aaacccgtct ttgtctgcac ggtaagatcc tagcatgtag | 11520 |
| aactgattaa ctgccttgta agggcagcag cccttctcta cgggtagaga gtatgcttga | 11580 |
| gcagcttttc gtagcgaagc gtgagtaagg gcaaaggtgt ctctgaccat gactttgaga | 11640 |
| aattggtatt tgaagtccat gtcgtcacag gctccctgtt cccagagttg gaagtctacc | 11700 |
| cgtttcttgt aggcggggtt gggcaaagcg aaagtaacat cattgaagag aatcttaccg | 11760 |
| gctctgggca taaaattgcg agtgatgcgg aaaggctgtg gtacttccgc tcgattgttg | 11820 |
| atcacctggg cagctaggac gatttcgtcg aaaccgttga tgttgtgtcc tacgatgtat | 11880 |
| aattctatga aacgcggcgt gcctctgacg tgaggtagct tactgagctc atcaaaggtt | 11940 |
| aggtctgtgg ggtcagataa ggcgtagtgt tcgagagccc attcgtgcag gtgaggattt | 12000 |
| gcatgtagga atgatgacca aagatctacc gccagtgctg tttgtaactg gtcccgatac | 12060 |
| tgacgaaaat gccggccaat tgccattttt tctggagtga cacagtagaa ggttctgggg | 12120 |
| tcttgttgcc atcgatccca cttgagttta atggctagat cgtgggccat gttgacgaga | 12180 |
| cgctcttctc ctgagagttt catgaccagc atgaaaggaa ctagttgttt gccaaaggat | 12240 |
| cccatccagg tgtaagtttc cacatcgtag gtcaggaaga gtctttctgt gcgaggatga | 12300 |
| gagccgatcg ggaagaactg gatttcctgc caccagttgg aggattggct gttgatgtga | 12360 |
| tggaagtaga agtttctgcg gcgcgccgag cattcgtgtt tgtgcttgta cagacggccg | 12420 |
| cagtagtcgc agcgttgcac gggttgtatc tcgtgaatga gctgtacctg gcttcccttg | 12480 |
| acgagaaatt tcagtgggaa gccgaggcct ggcgattgta tctcgtgctc ttctatattc | 12540 |
| gctgtatcgg cctgttcatc ttctgtttcg atggtggtca tgctgacgag ccccgcggg | 12600 |
| aggcaagtcc agacctcggc gcgggagggg cggagctgaa ggacgagagc gcgcaggctg | 12660 |
| gagctgtcca gagtcctgag acgctgcgga ctcaggttag taggtaggga cagaagatta | 12720 |
| acttgcatga tcttttccag ggcgtgcggg aggttcagat ggtacttgat ttccacaggt | 12780 |
| tcgtttgtag agacgtcaat ggcttgcagg gttccgtgtc cttttgggcgc cactaccgta | 12840 |
| cctttgtttt ttcttttgat cggtggtggc tctcttgctt cttgcatgct cagaagcggt | 12900 |
| gacggggacg cgcgccgggc ggcagcggtt gttccggacc cgggggcatg gctggtagtg | 12960 |
| gcacgtcggc gccgcgcacg ggcaggttct ggtattgcgc tctgagaaga cttgcgtgcg | 13020 |
| ccaccacgcg tcgattgacg tcttgtatct gacgtctctg ggtgaaagct accgcccccg | 13080 |
| tgagcttgaa cctgaaagag agttcaacag aatcaatttc ggtatcgtta acggcagctt | 13140 |
| gtctcagtat ttcttgtacg tcaccagagt tgtcctggta ggcgatctcc gccatgaact | 13200 |
| gctcgatttc ttcctcctga agatctccgc gacccgctct ttcgacggtg gccgcgaggt | 13260 |
| cattggagat acggcccatg agttgggaga atgcattcat gcccgcctcg ttccagacgc | 13320 |
| ggctgtaaac cacggccccc tcggagtctc ttgcgcgcat caccacctga gcgaggttaa | 13380 |
| gctccacgtg tctggtgaag accgcatagt tgcataggcg ctgaaaaagg tagttgagtg | 13440 |
| tggtggcaat gtgttcggcg acgaagaaat acatgatcca tcgtctcagc ggcatttcgc | 13500 |
| taacatcgcc cagagcttcc aagcgctcca tggcctcgta gaagtccacg gcaaaattaa | 13560 |
| aaaactggga gtttcgcgcg gacacggtca attcctcctc gagaagacgg atgagttcgg | 13620 |
| ctatggtggc ccgtacttcg cgttcgaagg ctcccgggat ctcttcttcc tcttctatct | 13680 |
| cttcttccac taacatctct tcttcgtctt caggcggggg cggaggggc acgcggcgac | 13740 |
| gtcgacggcg cacgggcaaa cggtcgatga atcgttcaat gacctctccg cggcggcggc | 13800 |
| gcatggtttc agtgacggcg cggccgttct cgcgcggtcg cagagtaaaa acaccgccgc | 13860 |

```
gcatctcctt aaagtggtga ctgggaggtt ctccgtttgg gagggagagg gcgctgatta    13920
tacattttat taattggccc gtagggactg cgcgcagaga tctgatcgtg tcaagatcca    13980
cgggatctga aaacctttcg acgaaagcgt ctaaccagtc acagtcacaa ggtaggctga    14040
gtacggcttc ttgtgggcgg gggtggttat gtgttcggtc tgggtcttct gtttcttctt    14100
catctcggga aggtgagacg atgctgctgg tgatgaaatt aaagtaggca gttctaagac    14160
ggcggatggt ggcgaggagc accaggtctt tgggtccggc ttgctggata cgcaggcgat    14220
tggccattcc ccaagcatta tcctgacatc tagcaagatc tttgtagtag tcttgcatga    14280
gccgttctac gggcacttct tcctcacccg ttctgccatg catacgtgtg agtccaaatc    14340
cgcgcattgg ttgtaccagt gccaagtcag ctacgactct ttcggcgagg atggcttgct    14400
gtacttgggt aagggtggct tgaaagtcat caaaatccac aaagcggtgg taagcccctg    14460
tattaatggt gtaagcacag ttggccatga ctgaccagtt aactgtctgg tgaccagggc    14520
gcacgagctc ggtgtattta aggcgcgaat aggcgcgggt gtcaaagatg taatcgttgc    14580
aggtgcgcac cagatactgg taccctataa gaaaatgcgg cggtggttgg cggtagagag    14640
gccatcgttc tgtagctgga gcgccagggg cgaggtcttc aacataagg cggtgatagc     14700 cgtagatgta cctggacatc caggtgattc ctgcggcggt agtagaagcc cgaggaaact    14760
cgcgtacgcg gttccaaatg ttgcgtagcg gcatgaagta gttcattgta ggcacggttt    14820
gaccagtgag gcgcgcgcag tcattgatgc tctatagaca cggagaaaat gaaagcgttc    14880
agcgactcga ctccgtagcc tggaggaacg tgaacgggtt gggtcgcggt gtaccccggt    14940
tcgagacttg tactcgagcc ggccggagcc gcggctaacg tggtattggc actcccgtct    15000
cgacccagcc tacaaaaatc caggatacgg aatcgagtcg ttttgctggt ttccgaatgg    15060
cagggaagtg agtcctattt tttttttttt tttgccgctc agatgcatcc cgtgctgcga    15120
cagatgcgcc cccaacaaca gccccctcg cagcagcagc agcagcaacc acaaaaggct     15180
gtccctgcaa ctactgcaac tgccgccgtg agcggtgcgg gacagcccgc ctatgatctg    15240
gacttggaag agggcgaagg actggcacgt ctaggtgcgc cttcgcccga gcggcatccg    15300
cgagttcaac tgaaaaaaga ttctcgcgag gcgtatgtgc cccaacagaa cctatttaga    15360
gacagaagcg gcgaggagcc ggaggagatg cgagcttccc gctttaacgc gggtcgtgag    15420
ctgcgtcacg gtttggaccg aagacgagtg ttgcgagacg aggatttcga agttgatgaa    15480
gtgacaggga tcagtcctgc cagggcacac gtggctgcag ccaaccttgt atcggcttac    15540
gagcagacag taaaggaaga gcgtaacttc caaaagtctt ttaataatca tgtgcgaacc    15600
ctgattgccc gcgaagaagt taccccttggt ttgatgcatt tgtgggattt gatggaagct    15660
atcattcaga accctactag caaacctctg accgcccagc tgtttctggt ggtgcaacac    15720
agcagagaca atgaggcttt cagagaggcg ctgctgaaca tcaccgaacc cgaggggaga    15780
tggttgtatg atcttatcaa cattctacag agtatcatag tgcaggagcg gagcctgggc    15840
ctggccgaga aggtagctgc catcaattac tcggttttga gcttgggaaa atattacgct    15900
cgcaaaatct acaagactcc atacgttccc atagacaagg aggtgaagat agatgggttc    15960
tacatgcgca tgacgctcaa ggtcttgacc ctgagcgatg atcttggggt gtatcgcaat    16020
gacagaatgc atcgcgcggt tagcgccagc aggaggcgcg agttaagcga cagggaactg    16080
atgcacagtt tgcaaagagc tctgactgga gctggaaccg agggtgagaa ttacttcgac    16140
atgggagctg acttgcagtg gcagcctagt cgcagggctc tgagcgccgc gacggcagga    16200
```

```
tgtgagcttc cttacataga agaggcggat gaaggcgagg aggaagaggg cgagtacttg    16260
gaagactgat ggcacaaccc gtgtttttttg ctagatggaa cagcaagcac cggatcccgc   16320
aatgcgggcg gcgctgcaga gccagccgtc cggcattaac tcctcggacg attggaccca   16380
ggccatgcaa cgtatcatgg cgttgacgac tcgcaacccc gaagccttta gacagcaacc   16440
ccaggccaac cgtctatcgg ccatcatgga agctgtagtg ccttcccgat ctaatcccac   16500
tcatgagaag gtcctggcca tcgtgaacgc gttggtggag aacaaagcta ttcgtccaga   16560
tgaggccgga ctggtataca acgctctctt agaacgcgtg gctcgctaca acagtagcaa   16620
tgtgcaaacc aatttggacc gtatgataac agatgtacgc gaagccgtgt ctcagcgcga   16680
aaggttccag cgtgatgcca acctgggttc gctggtggcg ttaaatgctt tcttgagtac   16740
tcagcctgct aatgtgccgc gtggtcaaca ggattatact aactttttaa gtgctttgag   16800
actgatggta tcagaagtac ctcagagcga agtgtatcag tccggtcctg attacttctt   16860
tcagactagc agacagggct tgcagacggt aaatctgagc caagctttta aaaaccttaa   16920
aggtttgtgg ggagtgcatg cccccggtagg agaaagagca accgtgtcta gcttgttaac   16980
tccgaactcc cgcctgttat tactgttggt agctcctttc accgacagcg gtagcatcga   17040
ccgtaattcc tatttgggtt acctactaaa cctgtatcgc gaagccatag ggcaaagtca   17100
ggtggacgag cagacctatc aagaaattac ccaagtcagt cgcgctttgg gacaggaaga   17160
cactggcagt ttggaagcca ctctgaactt cttgcttacc aatcggtctc aaaagatccc   17220
tcctcaatat gctcttactg cggaggagga gaggatcctt agatatgtgc agcagagcgt   17280
gggattgttt ctgatgcaag aggggcaac tccgactgca gcactggaca tgacagcgcg   17340
aaatatggag cccagcatgt atgccagtaa ccgacctttc attaacaaac tgctggacta   17400
cttgcacaga gctgccgcta tgaactctga ttatttcacc aatgccatct taaacccgca   17460
ctggctgccc ccacctggtt tctacacggg cgaatatgac atgcccgacc ctaatgacgg   17520
atttctgtgg gacgacgtgg acagcgatgt tttttcacct cttctgatc atcgcacgtg   17580 gaaaaaggaa ggcggtgata gaatgcattc ttctgcatcg ctgtccgggg tcatgggtgc   17640
taccgcggct gagcccgagt ctgcaagtcc tttcctagt ctaccctttt ctctacacag   17700
tgtacgtagc agcgaagtgg gtagaataag tcgcccgagt ttaatgggcg aagaggagta   17760
cctaaacgat tccttgctca gaccggcaag agaaaaaaat ttcccaaaca atggaataga   17820
aagtttggtg gataaaatga gtagatggaa gacttatgct caggatcaca gagacgagcc   17880
tgggatcatg gggactacaa gtagagcgag ccgtagacgc cagcgccatg acagacagag   17940
gggtcttgtg tgggacgatg aggattcggc cgatgatagc agcgtgttgg acttgggtgg   18000
gagaggaagg ggcaacccgt ttgctcattt gcgccctcgc ttgggtggta tgttgtgaaa   18060
aaaaataaaa aagaaaaact caccaaggcc atggcgacga gcgtacgttc gttcttcttt   18120
attatctgtg tctagtataa tgaggcgagt cgtgctaggc ggagcggtgg tgtatccgga   18180
gggtcctcct ccttcgtacg agagcgtgat gcagcagcag caggcgacgg cggtgatgca   18240
atccccactg gaggctccct ttgtgcctcc gcgatacctg gcacctacgg agggcagaaa   18300
cagcattcgt tactcggaac tggcacctca gtacgatacc accaggttgt atctggtgga   18360
caacaagtcg gcggacattg cttctctgaa ctatcagaat gaccacagca acttcttgac   18420
cacggtggtg cagaacaatg actttacccc tacggaagcc agcacccaga ccattaactt   18480
tgatgaacga tcgcggtggg gcggtcagct aaagaccatc atgcatacta acatgccaaa   18540
cgtgaacgag tatatgttta gtaacaagtt caaagcgcgt gtgatggtgt ccagaaaacc   18600
```

```
tcccgacggt gctgcagttg gggatactta tgatcacaag caggatattt tggaatatga   18660
gtggttcgag tttactttgc cagaaggcaa cttttcagtt actatgacta ttgatttgat   18720
gaacaatgcc atcatagata attacttgaa agtgggtaga cagaatggag tgcttgaaag   18780
tgacattggt gttaagttcg acaccaggaa cttcaagctg ggatgggatc ccgaaaccaa   18840
gttgatcatg cctggagtgt atacgtatga agccttccat cctgacattg tcttactgcc   18900
tggctgcgga gtggatttta ccgagagtcg tttgagcaac cttcttggta tcagaaaaaa   18960
acagccattt caagagggtt ttaagatttt gtatgaagat ttagaaggtg gtaatattcc   19020
ggccctcttg gatgtagatg cctatgagaa cagtaagaaa gaacaaaaag ccaaaataga   19080
agctgctaca gctgctgcag aagctaaggc aaacatagtt gccagcgact ctacaagggt   19140
tgctaacgct ggagaggtca gaggagacaa ttttgcgcca acacctgttc cgactgcaga   19200
atcattattg gccgatgtgt ctgaaggaac ggacgtgaaa ctcactattc aacctgtaga   19260
aaaagatagt aagaatagaa gctataatgt gttggaagac aaaatcaaca cagcctatcg   19320
cagttggtat ctttcgtaca attatggcga tcccgaaaaa ggagtgcgtt cctggacatt   19380
gctcaccacc tcagatgtca cctgcggagc agagcaggtt tactggtcgc ttccagacat   19440
gatgaaggat cctgtcactt tccgctccac tagacaagtc agtaactacc ctgtggtggg   19500
tgcagagctt atgcccgtct ctcaaagag cttctacaac gaacaagctg tgtactccca   19560
gcagctccgc cagtccacct cgcttacgca cgtcttcaac cgctttcctg agaaccagat   19620
tttaatccgt ccgccggcgc ccaccattac caccgtcagt gaaaacgttc ctgctctcac   19680
agatcacggg accctgccgt tgcgcagcag tatccgggga gtccaacgtg tgaccgttac   19740
tgacgccaga cgccgcacct gtccctacgt gtacaaggca ctgggcatag tcgcaccgcg   19800 cgtccttca agccgcactt tctaaaaaaa aaaaatgtcc attcttatct cgcccagtaa   19860
taacaccggt tggggtctgc gcgctccaag caagatgtac ggaggcgcac gcaaacgttc   19920
tacccaacat cccgtgcgtg ttcgcggaca ttttcgcgct ccatggggtg ccctcaaggg   19980
ccgcactcgc gttcgaacca ccgtcgatga tgtaatcgat caggtggttg ccgacgcccg   20040
taattatact cctactgcgc ctacatctac tgtggatgca gttattgaca gtgtagtggc   20100
tgacgctcgc aactatgctc gacgtaagag ccggcgaagg cgcattgcca gacgccaccg   20160
agctaccact gccatgcgag ccgcaagagc tctgctacga agctagac gcgtggggcg   20220 aagagccatg cttagggcgg ccagacgtgc agcttcgggc gccagcgccg gcaggtcccg   20280
caggcaagca gccgctgtcg cagcggcgac tattgccgac atggcccaat cgcgaagagg   20340
caatgtatac tgggtgcgtg acgctgccac cggtcaacgt gtacccgtgc gcacccgtcc   20400
ccctcgcact tagaagatac tgagcagtct ccgatgttgt gtcccagcgg cgaggatgtc   20460
caagcgcaaa tacaaggaag aaatgctgca ggttatcgca cctgaagtct acggccaacc   20520
gttgaaggat gaaaaaaaac cccgcaaaat caagcgggtt aaaaaggaca aaaagaaga   20580 ggaagatggc gatgatgggc tggcggagtt tgtgcgcgag tttgccccac ggcgacgcgt   20640 gcaatgcgt gggcgcaaag ttcgacatgt gttgagacct ggaacttcgg tggtcttttac   20700 acccggcgag cgttcaagcg ctactttaa gcgttcctat gatgaggtgt acggggatga   20760
tgatattctt gagcaggcgg ctgaccgatt aggcgagttt gcttatggca agcgtagtag   20820
aataacttcc aaggatgaga cagtgtcaat acccttggat catggaaatc ccaccccctag   20880 tcttaaaccg gtcactttgc agcaagtgtt acccgtaact ccgcgaacag gtgttaaacg   20940
```

```
cgaaggtgaa gatttgtatc ccactatgca actgatggta cccaaacgcc agaagttgga   21000
ggacgttttg gagaaagtaa aagtggatcc agatattcaa cctgaggtta aagtgagacc   21060
cattaagcag gtagcgcctg gtctgggggt acaaactgta gacattaaga ttcccactga   21120
aagtatggaa gtgcaaactg aacccgcaaa gcctactgcc acctccactg aagtgcaaac   21180
ggatccatgg atgcccatgc ctattacaac tgacgccgcc ggtcccactc gaagatcccg   21240
acgaaagtac ggtccagcaa gtctgttgat gcccaattat gttgtacacc catctattat   21300
tcctactcct ggttaccgag gcactcgcta ctatcgcagc cgaaacagta cctcccgccg   21360
tcgccgcaag acacctgcaa atcgcagtcg tcgccgtaga cgcacaagca aaccgactcc   21420
cggcgccctg gtgcggcaag tgtaccgcaa tggtagtgcg gaaccttga cactgccgcg   21480
tgcgcgttac catccgagta tcatcactta atcaatgttg ccgctgcctc cttgcagata   21540
tggccctcac ttgtcgcctt cgcgttccca tcactggtta ccgaggaaga aactcgcgcc   21600
gtagaagagg gatgttggga cgcggaatgc gacgctacag gcgacggcgt gctatccgca   21660
agcaattgcg gggtggtttt ttaccagcct taattccaat tatcgctgct gcaattggcg   21720
cgataccagg catagcttcc gtggcggttc aggcctcgca acgacattga cattggaaaa   21780
aaaacgtata aataaaaaaa aatacaatgg actctgacac tcctggtcct gtgactatgt   21840
tttcttagag atggaagaca tcaatttttc atccttggct ccgcgacacg gcacgaagcc   21900
gtacatgggc acctggagcg acatcggcac gagccaactg aacggggggcg ccttcaattg   21960
gagcagtatc tggagcgggc ttaaaaattt tggctcaacc ataaaaacat acgggaacaa   22020
agcttggaac agcagtacag gacaggcgct tagaaataaa cttaaagacc agaacttcca   22080
acaaaaagta gtcgatggga tagcttccgg catcaatgga gtggtagatt tggctaacca   22140
ggctgtgcag aaaaagataa acagtcgttt ggacccgccg ccagcaaccc caggtgaaat   22200
gcaagtggag gaagaaattc ctccgccaga aaaacgaggc gacaagcgtc cgcgtcccga   22260
tttggaagag acgctggtga cgcgcgtaga tgaaccgcct tcttatgagg aagcaacgaa   22320
gcttggaatg cccaccacta gaccgatagc cccaatggcc accggggtga tgaaaccttc   22380
tcagttgcat cgacccgtca ccttggattt gcccccctccc cctgctgcta ctgctgtacc   22440
cgcttctaag cctgtcgctg ccccgaaacc agtcgccgta gccaggtcac gtcccgggg   22500
cgctcctcgt ccaaatgcgc actggcaaaa tactctgaac agcatcgtgg gtctaggcgt   22560
gcaaagtgta aaacgccgtc gctgctttta attaaatatg gagtagcgct taacttgcct   22620
atctgtgtat atgtgtcatt acgccgtc acagcagcag aggaaaaaag gaagaggtcg   22680
tgcgtcgacg ctgagttact ttcaagatgg ccacccatc gatgctgccc caatgggcat   22740
acatgcacat cgccggacag gatgcttcgg agtacctgag tccgggtctg gtgcagttcg   22800
cccgcgccac agacacctac ttcaatctgg gaaataagtt tagaaatccc accgtagcgc   22860
cgacccacga tgtgaccacc gaccgtagcc agcggctcat gttgcgcttc gtgcccgttg   22920
accgggagga caatacatac tcttacaaag tgcggtacac cctggccgtg ggcgacaaca   22980
gagtgctgga tatggccagc acgttctttg acattagggg cgtgttggac agaggtccca   23040
gtttcaaacc ctattctggt acggcttaca actctctggc tcctaaaggc gctccaaatg   23100
catctcaatg gattgcaaaa ggcgtaccaa ctgcagcagc cgcaggcaat ggtgaagaag   23160
aacatgaaac agaggagaaa actgctactt cacttttgc caatgctcct gtaaaagccg   23220
aggctcaaat tacaaagag ggcttaccaa taggtttgga gatttcagct gaaaacgaat   23280
ctaaacccat ctatgcagat aaactttatc agccagaacc tcaagtggga gatgaaactt   23340
```

```
ggactgacct agacggaaaa accgaagagt atggaggcag ggctctaaag cctactacta   23400
acatgaaacc ctgttacggg tcctatgcga agcctactaa tttaaaaggt ggtcaggcaa   23460
aaccgaaaaa ctcggaaccg tcgagtgaaa aaattgaata tgatattgac atggaatttt   23520
ttgataactc atcgcaaaga acaaacttca gtcctaaaat tgtcatgtat gcagaaaatg   23580
taggtttgga aacgccagac actcatgtag tgtacaaacc tggaacagaa gacacaagtt   23640
ccgaagctaa tttgggacaa cagtctatgc ccaacagacc caactacatt ggcttcagag   23700
ataactttat tggactcatg tactataaca gtactggtaa catgggggtg ctggctggtc   23760
aagcgtctca gttaaatgca gtggttgact tgcaggacag aaacacagaa cttcttacc   23820 aactcttgct tgactctctg ggcgacagaa ccagatactt tagcatgtgg aatcaggctg   23880
tggacagtta tgatcctgat gtacgtgtta ttgaaaatca tggtgtggaa gatgaacttc   23940
ccaactattg ttttccactg gacggcatag gtgttccaac aaccagttac aaatcaatag   24000
ttccaaatgg agaagataat aataattgga aagaacctga agtaaatgga acaagtgaga   24060
tcggacaggg taatttgttt gccatggaaa ttaaccttca agccaatcta tggcgaagtt   24120
tcctttattc caatgtggct ctgtatctcc cagactcgta caaatacacc ccgtccaatg   24180
tcactcttcc agaaaacaaa aacacctacg actacatgaa cgggcgggtg gtgccgccat   24240
ctctagtaga cacctatgtg aacattggtg ccaggtggtc tctggatgcc atggacaatg   24300
tcaacccatt caaccaccac cgtaacgctg gcttgcgtta ccgatctatg cttctgggta   24360
acggacgtta tgtgcctttc cacatacaag tgcctcaaaa attcttcgct gttaaaaacc   24420
tgctgcttct cccaggctcc tacacttatg agtggaactt taggaaggat gtgaacatgg   24480
ttctacagag ttccctcggt aacgacctgc gggtagatgg cgccagcatc agtttcacga   24540
gcatcaacct ctatgctact ttttttcccca tggctcacaa caccgcttcc acccttgaag   24600
ccatgctgcg gaatgacacc aatgatcagt cattcaacga ctacctatct gcagctaaca   24660
tgctctaccc cattcctgcc aatgcaacca atattcccat ttccattcct tctcgcaact   24720
gggcggcttt cagaggctgg tcatttacca gactgaaaac caagaaaact ccctcttttgg   24780 ggtctggatt tgacccctac tttgtctatt ctggttctat tccctacctg gatggtacct   24840
tctacctgaa ccacactttt aagaaggttt ccatcatgtt tgactcttca gtgagctggc   24900
ctggaaatga caggttacta tctcctaacg aatttgaaat aaagcgcact gtggatggcg   24960
aaggctacaa cgtagcccaa tgcaacatga ccaaagactg gttcttggta cagatgctcg   25020
ccaactacaa catcggctat cagggcttct acattccaga aggatacaaa gatcgcatgt   25080
attcattttt cagaaacttc cagcccatga gcaggcaggt ggttgatgag gtcaattaca   25140
aagacttcaa ggccgtcgcc ataccctacc aacacaacaa ctctggcttt gtgggttaca   25200
tggctccgac catgcgccaa ggtcaaccct atcccgctaa ctatccctat ccactcattg   25260
gaacaactgc cgtaaatagt gttacgcaga aaaagttctt gtgtgacaga accatgtggc   25320
gcataccgtt ctcgagcaac ttcatgtcta tgggggccct tacagacttg ggacagaata   25380
tgctctatgc caactcagct catgctctgg acatgacctt tgaggtggat cccatggatg   25440
agcccaccct gctttatctt ctcttcgaag ttttcgacgt ggtcagagtg catcagccac   25500
accgcggcat catcgaggca gtctacctgc gtacaccgtt ctcggccggt aacgctacca   25560
cgtaagaagc ttcttgcttc ttgcaaatag cagctgcaac catggcctgc ggatcccaaa   25620
acggctccag cgagcaagag ctcagagcca ttgtccaaga cctgggttgc ggaccctatt   25680
```

```
ttttgggaac ctacgataag cgcttcccgg ggttcatggc ccccgataag ctcgcctgtg    25740
ccattgtaaa tacggccgga cgtgagacgg ggggagagca ctggttggct ttcggttgga    25800
acccacgttc taacacctgc tacctttttg atccttttgg attctcggat gatcgtctca    25860
aacagattta ccagtttgaa tatgagggtc tcctgcgccg cagcgctctt gctaccaagg    25920
accgctgtat tacgctggaa aaatctaccc agaccgtgca gggcccccgt tctgccgcct    25980
gcggactttt ctgctgcatg ttccttcacg cctttgtgca ctggcctgac cgtcccatgg    26040
acggaaaccc caccatgaaa ttgctaactg gagtgccaaa caacatgctt cattctccta    26100
aagtccagcc caccctgtgt gacaatcaaa aagcactcta ccatttttctt aatacccatt    26160
cgccttattt tcgctctcat cgtacacaca tcgaaagggc cactgcgttc gaccgtatgg    26220
atgttcaata atgactcatg taaacaacgt gttcaataaa catcacttta tttttttaca    26280
tgtatcaagg ctctggatta cttatttatt tacaagtcga atgggttctg acgagaatca    26340
gaatgacccg caggcagtga tacgttgcgg aactgatact tgggttgcca cttgaattcg    26400
ggaatcacca acttgggaac cggtatatcg ggcaggatgt cactccacag ctttctggtc    26460
agctgcaaag ctccaagcag gtcaggagcc gaaatcttga aatcacaatt aggaccagtg    26520
ctctgagcgc gagagttgcg gtacaccgga ttgcagcact gaaacaccat cagcgacgga    26580
tgtctcacgc ttgccagcac ggtgggatct gcaatcatgc ccacatccag atcttcagca    26640
ttggcaatgc tgaacggggt catcttgcag gtctgcctac ccatggcggg cacccaatta    26700
ggcttgtggt tgcaatcgca gtgcaggggg atcagtatca tcttggcctg atcctgtctg    26760
attcctggat acacggctct catgaaaagca tcatattgct tgaaagcctg ctgggcttta    26820
ctaccctcgg tataaaacat cccgcaggac ctgctcgaaa actggttagc tgcacagccg    26880
gcatcattca cacagcagcg ggcgtcattg ttggctattt gcaccacact tctgccccag    26940
cggttttggg tgattttggt tcgctcggga ttctccttta aggctcgttg tccgttctcg    27000
ctggccacat ccatctcgat aatctgctcc ttctgaatca taatattgcc atgcaggcac    27060
ttcagcttgc cctcataatc attgcagcca tgaggccaca acgcacagcc tgtacattcc    27120
caattatggt gggcgatctg agaaaaagaa tgtatcattc cctgcagaaa tcttcccatc    27180
atcgtgctca gtgtcttgtg actagtgaaa gttaactgga tgcctcggtg ctcttcgttt    27240
acgtactggt gacagatgcg cttgtattgt tcgtgttgct caggcattag tttaaaacag    27300
gttctaagtt cgttatccag cctgtacttc tccatcagca gacacatcac ttccatgcct    27360
ttctcccaag cagacaccag gggcaagcta atcggattct taacagtgca ggcagcagct    27420
cctttagcca gagggtcatc tttagcgatc ttctcaatgc ttcttttgcc atccttctca    27480
acgatgcgca cgggcgggta gctgaaaccc actgctacaa gttgcgcctc ttctcttttct    27540
tcttcgctgt cttgactgat gtcttgcatg gggatatgtt tggtcttcct tggcttcttt    27600
ttgggggta tcggaggagg aggactgtcg ctccgttccg gagacaggga ggattgtgac    27660
gtttcgctca ccattaccaa ctgactgtcg gtagaagaac ctgaccccac acggcgacag    27720
gtgtttttct tcggggcag aggtggaggc gattgcgaag ggctgcggtc cgacctggaa    27780
ggcggatgac tggcagaacc ccttccgcgt tcggggtgt gctccctgtg gcggtcgctt    27840
aactgatttc cttcgcggct ggccattgtg ttctcctagg cagagaaaca acagacatgg    27900
aaactcagcc attgctgtca acatcgccac gagtgccatc acatctcgtc ctcagcgacg    27960
aggaaaagga gcagagctta agcattccac cgcccagtcc tgccaccacc tctaccctag    28020
aagataagga ggtcgacgca tctcatgaca tgcagaataa aaaagcgaaa gagtctgaga    28080
```

```
cagacatcga gcaagacccg ggctatgtga caccggtgga acacgaggaa gagttgaaac    28140
gctttctaga gagagaggat gaaaactgcc caaaacagcg agcagataac tatcaccaag    28200
atgctggaaa tagggatcag aacaccgact acctcatagg gcttgacggg gaagacgcgc    28260
tccttaaaca tctagcaaga cagtcgctca tagtcaagga tgcattattg gacagaactg    28320
aagtgcccat cagtgtggaa gagctcagct gcgcctacga gcttaacctt ttttcacctc    28380
gtactccccc caaacgtcag ccaaacggca cctgcgagcc aaatcctcgc ttaaacttt    28440 atccagcttt tgctgtgcca gaagtactgg ctacctatca catctttttt aaaaatcaaa    28500
aaattccagt ctcctgccgc gctaatcgca cccgcgccga tgccctactc aatctgggac    28560
ctggttcacg cttacctgat atagcttcct tggaagaggt tccaaagatc ttcgagggtc    28620
tgggcaataa tgagactcgg gccgcaaatg ctctgcaaaa gggagaaaat ggcatggatg    28680
agcatcacag cgttctggtg gaattggaag gcgataatgc cagactcgca gtactcaagc    28740
gaagcgtcga ggtcacacac ttcgcatatc ccgctgtcaa cctgccccct aaagtcatga    28800
cggcggtcat ggaccagtta ctcattaagc gcgcaagtcc cctttcagaa gacatgcatg    28860
acccagatgc ctgtgatgag ggtaaaccag tggtcagtga tgagcagcta acccgatggc    28920
tgggcaccga ctctccccgg gatttggaag agcgtcgcaa gcttatgatg gccgtggtgc    28980
tggttaccgt agaactagag tgtctccgac gtttctttac cgattcagaa accttgcgca    29040
aactcgaaga gaatctgcac tacacttta gacacggctt tgtgcggcag gcatgcaaga    29100
tatctaacgt ggaactcacc aacctggttt cctacatggg tattctgcat gagaatcgcc    29160
taggacaaag cgtgctgcac agcacccctta aggggggaagc ccgccgtgat tacatccgcg    29220
attgtgtcta tctctacctg tgccacacgt ggcaaaccgg catgggtgta tggcagcaat    29280
gtttagaaga acagaacttg aaagagcttg acaagctctt acagaaatct cttaaggttc    29340
tgtggacagg gttcgacgag cgcaccgtcg cttccgacct ggcagacctc atcttcccag    29400
agcgtctcag ggttactttg cgaaacggat tgcctgactt tatgagccag agcatgctta    29460
acaattttcg ctctttcatc ctggaacgct ccggtatcct gcccgccacc tgctgcgcac    29520
tgccctccga ctttgtgcct ctcacctacc gcgagtgccc ccgccgcta tggagtcact    29580 gctacctgtt ccgtctggcc aactatctct cctaccactc ggatgtgatc gaggatgtga    29640
gcggagacgg cttgctggag tgccactgcc gctgcaatct gtgcacgccc caccggtccc    29700
tagcttgcaa ccccccagttg atgagcgaaa cccagataat aggcaccttt gaattgcaag    29760
gccccagcag ccaaggcgat gggtcttctc ctgggcaaag tttaaaactg accccgggac    29820
tgtggacctc cgcctacttg cgcaagtttg ctccggaaga ttaccacccc tatgaaatca    29880
agttctatga ggaccaatca cagcctccaa aggccgaact tcggcttgc gtcatcaccc    29940 aggggggcaat tctggcccaa ttgcaagcca tccaaaaatc ccgccaagaa tttctactga    30000
aaaagggtaa gggggtctac cttgaccccc agaccggcga ggaactcaac acaaggttcc    30060
ctcaggatgt cccaacgacg agaaaacaag aagttgaagg tgcagccgcc gcccccagaa    30120
gatatggagg aagattggga cagtcaggca gaggaggcgg aggaggacag tctggaggac    30180
agtctggagg aagacagttt ggaggaggaa acgaggagg cagaggaggt ggaagaagta    30240
accgccgaca aacagttatc ctcggctgcg gagacaagca acagcgctac catctccgct    30300
ccgagtcgag gaacccggcg gcgtcccagc agtagatggg acgagaccgg acgcttcccg    30360
aacccaacca gcgcttccaa gaccggtaag aaggatcggc agggatacaa gtcctggcgg    30420
```

```
gggcataaga atgccatcat ctcctgcttg catgagtgcg ggggcaacat atccttcacg   30480
cggcgctact tgctattcca ccatggggtg aactttccgc gcaatgtttt gcattactac   30540
cgtcacctcc acagcccta ctatagccag caaatcccga cagtctcgac agataaagac   30600
agcggcggcg acctccaaca gaaaaccagc agcggcagtt agaaaataca caacaagtgc   30660
agcaacagga ggattaaaga ttacagccaa cgagccagcg caaacccgag agttaagaaa   30720
tcggatcttt ccaaccctgt atgccatctt ccagcagagt cggggtcaag agcaggaact   30780
gaaaataaaa aaccgatctc tgcgttcgct caccagaagt tgtttgtatc acaagagcga   30840
agatcaactt cagcgcactc tcgaggacgc cgaggctctc ttcaacaagt actgcgcgct   30900
gactcttaaa gagtaggcag cgaccgcgct tattcaaaaa aggcgggaat tacatcatcc   30960
tcgacatgag taaagaaatt cccacgcctt acatgtggag ttatcaaccc caaatgggat   31020
tggcagcagg cgcctcccag gactactcca cccgcatgaa ttggctcagc gccgggcctt   31080
ctatgatttc tcgagttaat gatatacgcg cctaccgaaa ccaaatactt ttggaacagt   31140
cagtctttac caccacgccc cgccaacacc ttaatcccag aaattggccc gccgccctag   31200
tgtaccagga aagtcccgct cccaccactg tattacttcc tcgagacgcc caggccgaag   31260
tccaaatgac taatgcaggt gcgcagttag ctggcggctc caccctatgt cgtcacaggc   31320
ctcggcataa tataaaacgc ctgatgatca gaggccgagg tatccagctc aacgacgagt   31380
cggtgagctc tccgcttggt ctacgaccag acggaatctt tcagattgcc ggctgcggga   31440
gatcttcctt caccccctcgt caggctgttc tgactttgga aagttcgtct tcgcaacccc   31500
gctcgggcgg aatcgggacc gttcaatttg tagaggagtt tactccctct gtctacttca   31560
accccttctc cggatctcct gggcactacc cggacgagtt catacccgaac ttcgacgcga   31620 ttagcgagtc agtggacggc tacgattgat gtctggtgac gcggctgagc tatctcggct   31680
gcgacatcta gaccactgcc gccgcttttcg ctgctttgcc cgggaactta ttgagttcat   31740
ctacttcgaa ctccccaagg atcaccctca aggtccggcc cacggagtgc ggattactat   31800
cgaaggcaaa atagactctc gcctgcaacg aattttctcc cagcggcccg tgctgatcga   31860
gcgagaccag ggaaacacca cggtttccat ctactgcatt tgtaatcacc ccggattgca   31920
tgaaagcctt tgctgtctta tgtgtactga gtttaataaa aactgaatta agactctcct   31980
acggactgcc gcttcttcaa cccgattttt acaaccagaa gaacaaaact tttcctgtcg   32040
tccaggactc tgttaacttc acctttccta ctcacaaact agaagctcaa cgactacaac   32100
gcgtggccaa agagctcaga gatgtcatcc aaattcacca atgcaaaaaa ggcatattct   32160
gtttggtaaa acaagccaag atatcctacg agatcaccgc tactgaccat cgcctctctt   32220
acgaacttgg ccccccaacga caaaaattta cctgcatggt gggaatcaac cccatagtta   32280
tcacccaaca aagtggagat actaagggtt gcattcactg ctcctgcgat tccatcgagt   32340
gcacctacac cctgctgaag acccctatgcg gcctaagaga cctgctacca atgaattaaa   32400
aaaaaatgat taataaaaaa tcacttactt gaaatcagca ataaggtctc tgttgaaatt   32460
ttctcccagc agcacctcac ttccctcttc caactctgg tattctaaac cccgttcagc   32520
ggcatacttt ctccatactt taagggggat gtcaaatttt agctcctctc ctgtaccacc   32580
aatcttcatg tctttcttcc cagatgacca agagagtccg gctcagtgac tccttcaacc   32640
ctgtctaccc ctatgaagat gaaagcacct cccaacaccc ctttataaac ccagggttta   32700
tttccccaaa tggcttcaca caaagcccag acggagttct tactttaaaa tgtttaaccc   32760
cactaacaac cacaggcgga tctctacagc taaaagtggg agggggactt acagtggatg   32820
```

```
acactgatgg taccttacaa gaaaacatac gtgctacagc acccattact aaaaataatc   32880
actctgtaga actatccatt ggaaatggat tagaaactca aaacaataaa ctatgtgcca   32940
aattgggaaa tgggttaaaa tttaacaacg gtgacatttg tataaaggat agtattaaca   33000
ccttatggac tggaataaac cctccaccta actgtcaaat tgtggaaaac actaatacaa   33060
atgatggcaa acttacttta gtattagtaa aaaatggagg gcttgttaat ggctacgtgt   33120
ctctagttgg tgtatcagac actgtgaacc aaatgttcac acaaaagaca gcaaacatcc   33180
aattaagatt atattttgac tcttctggaa atctattaac tgaggaatca gacttaaaaa   33240
ttccacttaa aaataaatct tctacagcga ccagtgaaac tgtagccagc agcaaagcct   33300
ttatgccaag tactacagct tatcccttca acaccactac tagggatagt gaaaactaca   33360
ttcatggaat atgttactac atgactagtt atgatagaag tctatttccc ttgaacattt   33420
ctataatgct aaacagccgt atgatttctt ccaatgttgc ctatgccata caatttgaat   33480
ggaatctaaa tgcaagtgaa tctccagaaa gcaacatagc tacgctgacc acatccccct   33540
ttttctttct ttacattaca gaagacgaca actaaaataa agtttaagtg ttttttattta  33600
aaatcacaaa attcgagtag ttattttgcc tccaccttcc catttgacag aatacaccaa   33660
tctctcccca cgcacagctt taaacatttg gataccatta gagatagaca ttgttttaga   33720
ttccacattc caaacagttt cagagcgagc caatctgggg tcagtgatag ataaaaatcc   33780
atcgcgatag tcttttaaag cgctttcaca gtccaactgc tgcggatgcg actccggagt   33840
ttggatcacg gtcatctgga agaagaacga tgggaatcat aatccgaaaa cggtatcgga   33900
cgattgtgtc tcatcaaacc cacaagcagc cgctgtctgc gtcgctccgt gcgactgctg   33960
tttatgggat cagggtccac agtttcctga agcatgattt taatagccct taacatcaac   34020
tttctggtgc gatgcgcgca gcaacgcatt ctgatttcac tcaaatcttt gcagtaggta   34080
caacacatta ttacaatatt gtttaataaa ccataattaa aagcgctcca gccaaaactc   34140
atatctgata taatcgcccc tgcatgacca tcataccaaa gtttaatata aattaaatga   34200
cgttccctca aaaacacact acccacatac atgatctctt ttggcatgtg catattaaca   34260
atctgtctgt accatggaca acgttggtta atcatgcaac ccaatataac cttccggaac   34320
cacactgcca acaccgctcc cccagccatg cattgaagtg aaccctgctg attacaatga   34380
caatgaagaa cccaattctc tcgaccgtga atcacttgag aatgaaaaat atctatagtg   34440
gcacaacata gacataaatg catgcatctt ctcataattt ttaactcctc aggatttaga   34500
aacatatccc agggaatagg aagctcttgc agaacagtaa agctggcaga acaaggaaga   34560
ccacgaacac aacttacact atgcatagtc atagtatcac aatctggcaa cagcgggtgg   34620
tcttcagtca tagaagctcg ggtttcattt tcctcacaac gtggtaactg gctctggtg    34680
taagggtgat gtctggcgca tgatgtcgag cgtgcgcgca accttgtcat aatggagttg   34740
cttcctgaca ttctagaaag tacagcgggc acacaaacca caagctctaa agtcactctc   34800
caacctstcc acaatatata tacacaagcc ctaaactgac gtaatgggac taaagtgtaa   34860
aaaatcccgc caaacccaac acacacccc g aaactgcgtc accagggaaa agtcagttt   34920
cacttccgca atcccaacaa gcgtcacttc ctctttctca cggtacgtca catcccatta   34980
acttacaacg tcattttccc acggccgcgc cgccccttt t aaccgttaac cccacagcca   35040
atcaccacac ggcccacact ttttaaaatc acctcattta catattggca ccattccatc   35100
tataaggtat attattgatg atgatttaaa tgc                                35133
```

<210> SEQ ID NO 26
<211> LENGTH: 8027
<212> TYPE: DNA
<213> ORGANISM: Artificial Sequence
<220> FEATURE:
<223> OTHER INFORMATION: pAdApt35BSU.E1btg.Empty

<400> SEQUENCE: 26

```
gaattggtcg atggcaaaca gctattatgg gtattatggg ttcgaattaa ttaatcgaca      60
tcatcaataa tataccttat agatggaatg gtgccaatat gtaaatgagg tgattttaaa     120
aagtgtgggc cgtgtggtga ttggctgtgg ggttaacggt taaaagggc ggcgcggccg      180
tgggaaaatg acgttttatg ggggtggagt ttttttgcaa gttgtcgcgg gaaatgttac    240
gcataaaaag gcttcttttc tcacggaact acttagtttt cccacggtat ttaacaggaa    300
atgaggtagt tttgaccgga tgcaagtgaa aattgctgat tttcgcgcga aaactgaatg    360
aggaagtgtt tttctgaata atgtggtatt tatggcaggg tggagtattt gttcagggcc    420
aggtagactt tgacccatta cgtggaggtt tcgattaccg tgttttttac ctgaatttcc    480
gcgtaccgtg tcaaagtctt ctgttttttac gtaggtgtca gcctaggctg atcgctaggg    540
tatttatacc tcagggtttg tgtcaagagg ccactcttga gtgccagcga aaagagtttt    600
ctcctctgcg ccggcagttt aataataaaa aaatgagaga tttgcgattt ctgcctcagg    660
aaataatctc tgctgagact ggaaatgaaa tattggagct tgtggtgcac gccctgatgg    720
gagacgatcc ggagccacct gtgcagcttt ttgagcctcc tacgcttcag gaactgtatg    780
atttagaggt agagggatcg gaggattcta atgaggaagc tgtgaatggc ttttttaccg    840
attctatgct tttagctgct aatgaaggat tagaattaga tccgccttg gacactttca    900
atactccagg ggtgattgtg aaagcggta caggtgtaag aaaattacct gatttgagtt    960
ccgtggactg tgatttgcac tgctatgaag acgggtttcc tccgagtgat gaggaggacc   1020
atgaaaagga gcagtccatg cagactgcag cgggtgaggg agtgaaggct gccaatgttg   1080
gttttcagtt ggattgcccg gagcttcctg acatggctg taagtcttgt gaatttcaca   1140
ggaaaaatac tggagtaaag gaactgttat gttcgctttg ttatatgaga acgcactgcc   1200
actttattta cagtaagtgt gtttaagtta aaatttaaag gaatatgctg ttttttcacat   1260
gtatattgag tgtgagtttt gtgcttctta ttataggtcc tgtgtctgat gctgatgaat   1320
caccatctcc tgattctact acctcacctc ctgatattca agcacctgtt cctgtggacg   1380
tgcgcaagcc cattcctgtg aagcttaagc ctgggaaacg tccagcagtg gagaaacttg   1440
aggacttgtt acagggtggg gacggacctt tggacttgag tacacggaaa cgtccaagac   1500
aataagtgtt ccatatccgt gtttacttaa ggtgacgtca atatttgtgt gagagtgcaa   1560
tgtaataaaa atatgttaac tgttcactgg ttttttattgc ttttggggcg gggactcagg   1620
tatataagta gaagcagacc tgtgtggtta gctcatagga gctggcttc atccatggag   1680
gtttgggcca ttttggaaga ccttaggaag actaggcaac tgttagagag cgcttcggac   1740
ggagtctccg gttttggag attctggttc gctagtgaat tagctagggt agttttagg   1800
ataaaacagg actataaaca agaatttgaa aagttgttgg tagattgccc aggactttt   1860
gaagctctta atttgggcca tcaggttcac tttaaagaaa agtttttatc agtttagac   1920
ttttcaaccc caggtagaac tgctgctgct gtggcttttc ttacttttat attagataaa   1980
tggatcccgc agactcattt cagcagggga tacgttttgg atttcatagc cacagcattg   2040
tggagaacat ggaaggttcg caagatgagg acaatcttag gttactggcc agtgcagcct   2100
```

```
ttgggtgtag cgggaatcct gaggcatcca ccggtcatgc cagcggttct ggaggaggaa    2160
cagcaagagg acaacccgag agccggcctg gaccctccag tggaggaggc ggagtagctg    2220
acttgtctcc tgaactgcaa cgggtgctta ctggatctac gtccactgga cgggataggg    2280
gcgttaagag ggagagggca tccagtggta ctgatgctag atctgagttg ctttaagtt    2340
taatgagtcg cagacgtcct gaaaccattt ggtggcatga ggttcagaaa gagggaaggg    2400
atgaagtttc tgtattgcag gagaaatatt cactggaaca ggtgaaaaca tgttggttgg    2460
agccagagga tgattgggag gtggccatta aaaattatgc caagatagct ttgaggcctg    2520
ataaacagta taagatcagt agacggatta atatccggaa tgcttgttac atatctggaa    2580
atggggctga ggtggtaata gatactcaag acaagacagt tattagatgc tgcatgatgg    2640
atatgtggcc tggagtagtc ggtatggaag cagtcacttt tgtaaatgtt aagtttaggg    2700
gagatggtta taatggaata gtgtttatgg ccaataccaa acttatattg catggttgta    2760
gcttttttgg tttcaacaat acctgtgtag atgcctgggg acaggttagt gtacgggggt    2820
gtagtttcta tgcgtgttgg attgccacag ctggcagaac caagagtcaa ttgtctctga    2880
agaaatgcat attccaaaga tgtaacctgg gcattctgaa tgaaggcgaa gcaagggtcc    2940
gtcactgcgc ttctacagat actggatgtt ttatttaat caagggaaat gccagcgtaa    3000
agcataacat gatttgtggt gcttccgatg agaggcctta tcaaatgctc acttgtgctg    3060
gtgggcattg taatatgctg gctactgtgc atattgtttc ccatcaacgc aaaaaatggc    3120
ctgtttttga tcacaatgtg ttgaccaagt gcaccatgca tgcaggtggg cgtagaggaa    3180
tgtttatgcc ttaccagtgt aacatgaatc atgtgaaagt gttgttggaa ccagatgcct    3240
tttccagaat gagcctaaca ggaatctttg acatgaacac gcaaatctgg aagatcctga    3300
ggtatgatga tacgagatcg agggtgcgcg catgcgaatg cggaggcaag catgccaggt    3360
tccagccggt gtgtgtagat gtgaccgaag atctcagacc ggatcatttg gttattgccc    3420
gcactggagc agagttcgga tccagtggag aagaaactga ctaacctagg tggtcaatat    3480
tggccattag ccatattatt cattggttat atagcataaa tcaatattgg ctattggcca    3540
ttgcatacgt tgtatccata tcataatatg tacatttata ttggctcatg tccaacatta    3600
ccgccatgtt gacattgatt attgactagt tattaatagt aatcaattac ggggtcatta    3660
gttcatagcc catatatgga gttccgcgtt acataactta cggtaaatgg cccgcctggc    3720
tgaccgccca acgaccccccg cccattgacg tcaataatga cgtatgttcc catagtaacg    3780
ccaataggga ctttccattg acgtcaatgg gtggagtatt tacggtaaac tgcccacttg    3840
gcagtacatc aagtgtatca tatgccaagt acgcccccta ttgacgtcaa tgacggtaaa    3900
tggcccgcct ggcattatgc ccagtacatg accttatggg actttcctac ttggcagtac    3960
atctacgtat tagtcatcgc tattaccatg gtgatgcggt tttggcagta catcaatggg    4020
cgtggatagc ggtttgactc acggggattt ccaagtctcc accccattga cgtcaatggg    4080
agtttgtttt ggcaccaaaa tcaacgggac tttccaaaat gtcgtaacaa ctccgcccca    4140
ttgacgcaaa tgggcggtag gcgtgtacgg tgggaggtct atataagcag agctcgttta    4200
gtgaaccgtc agatcgcctg gagacgccat ccacgctgtt ttgacctcca tagaagacac    4260
cgggaccgat ccagcctccg cggccgggaa cggtgcattg gaagcttggt accggccggt    4320
gaattcggcg cgccgtcgac gatatcgata gcggccgcaa ttcgctagcg ttaacggatc    4380
ctctagacga gatccgaact tgtttattgc agcttataat ggttacaaat aaagcaatag    4440
```

-continued

```
catcacaaat ttcacaaata aagcattttt ttcactgcat tctagttgtg gtttgtccaa    4500
actcatcaat gtatcttatc atgtctagat ctgaggtatg atgatacgag atcgagggtg    4560
cgcgcatgcg aatgcggagg caagcatgcc aggttccagc cggtgtgtgt agatgtgacc    4620
gaagatctca gaccggatca tttggttatt gcccgcactg gagcagagtt cggatccagt    4680
ggagaagaaa ctgactaagg tgagtattgg gaaaactttg gggtgggatt ttcagatgga    4740
cagattgagt aaaaatttgt ttttttctgtc ttgcagctga catgagtgga aatgcttctt    4800 ttaaggggggg agtcttcagc ccttatctga cagggcgtct cccatcctgg gcaggagttc    4860
gtcagaatgt tatgggatct actgtggatg aagacccgt tcaacccgcc aattcttcaa     4920
cgctgaccta tgctacttta agttcttcac ctttggacgc agctgcagcc gctgccgccg    4980
cctctgtcgc cgctaacact gtgcttggaa tgggttacta tggaagcatc gtggctaatt    5040
ccacttcctc taataaccct tctacactga ctcaggacaa gttacttgtc cttttggccc    5100
agctggaggc tttgacccaa cgtctgggtg aactttctca gcaggtggcc gagttgcgag    5160
tacaaactga gtctgctgtc ggcacggcaa agtctaaata aaaaaaattc cagaatcaat    5220
gaataaataa acgagcttgt tgttgattta aaatcaagtg ttttatttc attttttcgcg    5280 cacggtatgc cctggaccac cgatctcgat cattgagaac tcgtggatt ttttccagaa     5340 tcctatagag gtgggattga atgtttagat acatgggcat taggccgtct ttggggtgga    5400
gatagctcca ttgaagggat tcatgctccg gggtagtgtt gtaaatcacc cagtcataac    5460
aaggtcgcag tgcatggtgt tgcacaatat cttttagaag taggctgatt gccacagata    5520
agcccttggt gtaggtgttt acaaaccggt tgagctggga ggggtgcatt cgaggtgaaa    5580
ttatgtgcat tttggattgg attttttaagt tggcaatatt gccgccaaga tcccgtcttg    5640
ggttcatgtt atgaaggact accaagacgg tgtatccggt acatttagga aatttatcgt    5700
gcagcttgga tggaaaagcg tggaaaaatt tggagacacc cttgtgtcct ccgagatttt    5760
ccatgcactc atccatgata atagcaatgg ggccgtgggc agcggcgcgg gcaaacacgt    5820
tccgtgggtc tgacacatca tagttatgtt cctgagttaa atcatcataa gccatttaa     5880 tgaatttggg gcgagcgta ccagattggg gtatgaatgt tccttcgggc cccggagcat     5940
agttcccctc acagatttgc atttcccttga attaattcga acccataata cccataatag    6000
ctgtttgcca tcgacgcgag gctggatggc cttccccatt atgattcttc tcgcttccgg    6060
cggcatcggg atgcccgcgt tgcaggccat gctgtccagg caggtagatg acgaccatca    6120
gggacagctt caaggatcgc tcgcggctct taccagccca gcaaaaggcc aggaaccgta    6180
aaaaggccgc gttgctggcg ttttttccata ggctccgccc cctgacgag catcacaaaa     6240 atcgacgctc aagtcagagg tggcgaaacc cgacaggact ataaagatac caggcgtttc    6300
cccctggaag ctccctcgtg cgctctcctg ttccgaccct gccgcttacc ggatacctgt    6360
ccgcctttct cccttcggga agcgtggcgc tttctcatag ctcacgctgt aggtatctca    6420
gttcggtgta ggtcgttcgc tccaagctgg gctgtgtgca cgaaccccc gttcagcccg     6480 accgctgcgc cttatccggt aactatcgtc ttgagtccaa cccggtaaga cacgacttat    6540
cgccactggc agcagccact ggtaacagga ttagcagagc gaggtatgta ggcggtgcta    6600
cagagttctt gaagtggtgg cctaactacg gctacactag aaggacagta tttggtatct    6660
gcgctctgct gaagccagtt accttcggaa aaagagttgg tagctcttga tccggcaaac    6720
aaaccaccgc tggtagcggt ggtttttttg tttgcaagca gcagattacg cgcagaaaaa    6780
aaggatctca agaagatcct ttgatctttt ctacggggtc tgacgctcag tggaacgaaa    6840
```

-continued

```
actcacgtta agggattttg gtcatgagat tatcaaaaag gatcttcacc tagatccttt    6900
taaattaaaa atgaagtttt aaatcaatct aaagtatata tgagtaaact tggtctgaca    6960
gttaccaatg cttaatcagt gaggcaccta tctcagcgat ctgtctattt cgttcatcca    7020
tagttgcctg actcccgtc gtgtagataa ctacgatacg ggagggctta ccatctggcc     7080
ccagtgctgc aatgataccg cgagaccac gctcaccggc tccagattta tcagcaataa      7140
accagccagc cggaagggcc gagcgcagaa gtggtcctgc aactttatcc gcctccatcc    7200
agtctattaa ttgttgccgg gaagctagag taagtagttc gccagttaat agtttgcgca    7260
acgttgttgc cattgctgca ggcatcgtgg tgtcacgctc gtcgtttggt atggcttcat    7320
tcagctccgg ttcccaacga tcaaggcgag ttacatgatc ccccatgttg tgcaaaaaag    7380
cggttagctc cttcggtcct ccgatcgttg tcagaagtaa gttggccgca gtgttatcac    7440
tcatggttat ggcagcactg cataattctc ttactgtcat gccatccgta agatgctttt    7500
ctgtgactgg tgagtactca accaagtcat tctgagaata gtgtatgcgg cgaccgagtt    7560
gctcttgccc ggcgtcaaca cgggataata ccgcgccaca tagcagaact ttaaaagtgc    7620
tcatcattgg aaaacgttct cggggcgaaa actctcaag gatcttaccg ctgttgagat     7680
ccagttcgat gtaacccact cgtgcaccca actgatcttc agcatctttt actttcacca    7740
gcgtttctgg gtgagcaaaa acaggaaggc aaaatgccgc aaaaaaggga ataagggcga    7800
cacggaaatg ttgaatactc atactcttcc tttttcaata ttattgaagc atttatcagg    7860
gttattgtct catgagcgga tacatatttg aatgtattta gaaaaataaa caaataggggg   7920 ttccgcgcac atttccccga aaagtgccac ctgacgtcta agaaaccatt attatcatga    7980
cattaaccta taaaaatagg cgtatcacga ggccctttcg tcttcaa                  8027
```

<210> SEQ ID NO 27
<211> LENGTH: 3424
<212> TYPE: DNA
<213> ORGANISM: Adenovirus Serotype 35

<400> SEQUENCE: 27

```
atgtctggtg acgcggctga gctatctcgg ctgcgacatc tagaccactg ccgccgcttt     60
cgctgctttg cccgggaact tattgagttc atctacttcg aactccccaa ggatcaccct   120
caaggtccgg cccacggagt gcggattact atcgaaggca aaatagactc tcgcctgcaa   180
cgaattttct cccagcggcc cgtgctgatc gagcgagacc agggaaacac cacggtttcc   240
atctactgca tttgtaatca ccccggattg catgaaagcc tttgctgtct tatgtgtact   300
gagtttaata aaaactgaat taagactctc ctacggactg ccgcttcttc aacccggatt   360
ttacaaccag aagaacaaaa cttttcctgt cgtccaggac tctgttaact tcaccttttcc  420 tactcacaaa ctagaagctc aacgactaca ccgcttttcc agaagcattt tccctactaa   480
tactactttc aaaaccggag gtgagctcca cggtctccct acagaaaacc cttgggtgga   540
agcgggcctt gtagtactag gaattcttgc gggtgggctt gtgattattc tttgctacct   600
atacacacct tgcttcactt tcctagtggt gttgtggtat tggtttaaaa atgggggccc   660
atactagtct tgcttgtttt actttcgctt ttggaaccgg gttctgccaa ttacgatcca   720
tgtctagact ttgacccaga aaactgcaca cttacttttg cacccgacac aagccgcatc   780
tgtggagttc ttattaagtg cggatgggaa tgcaggtccg ttgaaattac acacaataac   840
aaaacctgga acaatacctt atccaccaca tgggagccag gagttccgga gtggtacact   900
```

```
gtctctgtcc gaggtcctga cggttccatc cgcattagta acaacacttt cattttttct    960
gaaatgtgcg atctggccat gttcatgagc aaacagtatt ctctatggcc tcctagcaag   1020
gacaacatcg taacgttctc cattgcttat tgcttgtgcg cttgccttct tactgcttta   1080
ctgtgcgtat gcatacacct gcttgtaacc actcgcatca aaacgccaa taacaaagaa    1140
aaaatgcctt aacctctttc tgtttacaga catggcttct cttacatctc tcatatttgt   1200
cagcattgtc actgccgctc acggacaaac agtcgtctct atcccactag gacataatta   1260
cactctcata ggaccccaa tcacttcaga ggtcatctgg accaaactgg gaagcgttga    1320
ttactttgat ataatctgta acaaaacaaa accaataata gtaacttgca acatacaaaa   1380
tcttacattg attaatgtta gcaaagttta cagcggttac tattatggtt atgacagata   1440
cagtagtcaa tatagaaatt acttggttcg tgttacccag ttgaaaacca cgaaaatgcc   1500
aaatatggca aagattcgat ccgatgacaa ttctctagaa acttttacat ctcccaccac   1560
acccgacgaa aaaacatcc cagattcaat gattgcaatt gttgcagcgg tggcagtggt    1620
gatggcacta ataataatat gcatgctttt atatgcttgt cgctacaaaa agtttcatcc   1680
taaaaaacaa gatctcctac taaggcttaa catttaattt cttttttatac agccatggtt  1740
tccactacca cattccttat gcttactagt ctcgcaactc tgacttctgc tcgctcacac   1800
ctcactgtaa ctataggctc aaactgcaca ctaaaaggac tcaaggtgg tcatgtcttt    1860
tggtggagaa tatatgacaa tggatggttt acaaaaccat gtgaccaacc tggtagattt   1920
ttctgcaacg gcagagacct aaccattatc aacgtgacag caaatgacaa aggcttctat   1980
tatgaaccg actataaaag tagtttagat tataacatta ttgtactgcc atctaccact    2040
ccaccacccc gcacaactac tttctctagc agcagtgtcg ctaacaatac aatttccaat   2100
ccaacctttg ccgcgctttt aaaacgcact gtgaataatt ctacaacttc acatacaaca   2160
atttccactt caacaatcag catcatcgct gcagtgacaa ttggaatatc tattcttgtt   2220
tttaccataa cctactacgc ctgctgctat agaaaagaca aacataaagg tgatccatta   2280
cttagatttg atatttaatt tgttctttt ttttatttac agtatggtga acaccaatca    2340
tggtacctag aaatttcttc ttcaccatac tcatctgtgc ttttaatgtt tgcgctactt   2400
tcacagcagt agccacagca accccagact gtataggagc atttgcttcc tatgcacttt   2460
ttgcttttgt tacttgcatc tgcgtatgta gcatagtctg cctggttatt aattttttcc   2520
aacttctaga ctggatcctt gtgcgaattg cctacctgcg ccaccatccc gaataccgca   2580
accaaaatat cgcggcactt cttagactca tctaaaacca tgcaggctat actaccaata   2640
ttttgcttc tattgcttcc ctacgctgtc tcaacccag ctgcctatag tactccacca    2700
gaacacctta gaaaatgcaa attccaacaa ccgtggtcat ttcttgcttg ctatcgagaa   2760
aaatcagaaa tccccccaaa tttaataatg attgctggaa taattaatat aatctgttgc   2820
accataattt catttttgat ataccccta tttgatttg gctggaatgc tcccaatgca    2880
catgatcatc cacaagaccc agaggaacac attccccac aaaacatgca acatccaata    2940
gcgctaatag attacgaaag tgaaccacaa ccccactac tccctgctat tagttacttc    3000
aacctaaccg gcgagatga ctgaaacact caccacctcc aattccgccg aggatctgct    3060
cgatatggac ggccgcgtct cagaacaacg acttgcccaa ctacgcatcc gccagcagca   3120
ggaacgcgtg gccaaagagc tcagagatgt catccaaatt caccaatgca aaaaaggcat   3180
attctgtttg gtaaaacaag ccaagatatc ctacgagatc accgctactg accatcgcct   3240
ctcttacgaa cttggccccc aacgacaaaa atttacctgc atggtgggaa tcaaccccat   3300
```

```
agttatcacc caacaaagtg gagatactaa gggttgcatt cactgttcct gcgattccat    3360
cgagtgcacc tacaccctgc tgaagaccct atgcggccta agagacctgc taccaatgaa    3420
ttaa                                                                 3424
```

<210> SEQ ID NO 28
<211> LENGTH: 751
<212> TYPE: DNA
<213> ORGANISM: Adenovirus Serotype 35

<400> SEQUENCE: 28

```
atgtctggtg acgcggctga gctatctcgg ctgcgacatc tagaccactg ccgccgcttt     60
cgctgctttg cccgggaact tattgagttc atctacttcg aactccccaa ggatcaccct    120
caaggtccgg cccacggagt gcggattact atcgaaggca aaatagactc tcgcctgcaa    180
cgaattttct cccagcggcc cgtgctgatc gagcgagacc agggaaacac cacggtttcc    240
atctactgca tttgtaatca ccccggattg catgaaagcc tttgctgtct tatgtgtact    300
gagtttaata aaaactgaat taagactctc ctacggactg ccgcttcttc aacccggatt    360
ttacaaccag aagaacaaaa cttttcctgt cgtccaggac tctgttaact tcacctttcc    420
tactcacaaa ctagaagctc aacgactaca acgcgtggcc aaagagctca gagatgtcat    480
ccaaattcac caatgcaaaa aaggcatatt ctgtttggta aaacaagcca agatatccta    540
cgagatcacc gctactgacc atcgcctctc ttacgaactt ggcccccaac gacaaaaatt    600
tacctgcatg gtgggaatca accccatagt tatcacccaa caaagtggag atactaaggg    660
ttgcattcac tgctcctgcg attccatcga gtgcacctac accctgctga agaccctatg    720
cggcctaaga gacctgctac caatgaatta a                                   751
```

<210> SEQ ID NO 29
<211> LENGTH: 105
<212> TYPE: PRT
<213> ORGANISM: Adenovirus Serotype 35

<400> SEQUENCE: 29

```
Met Ser Gly Asp Ala Ala Glu Leu Ser Arg Leu Arg His Leu Asp His
 1               5                  10                  15
Cys Arg Arg Phe Arg Cys Phe Ala Arg Glu Leu Ile Glu Phe Ile Tyr
                20                  25                  30
Phe Glu Leu Pro Lys Asp His Pro Gln Gly Pro Ala His Gly Val Arg
            35                  40                  45
Ile Thr Ile Glu Gly Lys Ile Asp Ser Arg Leu Gln Arg Ile Phe Ser
        50                  55                  60
Gln Arg Pro Val Leu Ile Glu Arg Asp Gln Gly Asn Thr Thr Val Ser
65                  70                  75                  80
Ile Tyr Cys Ile Cys Asn His Pro Gly Leu His Glu Ser Leu Cys Cys
                85                  90                  95
Leu Met Cys Thr Glu Phe Asn Lys Asn
            100                 105
```

<210> SEQ ID NO 30
<211> LENGTH: 131
<212> TYPE: PRT
<213> ORGANISM: Adenovirus Serotype 35

<400> SEQUENCE: 30

Met Lys Ala Phe Ala Val Leu Cys Val Leu Ser Leu Ile Lys Thr Glu

```
1               5                   10                  15
Leu Arg Leu Ser Tyr Gly Leu Pro Leu Gln Pro Gly Phe Tyr Asn
                20                  25                  30

Gln Lys Asn Lys Thr Phe Pro Val Val Gln Asp Ser Val Asn Phe Thr
                35                  40                  45

Phe Pro Thr His Lys Leu Glu Ala Gln Arg Leu His Arg Phe Ser Arg
    50                  55                  60

Ser Ile Phe Pro Thr Asn Thr Thr Phe Lys Thr Gly Gly Glu Leu His
65                  70                  75                  80

Gly Leu Pro Thr Glu Asn Pro Trp Val Glu Ala Gly Leu Val Val Leu
                85                  90                  95

Gly Ile Leu Ala Gly Gly Leu Val Ile Ile Leu Cys Tyr Leu Tyr Thr
                100                 105                 110

Pro Cys Phe Thr Phe Leu Val Val Leu Trp Tyr Trp Phe Lys Lys Trp
                115                 120                 125

Gly Pro Tyr
    130
```

<210> SEQ ID NO 31
<211> LENGTH: 166
<212> TYPE: PRT
<213> ORGANISM: Adenovirus Serotype 35

<400> SEQUENCE: 31

```
Met Gly Pro Ile Leu Val Leu Val Leu Leu Ser Leu Leu Glu Pro
1               5                   10                  15

Gly Ser Ala Asn Tyr Asp Pro Cys Leu Asp Phe Asp Pro Glu Asn Cys
                20                  25                  30

Thr Leu Thr Phe Ala Pro Asp Thr Ser Arg Ile Cys Gly Val Leu Ile
                35                  40                  45

Lys Cys Gly Trp Glu Cys Arg Ser Val Glu Ile Thr His Asn Asn Lys
    50                  55                  60

Thr Trp Asn Asn Thr Leu Ser Thr Thr Trp Glu Pro Gly Val Pro Glu
65                  70                  75                  80

Trp Tyr Thr Val Ser Val Arg Gly Pro Asp Gly Ser Ile Arg Ile Ser
                85                  90                  95

Asn Asn Thr Phe Ile Phe Ser Glu Met Cys Asp Leu Ala Met Phe Met
                100                 105                 110

Ser Lys Gln Tyr Ser Leu Trp Pro Pro Ser Lys Asp Asn Ile Val Thr
                115                 120                 125

Phe Ser Ile Ala Tyr Cys Leu Cys Ala Cys Leu Leu Thr Ala Leu Leu
                130                 135                 140

Cys Val Cys Ile His Leu Leu Val Thr Thr Arg Ile Lys Asn Ala Asn
145                 150                 155                 160

Asn Lys Glu Lys Met Pro
                165
```

<210> SEQ ID NO 32
<211> LENGTH: 181
<212> TYPE: PRT
<213> ORGANISM: Adenovirus Serotype 35

<400> SEQUENCE: 32

```
Met Ala Ser Leu Thr Ser Leu Ile Phe Val Ser Ile Val Thr Ala Ala
1               5                   10                  15

His Gly Gln Thr Val Val Ser Ile Pro Leu Gly His Asn Tyr Thr Leu
```

```
            20                  25                  30
Ile Gly Pro Pro Ile Thr Ser Glu Val Ile Trp Thr Lys Leu Gly Ser
            35                  40                  45

Val Asp Tyr Phe Asp Ile Ile Cys Asn Lys Thr Lys Pro Ile Ile Val
 50                  55                  60

Thr Cys Asn Ile Gln Asn Leu Thr Leu Ile Asn Val Ser Lys Val Tyr
 65                  70                  75                  80

Ser Gly Tyr Tyr Tyr Gly Tyr Asp Arg Tyr Ser Ser Gln Tyr Arg Asn
                     85                  90                  95

Tyr Leu Val Arg Val Thr Gln Leu Lys Thr Thr Lys Met Pro Asn Met
                 100                 105                 110

Ala Lys Ile Arg Ser Asp Asp Asn Ser Leu Glu Thr Phe Thr Ser Pro
             115                 120                 125

Thr Thr Pro Asp Glu Lys Asn Ile Pro Asp Ser Met Ile Ala Ile Val
         130                 135                 140

Ala Ala Val Ala Val Met Ala Leu Ile Ile Ile Cys Met Leu Leu
145                 150                 155                 160

Tyr Ala Cys Arg Tyr Lys Lys Phe His Pro Lys Lys Gln Asp Leu Leu
                 165                 170                 175

Leu Arg Leu Asn Ile
             180

<210> SEQ ID NO 33
<211> LENGTH: 187
<212> TYPE: PRT
<213> ORGANISM: Adenovirus Serotype 35

<400> SEQUENCE: 33

Met Val Ser Thr Thr Thr Phe Leu Met Leu Thr Ser Leu Ala Thr Leu
  1               5                  10                  15

Thr Ser Ala Arg Ser His Leu Thr Val Thr Ile Gly Ser Asn Cys Thr
                 20                  25                  30

Leu Lys Gly Pro Gln Gly Gly His Val Phe Trp Trp Arg Ile Tyr Asp
             35                  40                  45

Asn Gly Trp Phe Thr Lys Pro Cys Asp Gln Pro Gly Arg Phe Phe Cys
 50                  55                  60

Asn Gly Arg Asp Leu Thr Ile Ile Asn Val Thr Ala Asn Asp Lys Gly
 65                  70                  75                  80

Phe Tyr Tyr Gly Thr Asp Tyr Lys Ser Ser Leu Asp Tyr Asn Ile Ile
                 85                  90                  95

Val Leu Pro Ser Thr Thr Pro Pro Arg Thr Thr Thr Phe Ser Ser
                 100                 105                 110

Ser Ser Val Ala Asn Asn Thr Ile Ser Asn Pro Thr Phe Ala Ala Leu
             115                 120                 125

Leu Lys Arg Thr Val Asn Asn Ser Thr Thr Ser His Thr Thr Ile Ser
         130                 135                 140

Thr Ser Thr Ile Ser Ile Ile Ala Ala Val Thr Ile Gly Ile Ser Ile
145                 150                 155                 160

Leu Val Phe Thr Ile Thr Tyr Tyr Ala Cys Cys Tyr Arg Lys Asp Lys
                 165                 170                 175

His Lys Gly Asp Pro Leu Leu Arg Phe Asp Ile
             180                 185

<210> SEQ ID NO 34
<211> LENGTH: 134
```

```
<212> TYPE: PRT
<213> ORGANISM: Adenovirus Serotype 35

<400> SEQUENCE: 34

Met Gln Ala Ile Leu Pro Ile Phe Leu Leu Leu Leu Pro Tyr Ala
1               5                   10                  15

Val Ser Thr Pro Ala Ala Tyr Ser Thr Pro Pro Glu His Leu Arg Lys
            20                  25                  30

Cys Lys Phe Gln Gln Pro Trp Ser Phe Leu Ala Cys Tyr Arg Glu Lys
            35                  40                      45

Ser Glu Ile Pro Pro Asn Leu Ile Met Ile Ala Gly Ile Ile Asn Ile
    50                  55                  60

Ile Cys Cys Thr Ile Ile Ser Phe Leu Ile Tyr Pro Leu Phe Asp Phe
65                  70                  75                  80

Gly Trp Asn Ala Pro Asn Ala His Asp His Pro Gln Asp Pro Glu Glu
                85                  90                  95

His Ile Pro Pro Gln Asn Met Gln His Pro Ile Ala Leu Ile Asp Tyr
            100                 105                 110

Glu Ser Glu Pro Gln Pro Pro Leu Leu Pro Ala Ile Ser Tyr Phe Asn
            115                 120                 125

Leu Thr Gly Gly Asp Asp
        130

<210> SEQ ID NO 35
<211> LENGTH: 135
<212> TYPE: PRT
<213> ORGANISM: Adenovirus Serotype 35

<400> SEQUENCE: 35

Met Thr Glu Thr Leu Thr Thr Ser Asn Ser Ala Glu Asp Leu Leu Asp
1               5                   10                  15

Met Asp Gly Arg Val Ser Glu Gln Arg Leu Ala Gln Leu Arg Ile Arg
            20                  25                  30

Gln Gln Gln Glu Arg Val Ala Lys Glu Leu Arg Asp Val Ile Gln Ile
            35                  40                  45

His Gln Cys Lys Lys Gly Ile Phe Cys Leu Val Lys Gln Ala Lys Ile
    50                  55                  60

Ser Tyr Glu Ile Thr Ala Thr Asp His Arg Leu Ser Tyr Glu Leu Gly
65                  70                  75                  80

Pro Gln Arg Gln Lys Phe Thr Cys Met Val Gly Ile Asn Pro Ile Val
            85                  90                  95

Ile Thr Gln Gln Ser Gly Asp Thr Lys Gly Cys Ile His Cys Ser Cys
            100                 105                 110

Asp Ser Ile Glu Cys Thr Tyr Thr Leu Leu Lys Thr Leu Cys Gly Leu
            115                 120                 125

Arg Asp Leu Leu Pro Met Asn
        130             135

<210> SEQ ID NO 36
<211> LENGTH: 2832
<212> TYPE: DNA
<213> ORGANISM: Adenovirus Serotype 35

<400> SEQUENCE: 36
atgagagatt tgcgatttct gcctcaggaa ataatctctg ctgagactgg aaatgaaata      60
ttggagcttg tggtgcacgc cctgatggga gacgatccgg agccacctgt gcagcttttt     120
```

-continued

```
gagcctccta cgcttcagga actgtatgat ttagaggtag agggatcgga ggattctaat      180
gaggaagctg tgaatggctt ttttaccgat tctatgcttt tagctgctaa tgaaggatta      240
gaattagatc cgcctttgga cactttcaat actccagggg tgattgtgga aagcggtaca      300
ggtgtaagaa aattacctga tttgagttcc gtggactgtg atttgcactg ctatgaagac      360
gggtttcctc cgagtgatga ggaggaccat gaaaaggagc agtccatgca gactgcagcg      420
ggtgagggag tgaaggctgc caatgttggt tttcagttgg attgcccgga gcttcctgga      480
catggctgta agtcttgtga atttcacagg aaaaatactg gagtaaagga actgttatgt      540
tcgctttgtt atatgagaac gcactgccac tttatttaca gtaagtgtgt ttaagttaaa      600
atttaaagga atatgctgtt tttcacatgt atattgagtg tgagttttgt gcttcttatt      660
ataggtcctg tgtctgatgc tgatgaatca ccatctcctg attctactac ctcacctcct      720
gatattcaag cacctgttcc tgtggacgtg cgcaagccca ttcctgtgaa gcttaagcct      780
gggaaacgtc cagcagtgga gaaacttgag gacttgttac agggtgggga cggacctttg      840
gacttgagta cacggaaacg tccaagacaa taagtgttcc atatccgtgt ttacttaagg      900
tgacgtcaat atttgtgtga gagtgcaatg taataaaaat atgttaactg ttcactggtt      960
tttattgctt tttgggcggg gactcaggta tataagtaga agcagacctg tgtggttagc     1020
tcataggagc tggctttcat ccatggaggt ttgggccatt ttggaagacc ttaggaagac     1080
taggcaactg ttagagagcg cttcggacgg agtctccggt ttttggagat tctggttcgc     1140
tagtgaatta gctagggtag ttttttagga taaaacaggac tataaacaag aatttgaaaa     1200
gttgttggta gattgcccag gactttttga agctcttaat ttgggccatc aggttcactt     1260
taaagaaaaa gttttatcag ttttagactt ttcaaccccca ggtagaactg ctgctgctgt     1320
ggcttttctt acttttatat tagataaatg gatcccgcag actcatttca gcagggggata     1380 cgttttggat ttcatagcca cagcattgtg gagaacatgg aaggttcgca agatgaggac     1440
aatcttaggt tactgccag tgcagccttt gggtgtagcg gaatcctga ggcatccacc     1500 ggtcatgcca gcggttctgg aggaggaaca gcaagaggac aacccgagag ccggcctgga     1560
ccctccagtg gaggaggcgg agtagctgac ttgtctcctg aactgcaacg ggtgcttact     1620
ggatctacgt ccactggacg ggatagggc gttaagaggg agagggcatc cagtggtact     1680
gatgctagat ctgagttggc tttaagttta atgagtcgca gacgtcctga aaccatttgg     1740
tggcatgagg ttcagaaaga gggaagggat gaagtttctg tattgcagga gaaatattca     1800
ctggaacagg tgaaaacatg ttggttggag ccagaggatg attgggaggt ggccattaaa     1860
aattatgcca agatagcttt gaggcctgat aaacagtata agatcagtag acggattaat     1920
atccggaatg cttgttacat atctggaaat ggggctgagg tggtaataga tactcaagac     1980
aagacagtta ttagatgctg catgatggat atgtggcctg gagtagtcgg tatggaagca     2040
gtcacttttg taaatgttaa gtttagggga gatggttata atggaatagt gtttatggcc     2100
aataccaaac ttatattgca tggttgtagc ttttttggtt tcaacaatac ctgtgtagat     2160
gcctggggac aggttagtgt acggggtgt agtttctatg cgtgttggat tgccacagct     2220
ggcagaacca agagtcaatt gtctctgaag aaatgcatat tccaaagatg taacctgggc     2280
attctgaatg aaggcgaagc aagggtccgt cactgcgctt ctacagatac tggatgtttt     2340 atttaatta agggaaatgc cagcgtaaag cataacatga tttgtggtgc ttccgatgag     2400
aggccttatc aaatgctcac ttgtgctggt gggcattgta atatgctggc tactgtgcat     2460
attgtttccc atcaacgcaa aaaatggcct gttttttgatc acaatgtgtt gaccaagtgc     2520
```

```
accatgcatg caggtgggcg tagaggaatg tttatgcctt accagtgtaa catgaatcat    2580
gtgaaagtgt tgttggaacc agatgccttt tccagaatga gcctaacagg aatctttgac    2640
atgaacacgc aaatctggaa gatcctgagg tatgatgata cgagatcgag ggtgcgcgca    2700
tgcgaatgcg gaggcaagca tgccaggttc cagccggtgt gtgtagatgt gaccgaagat    2760
ctcagaccgg atcatttggt tattgcccgc actggagcag agttcggatc cagtggagaa    2820
gaaactgact aa                                                        2832
```

<210> SEQ ID NO 37
<211> LENGTH: 193
<212> TYPE: PRT
<213> ORGANISM: Adenovirus Serotype 35

<400> SEQUENCE: 37

```
Met Arg Asp Leu Arg Phe Leu Pro Gln Glu Ile Ile Ser Ala Glu Thr
1               5                   10                  15

Gly Asn Glu Ile Leu Glu Leu Val Val His Ala Leu Met Gly Asp Asp
            20                  25                  30

Pro Glu Pro Pro Val Gln Leu Phe Glu Pro Pro Thr Leu Gln Glu Leu
        35                  40                  45

Tyr Asp Leu Glu Val Glu Gly Ser Glu Asp Ser Asn Glu Glu Ala Val
    50                  55                  60

Asn Gly Phe Phe Thr Asp Ser Met Leu Leu Ala Ala Asn Glu Gly Leu
65                  70                  75                  80

Glu Leu Asp Pro Pro Leu Asp Thr Phe Asn Thr Pro Gly Val Ile Val
                85                  90                  95

Glu Ser Gly Thr Gly Val Arg Lys Leu Pro Asp Leu Ser Ser Val Asp
            100                 105                 110

Cys Asp Leu His Cys Tyr Glu Asp Gly Phe Pro Pro Ser Asp Glu Glu
        115                 120                 125

Asp His Glu Lys Glu Gln Ser Met Gln Thr Ala Ala Gly Glu Gly Val
    130                 135                 140

Lys Ala Ala Asn Val Gly Phe Gln Leu Asp Cys Pro Glu Leu Pro Gly
145                 150                 155                 160

His Gly Cys Lys Ser Cys Glu Phe His Arg Lys Asn Thr Gly Val Lys
                165                 170                 175

Glu Leu Leu Cys Ser Leu Cys Tyr Met Arg Thr His Cys His Phe Ile
            180                 185                 190

Tyr
```

<210> SEQ ID NO 38
<211> LENGTH: 180
<212> TYPE: PRT
<213> ORGANISM: Adenovirus Serotype 35

<400> SEQUENCE: 38

```
Met Glu Val Trp Ala Ile Leu Glu Asp Leu Arg Lys Thr Arg Gln Leu
1               5                   10                  15

Leu Glu Ser Ala Ser Asp Gly Val Ser Gly Phe Trp Arg Phe Trp Phe
            20                  25                  30

Ala Ser Glu Leu Ala Arg Val Val Phe Arg Ile Lys Gln Asp Tyr Lys
        35                  40                  45

Gln Glu Phe Glu Lys Leu Leu Val Asp Cys Pro Gly Leu Phe Glu Ala
    50                  55                  60
```

```
Leu Asn Leu Gly His Gln Val His Phe Lys Glu Lys Val Leu Ser Val
 65                  70                  75                  80

Leu Asp Phe Ser Thr Pro Gly Arg Thr Ala Ala Val Ala Phe Leu
             85                  90                  95

Thr Phe Ile Leu Asp Lys Trp Ile Pro Gln Thr His Phe Ser Arg Gly
            100                 105                 110

Tyr Val Leu Asp Phe Ile Ala Thr Ala Leu Trp Arg Thr Trp Lys Val
            115                 120                 125

Arg Lys Met Arg Thr Ile Leu Gly Tyr Trp Pro Val Gln Pro Leu Gly
130                 135                 140

Val Ala Gly Ile Leu Arg His Pro Pro Val Met Pro Ala Val Leu Glu
145                 150                 155                 160

Glu Glu Gln Gln Glu Asp Asn Pro Arg Ala Gly Leu Asp Pro Val
            165                 170                 175

Glu Glu Ala Glu
        180

<210> SEQ ID NO 39
<211> LENGTH: 494
<212> TYPE: PRT
<213> ORGANISM: Adenovirus Serotype 35

<400> SEQUENCE: 39

Met Asp Pro Ala Asp Ser Phe Gln Gln Gly Ile Arg Phe Gly Phe His
  1               5                  10                  15

Ser His Ser Ile Val Glu Asn Met Glu Gly Ser Gln Asp Glu Asp Asn
             20                  25                  30

Leu Arg Leu Leu Ala Ser Ala Ala Phe Gly Cys Ser Gly Asn Pro Glu
         35                  40                  45

Ala Ser Thr Gly His Ala Ser Gly Ser Gly Gly Gly Thr Ala Arg Gly
 50                  55                  60

Gln Pro Glu Ser Arg Pro Gly Pro Ser Ser Gly Gly Gly Gly Val Ala
 65                  70                  75                  80

Asp Leu Ser Pro Glu Leu Gln Arg Val Leu Thr Gly Ser Thr Ser Thr
             85                  90                  95

Gly Arg Asp Arg Gly Val Lys Arg Glu Arg Ala Ser Ser Gly Thr Asp
            100                 105                 110

Ala Arg Ser Glu Leu Ala Leu Ser Leu Met Ser Arg Arg Arg Pro Glu
            115                 120                 125

Thr Ile Trp Trp His Glu Val Gln Lys Glu Gly Arg Asp Glu Val Ser
130                 135                 140

Val Leu Gln Glu Lys Tyr Ser Leu Glu Gln Val Lys Thr Cys Trp Leu
145                 150                 155                 160

Glu Pro Glu Asp Asp Trp Glu Val Ala Ile Lys Asn Tyr Ala Lys Ile
            165                 170                 175

Ala Leu Arg Pro Asp Lys Gln Tyr Lys Ile Ser Arg Arg Ile Asn Ile
            180                 185                 190

Arg Asn Ala Cys Tyr Ile Ser Gly Asn Gly Ala Glu Val Val Ile Asp
        195                 200                 205

Thr Gln Asp Lys Thr Val Ile Arg Cys Cys Met Met Asp Met Trp Pro
210                 215                 220

Gly Val Val Gly Met Glu Ala Val Thr Phe Val Asn Val Lys Phe Arg
225                 230                 235                 240

Gly Asp Gly Tyr Asn Gly Ile Val Phe Met Ala Asn Thr Lys Leu Ile
            245                 250                 255
```

Leu His Gly Cys Ser Phe Phe Gly Phe Asn Asn Thr Cys Val Asp Ala
            260                 265                 270

Trp Gly Gln Val Ser Val Arg Gly Cys Ser Phe Tyr Ala Cys Trp Ile
            275                 280                 285

Ala Thr Ala Gly Arg Thr Lys Ser Gln Leu Ser Leu Lys Lys Cys Ile
290                 295                 300

Phe Gln Arg Cys Asn Leu Gly Ile Leu Asn Glu Gly Glu Ala Arg Val
305                 310                 315                 320

Arg His Cys Ala Ser Thr Asp Thr Gly Cys Phe Ile Leu Ile Lys Gly
                325                 330                 335

Asn Ala Ser Val Lys His Asn Met Ile Cys Gly Ala Ser Asp Glu Arg
                340                 345                 350

Pro Tyr Gln Met Leu Thr Cys Ala Gly Gly His Cys Asn Met Leu Ala
                355                 360                 365

Thr Val His Ile Val Ser His Gln Arg Lys Lys Trp Pro Val Phe Asp
            370                 375                 380

His Asn Val Leu Thr Lys Cys Thr Met His Ala Gly Arg Arg Gly
385                 390                 395                 400

Met Phe Met Pro Tyr Gln Cys Asn Met Asn His Val Lys Val Leu Leu
                405                 410                 415

Glu Pro Asp Ala Phe Ser Arg Met Ser Leu Thr Gly Ile Phe Asp Met
            420                 425                 430

Asn Thr Gln Ile Trp Lys Ile Leu Arg Tyr Asp Asp Thr Arg Ser Arg
            435                 440                 445

Val Arg Ala Cys Glu Cys Gly Gly Lys His Ala Arg Phe Gln Pro Val
450                 455                 460

Cys Val Asp Val Thr Glu Asp Leu Arg Pro Asp His Leu Val Ile Ala
465                 470                 475                 480

Arg Thr Gly Ala Glu Phe Gly Ser Ser Gly Glu Glu Thr Asp
                485                 490

<210> SEQ ID NO 40
<211> LENGTH: 2341
<212> TYPE: DNA
<213> ORGANISM: Adenovirus Serotype 35

<400> SEQUENCE: 40
tcatctggaa gaagaacgat gggaatcata atccgaaaac ggtatcggac gattgtgtct     60
catcaaaccc acaagcagcc gctgtctgcg tcgctccgtg cgactgctgt ttatgggatc    120
agggtccaca gtttcctgaa gcatgatttt aatagccctt aacatcaact ttctggtgcg    180
atgcgcgcag caacgcattc tgatttcact caaatctttg cagtaggtac aacacattat    240
tacaatattg tttaataaac cataattaaa agcgctccag ccaaaactca tatctgatat    300
aatcgcccct gcatgaccat cataccaaag tttaatataa attaaatgac gttccctcaa    360
aaacacacta cccacataca tgatctcttt tggcatgtgc atattaacaa tctgtctgta    420
ccatggacaa cgttggttaa tcatgcaacc caatataacc ttccggaacc acactgccaa    480
caccgctccc ccagccatgc attgaagtga accctgctga ttacaatgac aatgaagaac    540
ccaattctct cgaccgtgaa tcacttgaga atgaaaaata tctatagtgg cacaacatag    600
acataaatgc atgcatcttc tcataatttt taactcctca ggatttagaa acatatccca    660
gggaatagga agctcttgca gaacagtaaa gctggcagaa caaggaagac cacgaacaca    720
acttacacta tgcatagtca tagtatcaca atctggcaac agcgggtggt cttcagtcat    780

```
agaagctcgg gtttcatttt cctcacaacg tggtaactgg gctctggtgt aagggtgatg    840
tctggcgcat gatgtcgagc gtgcgcgcaa ccttgtcata atggagttgc ttcctgacat    900
tctcgtattt tgtatagcaa aacgcggccc tggcagaaca cactcttcct cgccttctat    960
cctgccgctt agcgtgttcc gtgtgatagt tcaagtacag ccacactctt aagttggtca   1020
aaagaatgct ggcttcagtt gtaatcaaaa ctccatcgca tctaattgtt ctgaggaaat   1080
catccacggt agcatatgca aatcccaacc aagcaatgca actggattgc gtttcaagca   1140
ggagaggaga gggaagagac ggaagaacca tgttaatttt tattccaaac gatctcgcag   1200
tacttcaaat tgtagatcgc gcagatggca tctctcgccc ccactgtgtt ggtgaaaaag   1260
cacagctaaa tcaaaagaaa tgcgattttc aaggtgctca acggtggctt ccaacaaagc   1320
ctccacgcgc acatccaaga acaaaagaat accaaaagaa ggagcatttt ctaactcctc   1380
aatcatcata ttacattcct gcaccattcc cagataattt tcagctttcc agccttgaat   1440
tattcgtgtc agttcttgtg gtaaatccaa tccacacatt acaaacaggt cccggagggc   1500
gccctccacc accattctta aacacaccct cataatgaca aaatatcttg ctcctgtgtc   1560
acctgtagcg aattgagaat ggcaacatca attgacatgc ccttggctct aagttcttct   1620
ttaagttcta gttgtaaaaa ctctctcata ttatcaccaa actgcttagc cagaagcccc   1680
ccgggaacaa gagcagggga cgctacagtg cagtacaagc gcagacctcc ccaattggct   1740
ccagcaaaaa caagattgga ataagcatat tgggaaccac cagtaatatc atcgaagttg   1800
ctggaaatat aatcaggcag agtttcttgt agaaattgaa taaagaaaa atttgccaaa   1860
aaaacattca aaacctctgg gatgcaaatg caataggtta ccgcgctgcg ctccaacatt   1920
gttagttttg aattagtctg caaaaataaa aaaaaacaa gcgtcatatc atagtagcct   1980
gacgaacagg tggataaatc agtctttcca tcacaagaca agccacaggg tctccagctc   2040
gaccctcgta aaacctgtca tcgtgattaa acaacagcac cgaaagttcc tcgcggtgac   2100
cagcatgaat aagtcttgat gaagcataca atccagacat gttagcatca gttaaggaga   2160
aaaaacagcc aacatagcct ttgggtataa ttatgcttaa tcgtaagtat agcaaagcca   2220
ccctcgcgg atacaaagta aaaggcacag gagaataaaa aatataatta tttctctgct   2280
gctgtttagg caacgtcgcc cccggtccct ctaaatacac atacaaagcc tcatcagcca   2340
t                                                                  2341
```

<210> SEQ ID NO 41
<211> LENGTH: 897
<212> TYPE: DNA
<213> ORGANISM: Adenovirus Serotype 35

<400> SEQUENCE: 41

```
tctggaagaa gaacgatggg aatcataatc cgaaacggt atcggacgat tgtgtctcat      60
caaacccaca agcagccgct gtctgcgtcg ctccgtgcga ctgctgttta tgggatcagg    120
gtccacagtt tcctgaagca tgattttaat agcccttaac atcaactttc tggtgcgatg    180
cgcgcagcaa cgcattctga tttcactcaa atctttgcag taggtacaac acattattac    240
aatattgttt aataaaccat aattaaaagc gctccagcca aaactcatat ctgatataat    300
cgccctgca tgaccatcat accaaagttt aatataaatt aaatgacgtt ccctcaaaaa    360
cacactaccc acatacatga tctcttttgg catgtgcata ttaacaatct gtctgtacca    420
tggacaacgt tggttaatca tgcaacccaa tataaccttc cggaaccaca ctgccaacac    480
```

-continued

```
cgctccccca gccatgcatt gaagtgaacc ctgctgatta caatgacaat gaagaaccca    540
attctctcga ccgtgaatca cttgagaatg aaaaatatct atagtggcac aacatagaca    600
taaatgcatg catcttctca taattttttaa ctcctcagga tttagaaaca tatcccaggg    660
aataggaagc tcttgcagaa cagtaaagct ggcagaacaa ggaagaccac gaacacaact    720
tacactatgc atagtcatag tatcacaatc tggcaacagc gggtggtctt cagtcataga    780
agctcgggtt tcattttcct cacaacgtgg taactgggct ctggtgtaag ggtgatgtct    840
ggcgcatgat gtcgagcgtg cgcgcaacct tgtcataatg gagttgcttc ctgacat       897
```

<210> SEQ ID NO 42
<211> LENGTH: 125
<212> TYPE: PRT
<213> ORGANISM: Adenovirus Serotype 35

<400> SEQUENCE: 42

Met Ala Asp Glu Ala Leu Tyr Val Tyr Leu Glu Gly Pro Gly Ala Thr
1               5                   10                  15

Leu Pro Lys Gln Gln Arg Asn Asn Tyr Ile Phe Tyr Ser Pro Val
            20                  25                  30

Pro Phe Thr Leu Tyr Pro Arg Gly Val Ala Leu Leu Tyr Leu Arg Leu
        35                  40                  45

Ser Ile Ile Pro Lys Gly Tyr Val Gly Cys Phe Phe Ser Leu Thr
    50                  55                  60

Asp Ala Asn Met Ser Gly Leu Tyr Ala Ser Ser Arg Leu Ile His Ala
65                  70                  75                  80

Gly His Arg Glu Glu Leu Ser Val Leu Leu Phe Asn His Asp Asp Arg
                85                  90                  95

Phe Tyr Glu Gly Arg Ala Gly Asp Pro Val Ala Cys Leu Val Met Glu
            100                 105                 110

Arg Leu Ile Tyr Pro Pro Val Arg Gln Ala Thr Met Ile
        115                 120                 125

<210> SEQ ID NO 43
<211> LENGTH: 145
<212> TYPE: PRT
<213> ORGANISM: Adenovirus Serotype 35

<400> SEQUENCE: 43

Met Thr Leu Val Phe Phe Leu Phe Leu Gln Thr Asn Ser Lys Leu Thr
1               5                   10                  15

Met Leu Glu Arg Ser Ala Val Thr Tyr Cys Ile Cys Ile Pro Glu Val
            20                  25                  30

Leu Asn Val Phe Leu Ala Asn Phe Ser Phe Ile Gln Phe Leu Gln Glu
        35                  40                  45

Thr Leu Pro Asp Tyr Ile Ser Ser Asn Phe Asp Asp Ile Thr Gly Gly
    50                  55                  60

Ser Gln Tyr Ala Tyr Ser Asn Leu Val Phe Ala Gly Ala Asn Trp Gly
65                  70                  75                  80

Gly Leu Arg Leu Tyr Cys Thr Val Ala Ser Pro Ala Leu Val Pro Gly
                85                  90                  95

Gly Leu Leu Ala Lys Gln Phe Gly Asp Asn Met Arg Glu Phe Leu Gln
            100                 105                 110

Leu Glu Leu Lys Glu Glu Leu Arg Ala Lys Gly Met Ser Ile Asp Val
        115                 120                 125

Ala Ile Leu Asn Ser Leu Gln Val Thr Gln Glu Gln Asp Ile Leu Ser

Leu
145

<210> SEQ ID NO 44
<211> LENGTH: 117
<212> TYPE: PRT
<213> ORGANISM: Adenovirus Serotype 35

<400> SEQUENCE: 44

Met Arg Val Cys Leu Arg Met Val Val Glu Gly Ala Leu Arg Asp Leu
1               5                   10                  15

Phe Val Met Cys Gly Leu Asp Leu Pro Gln Glu Leu Thr Arg Ile Ile
            20                  25                  30

Gln Gly Trp Lys Ala Glu Asn Tyr Leu Gly Met Val Gln Glu Cys Asn
        35                  40                  45

Met Met Ile Glu Glu Leu Glu Asn Ala Pro Ser Phe Gly Ile Leu Leu
    50                  55                  60

Phe Leu Asp Val Arg Val Glu Ala Leu Leu Glu Ala Thr Val Glu His
65                  70                  75                  80

Leu Glu Asn Arg Ile Ser Phe Asp Leu Ala Val Leu Phe His Gln His
                85                  90                  95

Ser Gly Gly Glu Arg Cys His Leu Arg Asp Leu Gln Phe Glu Val Leu
            100                 105                 110

Arg Asp Arg Leu Glu
        115

<210> SEQ ID NO 45
<211> LENGTH: 121
<212> TYPE: PRT
<213> ORGANISM: Adenovirus Serotype 35

<400> SEQUENCE: 45

Met Val Leu Pro Ser Leu Pro Ser Pro Leu Leu Leu Glu Thr Gln Ser
1               5                   10                  15

Ser Cys Ile Ala Trp Leu Gly Phe Ala Tyr Ala Thr Val Asp Asp Phe
            20                  25                  30

Leu Arg Thr Ile Arg Cys Asp Gly Val Leu Ile Thr Thr Glu Ala Ser
        35                  40                  45

Ile Leu Leu Thr Asn Leu Arg Val Trp Leu Tyr Leu Asn Tyr His Thr
    50                  55                  60

Glu His Ala Lys Arg Gln Asp Arg Arg Arg Arg Val Cys Ser Ala
65                  70                  75                  80

Arg Ala Ala Phe Cys Tyr Thr Lys Tyr Glu Asn Val Arg Lys Gln Leu
                85                  90                  95

His Tyr Asp Lys Val Ala Arg Thr Leu Asp Ile Met Arg Gln Thr Ser
            100                 105                 110

Pro Leu His Gln Ser Pro Val Thr Thr
        115                 120

<210> SEQ ID NO 46
<211> LENGTH: 299
<212> TYPE: PRT
<213> ORGANISM: Adenovirus Serotype 35

<400> SEQUENCE: 46

Met Ser Gly Ser Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
                20                  25                  30

Glu Glu Asn Glu Thr Arg Ala Ser Met Thr Glu Asp His Pro Leu Leu
            35                  40                  45

Pro Asp Cys Asp Thr Met Thr Met His Ser Val Ser Cys Val Arg Gly
 50                  55                  60

Leu Pro Cys Ser Ala Ser Phe Thr Val Leu Gln Glu Leu Pro Ile Pro
 65                  70                  75                  80

Trp Asp Met Phe Leu Asn Pro Glu Glu Leu Lys Ile Met Arg Arg Cys
                85                  90                  95

Met His Leu Cys Leu Cys Cys Ala Thr Ile Asp Ile Phe His Ser Gln
               100                 105                 110

Val Ile His Gly Arg Glu Asn Trp Val Leu His Cys His Cys Asn Gln
               115                 120                 125

Gln Gly Ser Leu Gln Cys Met Ala Gly Gly Ala Val Leu Ala Val Trp
130                 135                 140

Phe Arg Lys Val Ile Leu Gly Cys Met Ile Asn Gln Arg Cys Pro Trp
145                 150                 155                 160

Tyr Arg Gln Ile Val Asn Met His Met Pro Lys Glu Ile Met Tyr Val
                165                 170                 175

Gly Ser Val Phe Leu Arg Glu Arg His Leu Ile Tyr Ile Lys Leu Trp
                180                 185                 190

Tyr Asp Gly His Ala Gly Ala Ile Ile Ser Asp Met Ser Phe Gly Trp
                195                 200                 205

Ser Ala Phe Asn Tyr Gly Leu Leu Asn Asn Ile Val Ile Met Cys Cys
        210                 215                 220

Thr Tyr Cys Lys Asp Leu Ser Glu Ile Arg Met Arg Cys Cys Ala His
225                 230                 235                 240

Arg Thr Arg Lys Leu Met Leu Arg Ala Ile Lys Ile Met Leu Gln Glu
                245                 250                 255

Thr Val Asp Pro Asp Pro Ile Asn Ser Ser Arg Thr Glu Arg Arg Arg
                260                 265                 270

Gln Arg Leu Leu Val Gly Leu Met Arg His Asn Arg Pro Ile Pro Phe
        275                 280                 285

Ser Asp Tyr Asp Ser His Arg Ser Ser Ser Arg
        290                 295

<210> SEQ ID NO 47
<211> LENGTH: 2055
<212> TYPE: DNA
<213> ORGANISM: Artificial Sequence
<220> FEATURE:
<223> OTHER INFORMATION: Mos1ENV

<400> SEQUENCE: 47
atgcgggtga ccggcatccg aagaactac cagcacctgt ggcggtgggg caccatgctg      60
ctgggcatcc tgatgatttg ctctgccgcc ggaaagctgt gggtgaccgt gtactacggc     120
gtgcccgtgt ggaaagaggc caccaccacc ctgttctgcg ccagcgacgc caaggcctac     180
gacaccgagg tgcacaacgt gtgggccacc cacgcctgcg tgcccaccga ccccaacccc     240
caggaagtgg tcctggaaaa cgtgaccgag aacttcaaca tgtggaagaa caacatggtg     300
gagcagatgc acgaggacat catcagcctg tgggaccaga gcctgaagcc ctgcgtgaag     360
ctgacccccc tgtgcgtgac cctgaactgc accgacgacg tgcggaacgt gaccaacaac     420

-continued

```
gccaccaaca ccaacagcag ctggggcgag cctatggaaa agggcgagat caagaactgc      480
agcttcaaca tcaccacctc catccggaac aaggtgcaga agcagtacgc cctgttctac      540
aagctggacg tggtgcccat cgacaacgac agcaacaaca ccaactaccg gctgatcagc      600
tgcaacacca gcgtgatcac ccaggcctgc cccaaggtgt ccttcgagcc catccccatc      660
cactactgcg cccctgccgg cttcgccatc ctgaagtgca cgacaagaa gttcaacggc       720 accggcccct gcaccaacgt gagcaccgtg cagtgcaccc acggcatccg gcccgtggtg      780
tccacccagc tgctgctgaa cggcagcctg gccgaggaag aggtggtgat cagaagcgag      840
aatttcacca caatgccaa gaccatcatg gtgcagctga acgtgagcgt ggagatcaac       900
tgcacccggc ccaacaacaa cacccggaag agcatccaca tcggccctgg cagggccttc      960
tacacagccg cgacatcat cggcgacatc cggcaggccc actgcaacat cagccgggcc     1020
aactggaaca cacccctgcg gcagatcgtg gagaagctgg gcaagcagtt cggcaacaac     1080
aagaccatcg tgttcaacca cagcagcggc ggagaccccg agatcgtgat gcacagcttc     1140
aactgtggcg gcgagttctt ctactgcaac agcaccaagc tgttcaacag cacctggacc     1200
tggaacaact ccacctggaa taacaccaag cggagcaacg acaccgaaga gcacatcacc     1260
ctgccctgcc ggatcaagca gattatcaat atgtggcagg aggtcggcaa ggccatgtac     1320
gcccctccca tccggggcca gatccggtgc agcagcaaca tcaccggcct gctgctgacc     1380
cgggacggcg gcaacgatac cagcggcacc gagatcttcc ggcctggcgg cggagatatg     1440
cgggacaact ggcggagcga gctgtacaag tacaaggtgg tgaagatcga gcccctgggc     1500
gtggctccca ccaaggccaa gcggcgggtg gtgcagagcg agaagagcgc cgtgggcatc     1560
ggcgccgtgt ttctgggctt cctgggagcc gccggaagca ccatgggagc cgccagcatg     1620
accctgaccg tgcaggcccg gctgctgctg tccggcatcg tgcagcagca gaacaacctg     1680
ctccgggcca tcgaggccca gcagcacctg ctgcagctga ccgtgtgggg catcaagcag     1740
ctgcaggcca gggtgctggc cgtggagaga tacctgaagg atcagcagct cctggggatc     1800
tggggctgca gcggcaagct gatctgcacc accaccgtgc cctggaacgc agctggtcc      1860 aacaagagcc tggacaagat ctggaacaat atgacctgga tggaatggga gcgcgagatc     1920
aacaattaca ccagcctgat ctacaccctg atcgaggaaa gccagaacca gcaggaaaag     1980
aacgagcagg aactgctgga actggacaag tgggccagcc tgtggaactg gttcgacatc     2040
agcaactggc tgtgg                                                      2055
```

<210> SEQ ID NO 48
<211> LENGTH: 685
<212> TYPE: PRT
<213> ORGANISM: Artificial Sequence
<220> FEATURE:
<223> OTHER INFORMATION: Mos1ENV

<400> SEQUENCE: 48

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro

```
                65                  70                  75                  80
        Gln Glu Val Val Leu Glu Asn Val Thr Glu Asn Phe Asn Met Trp Lys
                            85                  90                  95
        Asn Asn Met Val Glu Gln Met His Glu Asp Ile Ile Ser Leu Trp Asp
                        100                 105                 110
        Gln Ser Leu Lys Pro Cys Val Lys Leu Thr Pro Leu Cys Val Thr Leu
                    115                 120                 125
        Asn Cys Thr Asp Asp Val Arg Asn Val Thr Asn Ala Thr Asn Thr
        130                 135                 140
        Asn Ser Ser Trp Gly Glu Pro Met Glu Lys Gly Glu Ile Lys Asn Cys
        145                 150                 155                 160
        Ser Phe Asn Ile Thr Thr Ser Ile Arg Asn Lys Val Gln Lys Gln Tyr
                        165                 170                 175
        Ala Leu Phe Tyr Lys Leu Asp Val Val Pro Ile Asp Asn Asp Ser Asn
                    180                 185                 190
        Asn Thr Asn Tyr Arg Leu Ile Ser Cys Asn Thr Ser Val Ile Thr Gln
                    195                 200                 205
        Ala Cys Pro Lys Val Ser Phe Glu Pro Ile Pro Ile His Tyr Cys Ala
        210                 215                 220
        Pro Ala Gly Phe Ala Ile Leu Lys Cys Asn Asp Lys Lys Phe Asn Gly
        225                 230                 235                 240
        Thr Gly Pro Cys Thr Asn Val Ser Thr Val Gln Cys Thr His Gly Ile
                        245                 250                 255
        Arg Pro Val Val Ser Thr Gln Leu Leu Leu Asn Gly Ser Leu Ala Glu
                    260                 265                 270
        Glu Glu Val Val Ile Arg Ser Glu Asn Phe Thr Asn Asn Ala Lys Thr
                    275                 280                 285
        Ile Met Val Gln Leu Asn Val Ser Val Glu Ile Asn Cys Thr Arg Pro
                290                 295                 300
        Asn Asn Asn Thr Arg Lys Ser Ile His Ile Gly Pro Gly Arg Ala Phe
        305                 310                 315                 320
        Tyr Thr Ala Gly Asp Ile Ile Gly Asp Ile Arg Gln Ala His Cys Asn
                        325                 330                 335
        Ile Ser Arg Ala Asn Trp Asn Asn Thr Leu Arg Gln Ile Val Glu Lys
                    340                 345                 350
        Leu Gly Lys Gln Phe Gly Asn Asn Lys Thr Ile Val Phe Asn His Ser
                    355                 360                 365
        Ser Gly Gly Asp Pro Glu Ile Val Met His Ser Phe Asn Cys Gly Gly
                370                 375                 380
        Glu Phe Phe Tyr Cys Asn Ser Thr Lys Leu Phe Asn Ser Thr Trp Thr
        385                 390                 395                 400
        Trp Asn Asn Ser Thr Trp Asn Asn Thr Lys Arg Ser Asn Asp Thr Glu
                        405                 410                 415
        Glu His Ile Thr Leu Pro Cys Arg Ile Lys Gln Ile Ile Asn Met Trp
                    420                 425                 430
        Gln Glu Val Gly Lys Ala Met Tyr Ala Pro Pro Ile Arg Gly Gln Ile
                    435                 440                 445
        Arg Cys Ser Ser Asn Ile Thr Gly Leu Leu Leu Thr Arg Asp Gly Gly
                450                 455                 460
        Asn Asp Thr Ser Gly Thr Glu Ile Phe Arg Pro Gly Gly Gly Asp Met
        465                 470                 475                 480
        Arg Asp Asn Trp Arg Ser Glu Leu Tyr Lys Tyr Lys Val Val Lys Ile
                        485                 490                 495
```

```
Glu Pro Leu Gly Val Ala Pro Thr Lys Ala Lys Arg Val Val Gln
            500                 505                 510
Ser Glu Lys Ser Ala Val Gly Ile Gly Ala Val Phe Leu Gly Phe Leu
    515                 520                 525
Gly Ala Ala Gly Ser Thr Met Gly Ala Ala Ser Met Thr Leu Thr Val
    530                 535                 540
Gln Ala Arg Leu Leu Leu Ser Gly Ile Val Gln Gln Asn Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Ala Arg Val Leu Ala Val Glu Arg Tyr Leu
            580                 585                 590
Lys Asp Gln Gln Leu Leu Gly Ile Trp Gly Cys Ser Gly Lys Leu Ile
                595                 600                 605
Cys Thr Thr Thr Val Pro Trp Asn Ala Ser Trp Ser Asn Lys Ser Leu
610                 615                 620
Asp Lys Ile Trp Asn Asn Met Thr Trp Met Glu Trp Glu Arg Glu Ile
625                 630                 635                 640
Asn Asn Tyr Thr Ser Leu Ile Tyr Thr Leu Ile Glu Glu Ser Gln Asn
                645                 650                 655
Gln Gln Glu Lys Asn Glu Gln Glu Leu Leu Glu Leu Asp Lys Trp Ala
            660                 665                 670
Ser Leu Trp Asn Trp Phe Asp Ile Ser Asn Trp Leu Trp
            675                 680                 685

<210> SEQ ID NO 49
<211> LENGTH: 4050
<212> TYPE: DNA
<213> ORGANISM: Artificial Sequence
<220> FEATURE:
<223> OTHER INFORMATION: Mos1GagPol

<400> SEQUENCE: 49
atgggagcca gagccagcgt gctgtccgga ggggagctgg accgctggga gaagatcagg      60
ctgaggcctg gagggaagaa gaagtacagg ctgaagcaca tcgtgtgggc cagcagagag     120
ctggaacggt ttgccgtgaa ccctggcctg ctggaaacca gcgagggctg taggcagatt     180
ctgggacagc tgcagcccag cctgcagaca ggcagcgagg aactgcggag cctgtacaac     240
accgtggcca ccctgtactg cgtgcaccag cggatcgaga tcaaggacac caaagaagcc     300
ctggaaaaga tcgaggaaga gcagaacaag agcaagaaga agcccagca ggctgccgct      360
gacacaggca acagcagcca ggtgtcccag aactacccca tcgtgcagaa catccaggga     420
cagatggtgc accaggccat cagccctcgg accctgaacg cctgggtgaa ggtggtggag     480
gaaaaggcct tcagccctga ggtgatcccc atgttctctg ccctgagcga gggagccaca     540
ccccaggacc tgaacaccat gctgaacacc gtgggagggc accaggctgc catgcagatg     600
ctgaaagaga caatcaacga ggaagctgcc gagtgggaca gggtccaccc agtgcacgct     660
ggacctatcg ctcctggcca gatgagagag cccagaggca gcgatattgc tggcaccacc     720
tccacactgc aggaacagat cggctggatg accaacaacc ctcccatccc tgtgggagag     780
atctacaagc ggtggatcat tctgggactg aacaagatcg tgcggatgta cagccctgtg     840
agcatcctgg acatcaggca gggacccaaa gagcccttca ggactacgt ggaccggttc      900
tacaagaccc tgagagccga gcaggccagc caggacgtga gaactggat gaccgagaca      960
```

```
ctgctggtgc agaacgccaa ccctgactgc aagaccatcc tgaaagccct gggacctgct    1020
gccaccctgg aagagatgat gacagcctgc agggagtgg gaggacctgg ccacaaggcc     1080
agggtgctgg ccgaggccat gagccaggtg accaactctg ccaccatcat gatgcagaga   1140
ggcaacttcc ggaaccagag aaagaccgtg aagtgcttca actgtggcaa agagggacac   1200
attgccaaga actgcagggc tcccaggaag aaaggctgct ggaagtgcgg aaaagaaggc   1260
caccagatga aggactgcac cgagaggcag gccaacttcc tgggcaagat ctggcctagc   1320
aacaagggca ggcctggcaa cttcctgcag aacagacccg agcccaccgc tcctcccgag   1380
gaaagcttcc ggtttggcga ggaaaccacc accccctagcc agaagcagga acccatcgac   1440
aaagagatgt accctctggc cagcctgaag agcctgttcg gcaacgaccc cagcagccag   1500
atggctccca tcagcccaat cgagacagtg cctgtgaagc tgaagcctgg catggacgga   1560
cccagggtga agcagtggcc tctgaccgag gaaaagatca agccctgac agccatctgc    1620
gaggaaatgg aaaagagggg caagatcacc aagatcggac ccgagaaccc ctacaacacc   1680
cctgtgttcg ccatcaagaa gaaagacagc accaagtgga gaaactggt ggacttcaga    1740
gagctgaaca gcggacccca ggacttctgg gaggtgcagc tgggcatccc tcaccctgct   1800
ggcctgaaga aaagaaaag cgtgaccgtg ctggctgtgg gagatgccta cttcagcgtg    1860
cctctggacg agggcttccg gaagtacaca gccttcacca tccccagcac caacaacgag   1920
acacctggca tcagatacca gtacaacgtg ctgcctcagg gctggaaagg cagccctgcc   1980
atcttccagt gcagcatgac cagaatcctg gaacccttca gagccaagaa ccctgagatc   2040
gtgatctacc agtatatggc tgccctctac gtgggcagcg acctggaaat cggacagcac   2100
agagccaaaa tcgaagaact ccgcgagcac ctgctgaagt ggggattcac caccccctgac  2160
aagaagcacc agaaagagcc tccccttcctg tggatgggct acgagctgca ccctgacaag   2220
tggaccgtgc agcccatcca gctgccagag aaggactcct ggaccgtgaa cgacatccag   2280
aaactggtcg gcaagctgaa ctgggccagc cagatctacc ctggcatcaa agtcagacag   2340
ctgtgtaagc tgctgagggg agccaaagca ctgaccgaca tcgtgcctct gacagaagaa   2400
gccgagctgg aactgccga gaacagagag atcctgaaag acccgtgca cggagtgtac    2460
tacgaccccct ccaaggacct gattgccgag atccagaaac agggacacga ccagtggacc   2520
taccagatct atcaggaacc tttcaagaac ctgaaaacag gcaagtacgc caagatgcgg   2580
acagcccaca ccaacgacgt gaagcagctg accgaagccg tgcagaaaat cgccatggaa   2640
agcatcgtga tctggggaaa gacacccaag ttcaggctgc ccatccagaa agagacatgg   2700
gaaacctggt ggaccgacta ctggcaggcc acctggattc ccgagtggga gttcgtgaac   2760
accccacccc tggtgaagct gtggtatcag ctggaaaagg accctatcgc tggcgtggag   2820
acattctacg tggctggagc tgccaacaga gagacaaagc tgggcaaggc tggctacgtg   2880
accgacagag gcagacagaa aatcgtgagc ctgaccgaaa ccaccaacca gaaaacagcc   2940
ctgcaggcca tctatctggc actgcaggac agcggaagcg aggtgaacat cgtgacagcc   3000
agccagtatg ccctgggcat catccaggcc cagcctgaca gagcgagag cgagctggtg   3060
aaccagatca tcgagcagct gatcaagaaa gaacgggtgt acctgagctg ggtgccagcc   3120
cacaagggca tcggagggaa cgagcaggtg gacaagctgg tgtccagcgg aatccggaag   3180
gtgctgttcc tggacggcat cgataaagcc caggaagagc acgagaagta ccacagcaat   3240
tggagagcca tggccagcga cttcaacctg cctcccgtgg tggccaaaga aatcgtggcc   3300
agctgcgacc agtgccagct gaaaggcgag gccatgcacg acaggtgga ctgctcccct   3360
```

```
ggcatctggc agctggcatg cacccacctg gaaggcaaga tcattctggt ggccgtgcac    3420
gtggccagcg gatacatcga agccgaagtg atccctgccg agacagggca ggaaacagcc    3480
tacttcatcc tgaagctggc tggcagatgg cctgtgaagg tgatccacac agccaacggc    3540
agcaacttca cctctgctgc cgtgaaggct gcctgttggt gggctggcat tcagcaggaa    3600
tttggcatcc cctacaatcc ccagtctcag ggagtggtgg ccagcatgaa caaagagctg    3660
aagaagatca tcggacaggt cagggatcag gccgagcacc tgaaaactgc cgtccagatg    3720
gccgtgttca tccacaactt caagcggaag ggagggatcg agggtactc tgctggcgag    3780 cggatcatcg acatcattgc caccgatatc cagaccaaag agctgcagaa acagatcatc    3840
aagatccaga acttcagggt gtactacagg gacagcaggg accccatctg aagggacct    3900 gccaagctgc tgtggaaagg cgaaggagcc gtcgtcatcc aggacaacag cgacatcaag    3960
gtggtgccca gacggaaggt gaaaatcatc aaggactacg gcaaacagat ggctggagcc    4020
gactgtgtcg ctggcaggca ggacgaggac                                     4050
```

<210> SEQ ID NO 50
<211> LENGTH: 1350
<212> TYPE: PRT
<213> ORGANISM: Artificial Sequence
<220> FEATURE:
<223> OTHER INFORMATION: Mos1GagPol

<400> SEQUENCE: 50

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240
```

-continued

```
Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
        260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
        515                 520                 525

Thr Glu Glu Lys Ile Lys Ala Leu Thr Ala Ile Cys Glu Glu Met Glu
    530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Ser Val
        595                 600                 605

Thr Val Leu Ala Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655
```

```
Gly Ser Pro Ala Ile Phe Gln Cys Ser Met Thr Arg Ile Leu Glu Pro
            660                 665                 670

Phe Arg Ala Lys Asn Pro Glu Ile Val Ile Tyr Gln Tyr Met Ala Ala
            675                 680                 685

Leu Tyr Val Gly Ser Asp Leu Glu Ile Gly Gln His Arg Ala Lys Ile
            690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
            755                 760                 765

Ala Ser Gln Ile Tyr Pro Gly Ile Lys Val Arg Gln Leu Cys Lys Leu
            770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
            835                 840                 845

Lys Asn Leu Lys Thr Gly Lys Tyr Ala Lys Met Arg Thr Ala His Thr
850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
            900                 905                 910

Ile Pro Glu Trp Glu Phe Val Asn Thr Pro Pro Leu Val Lys Leu Trp
            915                 920                 925

Tyr Gln Leu Glu Lys Asp Pro Ile Ala Gly Val Glu Thr Phe Tyr Val
930                 935                 940

Ala Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Ala Leu Gln Ala Ile Tyr Leu Ala Leu Gln Asp Ser Gly
            980                 985                 990

Ser Glu Val Asn Ile Val Thr Ala Ser Gln Tyr Ala Leu Gly Ile Ile
            995                 1000                1005

Gln Ala Gln Pro Asp Lys Ser Glu Ser Glu Leu Val Asn Gln Ile
    1010                1015                1020

Ile Glu Gln Leu Ile Lys Lys Glu Arg Val Tyr Leu Ser Trp Val
    1025                1030                1035

Pro Ala His Lys Gly Ile Gly Gly Asn Glu Gln Val Asp Lys Leu
    1040                1045                1050

Val Ser Ser Gly Ile Arg Lys Val Leu Phe Leu Asp Gly Ile Asp
    1055                1060                1065

Lys Ala Gln Glu Glu His Glu Lys Tyr His Ser Asn Trp Arg Ala
```

Met Ala Ser Asp Phe Asn Leu Pro Pro Val Val Ala Lys Glu Ile
1085                1090                1095

Val Ala Ser Cys Asp Gln Cys Gln Leu Lys Gly Glu Ala Met His
1100                1105                1110

Gly Gln Val Asp Cys Ser Pro Gly Ile Trp Gln Leu Ala Cys Thr
1115                1120                1125

His Leu Glu Gly Lys Ile Ile Leu Val Ala Val His Val Ala Ser
1130                1135                1140

Gly Tyr Ile Glu Ala Glu Val Ile Pro Ala Glu Thr Gly Gln Glu
1145                1150                1155

Thr Ala Tyr Phe Ile Leu Lys Leu Ala Gly Arg Trp Pro Val Lys
1160                1165                1170

Val Ile His Thr Ala Asn Gly Ser Asn Phe Thr Ser Ala Ala Val
1175                1180                1185

Lys Ala Ala Cys Trp Trp Ala Gly Ile Gln Gln Glu Phe Gly Ile
1190                1195                1200

Pro Tyr Asn Pro Gln Ser Gln Gly Val Val Ala Ser Met Asn Lys
1205                1210                1215

Glu Leu Lys Lys Ile Ile Gly Gln Val Arg Asp Gln Ala Glu His
1220                1225                1230

Leu Lys Thr Ala Val Gln Met Ala Val Phe Ile His Asn Phe Lys
1235                1240                1245

Arg Lys Gly Gly Ile Gly Gly Tyr Ser Ala Gly Glu Arg Ile Ile
1250                1255                1260

Asp Ile Ile Ala Thr Asp Ile Gln Thr Lys Glu Leu Gln Lys Gln
1265                1270                1275

Ile Ile Lys Ile Gln Asn Phe Arg Val Tyr Tyr Arg Asp Ser Arg
1280                1285                1290

Asp Pro Ile Trp Lys Gly Pro Ala Lys Leu Leu Trp Lys Gly Glu
1295                1300                1305

Gly Ala Val Val Ile Gln Asp Asn Ser Asp Ile Lys Val Val Pro
1310                1315                1320

Arg Arg Lys Val Lys Ile Ile Lys Asp Tyr Gly Lys Gln Met Ala
1325                1330                1335

Gly Ala Asp Cys Val Ala Gly Arg Gln Asp Glu Asp
1340                1345                1350

<210> SEQ ID NO 51
<211> LENGTH: 829
<212> TYPE: DNA
<213> ORGANISM: Cytomegalovirus

<400> SEQUENCE: 51
tcaatattgg ccattagcca tattattcat tggttatata gcataaatca atattggcta     60
ttggccattg catacgttgt atccatatca taatatgtac atttatattg gctcatgtcc    120
aacattaccg ccatgttgac attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat    300
agtaacgcca tagggacttt ccattgacg tcaatgggtg gagtatttac ggtaaactgc    360
ccacttggca gtacatcaag tgtatcatat gccaagtacg ccccctattg acgtcaatga    420
cggtaaatgg cccgcctggc attatgccca gtacatgacc ttatgggact ttcctacttg    480

```
gcagtacatc tacgtattag tcatcgctat taccatggtg atgcggtttt ggcagtacat      540
caatgggcgt ggatagcggt ttgactcacg gggatttcca agtctccacc ccattgacgt      600
caatgggagt ttgttttggc accaaaatca acgggacttt ccaaaatgtc gtaacaactc      660
cgccccattg acgcaaatgg gcggtaggcg tgtacggtgg gaggtctata taagcagagc      720
tcgtttagtg aaccgtcaga tcgcctggag acgccatcca cgctgttttg acctccatag      780
aagacaccgg gaccgatcca gcctccgcgg ccgggaacgg tgcattgga                  829
```

<210> SEQ ID NO 52
<211> LENGTH: 24
<212> TYPE: DNA
<213> ORGANISM: Artificial Sequence
<220> FEATURE:
<223> OTHER INFORMATION: AdApt26.NdeI.fwd primer

<400> SEQUENCE: 52

```
gtgtatcata tgccaagtac gccc                                              24
```

<210> SEQ ID NO 53
<211> LENGTH: 38
<212> TYPE: DNA
<213> ORGANISM: Artificial Sequence
<220> FEATURE:
<223> OTHER INFORMATION: AdApt26.MluI.rev primer

<400> SEQUENCE: 53

```
cgatcacgcg tatctagaca tgataagata cattgatg                               38
```

<210> SEQ ID NO 54
<211> LENGTH: 34
<212> TYPE: DNA
<213> ORGANISM: Artificial Sequence
<220> FEATURE:
<223> OTHER INFORMATION: Ad26WT.463.MluI.fwd primer

<400> SEQUENCE: 54

```
acagacgcgt atcagctgat ccgcagggta ttta                                   34
```

<210> SEQ ID NO 55
<211> LENGTH: 24
<212> TYPE: DNA
<213> ORGANISM: Artificial Sequence
<220> FEATURE:
<223> OTHER INFORMATION: Ad26WT.XhoI.rev primer

<400> SEQUENCE: 55

```
ctgggcatgt agctcgaggc cagt                                              24
```

<210> SEQ ID NO 56
<211> LENGTH: 27
<212> TYPE: DNA
<213> ORGANISM: Artificial Sequence
<220> FEATURE:
<223> OTHER INFORMATION: Ad26.E4orf6.fwd primer

<400> SEQUENCE: 56

```
ctatttgatg agaatggaat tctatta                                           27
```

<210> SEQ ID NO 57
<211> LENGTH: 24
<212> TYPE: DNA
<213> ORGANISM: Artificial Sequence
<220> FEATURE:

<223> OTHER INFORMATION: Ad26.E4orf6.rev primer

<400> SEQUENCE: 57
cttatgctgg atgtacgcgt agag                                      24

<210> SEQ ID NO 58
<211> LENGTH: 25
<212> TYPE: DNA
<213> ORGANISM: Artificial Sequence
<220> FEATURE:
<223> OTHER INFORMATION: Ad26.dE4.EcoRI-MluI.fwd primer

<400> SEQUENCE: 58
gactgctact acaaagaagg atgta                                     25

<210> SEQ ID NO 59
<211> LENGTH: 37
<212> TYPE: DNA
<213> ORGANISM: Artificial Sequence
<220> FEATURE:
<223> OTHER INFORMATION: Ad26.dE4.EcoRI-MluI.rev primer

<400> SEQUENCE: 59
tattcaacgc gtagtacgac aaggtacgca agagaat                        37

<210> SEQ ID NO 60
<211> LENGTH: 35
<212> TYPE: DNA
<213> ORGANISM: Artificial Sequence
<220> FEATURE:
<223> OTHER INFORMATION: Ad26.dE4.MluI-SrfI.fwd primer

<400> SEQUENCE: 60
tattcaacgc gtagctcagc ccgcttacca gtaga                          35

<210> SEQ ID NO 61
<211> LENGTH: 22
<212> TYPE: DNA
<213> ORGANISM: Artificial Sequence
<220> FEATURE:
<223> OTHER INFORMATION: Ad26.dE4.MluI-SrfI.rev  primer

<400> SEQUENCE: 61
gcgtctggcg cggcgcagca ga                                        22

<210> SEQ ID NO 62
<211> LENGTH: 37
<212> TYPE: DNA
<213> ORGANISM: Artificial Sequence
<220> FEATURE:
<223> OTHER INFORMATION: Ad35.lITR.PacI.fwd primer

<400> SEQUENCE: 62
ggttaattaa catcatcaat aatatacctt atagatg                        37

<210> SEQ ID NO 63
<211> LENGTH: 34
<212> TYPE: DNA
<213> ORGANISM: Artificial Sequence
<220> FEATURE:
<223> OTHER INFORMATION: Ad35.E1B.AvrII.rev primer

<400> SEQUENCE: 63
aacctagggt cagctgcaag acagaaaaaa caaa                           34

```
<210> SEQ ID NO 64
<211> LENGTH: 27
<212> TYPE: DNA
<213> ORGANISM: Artificial Sequence
<220> FEATURE:
<223> OTHER INFORMATION: rcAd35.E1mut.fwd primer

<400> SEQUENCE: 64
gttttatttt aatcaaggga aatgcca                                         27

<210> SEQ ID NO 65
<211> LENGTH: 27
<212> TYPE: DNA
<213> ORGANISM: Artificial Sequence
<220> FEATURE:
<223> OTHER INFORMATION: rcAd35.E1mut.rev primer

<400> SEQUENCE: 65
tggcatttcc cttgattaaa ataaaac                                         27

<210> SEQ ID NO 66
<211> LENGTH: 37
<212> TYPE: DNA
<213> ORGANISM: Artificial Sequence
<220> FEATURE:
<223> OTHER INFORMATION: pWe.NotI.fwd primer

<400> SEQUENCE: 66
aatttagcgg ccgcatcgtc cattccgaca gcatcgc                              37

<210> SEQ ID NO 67
<211> LENGTH: 22
<212> TYPE: DNA
<213> ORGANISM: Artificial Sequence
<220> FEATURE:
<223> OTHER INFORMATION: pWe.NotI.rev primer

<400> SEQUENCE: 67
gaagcatttc cactcatgtc gc                                              22

<210> SEQ ID NO 68
<211> LENGTH: 2052
<212> TYPE: DNA
<213> ORGANISM: Artificial Sequence
<220> FEATURE:
<223> OTHER INFORMATION: Mos2ENV

<400> SEQUENCE: 68
atgagagtgc ggggcatcca gcggaactgg ccccagtggt ggatctgggg catcctgggc     60
ttttggatga tcatcatctg ccgggtgatg ggcaacctgt gggtgaccgt gtactacggc    120
gtgcccgtgt ggaaagaggc caagaccacc ctgttctgcg ccagcgacgc caaggcctac    180
gagaaagagg tgcacaacgt gtgggccacc cacgcctgcg tgcccaccga ccccaacccc    240
caggaaatgg tcctggaaaa cgtgaccgag aacttcaaca tgtggaagaa cgacatggtg    300
gaccagatgc acgaggacat catccggctg tgggaccaga gcctgaagcc ctgcgtgaag    360 ctgaccccccc tgtgcgtgac cctggaatgc ggaacgtga gaaacgtgag cagcaacggc    420
acctacaaca tcatccacaa cgagacctac aaagagatga gaactgcag cttcaacgcc    480 accaccgtgg tggaggaccg gaagcagaag gtgcacgccc tgttctaccg gctggacatc    540
gtgcccctgg acgagaacaa cagcagcgag aagtccagcg agaacagctc cgagtactac    600
cggctgatca actgcaacac cagcgccatc acccaggcct gccccaaggt gtccttcgac    660
```

```
cccatcccca tccactactg cgcccctgcc ggctacgcca tcctgaagtg caacaacaag    720
accttcaacg gcaccggccc ctgcaacaac gtgagcaccg tgcagtgcac ccacggcatc    780
aagcccgtgg tgtccaccca gctgctgctg aacggcagcc tggccgagga agagatcatc    840
atccggtccg agaacctgac caacaacgcc aagaccatca tcgtgcacct gaatgagacc    900
gtgaacatca cctgcacccg gcccaacaac aacacccgga gagcatccg gatcggccct    960
ggccagacct tttacgccac cggcgacatc atcggcgaca tccggcaggc ccactgcaac    1020
ctgagccggg acggctggaa caagaccctg cagggcgtga agaagaagct ggccgagcac    1080
ttccccaata agaccatcaa cttcaccagc agcagcggcg agacctggaa atcaccacc     1140
cacagcttca actgcagggg cgagttcttc tactgcaata cctccggcct gttcaatggc    1200
acctacatgc ccaacggcac caacagcaac agcagcagca acatcaccct gccctgccgg    1260
atcaagcaga tcatcaatat gtggcaggag gtcggcaggg ccatgtacgc ccctcccatc    1320
gccggcaata tcacctgccg gtccaacatc accggcctgc tgctgaccag ggacggcggc    1380
agcaacaacg gcgtgcctaa cgacaccgag accttccggc tggcggcgg agatatgcgg     1440
aacaactggc ggagcgagct gtacaagtac aaggtggtgg aggtgaagcc cctgggcgtg    1500
gctcctaccg aggccaagcg gcgggtggtg gagagcgaga gagcgccgt gggcatcggc     1560
gccgtgtttc tgggcattct gggagccgcc ggaagcacca tgggagccgc cagcatcacc    1620
ctgaccgtgc aggcccggca gctgctgtcc ggcatcgtgc agcagcagag caacctgctg    1680
agagccatcg aggcccagca gcacatgctg cagctgaccg tgtggggcat caagcagctg    1740
cagacccggg tgctggccat cgagagatac ctgcaggatc agcagctcct gggcctgtgg    1800
ggctgcagcg gcaagctgat ctgcaccacc gccgtgccct ggaacaccag ctggtccaac    1860
aagagccaga ccgacatctg gacaacatg acctggatgc agtgggacaa agagatcggc     1920
aactacaccg gcgagatcta caggctgctg aagagagcc agaaccagca ggaaaagaac    1980
gagaaggacc tgctggccct ggacagctgg aagaacctgt ggaactggtt cgacatcacc    2040
aactggctgt gg                                                      2052
```

<210> SEQ ID NO 69
<211> LENGTH: 684
<212> TYPE: PRT
<213> ORGANISM: Artificial Sequence
<220> FEATURE:
<223> OTHER INFORMATION: Mos2ENV

<400> SEQUENCE: 69

```
Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110
```

-continued

```
Gln Ser Leu Lys Pro Cys Val Lys Leu Thr Pro Leu Cys Val Thr Leu
            115                 120                 125

Glu Cys Arg Asn Val Arg Asn Val Ser Ser Asn Gly Thr Tyr Asn Ile
130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445

Asn Ile Thr Gly Leu Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Ser
            500                 505                 510

Glu Lys Ser Ala Val Gly Ile Gly Ala Val Phe Leu Gly Ile Leu Gly
        515                 520                 525

Ala Ala Gly Ser Thr Met Gly Ala Ala Ser Ile Thr Leu Thr Val Gln
```

```
            530                 535                 540
Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
                580                 585                 590

Asp Gln Gln Leu Leu Gly Leu Trp Gly Cys Ser Gly Lys Leu Ile Cys
                595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
                660                 665                 670

Leu Trp Asn Trp Phe Asp Ile Thr Asn Trp Leu Trp
            675                 680

<210> SEQ ID NO 70
<211> LENGTH: 4023
<212> TYPE: DNA
<213> ORGANISM: Artificial Sequence
<220> FEATURE:
<223> OTHER INFORMATION: Mos2GagPol

<400> SEQUENCE: 70
atgggagcca gagccagcat cctgcgagga gggaagctgg acaagtggga gaagatcagg       60
ctgaggcctg gagggaagaa acactacatg ctgaagcacc tggtctgggc cagcagagag      120
ctggaacggt ttgccctcaa tcctggcctg ctggaaacca gcgagggctg caagcagatc      180
atcaagcagc tgcagcctgc cctgcagaca ggcaccgagg aactgcggag cctgttcaac      240
accgtggcca ccctgtactg cgtgcatgcc gagatcgaag tgagggacac caaagaagcc      300
ctggacaaga tcgaggaaga gcagaacaag agccagcaga aacccagca ggccaaagaa       360
gccgacggca aggtctccca gaactacccc atcgtgcaga acctgcaggg acagatggtg      420
caccagccca tcagccctcg gacactgaat gcctgggtga aggtgatcga ggaaaaggcc      480
ttcagccctg aggtgatccc catgttcaca gccctgagcg agggagccac accccaggac      540
ctgaacacca tgctgaacac cgtgggaggg caccaggctg ccatgcagat gctgaaggac      600
accatcaacg aggaagctgc cgagtgggac aggctgcacc tgtgcacgc tggacctgtg       660
gctcctggcc agatgagaga gcccagaggc agcgatattg ctggcaccac ctccaatctg      720
caggaacaga tcgcctggat gaccagcaac cctcccatcc tgtgtggaga catctacaag      780
cggtggatca tcctgggact gaacaagatc gtgcggatgt acagccctac ctccatcctg      840
gacatcaagc agggacccaa agagcctttc agggactacg tggaccggtt cttcaagacc      900
ctgagagccg agcaggccac ccaggacgtg aagaactgga tgaccgacac cctgctggtg      960
cagaacgcca accctgactg caagaccatc ctgagagccc tgggacctgg agccaccctg     1020
aagagatga tgacagcctg ccagggagtg gaggaccct ctcacaaggc tagggtgctg       1080
gccgaggcca tgagccagac caacagcacc atcctgatgc agcggagcaa cttcaagggc     1140
agcaagcgga tcgtgaagtg cttcaactgt ggcaaagagg gacacattgc cagaaactgt     1200
```

```
agggcaccca ggaagaaagg ctgctggaag tgcggaaaag aaggccacca gatgaaggac    1260
tgcaccgaga ggcaggccaa cttcctgggc aagatctggc ctagccacaa gggcagacct    1320
ggcaacttcc tgcagagcag acccgagccc accgctcctc cagccgagag cttccggttc    1380
gaggaaacca cccctgctcc caagcaggaa cctaaggaca gagagcctct gaccagcctg    1440
agaagcctgt tcggcagcga ccctctgagc cagatggctc ccatctcccc tatcgagaca    1500
gtgcctgtga agctgaagcc tggcatggac ggacccaagg tgaaacagtg gcctctgacc    1560
gaggaaaaga tcaaagccct ggtggagatc tgtaccgaga tggaaaaaga gggcaagatc    1620
agcaagatcg acccgagaa ccctacaac acccctatct cgccatcaa gaagaaagac    1680
agcaccaagt ggaggaaact ggtggacttc agagagctga acaagcggac ccaggacttc    1740
tgggaggtgc agctgggcat ccctcaccct gctggcctga agaaaaagaa aagcgtgacc    1800
gtgctggccg tgggagatgc ctacttcagc gtgcctctgg acgaggactt cagaaagtac    1860
acagccttca ccatccccag catcaacaac gagacacctg gcatcagata ccagtacaac    1920
gtgctgcctc agggatggaa gggctctcct gcaatcttcc agagcagcat gaccaagatc    1980
ctggaaccct tccggaagca gaaccctgac atcgtgatct accagtacat ggcagccctg    2040
tacgtcggca gcgacctgga aatcggacag caccggacca gatcgaaga actcaggcag    2100
cacctgctgc ggtgggatt caccacccct gacaagaagc accagaaaga gcctcccttc    2160
ctgtggatgg gctacgagct gcacccagac aagtggaccg tgcagcccat cgtgctgcct    2220
gagaaggact cctggaccgt gaacgacatc cagaaactgg tcggcaagct gaactgggcc    2280
agccagatct acgctggcat caaagtgaag cagctgtgta agctcctgag aggcaccaaa    2340
gccctgaccg aggtggtgcc actgacagag gaagccgagc tggaactggc cgagaacaga    2400
gagatcctga agaacccgt gcacggagtg tactacgacc ccagcaagga cctgattgcc    2460
gagatccaga gcagggaca gggacagtgg acctaccaga tctaccagga acccttcaag    2520
aacctgaaaa caggcaagta cgccaggatg aggggagccc acaccaacga cgtcaaacag    2580
ctgaccgaag ccgtgcagaa gatcgccacc gagagcatcg tgatttgggg aaagacaccc    2640
aagttcaagc tgcccatcca gaaagagaca tgggaggcct ggtggaccga gtactggcag    2700
gccacctgga ttcccgagtg ggagttcgtg aacaccccac ccctggtgaa gctgtggtat    2760
cagctggaaa agaacccat cgtgggagcc gagacattct acgtggctgg agctgccaac    2820
agagagacaa agctgggcaa ggctggctac gtgaccgaca gaggcaggca gaaagtggtg    2880
tccctgaccg ataccaccaa ccagaaaaca gccctgcagg ccatccacct ggctctgcag    2940
gactctggcc tggaagtgaa catcgtgaca gccagccagt atgccctggg catcattcag    3000
gcacagcctg acaagagcga gagcgagctg gtgtctcaga tcattgagca gctgatcaag    3060
aaagaaaagg tgtacctggc ctgggtgcca gcccacaagg ggatcggagg gaacgagcag    3120
gtggacaagc tggtgtccag gggcatccgg aaggtgctgt ttctggacgg catcgacaaa    3180
gcccaggaag agcacgagaa gtaccacagc aattggagag ccatgccagc gagttcaac    3240
ctgcctccca tcgtggccaa agaaatcgtg gcctcttgcg acaagtgcca gctgaaaggc    3300
gaggccattc acggacaggt ggactgcagc ccaggcatct ggcagctggc ctgcacccac    3360
ctggaaggca aggtgatcct ggtggccgtg cacgtggcct ctggatacat cgaagccgaa    3420
gtgatccctg ccgagacagg ccaggaaaca gcctacttcc tgctgaagct ggctggcagg    3480
tggcctgtga aaaccatcca cacagccaac ggcagcaact tcacctctgc caccgtgaag    3540
gctgcctgtt ggtgggctgg cattaagcag gaatttggca tcccctacaa ccctcagtct    3600
```

-continued

```
cagggagtgg tggcctccat caacaaagag ctgaagaaga tcatcggaca ggtcagggat    3660
caggccgagc atctgaaaac agccgtccag atggccgtgt tcatccacaa cttcaagcgg    3720
aagggaggga tcggagagta ctctgctggc gagaggatcg tggacattat cgccagcgat    3780
atccagacca agaactgca gaagcagatc acaaagatcc agaacttcag ggtgtactac    3840
agggacagca gagatcccct gtggaaggga cctgccaagc tgctgtggaa aggcgaagga    3900
gccgtcgtca tccaggacaa cagcgacatc aaggtggtgc ccagacgaa ggccaagatc    3960 atcagagact acggcaaaca gatggctggc gacgactgcg tcgcctctag gcaggacgag    4020
gat                                                                   4023
```

<210> SEQ ID NO 71
<211> LENGTH: 1341
<212> TYPE: PRT
<213> ORGANISM: Artificial Sequence
<220> FEATURE:
<223> OTHER INFORMATION: Mos2GagPol

<400> SEQUENCE: 71

```
Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
```

```
            275                 280                 285
Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                    325                 330                 335

Gly Ala Thr Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                    405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
            435                 440                 445

Glu Pro Thr Ala Pro Ala Glu Ser Phe Arg Phe Glu Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                    485                 490                 495

Pro Ile Glu Thr Val Pro Val Lys Leu Lys Pro Gly Met Asp Gly Pro
                500                 505                 510

Lys Val Lys Gln Trp Pro Leu Thr Glu Glu Lys Ile Lys Ala Leu Val
            515                 520                 525

Glu Ile Cys Thr Glu Met Glu Lys Glu Gly Lys Ile Ser Lys Ile Gly
530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                    565                 570                 575

Thr Gln Asp Phe Trp Glu Val Gln Leu Gly Ile Pro His Pro Ala Gly
                580                 585                 590

Leu Lys Lys Lys Lys Ser Val Thr Val Leu Ala Val Gly Asp Ala Tyr
            595                 600                 605

Phe Ser Val Pro Leu Asp Glu Asp Phe Arg Lys Tyr Thr Ala Phe Thr
610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
                    645                 650                 655

Met Thr Lys Ile Leu Glu Pro Phe Arg Lys Gln Asn Pro Asp Ile Val
                660                 665                 670

Ile Tyr Gln Tyr Met Ala Ala Leu Tyr Val Gly Ser Asp Leu Glu Ile
            675                 680                 685

Gly Gln His Arg Thr Lys Ile Glu Glu Leu Arg Gln His Leu Leu Arg
690                 695                 700
```

-continued

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
            725                 730                 735

Ile Val Leu Pro Glu Lys Asp Ser Trp Thr Val Asn Asp Ile Gln Lys
        740                 745                 750

Leu Val Gly Lys Leu Asn Trp Ala Ser Gln Ile Tyr Ala Gly Ile Lys
    755                 760                 765

Val Lys Gln Leu Cys Lys Leu Leu Arg Gly Thr Lys Ala Leu Thr Glu
770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
            805                 810                 815

Asp Leu Ile Ala Glu Ile Gln Lys Gln Gly Gln Gly Gln Trp Thr Tyr
        820                 825                 830

Gln Ile Tyr Gln Glu Pro Phe Lys Asn Leu Lys Thr Gly Lys Tyr Ala
    835                 840                 845

Arg Met Arg Gly Ala His Thr Asn Asp Val Lys Gln Leu Thr Glu Ala
850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
            885                 890                 895

Glu Tyr Trp Gln Ala Thr Trp Ile Pro Glu Trp Glu Phe Val Asn Thr
        900                 905                 910

Pro Pro Leu Val Lys Leu Trp Tyr Gln Leu Glu Lys Glu Pro Ile Val
    915                 920                 925

Gly Ala Glu Thr Phe Tyr Val Ala Gly Ala Ala Asn Arg Glu Thr Lys
930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
            965                 970                 975

Leu Ala Leu Gln Asp Ser Gly Leu Glu Val Asn Ile Val Thr Ala Ser
        980                 985                 990

Gln Tyr Ala Leu Gly Ile Ile Gln Ala Gln Pro Asp Lys Ser Glu Ser
    995                 1000                1005

Glu Leu Val Ser Gln Ile Ile Glu Gln Leu Ile Lys Lys Glu Lys
    1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

| | | | | | | | | | | |
|---|---|---|---|---|---|---|---|---|---|---|
| Trp | Gln | Leu | Ala | Cys | Thr | His | Leu | Glu | Gly | Lys | Val | Ile | Leu | Val |
| 1115 | | | | | 1120 | | | | | 1125 | | | | |
| Ala | Val | His | Val | Ala | Ser | Gly | Tyr | Ile | Glu | Ala | Glu | Val | Ile | Pro |
| 1130 | | | | | 1135 | | | | | 1140 | | | | |
| Ala | Glu | Thr | Gly | Gln | Glu | Thr | Ala | Tyr | Phe | Leu | Leu | Lys | Leu | Ala |
| 1145 | | | | | 1150 | | | | | 1155 | | | | |
| Gly | Arg | Trp | Pro | Val | Lys | Thr | Ile | His | Thr | Ala | Asn | Gly | Ser | Asn |
| 1160 | | | | | 1165 | | | | | 1170 | | | | |
| Phe | Thr | Ser | Ala | Thr | Val | Lys | Ala | Ala | Cys | Trp | Trp | Ala | Gly | Ile |
| 1175 | | | | | 1180 | | | | | 1185 | | | | |
| Lys | Gln | Glu | Phe | Gly | Ile | Pro | Tyr | Asn | Pro | Gln | Ser | Gln | Gly | Val |
| 1190 | | | | | 1195 | | | | | 1200 | | | | |
| Val | Ala | Ser | Ile | Asn | Lys | Glu | Leu | Lys | Lys | Ile | Ile | Gly | Gln | Val |
| 1205 | | | | | 1210 | | | | | 1215 | | | | |
| Arg | Asp | Gln | Ala | Glu | His | Leu | Lys | Thr | Ala | Val | Gln | Met | Ala | Val |
| 1220 | | | | | 1225 | | | | | 1230 | | | | |
| Phe | Ile | His | Asn | Phe | Lys | Arg | Lys | Gly | Gly | Ile | Gly | Glu | Tyr | Ser |
| 1235 | | | | | 1240 | | | | | 1245 | | | | |
| Ala | Gly | Glu | Arg | Ile | Val | Asp | Ile | Ile | Ala | Ser | Asp | Ile | Gln | Thr |
| 1250 | | | | | 1255 | | | | | 1260 | | | | |
| Lys | Glu | Leu | Gln | Lys | Gln | Ile | Thr | Lys | Ile | Gln | Asn | Phe | Arg | Val |
| 1265 | | | | | 1270 | | | | | 1275 | | | | |
| Tyr | Tyr | Arg | Asp | Ser | Arg | Asp | Pro | Leu | Trp | Lys | Gly | Pro | Ala | Lys |
| 1280 | | | | | 1285 | | | | | 1290 | | | | |
| Leu | Leu | Trp | Lys | Gly | Glu | Gly | Ala | Val | Val | Ile | Gln | Asp | Asn | Ser |
| 1295 | | | | | 1300 | | | | | 1305 | | | | |
| Asp | Ile | Lys | Val | Val | Pro | Arg | Arg | Lys | Ala | Lys | Ile | Ile | Arg | Asp |
| 1310 | | | | | 1315 | | | | | 1320 | | | | |
| Tyr | Gly | Lys | Gln | Met | Ala | Gly | Asp | Asp | Cys | Val | Ala | Ser | Arg | Gln |
| 1325 | | | | | 1330 | | | | | 1335 | | | | |
| Asp | Glu | Asp | | | | | | | | | | | | |
| 1340 | | | | | | | | | | | | | | |

<210> SEQ ID NO 72
<211> LENGTH: 11126
<212> TYPE: DNA
<213> ORGANISM: Artificial Sequence
<220> FEATURE:
<223> OTHER INFORMATION: pAdApt26.26E1.Mos1-HIVENV

<400> SEQUENCE: 72

```
aaagtaaaca aaagttaata tgcaaatgag cttttgaatt ttaacggttt tggggcggag      60
ccaacgctga ttggacgaga aacggtgatg caaatgacgt cacgacgcac ggctaacggt     120
cgccgcggag gcgtggccta gcccggaagc aagtcgcggg gctgatgacg tataaaaaag     180
cggactttag acccggaaac ggccgatttt cccgcggcca cgcccggata tgaggtaatt     240
ctgggcggat gcaagtgaaa ttaggtcatt ttggcgcgaa aactgaatga ggaagtgaaa     300
agcgaaaaat accggtccct cccagggcgg aatatttacc gagggccgag agactttgac     360
cgattacgtg ggggtttcga ttgcggtgtt ttttcgcga atttccgcgt ccgtgtcaaa     420
gtccggtgtt tatgtcacag atcagctgac ctaggtggtc aatattggcc attagccata     480
ttattcattg gttatatagc ataaatcaat attggctatt ggccattgca tacgttgtat     540
ccatatcata atatgtacat ttatattggc tcatgtccaa cattaccgcc atgttgacat     600
tgattattga ctagttatta atagtaatca attacggggt cattagttca tagcccatat     660
```

```
atggagttcc gcgttacata acttacggta aatggcccgc ctggctgacc gcccaacgac    720
ccccgcccat tgacgtcaat aatgacgtat gttcccatag taacgccaat agggactttc    780
cattgacgtc aatgggtgga gtatttacgg taaactgccc acttggcagt acatcaagtg    840
tatcatatgc caagtacgcc ccctattgac gtcaatgacg gtaaatggcc cgcctggcat    900
tatgcccagt acatgacctt atgggacttt cctacttggc agtacatcta cgtattagtc    960
atcgctatta ccatggtgat gcggttttgg cagtacatca atgggcgtgg atagcggttt   1020
gactcacggg gatttccaag tctccacccc attgacgtca atgggagttt gttttggcac   1080
caaaatcaac gggactttcc aaaatgtcgt aacaactccg ccccattgac gcaaatgggc   1140
ggtaggcgtg tacggtggga ggtctatata agcagagctc gtttagtgaa ccgtcagatc   1200
gcctggagac gccatccacg ctgttttgac ctccatagaa gacaccggga ccgatccagc   1260
ctccgcggcc gggaacggtg cattggaagc ttggtaccgg tgaattcgcc accatgcggg   1320
tgaccggcat ccggaagaac taccagcacc tgtggcggtg gggcaccatg ctgctgggca   1380
tcctgatgat ttgctctgcc gccggaaagc tgtgggtgac cgtgtactac ggcgtgcccg   1440
tgtggaaaga ggccaccacc accctgttct gcgccagcga cgccaaggcc tacgacaccg   1500
aggtgcacaa cgtgtgggcc acccacgcct gcgtgcccac cgaccccaac ccccaggaag   1560
tggtcctgga aaacgtgacc gagaacttca acatgtggaa gaacaacatg gtggagcaga   1620
tgcacgagga catcatcagc ctgtgggacc agagcctgaa gcccgcgtg aagctgaccc   1680 ccctgtgcgt gaccctgaac tgcaccgacg acgtgcggaa cgtgaccaac aacgccacca   1740
acaccaacag cagctggggc gagcctatgg aaaagggcga gatcaagaac tgcagcttca   1800
acatcaccac ctccatccgg aacaaggtgc agaagcagta cgccctgttc tacaagctgg   1860
acgtggtgcc catcgacaac gacagcaaca acaccaacta ccggctgatc agctgcaaca   1920
ccagcgtgat cacccaggcc tgccccaagg tgtccttcga gcccatcccc atccactact   1980
gcgcccctgc cggcttcgcc atcctgaagt gcaacgacaa gaagttcaac ggcaccggcc   2040
cctgcaccaa cgtgagcacc gtgcagtgca cccacggcat ccggcccgtg gtgtccaccc   2100
agctgctgct gaacggcagc ctggccgagg aagaggtggt gatcagaagc gagaatttca   2160
ccaacaatgc caagaccatc atggtgcagc tgaacgtgag cgtggagatc aactgcaccc   2220
ggcccaacaa caacacccgg aagagcatcc acatcggccc tggcagggcc ttctacacag   2280
ccggcgacat catcggcgac atccggcagg cccactgcaa catcagccgg gccaactgga   2340
acaacaccct gcggcagatc gtggagaagc tgggcaagca gttcggcaac aacaagacca   2400
tcgtgttcaa ccacagcagc ggcggagacc ccgagatcgt gatgcacagc ttcaactgtg   2460
gcggcgagtt cttctactgc aacagcacca agctgttcaa cagcacctgg acctggaaca   2520
actccacctg gaataacacc aagcggagca acgacaccga agagcacatc accctgccct   2580
gccggatcaa gcagattatc aatatgtggc aggaggtcgg caaggccatg tacgcccctc   2640
ccatccgggg ccagatccgg tgcagcagca acatcaccgg cctgctgctg acccgggacg   2700
gcggcaacga taccagcggc accgagatct tccggcctgg cggcggagat atgcgggaca   2760
actggcggag cgagctgtac aagtacaagg tggtgaagat cgagcccctg ggcgtggctc   2820
ccaccaaggc caagcggcgg gtggtgcaga gcgagaagag cgccgtgggc atcggcgccg   2880
tgtttctggg cttcctggga gccgccgaaa gcaccatggg agccgccagc atgaccctga   2940
ccgtgcaggc ccggctgctg ctgtccggca tcgtgcagca gcagaacaac ctgctccggg   3000
```

```
ccatcgaggc ccagcagcac ctgctgcagc tgaccgtgtg gggcatcaag cagctgcagg    3060
ccagggtgct ggccgtggag agatacctga aggatcagca gctcctgggg atctggggct    3120
gcagcggcaa gctgatctgc accaccaccg tgccctggaa cgccagctgg tccaacaaga    3180
gcctggacaa gatctggaac aatatgacct ggatggaatg ggagcgcgag atcaacaatt    3240
acaccagcct gatctacacc ctgatcgagg aaagccagaa ccagcaggaa agaacgagc     3300 aggaactgct ggaactggac aagtgggcca gcctgtggaa ctggttcgac atcagcaact    3360
ggctgtggta atgaggatcc tctagacgag atccgaactt gtttattgca gcttataatg    3420
gttacaaata aagcaatagc atcacaaatt cacaaataa agcattttt tcactgcatt      3480 ctagttgtgg tttgtccaaa ctcatcaatg tatcttatca tgtctagata cgcgtatcag    3540
ctgatccgca gggtatttaa accagtcgag tccgtcaaga ggccactctt gagtgccagc    3600
gagtagagat ttctctgagc tccgctccca gagaccgaga aaaatgagac acctgcgcct    3660
cctgccttca actgtgcccg gtgagctggc tgtgcttatg ctggaggact ttgtggatac    3720
agtattggag gacgaactgc atccaagtcc gttcgagctg ggaccacac ttcaggatct     3780 ctatgatctg gaggtagatg cccatgatga cgaccctaac gaggaggctg tgaatttaat    3840
atttccagaa tctatgattc ttcaggctga catagccaac gaatctactc cacttcatac    3900
accgactctg tcaccatac ctgaattgga agaggaggac gaactagacc tccggtgtta     3960
tgaggaaggt tttcctccca gcgattcaga ggatgaacgg ggtgagcaga ccatggctct    4020
gatctcagac tatgcttgtg tgattgtgga ggaacaagta gtgattgaaa attctaccga    4080
gccagtggag ggctgtagaa aatgccagta ccaccgggat aagtctggag acccgaacgc    4140
atcatgcgct ttgtgctata tgaaacagac tttcagcttt atttacagta agtggagtga    4200
atgtgagaga ggctgagtgc ttaacacatc actgtgtatt gcttgaacag ctgtgctaag    4260
tgtggtttat ttttgtttct aggtccggtg tcagaggatg agtcatcacc ctcagaagaa    4320
gaccacccgt ctcccctga tctcacagat gacacgcccc tgcaagtgca cagacccacc     4380
ccagtcagag ccagtggcga gaggcgagca gctgttgaaa aaattgagga cttgttacat    4440
gacatgggtg gggatgaacc tttggacctg agcttgaaac gccccaggaa ctaggcgcag    4500
ctgcgcttag tcatgtgtaa ataaagttgt acaataaaag tatatgtgac gcatgcaagg    4560
tgtggtttat gactcatggg cggggcttag tcctatataa gtggcaacac ctgggcactg    4620
ggcacagacc ttcagggagt tcctgatgga tgtgtggact atccttgcag actttagcaa    4680
gacacgccgg cttgtagagg atagttcaga cgggtgctcc gggttctgga gacactggtt    4740
tggaactcct ctatctcgcc tggtgtacac agttaagaag gattataaag aggaatttga    4800 aaatatttt gctgactgct ctggcctgct agattctctg aatcttggcc accagtccct     4860
tttccaggaa agggtactcc acagccttga ttttccagc ccagggcgca ctacagccgg     4920
ggttgctttt gtggttttc tggttgacaa atggagccag acacccaac tgagcagggg      4980 ctacatcctg gacttcgcag ccatgcacct gtggagggcc tggatcaggc agcggggaca    5040
gagaatcttg aattactggc ttctacagcc agcagctccg ggtcttcttc gtctacacag    5100
acaaacatcc atgttggagg aagaaatgag gcaggccatg gacgagaacc cgaggagcgg    5160
cctggaccct ccgtcggaag aggagctgga ttgaatcagg tatccagcct gtacccagag    5220
cttagcaagg tgctgacatc catggccagg ggagttaaga gggagaggag cgatgggggt    5280
aataccggga tgatgaccga gctgacggcc agcctgatga tcggaagcg cccagagcgc     5340 cttacctggt acgagctaca gcaggagtgc aggatgagt tgggcctgat gcaggataaa     5400
```

```
tatggcctgg agcagataaa aacccattgg ttgaacccag atgaggattg ggaggaggct      5460
attaagaagt atgccaagat agccctgcgc ccagattgca agtacatagt gaccaagacc      5520
gtgaatatca gacatgcctg ctacatctcg gggaacgggg cagaggtggt catcgatacc      5580
ctggacaagg ccgccttcag gtgttgcatg atgggaatga gagcaggagt gatgaatatg      5640
aattccatga tcttcatgaa catgaagttc aatggagaga agtttaatgg ggtgctgttc      5700
atggccaaca gccacatgac cctgcatggc tgcagtttct tcggcttcaa caatatgtgc      5760
gcagaggtct ggggcgcttc caagatcagg ggatgtaagt tttatggctg ctggatgggc      5820
gtggtcggaa gacccaagag cgagatgtct gtgaagcagt gtgtgtttga gaaatgctac      5880 ctggagtct ctaccgaggg caatgctaga gtgagacact gctcttccct ggagacgggc       5940
tgcttctgcc tggtgaaggg cacagcctct ctgaagcata atatggtgaa gggctgcacg      6000
gatgagcgca tgtacaacat gctgacctgc gattcggggg tctgccatat cctgaagaac      6060
atccatgtga cctcccaccc cagaaagaag tggccagtgt tgagaataa cctgctgatc       6120 aagtgccata tgcacctggg agccagaagg ggcaccttcc agccgtacca gtgcaacttt      6180
agccagacca agctgctgtt ggagaacgat gccttctcca gggtgaacct gaacggcatc      6240
tttgacatgg atgtctcggt gtacaagatc ctgagatacg atgagaccaa gtccagggtg      6300
cgcgcttgcg agtgcggggg cagacacacc aggatgcagc cagtggccct ggatgtgacc      6360
gaggagctga gaccagacca cctggtgatg gcctgtaccg ggaccgagtt cagctccagt      6420
ggggaggata cagattagag gtaggtttga gtagtgggcg tggctaaggt gactataaag      6480
gcgggtgtct tacgagggtc ttttttgcttt tctgcagaca tcatgaacgg gactggcggg      6540
gccttcgaag gggggctttt tagcccttat ttgacaaccc gcctgccggg atgggccgga      6600
gttcgtcaga atgtgatggg atcgacggtg gatgggcgcc cagtgcttcc agcaaattcc      6660
tcgaccatga cctacgcgac cgtgggaac tcgtcgctcg acagcaccgc cgcagccgcg       6720
gcagccgcag ccgccatgac agcgacgaga ctggcctcga gctacatgcc cagcagcggt      6780
agtagcccct ctgtgcccag ttccatcatc gccgaggaga aactgctggc cctgctggcc      6840
gagctggaag ccctgagccg ccagctggcc gccctgaccc agcaggtgtc cgagctccgc      6900
gaacagcagc agcagcaaaa taatgattc aataaacaca gattctgatt caaacagcaa       6960 agcatctta ttatttattt tttcgcgcgc ggtaggccct ggtccacctc tcccgatcat       7020
tgagagtgcg gtggattttt tccaggaccc ggtagaggtg ggattggatg ttgaggtaca      7080
tgggcatgag cccgtcccgt gggtggaggt agcaccactg catggcctcg tgctctgggg      7140
tcgtgttgta gatgatccag tcatagcagg ggcgctgggc gtggtgctgg atgatgtcct      7200
tgaggaggag actgatggcc acggggagcc ccttggtgta ggtgttggca aaacggttga      7260
gctgggaggg atgcatgcgg ggggagatga tgtgcagttt ggcctggatc ttgaggttgg      7320
cgatgttgcc acccagatcc cgccggggt tcatgttgtg caggaccacc agaacgtgt       7380 agcccgtgca cttggggaac ttgtcatgca acttggaagg gaatgcgtgg aagaatttgg      7440
agacgccctt gtgcccgccc aggttttcca tgcactcatc catgatgatg caatgggcc       7500 cgtgggctgc ggctttggca aagacgtttc tgggtcaga gacatcgtaa ttatgctcct       7560
gggtgagatc atcataagac attttaatga atttggggcg gagggtgcca gattggggga      7620
cgatggttcc ctcgggcccc ggggcgaagt tccctcgca gatctgcatc tcccaggctt       7680
tcatctcgga gggggggatc atgtccacct gcgggggcgat gaaaaaaacg gtttccgggg      7740
```

```
cggggggtgat gagctgcgag gagagcaggt ttctcaacag ctgggacttg ccgcacccgg    7800
tcgggccgta gatgaccccg atgacgggtt gcaggtggta gttcaaggac atgcagctgc    7860
cgtcgtcccg gaggaggggg gccacctcgt tgagcttgtc tctgacttgg aggttttccc    7920
ggacgagctc gccgaggagg cggtcccccgc ccagcgagag aagctcttgc agggaagcaa   7980
agttttcag gggcttgagc ccgtcggcca tgggcatctt ggcgagggtc tgcgagagga     8040
gctccaggcg gtcccagagc tcggtgacgt gctctacggc atctcgatcc agcagacttc    8100
ctcgtttcgg gggttgggac gactgcgact gtagggcacg agacgatggg cgtccagcgc    8160
ggccagcgtc atgtccttcc agggtctcag ggtccgcgtg agggtggtct ccgtcacggt    8220
gaagggtgg gccgcgggct gggcgcttgc aagggtgcgc ttgagactca tcctgctggt     8280
gctgaaacgg gcacggtctt cgccctgcgc gtcggcgaga tagcagttga ccatgagctc    8340
gtagttgagg gcctcggcgg cgtggccctt ggcgcggagc ttgcccttgg aagagcgccc    8400
gcaggcggga cagaggaggg attgcagggc gtagagcttg ggcgcgagaa agacggactc    8460
gggggcgaag gcgtccgctc cgcagtgggc gcagacggtc tcgcactcga ctagccaggt    8520
gagctcgggc tgctcggggt caaaaaccag ttttccccccg ttcttttttga tgcgcttctt   8580
acctcgcgtc tccatgagtc tgtgtccgcg ctcggtgaca acaggctgt ctgtgtcccc     8640
gtagacggac ttgatgggcc tgtcctgcag gggcgtcccg cggtcctcct cgtagagaaa    8700
ctcagaccac tctgagacga aggcgcgcgt ccacgccaag acaaaggagg ccacgtgcga    8760
ggggtagcgg tcgttgtcca ccaggggtc caccttttcc acggtatgca ggcacatgtc     8820
cccctcctcc gcatccaaga aggtgattgg cttgtaggtg taggcacgt gacctgggt      8880
tcccgacggg ggggtataaa aggggggcggg tctgtgctcg tcctcactct cttccgcgtc   8940
gctgtccacg agcgccagct gttggggtag gtattccctc tcaagattaa ttaattcgaa    9000
cccataatac ccataatagc tgtttgccat cgacgcgagg ctggatggcc ttccccatta    9060
tgattcttct cgcttccggc ggcatcggga tgcccgcgtt gcaggccatg ctgtccaggc    9120
aggtagatga cgaccatcag ggacagcttc aaggatcgct cgcggctctt accagcccag    9180
caaaaggcca ggaaccgtaa aaaggccgcg ttgctggcgt ttttccatag gctccgcccc    9240
cctgacgagc atcacaaaaa tcgacgctca agtcagaggt ggcgaaaccc gacaggacta    9300
taaagatacc aggcgtttcc ccctggaagc tccctcgtgc gctctcctgt tccgaccctg    9360
ccgcttaccg gatacctgtc cgcctttctc ccttcgggaa gcgtggcgct ttctcatagc    9420
tcacgctgta ggtatctcag ttcggtgtag gtcgttcgct ccaagctggg ctgtgtgcac    9480
gaaccccccg ttcagcccga ccgctgcgcc ttatccggta actatcgtct tgagtccaac    9540
ccggtaagac acgacttatc gccactggca gcagccactg gtaacaggat tagcagagcg    9600
aggtatgtag gcggtgctac agagttcttg aagtggtggc ctaactacgg ctacactaga    9660
aggacagtat ttggtatctg cgctctgctg aagccagtta ccttcggaaa aagagttggt    9720
agctcttgat ccggcaaaca aaccaccgct ggtagcggtg ttttttttgt ttgcaagcag    9780
cagattacgc gcagaaaaaa aggatctcaa gaagatcctt tgatcttttc tacgggtct    9840
gacgctcagt ggaacgaaaa ctcacgttaa gggattttgg tcatgagatt atcaaaaagg    9900
atcttcacct agatcctttt aaattaaaaa tgaagtttta aatcaatcta agtatatat    9960
gagtaaactt ggtctgacag ttaccaatgc ttaatcagtg aggcacctat ctcagcgatc    10020
tgtctatttc gttcatccat agttgcctga ctccccgtcg tgtagataac tacgatacgg    10080
gagggcttac catctggccc cagtgctgca atgataccgc gagacccacg ctcaccggct    10140
```

```
ccagatttat cagcaataaa ccagccagcc ggaagggccg agcgcagaag tggtcctgca   10200
actttatccg cctccatcca gtctattaat tgttgccggg aagctagagt aagtagttcg   10260
ccagttaata gtttgcgcaa cgttgttgcc attgctgcag gcatcgtggt gtcacgctcg   10320
tcgtttggta tggcttcatt cagctccggt tcccaacgat caaggcgagt tacatgatcc   10380
cccatgttgt gcaaaaaagc ggttagctcc ttcggtcctc cgatcgttgt cagaagtaag   10440
ttggccgcag tgttatcact catggttatg gcagcactgc ataattctct tactgtcatg   10500
ccatccgtaa gatgcttttc tgtgactggt gagtactcaa ccaagtcatt ctgagaatag   10560
tgtatgcggc gaccgagttg ctcttgcccg gcgtcaacac gggataatac cgcgccacat   10620
agcagaactt taaaagtgct catcattgga aaacgttctt cggggcgaaa actctcaagg   10680
atcttaccgc tgttgagatc cagttcgatg taacccactc gtgcacccaa ctgatcttca   10740
gcatctttta ctttcaccag cgtttctggg tgagcaaaaa caggaaggca aaatgccgca   10800
aaaaagggaa taagggcgac acggaaatgt tgaatactca tactcttcct ttttcaatat   10860
tattgaagca tttatcaggg ttattgtctc atgagcggat acatatttga atgtatttag   10920
aaaaataaac aaataggggt tccgcgcaca tttccccgaa aagtgccacc tgacgtctaa   10980
gaaaccatta ttatcatgac attaacctat aaaaataggc gtatcacgag gccctttcgt   11040
cttcaagaat tggtcgatgg caaacagcta ttatgggtat tatgggttcg aattaattaa   11100
tcgacatcat caataatata ccccac                                        11126
```

<210> SEQ ID NO 73
<211> LENGTH: 21
<212> TYPE: DNA
<213> ORGANISM: Artificial Sequence
<220> FEATURE:
<223> OTHER INFORMATION: CMV.fwd (Ad26_1)

<400> SEQUENCE: 73
gatcagctga cctaggtggt c                                             21

<210> SEQ ID NO 74
<211> LENGTH: 21
<212> TYPE: DNA
<213> ORGANISM: Artificial Sequence
<220> FEATURE:
<223> OTHER INFORMATION: E1.rev (Ad26_7)

<400> SEQUENCE: 74
ctcctcgtta gggtcgtcat c                                             21

<210> SEQ ID NO 75
<211> LENGTH: 22
<212> TYPE: DNA
<213> ORGANISM: Artificial Sequence
<220> FEATURE:
<223> OTHER INFORMATION: polyA.fwd (Ad26_8)

<400> SEQUENCE: 75
tgtggtttgt ccaaactcat ca                                            22

<210> SEQ ID NO 76
<211> LENGTH: 19
<212> TYPE: DNA
<213> ORGANISM: Artificial Sequence
<220> FEATURE:
<223> OTHER INFORMATION: Ad26.pIX.rev (Ad26_9)

```
<400> SEQUENCE: 76
tcgcgtaggt catggtcga                                              19

<210> SEQ ID NO 77
<211> LENGTH: 21
<212> TYPE: DNA
<213> ORGANISM: Artificial Sequence
<220> FEATURE:
<223> OTHER INFORMATION: Ad26.E3.fwd (Ad26_3

<400> SEQUENCE: 77
gagtctcacc tggtcaggtt c                                           21

<210> SEQ ID NO 78
<211> LENGTH: 22
<212> TYPE: DNA
<213> ORGANISM: Artificial Sequence
<220> FEATURE:
<223> OTHER INFORMATION: Ad26.E3.rev (Ad26_4)

<400> SEQUENCE: 78
gctgaacaac tacaccagag ac                                          22

<210> SEQ ID NO 79
<211> LENGTH: 22
<212> TYPE: DNA
<213> ORGANISM: Artificial Sequence
<220> FEATURE:
<223> OTHER INFORMATION: Ad26.E4.fwd (Ad26_5)

<400> SEQUENCE: 79
ttacaccagc acgggtagtc ag                                          22

<210> SEQ ID NO 80
<211> LENGTH: 22
<212> TYPE: DNA
<213> ORGANISM: Artificial Sequence
<220> FEATURE:
<223> OTHER INFORMATION: Ad26.E4.rev (Ad26_6)

<400> SEQUENCE: 80
cggaagttga gtcacgaaat cg                                          22

<210> SEQ ID NO 81
<211> LENGTH: 21
<212> TYPE: DNA
<213> ORGANISM: Artificial Sequence
<220> FEATURE:
<223> OTHER INFORMATION: Ad26_10

<400> SEQUENCE: 81
aattcacagc ctcctcgtta g                                           21

<210> SEQ ID NO 82
<211> LENGTH: 37
<212> TYPE: DNA
<213> ORGANISM: Artificial Sequence
<220> FEATURE:
<223> OTHER INFORMATION: 35BSU.E1btg.AvrII.fwd

<400> SEQUENCE: 82
ataacaccta ggctgatcgc tagggtattt atacctc                          37

<210> SEQ ID NO 83
<211> LENGTH: 37
```

```
<212> TYPE: DNA
<213> ORGANISM: Artificial Sequence
<220> FEATURE:
<223> OTHER INFORMATION: 35BSU.E1btg.AvrII.rev

<400> SEQUENCE: 83
ataacaccta ggttagtcag tttcttctcc actggat                                37

<210> SEQ ID NO 84
<211> LENGTH: 9864
<212> TYPE: DNA
<213> ORGANISM: Artificial Sequence
<220> FEATURE:
<223> OTHER INFORMATION: pAdApt35BSU.E1atg.Mos1-HIVenv

<400> SEQUENCE: 84
gaattggtcg atggcaaaca gctattatgg gtattatggg ttcgaattaa ttaatcgaca      60
tcatcaataa tataccttat agatggaatg gtgccaatat gtaaatgagg tgattttaaa    120
aagtgtgggc cgtgtggtga ttggctgtgg ggttaacggt taaaagggc ggcgcggccg    180
tgggaaaatg acgttttatg ggggtggagt ttttttgcaa gttgtcgcgg gaaatgttac    240
gcataaaaag gcttcttttc tcacggaact acttagtttt cccacggtat ttaacaggaa    300
atgaggtagt tttgaccgga tgcaagtgaa aattgctgat tttcgcgcga aaactgaatg    360
aggaagtgtt tttctgaata atgtggtatt tatggcaggg tggagtattt gttcagggcc    420
aggtagactt tgacccatta cgtggaggtt tcgattaccg tgttttttac ctgaatttcc    480
gcgtaccgtg tcaaagtctt ctgtttttac gtaggtgtca gcctaggtgg tcaatattgg    540
ccattagcca tattattcat tggttatata gcataaatca atattggcta ttggccattg    600
catacgttgt atccatatca taatatgtac atttatattg gctcatgtcc aacattaccg    660
ccatgttgac attgattatt gactagttat taatagtaat caattacggg gtcattagtt    720
catagcccat atatggagtt ccgcgttaca taacttacgg taaatggccc gcctggctga    780
ccgcccaacg acccccgccc attgacgtca ataatgacgt atgttccat agtaacgcca     840
atagggactt tccattgacg tcaatgggtg gagtatttac ggtaaactgc ccacttggca    900
gtacatcaag tgtatcatat gccaagtacg ccccctattg acgtcaatga cggtaaatgg    960
cccgcctggc attatgccca gtacatgacc ttatgggact ttcctacttg gcagtacatc   1020
tacgtattag tcatcgctat taccatggtg atgcggtttt ggcagtacat caatgggcgt   1080
ggatagcggt ttgactcacg gggatttcca agtctccacc ccattgacgt caatgggagt   1140
ttgttttggc accaaaatca acgggacttt ccaaaatgtc gtaacaactc cgccccattg   1200
acgcaaatgg gcggtaggcg tgtacggtgg gaggtctata taagcagagc tcgtttagtg   1260
aaccgtcaga tcgcctggag acgccatcca cgctgttttg acctccatag aagacaccgg   1320
gaccgatcca gcctccgcgg ccgggaacgg tgcattggaa gcttggtacc ggccggtgaa   1380
ttcgccacca tgcgggtgac cggcatccgg aagaactacc agcacctgtg gcggtggggc   1440
accatgctgc tgggcatcct gatgatttgc tctgccgccg aaagctgtgg ggtgaccgtg   1500
tactacggcg tgcccgtgtg gaaagaggcc accaccaccc tgttctgcgc cagcgacgcc   1560
aaggcctacg acaccgaggt gcacaacgtg tgggccaccc acgcctgcgt gcccaccgac   1620
ccaaccccc aggaagtggt cctggaaaac gtgaccgaga cttcaacat gtggaagaac   1680
aacatggtgg agcagatgca cgaggacatc atcagcctgt gggaccagag cctgaagccc   1740
tgcgtgaagc tgacccccct gtgcgtgacc ctgaactgca ccgacgacgt gcggaacgtg   1800
```

-continued

```
accaacaacg ccaccaacac caacagcagc tggggcgagc ctatggaaaa gggcgagatc    1860
aagaactgca gcttcaacat caccacctcc atccggaaca aggtgcagaa gcagtacgcc    1920
ctgttctaca agctggacgt ggtgcccatc gacaacgaca gcaacaacac caactaccgg    1980
ctgatcagct gcaacaccag cgtgatcacc caggcctgcc ccaaggtgtc cttcgagccc    2040
atccccatcc actactgcgc ccctgccggc ttcgccatcc tgaagtgcaa cgacaagaag    2100
ttcaacggca ccggcccctg caccaacgtg agcaccgtgc agtgcaccca cggcatccgg    2160
cccgtggtgt ccacccagct gctgctgaac ggcagcctgg ccgaggaaga ggtggtgatc    2220
agaagcgaga atttcaccaa caatgccaag accatcatgg tgcagctgaa cgtgagcgtg    2280
gagatcaact gcacccggcc caacaacaac acccggaaga gcatccacat cggccctggc    2340
agggccttct acacagccgg cgacatcatc ggcgacatcc ggcaggccca ctgcaacatc    2400
agccgggcca actggaacaa caccctgcgg cagatcgtgg agaagctggg caagcagttc    2460
ggcaacaaca agaccatcgt gttcaaccac agcagcggcg agaccccga gatcgtgatg    2520
cacagcttca actgtggcgg cgagttcttc tactgcaaca gcaccaagct gttcaacagc    2580
acctggacct ggaacaactc cacctggaat aacaccaagc ggagcaacga caccgaagag    2640
cacatcaccc tgccctgccg gatcaagcag attatcaata tgtggcagga ggtcggcaag    2700
gccatgtacg cccctcccat ccggggccag atccggtgca gcagcaacat caccggcctg    2760
ctgctgaccc gggacggcgg caacgatacc agcggcaccg agatcttccg gcctggcggc    2820
ggagatatgc gggacaactg gcggagcgag ctgtacaagt acaaggtggt gaagatcgag    2880
cccctgggcg tggctcccac caaggccaag cggcgggtgg tgcagagcga aagagcgcc    2940
gtgggcatcg gcgccgtgtt tctgggcttc ctgggagccg ccggaagcac catgggagcc    3000
gccagcatga ccctgaccgt gcaggcccgg ctgctgctgt ccggcatcgt gcagcagcag    3060
aacaacctgc tccgggccat cgaggcccag cagcacctgc tgcagctgac cgtgtgggc    3120
atcaagcagc tgcaggccag ggtgctggcc gtggagagat acctgaagga tcagcagctc    3180
ctggggatct ggggctgcag cggcaagctg atctgcacca ccaccgtgcc ctggaacgcc    3240
agctggtcca acaagagcct ggacaagatc tggaacaata tgacctggat ggaatgggag    3300
cgcgagatca acaattacac cagcctgatc tacaccctga tcgaggaaag ccagaaccag    3360
caggaaaaga cgagcagga actgctggaa ctggacaagt gggccagcct gtggaactgg    3420
ttcgacatca gcaactggct gtggtaagct agcgttaacg gatcctctag acgagatccg    3480
aacttgttta ttgcagctta taatggttac aaataaagca atagcatcac aaatttcaca    3540
aataaagcat ttttttcact gcattctagt tgtggtttgt ccaaactcat caatgtatct    3600
tatcatgtct agatacgcgt ctgatcgcta gggtatttat acctcagggt tgtgtcaag    3660
aggccactct tgagtgccag cgagaagagt tttctcctct gcgccggcag tttaataata    3720
aaaaaatgag agatttgcga tttctgcctc aggaaataat ctctgctgag actgaaatg    3780
aaatattgga gcttgtggtg cacgcccga tgggagacga tccggagcca cctgtgcagc    3840
tttttgagcc tcctacgctt caggaactgt atgatttaga ggtagaggga tcggaggatt    3900
ctaatgagga agctgtgaat ggctttttta ccgattctat gcttttagct gctaatgaag    3960
gattagaatt agatccgcct ttggacactt tcaatactcc aggggtgatt gtggaaagcg    4020
gtacaggtgt aagaaaatta cctgattga gttccgtgga ctgtgatttg cactgctatg    4080
aagacgggtt tcctccgagt gatgaggagg accatgaaaa ggagcagtcc atgcagactc    4140
cagcgggtga gggagtgaag gctgccaatg ttggttttca gttggattgc ccggagcttc    4200
```

```
ctggacatgg ctgtaagtct tgtgaatttc acaggaaaaa tactggagta aaggaactgt   4260
tatgttcgct ttgttatatg agaacgcact gccactttat ttacagtaag tgtgtttaag   4320
ttaaaattta aaggaatatg ctgttttttca catgtatatt gagtgtgagt tttgtgcttc   4380
ttattatagg tcctgtgtct gatgctgatg aatcaccatc tcctgattct actacctcac   4440
ctcctgatat tcaagcacct gttcctgtgg acgtgcgcaa gcccattcct gtgaagctta   4500
agcctgggaa acgtccagca gtggagaaac ttgaggactt gttacagggt ggggacggac   4560
ctttggactt gagtacacgg aaacgtccaa gacaataagt gttccatatc cgtgtttact   4620
taaggtgacg tcaatatttg tgtgagagtg caatgtaata aaaatatgtt aactgttcac   4680 tggttttttat tgcttttttgg gcggggactc aggtatataa gtagaagcag acctgtgtgg   4740
ttagctcata ggagctggct ttcatccatg gaggtttggg ccattttgga agaccttagg   4800
aagactaggc aactgttaga gagcgcttcg gacggagtct ccggtttttg gagattctgg   4860
ttcgctagtg aattagctag ggtagttttt aggataaaac aggactataa acaagaattt   4920
gaaaagttgt tggtagattg cccaggactt tttgaagctc ttaatttggg ccatcaggtt   4980
cactttaaag aaaaagtttt atcagttttta gacttttcaa ccccaggtag aactgctgct   5040
gctgtggctt ttcttacttt tatattagat aaatggatcc cgcagactca tttcagcagg   5100
ggatacgttt tggatttcat agccacagca ttgtggagaa catggaaggt tcgcaagatg   5160
aggacaatct taggttactg gccagtgcag cctttgggtg tagcgggaat cctgaggcat   5220
ccaccggtca tgccagcggt tctggaggag gaacagcaag aggacaaccc gagagccggc   5280
ctggaccctc cagtggagga ggcggagtag ctgacttgtc tcctgaactg caacgggtgc   5340
ttactggatc tacgtccact ggacgggata ggggcgttaa gagggagagg gcatccagtg   5400
gtactgatgc tagatctgag ttggctttaa gtttaatgag tcgcagacgt cctgaaacca   5460
tttggtggca tgaggttcag aaagagggaa gggatgaagt ttctgtattg caggagaaat   5520
attcactgga acaggtgaaa acatgttggt tggagccaga ggatgattgg gaggtggcca   5580
ttaaaaatta tgccaagata gctttgaggc ctgataaaca gtataagatc agtgagacgga   5640 ttaatatccg gaatgcttgt tacatatctg gaaatggggc tgaggtggta atagatactc   5700
aagacaagac agttattaga tgctgcatga tggatatgtg gcctggagta gtcggtatgg   5760
aagcagtcac ttttgtaaat gttaagttta ggggagatgg ttataatgga atagtgttta   5820
tggccaatac caaacttata ttgcatggtt gtagcttttt tggtttcaac aatacctgtg   5880
tagatgcctg gggacaggtt agtgtacggg ggtgtagttt ctatgcgtgt tggattgcca   5940
cagctggcag aaccaagagt caattgtctc tgaagaaatg catattccaa agatgtaacc   6000
tgggcattct gaatgaaggc gaagcaaggg tccgtcactg cgcttctaca gatactggat   6060 gtttttatttt aatcaaggga aatgccagcg taaagcataa catgatttgt ggtgcttccg   6120
atgagaggcc ttatcaaatg ctcacttgtg ctggtgggca ttgtaatatg ctggctactg   6180
tgcatattgt ttcccatcaa cgcaaaaaat ggcctgtttt tgatcacaat gtgttgacca   6240
agtgcaccat gcatgcaggt gggcgtagag gaatgtttat gccttaccag tgtaacatga   6300
atcatgtgaa agtgttgttg gaaccagatg cctttttccag aatgagccta acaggaatct   6360
ttgacatgaa cacgcaaatc tggaagatcc tgaggtatga tgatacgaga tcgagggtgc   6420
gcgcatgcga atgcggaggc aagcatgcca ggttccagcc ggtgtgtgta gatgtgaccg   6480
aagatctcag accggatcat ttggttattg cccgcactgg agcagagttc ggatccagtg   6540
```

```
gagaagaaac tgactaaggt gagtattggg aaaactttgg ggtgggattt tcagatggac    6600
agattgagta aaaatttgtt ttttctgtct tgcagctgac atgagtggaa atgcttcttt    6660
taagggggga gtcttcagcc cttatctgac agggcgtctc ccatcctggg caggagttcg    6720
tcagaatgtt atgggatcta ctgtggatgg aagacccgtt caacccgcca attcttcaac    6780
gctgacctat gctactttaa gttcttcacc tttggacgca gctgcagccg ctgccgccgc    6840
ctctgtcgcc gctaacactg tgcttggaat gggttactat ggaagcatcg tggctaattc    6900
cacttcctct aataaccctt ctacactgac tcaggacaag ttacttgtcc ttttggccca    6960
gctggaggct ttgacccaac gtctgggtga actttctcag caggtggccg agttgcgagt    7020
acaaactgag tctgctgtcg gcacggcaaa gtctaaataa aaaaaattcc agaatcaatg    7080
aataaataaa cgagcttgtt gttgatttaa aatcaagtgt ttttatttca tttttcgcgc    7140
acggtatgcc ctgaccacc gatctcgatc attgagaact cggtggattt tttccagaat    7200
cctatagagg tgggattgaa tgtttagata catgggcatt aggccgtctt tggggtggag    7260
atagctccat tgaagggatt catgctccgg ggtagtgttg taaatcaccc agtcataaca    7320
aggtcgcagt gcatggtgtt gcacaatatc ttttagaagt aggctgattg ccacagataa    7380
gcccttggtg taggtgttta caaaccggtt gagctgggag gggtgcattc gaggtgaaat    7440
tatgtgcatt ttggattgga ttttttaagtt ggcaatattg ccgccaagat cccgtcttgg    7500
gttcatgtta tgaaggacta ccaagacggt gtatccggta catttaggaa atttatcgtg    7560
cagcttggat ggaaaagcgt ggaaaaattt ggagacaccc ttgtgtcctc cgagattttc    7620
catgcactca tccatgataa tagcaatggg gccgtgggca gcggcgcggg caaacacgtt    7680
ccgtgggtct gacacatcat agttatgttc ctgagttaaa tcatcataag ccattttaat    7740
gaatttgggg cggagcgtac cagattgggg tatgaatgtt ccttcgggcc ccggagcata    7800
gttcccctca cagatttgca tttcccttaa ttaattcgaa cccataatac ccataatagc    7860
tgtttgccat cgacgcgagg ctggatggcc ttccccatta tgattcttct cgcttccggc    7920
ggcatcggga tgcccgcgtt gcaggccatg ctgtccaggc aggtagatga cgaccatcag    7980
ggacagcttc aaggccagca aaaggccagg aaccgtaaaa aggccgcgtt gctggcgttt    8040
ttccataggc tccgcccccc tgacgagcat cacaaaaatc gacgctcaag tcagaggtgg    8100
cgaaacccga caggactata aagataccag gcgtttcccc ctggaagctc cctcgtgcgc    8160
tctcctgttc cgaccctgcc gcttaccgga tacctgtccg cctttctccc ttcgggaagc    8220
gtggcgcttt ctcatagctc acgctgtagg tatctcagtt cggtgtaggt cgttcgctcc    8280
aagctgggct gtgtgcacga accccccgtt cagcccgacc gctgcgcctt atccggtaac    8340
tatcgtcttg agtccaaccc ggtaagacac gacttatcgc cactggcagc agccactggt    8400
aacaggatta gcagagcgag gtatgtaggc ggtgctacag agttcttgaa gtggtggcct    8460
aactacggct acactagaag gacagtattt ggtatctgcg ctctgctgaa gccagttacc    8520
ttcggaaaaa gagttggtag ctcttgatcc ggcaaacaaa ccaccgctgg tagcggtggt    8580
ttttttgttt gcaagcagca gattacgcgc agaaaaaaag gatctcaaga agatcctttg    8640
atcttttcta cggggtctga cgctcagtgg aacgaaaact cacgttaagg gattttggtc    8700
atgagattat caaaaaggat cttcacctag atccttttaa attaaaaatg aagttttaaa    8760
tcaatctaaa gtatatatga gtaaacttgg tctgacagtt accaatgctt aatcagtgag    8820
gcacctatct cagcgatctg tctatttcgt tcatccatag ttgcctgact ccccgtcgtg    8880
tagataacta cgatacggga gggcttacca tctggcccca gtgctgcaat gataccgcga    8940
```

```
gacccacgct caccggctcc agatttatca gcaataaacc agccagccgg aagggccgag     9000
cgcagaagtg gtcctgcaac tttatccgcc tccatccagt ctattaattg ttgccgggaa     9060
gctagagtaa gtagttcgcc agttaatagt ttgcgcaacg ttgttgccat tgctgcaggc     9120
atcgtggtgt cacgctcgtc gtttggtatg gcttcattca gctccggttc caacgatca     9180
aggcgagtta catgatcccc catgttgtgc aaaaaagcgg ttagctcctt cggtcctccg     9240
atcgttgtca gaagtaagtt ggccgcagtg ttatcactca tggttatggc agcactgcat     9300
aattctctta ctgtcatgcc atccgtaaga tgcttttctg tgactggtga gtactcaacc     9360
aagtcattct gagaatagtg tatgcggcga ccgagttgct cttgcccggc gtcaacacgg     9420
gataataccg cgccacatag cagaacttta aaagtgctca tcattggaaa acgttcttcg     9480
gggcgaaaac tctcaaggat cttaccgctg ttgagatcca gttcgatgta acccactcgt     9540
gcacccaact gatcttcagc atcttttact ttcaccagcg tttctgggtg agcaaaaaca     9600
ggaaggcaaa atgccgcaaa aaagggaata agggcgacac ggaaatgttg aatactcata     9660
ctcttccttt ttcaatatta ttgaagcatt tatcagggtt attgtctcat gagcggatac     9720
atatttgaat gtatttagaa aaataaacaa ataggggttc cgcgcacatt tccccgaaaa     9780
gtgccacctg acgtctaaga aaccattatt atcatgacat taacctataa aaataggcgt     9840
atcacgaggc cctttcgtct tcaa                                            9864

<210> SEQ ID NO 85
<211> LENGTH: 10054
<212> TYPE: DNA
<213> ORGANISM: Artificial Sequence
<220> FEATURE:
<223> OTHER INFORMATION: pAdApt35BSU.E1btg.Mos1-HIVenv

<400> SEQUENCE: 85
gaattggtcg atggcaaaca gctattatgg gtattatggg ttcgaattaa ttaatcgaca       60
tcatcaataa tataccttat agatggaatg gtgccaatat gtaaatgagg tgattttaaa      120
aagtgtgggc cgtgtggtga ttggctgtgg ggttaacggt taaaaggggc ggcgcggccg      180
tgggaaaatg acgttttatg ggggtggagt ttttttgcaa gttgtcgcgg gaaatgttac      240
gcataaaaag gcttcttttc tcacggaact acttagtttt cccacggtat ttaacaggaa      300
atgaggtagt tttgaccgga tgcaagtgaa aattgctgat tttcgcgcga aaactgaatg      360
aggaagtgtt tttctgaata atgtggtatt tatggcaggg tggagtattt gttcagggcc      420
aggtagactt tgacccatta cgtggaggtt tcgattaccg tgttttttac ctgaatttcc      480
gcgtaccgtg tcaaagtctt ctgttttttac gtaggtgtca gcctaggctg atcgctaggg      540
tatttatacc tcagggtttg tgtcaagagg ccactcttga gtgccagcga gaagagtttt      600
ctcctctgcg ccggcagttt aataataaaa aaatgagaga tttgcgattt ctgcctcagg      660
aaataatctc tgctgagact ggaaatgaaa tattggagct tgtggtgcac gccctgatgg      720
gagacgatcc ggagccacct gtgcagcttt ttgagcctcc tacgcttcag gaactgtatg      780
atttagaggt agagggatcg gaggattcta atgaggaagc tgtgaatggc ttttttaccg      840
attctatgct tttagctgct aatgaaggat tagaattaga tccgccttg gacactttca      900
atactccagg ggtgattgtg gaaagcggta caggtgtaag aaaattacct gatttgagtt      960
ccgtggactg tgatttgcac tgctatgaag acgggtttcc tccgagtgat gaggaggacc     1020
atgaaaagga gcagtccatg cagactgcag cgggtgaggg agtgaaggct gccaatgttg     1080
```

-continued

| | | | | |
|---|---|---|---|---|
| gttttcagtt | ggattgcccg | gagcttcctg | gacatggctg | taagtcttgt gaatttcaca | 1140 |
| ggaaaaatac | tggagtaaag | gaactgttat | gttcgctttg | ttatatgaga acgcactgcc | 1200 |
| actttattta | cagtaagtgt | gtttaagtta | aaatttaaag | gaatatgctg tttttcacat | 1260 |
| gtatattgag | tgtgagtttt | gtgcttctta | ttataggtcc | tgtgtctgat gctgatgaat | 1320 |
| caccatctcc | tgattctact | acctcacctc | ctgatattca | agcacctgtt cctgtggacg | 1380 |
| tgcgcaagcc | cattcctgtg | aagcttaagc | ctgggaaacg | tccagcagtg gagaaacttg | 1440 |
| aggacttgtt | acagggtggg | gacggacctt | tggacttgag | tacacggaaa cgtccaagac | 1500 |
| aataagtgtt | ccatatccgt | gtttacttaa | ggtgacgtca | atatttgtgt gagagtgcaa | 1560 |
| tgtaataaaa | atatgttaac | tgttcactgg | ttttttattgc | ttttttgggcg gggactcagg | 1620 |
| tatataagta | gaagcagacc | tgtgtggtta | gctcatagga | gctggctttc atccatggag | 1680 |
| gtttgggcca | ttttggaaga | ccttaggaag | actaggcaac | tgttagagag cgcttcggac | 1740 |
| ggagtctccg | gttttttggag | attctggttc | gctagtgaat | tagctagggt agttttttagg | 1800 |
| ataaaacagg | actataaaca | agaatttgaa | aagttgttgg | tagattgccc aggacttttt | 1860 |
| gaagctctta | atttgggcca | tcaggttcac | tttaaagaaa | aagttttatc agttttagac | 1920 |
| ttttcaaccc | caggtagaac | tgctgctgct | gtggcttttc | ttacttttat attagataaa | 1980 |
| tggatcccgc | agactcattt | cagcagggga | tacgttttgg | atttcatagc cacagcattg | 2040 |
| tggagaacat | ggaaggttcg | caagatgagg | acaatcttag | gttactggcc agtgcagcct | 2100 |
| ttgggtgtag | cgggaatcct | gaggcatcca | ccggtcatgc | cagcggttct ggaggaggaa | 2160 |
| cagcaagagg | acaacccgag | agccggcctg | gaccctccag | tggaggaggc ggagtagctg | 2220 |
| acttgtctcc | tgaactgcaa | cgggtgctta | ctggatctac | gtccactgga cgggataggg | 2280 |
| gcgttaagag | ggagagggca | tccagtggta | ctgatgctag | atctgagttg gctttaagtt | 2340 |
| taatgagtcg | cagacgtcct | gaaaccattt | ggtggcatga | ggttcagaaa gagggaaggg | 2400 |
| atgaagtttc | tgtattgcag | gagaaatatt | cactggaaca | ggtgaaaaca tgttggttgg | 2460 |
| agccagagga | tgattgggag | gtggccatta | aaaattatgc | caagatagct ttgaggcctg | 2520 |
| ataaacagta | taagatcagt | agacggatta | atatccggaa | tgcttgttac atatctggaa | 2580 |
| atggggctga | ggtggtaata | gatactcaag | acaagacagt | tattagatgc tgcatgatgg | 2640 |
| atatgtggcc | tggagtagtc | ggtatggaag | cagtcacttt | tgtaaatgtt aagtttaggg | 2700 |
| gagatggtta | taatggaata | gtgtttatgg | ccaataccaa | acttatattg catggttgta | 2760 |
| gcttttttgg | tttcaacaat | acctgtgtag | atgcctgggg | acaggttagt gtacgggggt | 2820 |
| gtagtttcta | tgcgtgttgg | attgccacag | ctggcagaac | caagagtcaa ttgtctctga | 2880 |
| agaaatgcat | attccaaaga | tgtaacctgg | gcattctgaa | tgaaggcgaa gcaagggtcc | 2940 |
| gtcactgcgc | ttctacagat | actggatgtt | ttattttaat | caagggaaat gccagcgtaa | 3000 |
| agcataacat | gatttgtggt | gcttccgatg | agaggcctta | tcaaatgctc acttgtgctg | 3060 |
| gtgggcattg | taatatgctg | gctactgtgc | atattgtttc | ccatcaacgc aaaaaatggc | 3120 |
| ctgttttttga | tcacaatgtg | ttgaccaagt | gcaccatgca | tgcaggtggg cgtagaggaa | 3180 |
| tgtttatgcc | ttaccagtgt | aacatgaatc | atgtgaaagt | gttgttggaa ccagatgcct | 3240 |
| tttccagaat | gagcctaaca | ggaatctttg | acatgaacac | gcaaatctgg aagatcctga | 3300 |
| ggtatgatga | tacgagatcg | agggtgcgcg | catgcgaatg | cggaggcaag catgccaggt | 3360 |
| tccagccggt | gtgtgtagat | gtgaccgaag | atctcagacc | ggatcatttg gttattgccc | 3420 |
| gcactggagc | agagttcgga | tccagtggag | aagaaactga | ctaacctagg tggtcaatat | 3480 |

```
tggccattag ccatattatt cattggttat atagcataaa tcaatattgg ctattggcca    3540
ttgcatacgt tgtatccata tcataatatg tacatttata ttggctcatg tccaacatta    3600
ccgccatgtt gacattgatt attgactagt tattaatagt aatcaattac ggggtcatta    3660
gttcatagcc catatatgga gttccgcgtt acataactta cggtaaatgg cccgcctggc    3720
tgaccgccca acgaccccg cccattgacg tcaataatga cgtatgttcc catagtaacg    3780
ccaataggga ctttccattg acgtcaatgg gtggagtatt tacggtaaac tgcccacttg    3840
gcagtacatc aagtgtatca tatgccaagt acgccccta ttgacgtcaa tgacggtaaa    3900
tggcccgcct ggcattatgc ccagtacatg accttatggg actttcctac ttggcagtac    3960
atctacgtat tagtcatcgc tattaccatg gtgatgcggt tttggcagta catcaatggg    4020
cgtggatagc ggtttgactc acggggattt ccaagtctcc accccattga cgtcaatggg    4080
agtttgtttt ggcaccaaaa tcaacgggac tttccaaaat gtcgtaacaa ctccgcccca    4140
ttgacgcaaa tgggcggtag gcgtgtacgg tgggaggtct atataagcag agctcgttta    4200
gtgaaccgtc agatcgcctg gagacgccat ccacgctgtt tgacctccat agaagacac    4260 cgggaccgat ccagcctccg cggccgggaa cggtgcattg gaagcttggt accgccggt    4320 gaattcgcca ccatgcgggt gaccggcatc cggaagaact accagcacct gtggcggtgg    4380 ggaccatgc tgctgggcat cctgatgatt tgctctgccg ccggaaagct gtgggtgacc    4440
gtgtactacg gcgtgcccgt gtggaaagag gccaccacca ccctgttctg cgccagcgac    4500
gccaaggcct acgacaccga ggtgcacaac gtgtgggcca cccacgcctg cgtgcccacc    4560
gaccccaacc cccaggaagt ggtcctggaa aacgtgaccg agaacttcaa catgtggaag    4620
aacaacatgg tggagcagat gcacgaggac atcatcagcc tgtgggacca gagcctgaag    4680
ccctgcgtga agctgacccc cctgtgcgtg accctgaact gcaccgacga cgtgcggaac    4740
gtgaccaaca cgccaccaa caccaacagc agctggggcg agcctatgga aaagggcgag    4800
atcaagaact gcagcttcaa catcaccacc tccatccgga acaaggtgca gaagcagtac    4860
gccctgttct acaagctgga cgtggtgccc atcgacaacg acagcaacaa caccaactac    4920
cggctgatca gctgcaacac cagcgtgatc acccaggcct gccccaaggt gtccttcgag    4980
cccatcccca tccactactg cgcccctgcc ggcttcgcca tcctgaagtg caacgacaag    5040
aagttcaacg gcaccggccc ctgcaccaac gtgagcaccg tgcagtgcac ccacggcatc    5100
cggcccgtgg tgtccaccca gctgctgctg aacggcagcc tggccgagga agaggtggtg    5160
atcagaagcg agaatttcac caacaatgcc aagaccatca tggtgcagct gaacgtgagc    5220
gtggagatca actgcacccg gcccaacaac aacacccgga agagcatcca catcggccct    5280
ggcagggcct tctacacagc cggcgacatc atcggcgaca tccggcaggc ccactgcaac    5340
atcagccggg ccaactggaa caacaccctg cggcagatcg tggagaagct gggcaagcag    5400
ttcggcaaca acaagaccat cgtgttcaac cacagcagcg gcggagaccc cgagatcgtg    5460
atgcacagct tcaactgtgg cggcgagttc ttctactgca cagcaccaa gctgttcaac    5520 agcacctgga cctggaacaa ctccacctgg aataacacca gcggagcaa cgacaccgaa    5580 gagcacatca ccctgccctg ccggatcaag cagattatca atatgtggca ggaggtcggc    5640
aaggccatgt acgcccctcc catccggggc cagatccggt gcagcagcaa catcaccggc    5700
ctgctgctga cccgggacgg cggcaacgat accagcggca ccgagatctt ccggcctggc    5760
ggcggagata tgcgggacaa ctggcggagc gagctgtaca agtacaaggt ggtgaagatc    5820
```

-continued

| | |
|---|---|
| gagcccctgg gcgtggctcc caccaaggcc aagcggcggg tggtgcagag cgagaagagc | 5880 |
| gccgtgggca tcggcgccgt gtttctgggc ttcctgggag ccgccggaag caccatggga | 5940 |
| gccgccagca tgaccctgac cgtgcaggcc cggctgctgc tgtccggcat cgtgcagcag | 6000 |
| cagaacaacc tgctccgggc catcgaggcc agcagcacc tgctgcagct gaccgtgtgg | 6060 |
| ggcatcaagc agctgcaggc cagggtgctg gccgtggaga gatacctgaa ggatcagcag | 6120 |
| ctcctgggga tctggggctg cagcggcaag ctgatctgca ccaccaccgt gccctggaac | 6180 |
| gccagctggt ccaacaagag cctggacaag atctggaaca atatgacctg gatggaatgg | 6240 |
| gagcgcgaga tcaacaatta caccagcctg atctacaccc tgatcgagga aagccagaac | 6300 |
| cagcaggaaa agaacgagca ggaactgctg gaactggaca agtgggccag cctgtggaac | 6360 |
| tggttcgaca tcagcaactg gctgtggtaa gctagcgtta acggatcctc tagacgagat | 6420 |
| ccgaacttgt ttattgcagc ttataatggt tacaaataaa gcaatagcat cacaaatttc | 6480 |
| acaaataaag cattttttc actgcattct agttgtggtt tgtccaaact catcaatgta | 6540 |
| tcttatcatg tctagatctg aggtatgatg atacgagatc gagggtgcgc gcatgcgaat | 6600 |
| gcggaggcaa gcatgccagg ttccagccgg tgtgtgtaga tgtgaccgaa gatctcagac | 6660 |
| cggatcattt ggttattgcc cgcactggag cagagttcgg atccagtgga gaagaaactg | 6720 |
| actaaggtga gtattgggaa aactttgggg tgggattttc agatggacag attgagtaaa | 6780 |
| aatttgtttt ttctgtcttg cagctgacat gagtggaaat gcttctttta agggggagt | 6840 |
| cttcagccct tatctgacag ggcgtctccc atcctgggca ggagttcgtc agaatgttat | 6900 |
| gggatctact gtggatggaa gacccgttca acccgccaat tcttcaacgc tgacctatgc | 6960 |
| tactttaagt tcttcacctt tggacgcagc tgcagccgct gccgccgcct ctgtcgccgc | 7020 |
| taacactgtg cttggaatgg gttactatgg aagcatcgtg gctaattcca cttcctctaa | 7080 |
| taacccttct acactgactc aggacaagtt acttgtcctt ttggcccagc tggaggcttt | 7140 |
| gacccaacgt ctgggtgaac tttctcagca ggtggccgag ttgcgagtac aaactgagtc | 7200 |
| tgctgtcggc acggcaaagt ctaaataaaa aaaattccag aatcaatgaa taaataaacg | 7260 |
| agcttgttgt tgatttaaaa tcaagtgttt ttatttcatt tttcgcgcac ggtatgccct | 7320 |
| ggaccaccga tctcgatcat tgagaactcg gtggattttt tccagaatcc tatagaggtg | 7380 |
| ggattgaatg tttagataca tgggcattag gccgtctttg gggtggagat agctccattg | 7440 |
| aagggattca tgctccgggg tagtgttgta aatcacccag tcataacaag gtcgcagtgc | 7500 |
| atggtgttgc acaatatctt ttagaagtag gctgattgcc acagataagc ccttggtgta | 7560 |
| ggtgtttaca aaccggttga gctgggaggg gtgcattcga ggtgaaatta tgtgcatttt | 7620 |
| ggattggatt tttaagttgg caatattgcc gccaagatcc cgtcttggt tcatgttatg | 7680 |
| aaggactacc aagacggtgt atccggtaca tttaggaaat ttatcgtgca gcttggatgg | 7740 |
| aaaagcgtgg aaaatttgg agacacccct gtgtcctccg agattttcca tgcactcatc | 7800 |
| catgataata gcaatgggc cgtgggcagc ggcgcgggca acacgttcc gtgggtctga | 7860 |
| cacatcatag ttatgttcct gagttaaatc atcataagcc atttaatga atttggggcg | 7920 |
| gagcgtacca gattggggta tgaatgtcc ttcgggcccc ggagcatagt tcccctcaca | 7980 |
| gatttgcatt tcccttaatt aattcgaacc cataataccc ataatagctg tttgccatcg | 8040 |
| acgcgaggct ggatgccctt ccccattatg attcttctcg cttccggcgg catcgggatg | 8100 |
| cccgcgttgc aggccatgct gtccaggcag gtagatgacg accatcaggg acagcttcaa | 8160 |
| ggatcgctcg cggctcttac cagcccagca aaaggccagg aaccgtaaaa aggccgcgtt | 8220 |

| | |
|---|---|
| gctggcgttt tccataggc tccgcccccc tgacgagcat cacaaaaatc gacgctcaag | 8280 |
| tcagaggtgg cgaaacccga caggactata aagataccag gcgtttcccc ctggaagctc | 8340 |
| cctcgtgcgc tctcctgttc cgaccctgcc gcttaccgga tacctgtccg cctttctccc | 8400 |
| ttcgggaagc gtggcgcttt ctcatagctc acgctgtagg tatctcagtt cggtgtaggt | 8460 |
| cgttcgctcc aagctgggct gtgtgcacga accccccgtt cagcccgacc gctgcgcctt | 8520 |
| atccggtaac tatcgtcttg agtccaaccc ggtaagacac gacttatcgc cactggcagc | 8580 |
| agccactggt aacaggatta gcagagcgag gtatgtaggc ggtgctacag agttcttgaa | 8640 |
| gtggtggcct aactacggct acactagaag gacagtattt ggtatctgcg ctctgctgaa | 8700 |
| gccagttacc ttcggaaaaa gagttggtag ctcttgatcc ggcaaacaaa ccaccgctgg | 8760 |
| tagcggtggt ttttttgttt gcaagcagca gattacgcgc agaaaaaaag gatctcaaga | 8820 |
| agatcctttg atcttttcta cggggtctga cgctcagtgg aacgaaaact cacgttaagg | 8880 |
| gattttggtc atgagattat caaaaaggat cttcacctag atccttttaa attaaaaatg | 8940 |
| aagttttaaa tcaatctaaa gtatatatga gtaaacttgg tctgacagtt accaatgctt | 9000 |
| aatcagtgag gcacctatct cagcgatctg tctatttcgt tcatccatag ttgcctgact | 9060 |
| ccccgtcgtg tagataacta cgatacggga gggcttacca tctggcccca gtgctgcaat | 9120 |
| gataccgcga gacccacgct caccggctcc agatttatca gcaataaacc agccagccgg | 9180 |
| aagggccgag cgcagaagtg gtcctgcaac tttatccgcc tccatccagt ctattaattg | 9240 |
| ttgccgggaa gctagagtaa gtagttcgcc agttaatagt ttgcgcaacg ttgttgccat | 9300 |
| tgctgcaggc atcgtggtgt cacgctcgtc gtttggtatg gcttcattca gctccggttc | 9360 |
| ccaacgatca aggcgagtta catgatcccc catgttgtgc aaaaaagcgg ttagctcctt | 9420 |
| cggtcctccg atcgttgtca gaagtaagtt ggccgcagtg ttatcactca tggttatggc | 9480 |
| agcactgcat aattctctta ctgtcatgcc atccgtaaga tgcttttctg tgactggtga | 9540 |
| gtactcaacc aagtcattct gagaatagtg tatgcggcga ccgagttgct cttgcccggc | 9600 |
| gtcaacacgg gataataccg cgccacatag cagaacttta aaagtgctca tcattggaaa | 9660 |
| acgttcttcg gggcgaaaac tctcaaggat cttaccgctg ttgagatcca gttcgatgta | 9720 |
| acccactcgt gcacccaact gatcttcagc atcttttact ttcaccagcg tttctgggtg | 9780 |
| agcaaaaaca ggaaggcaaa atgccgcaaa aaagggaata agggcgacac ggaaatgttg | 9840 |
| aatactcata ctcttccttt ttcaatatta ttgaagcatt tatcagggtt attgtctcat | 9900 |
| gagcggatac atatttgaat gtatttagaa aaataaacaa ataggggttc cgcgcacatt | 9960 |
| tccccgaaaa gtgccacctg acgtctaaga aaccattatt atcatgacat taacctataa | 10020 |
| aaataggcgt atcacgaggc cctttcgtct tcaa | 10054 |

<210> SEQ ID NO 86
<211> LENGTH: 20
<212> TYPE: DNA
<213> ORGANISM: Artificial Sequence
<220> FEATURE:
<223> OTHER INFORMATION: Ad26.RT.fwd

<400> SEQUENCE: 86
tgcttacttt gacgtccctg                                          20

<210> SEQ ID NO 87
<211> LENGTH: 22
<212> TYPE: DNA
<213> ORGANISM: Artificial Sequence

```
<220> FEATURE:
<223> OTHER INFORMATION: Ad26.RT.Rev

<400> SEQUENCE: 87
actgttatct gaagttcctg gc                                           22

<210> SEQ ID NO 88
<211> LENGTH: 26
<212> TYPE: DNA
<213> ORGANISM: Artificial Sequence
<220> FEATURE:
<223> OTHER INFORMATION: Ad26.RT.probe

<400> SEQUENCE: 88
ttgtattctt ccccactacc acctgc                                       26

<210> SEQ ID NO 89
<211> LENGTH: 24
<212> TYPE: DNA
<213> ORGANISM: Artificial Sequence
<220> FEATURE:
<223> OTHER INFORMATION: AdApt35BSU.NdeI.fwd

<400> SEQUENCE: 89
gtgtatcata tgccaagtac gccc                                         24

<210> SEQ ID NO 90
<211> LENGTH: 38
<212> TYPE: DNA
<213> ORGANISM: Artificial Sequence
<220> FEATURE:
<223> OTHER INFORMATION: AdApt35BSU.MluI.rev

<400> SEQUENCE: 90
cgatcacgcg tatctagaca tgataagata cattgatg                          38

<210> SEQ ID NO 91
<211> LENGTH: 35
<212> TYPE: DNA
<213> ORGANISM: Artificial Sequence
<220> FEATURE:
<223> OTHER INFORMATION: Ad35WT.464.MluI.fwd

<400> SEQUENCE: 91
acagacgcgt ctgatcgcta gggtatttat acctc                             35

<210> SEQ ID NO 92
<211> LENGTH: 24
<212> TYPE: DNA
<213> ORGANISM: Artificial Sequence
<220> FEATURE:
<223> OTHER INFORMATION: Ad35WT.AleI.rev

<400> SEQUENCE: 92
ggaggacaca agggtgtctc caaa                                         24

<210> SEQ ID NO 93
<211> LENGTH: 3387
<212> TYPE: DNA
<213> ORGANISM: Artificial Sequence
<220> FEATURE:
<223> OTHER INFORMATION: CMV-MOs1Env-polyA Transgene PCR Product Ref.
      Seq.
```

<400> SEQUENCE: 93

```
gatcagctga cctaggtggt caatattggc cattagccat attattcatt ggttatatag    60
cataaatcaa tattggctat tggccattgc atacgttgta tccatatcat aatatgtaca   120
tttatattgg ctcatgtcca acattaccgc catgttgaca ttgattattg actagttatt   180
aatagtaatc aattacgggg tcattagttc atagcccata tatggagttc cgcgttacat   240
aacttacggt aaatggcccg cctggctgac cgcccaacga cccccgccca ttgacgtcaa   300
taatgacgta tgttcccata gtaacgccaa tagggacttt ccattgacgt caatgggtgg   360
agtatttacg gtaaactgcc cacttggcag tacatcaagt gtatcatatg ccaagtacgc   420
cccctattga cgtcaatgac ggtaaatggc ccgcctggca ttatgcccag tacatgacct   480
tatgggactt tcctacttgg cagtacatct acgtattagt catcgctatt accatggtga   540
tgcggttttg gcagtacatc aatgggcgtg gatagcggtt tgactcacgg ggatttccaa   600
gtctccaccc cattgacgtc aatgggagtt tgttttggca ccaaaatcaa cgggactttc   660
caaaatgtcg taacaactcc gccccattga cgcaaatggg cggtaggcgt gtacggtggg   720
aggtctatat aagcagagct cgtttagtga accgtcagat cgcctggaga cgccatccac   780
gctgttttga cctccataga agacaccggg accgatccag cctccgcggc cgggaacggt   840
gcattggaag cttggtaccg gtgaattcgc caccatgcgg gtgaccggca tccggaagaa   900
ctaccagcac ctgtggcggt ggggcaccat gctgctgggc atcctgatga tttgctctgc   960
cgccggaaag ctgtgggtga ccgtgtacta cggcgtgccc gtgtggaaag aggccaccac  1020
cacccctgttc tgcgccagcg acgccaaggc ctacgacacc gaggtgcaca acgtgtgggc  1080
cacccacgcc tgcgtgccca ccgaccccaa ccccaggaa gtggtcctgg aaaacgtgac  1140
cgagaacttc aacatgtgga gaacaacat ggtggagcag atgcacgagg acatcatcag  1200
cctgtgggac cagagcctga agccctgcgt gaagctgacc cccctgtgcg tgaccctgaa  1260
ctgcaccgac gacgtgcgga acgtgaccaa caacgccacc aacaccaaca gcagctgggg  1320
cgagcctatg gaaaagggcg agatcaagaa ctgcagcttc aacatcacca cctccatccg  1380
gaacaaggtg cagaagcagt acgccctgtt ctacaagctg gacgtggtgc catcgacaa  1440
cgacagcaac aacaccaact accggctgat cagctgcaac accagcgtga tcacccaggc  1500
ctgccccaag gtgtccttcg agcccatccc catccactac tgcgcccctg ccggcttcgc  1560
catcctgaag tgcaacgaca gaagttcaa cggcaccggc cctgcacca cgtgagcac  1620
cgtgcagtgc acccacggca tccggcccgt ggtgtccacc cagctgctgc tgaacggcag  1680
cctggccgag gaagaggtgg tgatcagaag cgagaatttc accaacaatg ccaagaccat  1740
catggtgcag ctgaacgtga gcgtggagat caactgcacc cggcccaaca caacacccg  1800
gaagagcatc cacatcggcc ctggcagggc cttctacaca gccggcgaca tcatcggcga  1860
catccggcag gcccactgca acatcagccg ggccaactgg aacaacaccc tgcggcagat  1920
cgtggagaag ctgggcaagc agttcggcaa caacaagacc atcgtgttca accacagcag  1980
cggcggagac cccgagatcg tgatgcacag cttcaactgt ggcggcgagt tcttctactg  2040
caacagcacc aagctgttca acagcacctg gacctgaac aactccacct ggaataacac  2100
caagcggagc aacgacaccg aagagcacat caccctgccc tgccggatca gcagattat  2160
caatatgtgg caggaggtcg gcaaggccat gtacgcccct cccatccggg ccagatccg  2220
gtgcagcagc aacatcaccg gcctgctgct gacccgggac ggcggcaacg ataccagcgg  2280
caccgagatc ttccggcctg gcggcggaga tatgcgggac aactggcgga gcgagctgta  2340
```

-continued

```
caagtacaag gtggtgaaga tcgagcccct gggcgtggct cccaccaagg ccaagcggcg    2400
ggtggtgcag agcgagaaga gcgccgtggg catcggcgcc gtgtttctgg gcttcctggg    2460
agccgccgga agcaccatgg gagccgccag catgaccctg accgtgcagg cccggctgct    2520
gctgtccggc atcgtgcagc agcagaacaa cctgctccgg gccatcgagg cccagcagca    2580
cctgctgcag ctgaccgtgt ggggcatcaa gcagctgcag gccagggtgc tggccgtgga    2640
gagatacctg aaggatcagc agctcctggg gatctgggc tgcagcggca agctgatctg     2700
caccaccacc gtgccctgga acgccagctg gtccaacaag agcctggaca agatctggaa    2760
caatatgacc tggatggaat gggagcgcga gatcaacaat tacaccagcc tgatctacac    2820
cctgatcgag gaaagccaga accagcagga aaagaacgag caggaactgc tggaactgga    2880
caagtgggcc agcctgtgga actggttcga catcagcaac tggctgtggt aatgaggatc    2940
ctctagacga gatccgaact tgtttattgc agcttataat ggttacaaat aaagcaatag    3000
catcacaaat ttcacaaata aagcattttt ttcactgcat tctagttgtg gtttgtccaa    3060
actcatcaat gtatcttatc atgtctagat acgcgtatca gctgatccgc agggtattta    3120
aaccagtcga gtccgtcaag aggccactct tgagtgccag cgagtagaga tttctctgag    3180
ctccgctccc agagaccgag aaaaatgaga cacctgcgcc tcctgccttc aactgtgccc    3240
ggtgagctgg ctgtgcttat gctggaggac tttgtggata cagtattgga ggacgaactg    3300
catccaagtc cgttcgagct gggacccaca cttcaggatc tctatgatct ggaggtagat    3360
gcccatgatg acgaccctaa cgaggag                                        3387
```